(12) United States Patent
Fujiwara et al.

(10) Patent No.: US 7,396,842 B2
(45) Date of Patent: Jul. 8, 2008

(54) FIVE-MEMBERED CYCLIC COMPOUNDS

(75) Inventors: Norio Fujiwara, Yao (JP); Hitoshi Fujita, Takatsuki (JP); Fujio Antoku, Nishinomiya (JP); Toshinari Sugasawa, Nishinomiya (JP); Hajime Kawakami, Nishinomiya (JP)

(73) Assignee: Dianippon Sumitomo Pharma Co., Ltd., Osaka (JP)

( * ) Notice: Subject to any disclaimer, the term of this patent is extended or adjusted under 35 U.S.C. 154(b) by 370 days.

(21) Appl. No.: 11/111,845

(22) Filed: Apr. 22, 2005

(65) Prior Publication Data

US 2005/0222226 A1 Oct. 6, 2005

Related U.S. Application Data

(62) Division of application No. 10/312,692, filed on Dec. 30, 2002, now Pat. No. 6,919,361.

(51) Int. Cl.
*A61K 31/44* (2006.01)
*C07D 417/00* (2006.01)

(52) U.S. Cl. .................. 514/342; 514/235.5; 546/269.7; 544/124; 544/133

(58) Field of Classification Search .................. 544/124, 544/133; 546/269.7; 514/235.5, 342
See application file for complete search history.

(56) References Cited

U.S. PATENT DOCUMENTS 6,639,077 B2 * 10/2003 Cote et al. ............... 546/269.7

FOREIGN PATENT DOCUMENTS

| DE | 941288 C | 4/1956 |
|---|---|---|
| WO | WO98/26065 A1 | 6/1998 |
| WO | WO01/07424 A1 | 2/2001 |
| WO | WO01/32604 A1 | 5/2001 |

OTHER PUBLICATIONS

Kaye et al., J. Am. Chem. Soc., vol. 74, pp. 2921-2922, (1952).
Druey et al., Helv. Chim. Acta, vol. 24, pp. 226E-233E, (1941).
Previtera et al., Farmaco Soc. Chim. Ital., vol. 49, No. 1, pp. 33-40, (1994).
Nemes et al., Acta Chimica Academiae Scientiarum Hungaricae, Tomus, vol. 78, No. 3, pp. 283-291, (1973).
Acheson et al., Journal of Chemical Society, Perkin Transactions 1, vol. 8, pp. 1773-1778, (1980).
Yamamoto et al., Chemical & Pharmaceutical Bulletin, vol. 32, No. 11, pp. 4292-4299, (1984).
Tsatsas et al., Chimika Chronika New Series 1, vol. 1, No. 3-4, pp. 188-192, (1972).
Selwood et al., 2001, CAS:134:353175.
Matsuura et al., 2002, CAS:138:39276.
Christensen et al., 1999, CAS:130:237560.

* cited by examiner

*Primary Examiner*—Rei-Tsang Shiao
(74) *Attorney, Agent, or Firm*—Birch Stewart Kolasch & Birch LLP

(57) ABSTRACT

A 5-membered cyclic compound of the formula:

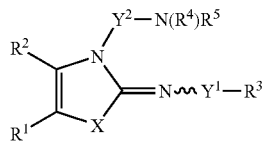

wherein X is oxygen or sulfur, $R^1$ is hydrogen, substituted or unsubstituted alkyl, etc., $R^2$ is hydrogen, substituted or unsubstituted alkyl, substituted or unsubstituted aryl, etc., $Y^1$ is a direct bond, substituted or unsubstituted alkylene, —CO$(CH_2)_n$—, etc., the wavy line means (E)-configuration or (Z)-configuration, $R^3$ is substituted or unsubstituted aryl, etc., $Y^2$ is substituted or unsubstituted alkylene, etc., $R^4$ is hydrogen, substituted or unsubstituted alkanoyl, substituted or unsubstituted alkyl, etc., $R^5$ is hydrogen, etc., or a salt thereof, these compound being able to inhibit infiltration of leukocytes such as eosinophils and lymphocytes, by which being useful for the treatment of various kinds of inflammation.

14 Claims, No Drawings

FIVE-MEMBERED CYCLIC COMPOUNDS

This application is a Divisional of application Ser. No. 10/312,692, filed on Dec. 30, 2002, now U.S. Pat. No. 6,919,361 and for which priority is claimed under 35 U.S.C. § 120; and this application claims priority of Application No. 2000-198074 filed in Japan on Jun. 30, 2000 under 35 U.S.C. § 119; the entire contents of all are hereby incorporated by reference.

TECHNICAL FIELD

The present invention relates to a novel 5-membered cyclic compound or a salt thereof, and a clinical use thereof. More particularly, the present invention relates to a novel 5-membered cyclic compound or a salt thereof, which binds in vivo to a specific binding site of L-threo-3-(3,4-dihydroxyphenyl)-N-[3-(4-fluorophenyl)propyl]serine-pyrrolidinamide, and inhibits the infiltration by leukocytes such as eosinophil or lymphocyte, whereby being useful in the treatment of various inflammations, and a pharmaceutical composition thereof.

BACKGROUND ART

A method of inducing immediate asthmatic response (IAR) by inhalation of an allergen in a patient with atopic asthma has been employed as an experimental model for respiratory distress in bronchial asthma. Namely, when a patient with atopic asthma inhales an allergen, then the patient has an asthmatic response (broncho-constriction) after about 20 minutes, and further 2 hours thereafter, the symptom returns to the original condition. Then, keeping on observation of the patient who had immediate asthmatic response, it has been confirmed that about half of the patients who have immediate asthmatic response showed again a bronchoconstriction 6 to 10 hours thereafter, and it was named as late asthmatic response (LAR) (cf., Booji-Noord, H, et al., J. Allergy Clin. Immunol., 48, 344-354, 1971). In late asthmatic response, the bronchial obstruction lasts for a long period, and pulmonary overexpansion is accompanied thereto, but this response is strongly suppressed by corticosteroids. From this fact, the above bronchial asthma induced by an allergen has been recognized as an important clinical model for steroid-dependent respiratory distress of serious bronchial asthma. Immediate asthmatic response has been considered as type I allergy induced as a result of a mast cell activation by IgE antibody, while late asthmatic response has been considered as T lymphocyte- and eosinophilic-induced allergic responses (eosinophilic inflammation). It has been clarified that these immediate asthmatic response and late asthmatic response are also induced in the allergic rhinitis or atopic dermatitides (cf., OKUDAIRA Hirokazu, medicina 34, p. 200-203 (1997)). In addition, the bronchoalveolar eosinophilia during allergen-induced late asthmatic reactions has been reported in a patient with bronchial asthma (cf., De Monchy, J. G., et al., Am. Rev. Respir. Dis., 131, 373-376 (1985)). From the increase of eosinophils in the peripheral blood and sputum of many patients with bronchial asthma, massive infiltration by eosinophils in the pulmonary tissue of a patient who died by asthma, and the deposition of major basic protein (MBP) at bronchial wall and mucous plug of patients, which is a tissue toxic protein derived from eosinophils, certain product derived from eosinophils has been considered to play an important role in bronchial epithelium injury accompanying to late asthmatic response (cf., Filley, W. V., et al., Lancet. 2 (8288), 11-6 (1982)).

At present, the concept of developing bronchial asthma has been considered as a chronic inflammatory disease from a simple reversible bronchial spasm, and according to this change of the concept, a method for treatment thereof should also have been changed. US National Institute of Health National Heart Lung Blood Institute (NIH/NHLBI) and WHO announced a Global Initiative for Asthma (GINA) for controlling and preventing asthma in 1995, and it has been an international guidance for treatment of a patient with bronchial asthma. As mentioned above, until comparatively lately, bronchial asthma had been considered as type 1 allergy in which IgE antibody participates, and a medicament for treatment thereof had been developed based on a role of mast cell in the mechanism of pathogeny thereof. However, at present, as shown in the opinion of NIH/NHLBI, bronchial asthma is positioned to be an inflammatory disease at airway, and bronchial asthma is considered to be "chronic epithelium desquamative eosinophilic infiltrative bronchial infection" as inflammation of airway induced by inflammatory cells which are mainly eosinophils/T lymphocytes (cf., Miwa MISAWA, Folia Pharmacologica Japonica, 111, 193-194 (1998)). In the above-mentioned GINA, conventional methods in Europe and the United States for treatment of asthma have mainly been employed, and inhaled corticosteroids are used as a primary choice. According to this guide line, there is established a guide line for treatment of asthma having inhaled corticosteroids as basal medication in Japan (cf., under the editorship of Sohei MAKINO, Japanese Society of Allergology, Guide Line for treatment of Allergic diseases, p. 3-65, Life Science Medica (1995)).

Corticosteroids are considered to be the only remedy for serious bronchial asthma and atopic dermatitis, but they exhibit their potent effects as well as side effects such as hypertension, diabetes mellitus, obesity, immune suppression, cataracta, mental disorder, atrophy cutis, etc. Inhaled corticosteroids have been developed in order to reduce such systemic side effects of steroids, but it is difficult to prove that corticosteroids administered by inhalation do not circulate in entire body, and fears for inherent side effects of corticosteroids cannot be eradicated. Recently, side effects of inhaled corticosteroids have been reported in Europe and the United States, and FDA of the United States instructs to attach a warning as to the risk of side effects to inhalant corticosteroids for treatment of bronchial asthma and nasal inhalant corticosteroids for treatment of allergic rhinitis (Konig, P., Allergol. Int., 49, 1-6 (2000)).

As mentioned above, the infiltration by eosinophils into lesion plays an important role in the onset and exacerbation of late response of not only bronchial asthma but also of allergic dermatitis or rhinitis. However, by suppressing the infiltration and activation of eosinophils, only corticosteroids are specific remedies for treatment of allergic diseases, for example, bronchial asthma, and in the clinical field, it has been desired to develop an anti-inflammatory agent, which can take the place of corticosteroids, and have fewer side effects and also can be orally administered. For example, as a trial of developing an agent for suppressing eosinophilic inflammation, an antibody neutralizing interleukin-5 (anti-IL-5 neutralization antibody), which induces the proliferation-differentiation of eosinophilic precursor cell, extension of survival of mature eosinophils (cf., Garlisi, C. G., Pulm. Pharmacol. Ther., 12, 81-85 (1999)), a low molecular inhibitor of Very Late Antigen 4 (VLA-4), which is an adhesive factor being specific to eosinophil (cf., Haworth, D., et al., Br. J. Pharmacol., 126, 1751-1760 (1999)), a low molecular antagonist against CCR3, a receptor of eotaxin, which is a chemokine being specific to eosinophil and induces eosinophil migration (cf., Wells, T. N. C., et al., Inflammation Res., 48, 353-62, (1999)) have been studied, but they cannot take the place of corticosteroids yet.

On the other hand, L-threo-3-(3,4-dihydroxyphenyl)-N-[3-(4-fluorophenyl)propyl]serinepyrrolidinamide has been known to exhibit an inhibitory effect of eosinophil migration (cf., Sugasawa, T. and Morooka, S., Recent Advances in Cellular and Molecular Biology, 3, 223-227, Peeters Press, Leuven, Belgium (1992), Sugasawa, T. et al., J. Biol. Chem., 272, 21244-21252 (1997), WO 98/26065). The in vivo specific binding site of this L-threo-3-(3,4-dihydroxyphenyl)-N-[3-(4-fluorophenyl)propyl]serinepyrrolidinamide is a receptor-like membrane protein and referred to as SMBS protein (SMBP) (cf., Sugasawa, T. et al., J. Biol. Chem., 267, 21244-21252 (1997), WO 98/26065).

Therefore, if the eosinophil migration can be inhibited by binding to this SMBS protein, then it may be possible to treat allergic diseases such as asthma, etc.

DISCLOSURE OF INVENTION

An object of the present invention is to provide a compound being useful as an agent for treatment of various inflammations by inhibiting the infiltration of leukocyte such as eosinophils, lymphocytes, etc., and to provide a pharmaceutical composition containing the same.

The present inventors have intensively studied in order to solve the above problems, and have found that SMBS appears on rat's lung membranes. Combining this fact and the report that L-threo-3-(3,4-dihydroxyphenyl)-N-[3-(4-fluorophenyl)propyl]serinepyrrolidinamide and [$^{125}$I]iodocyanopindorole can combine together (cf., Sugasawa, T. et al., J. Biol. Chem., 272, 21244-21252 (1997), WO 98/26065), they have constructed a new method for testing inhibition of onset of late response, and subjected various compounds to screening by using said method, and finally found that certain 5-membered cyclic compounds bind to SMBS and suppress the infiltration of leukocytes such as eosinophils, lymphocytes, etc., and finally have accomplished the present invention.

The present invention relates to the following:

[1] A 5-membered cyclic compound of the formula:

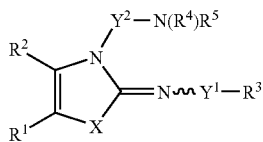

wherein X is an oxygen atom or a sulfur atom, $R^1$ is a hydrogen atom, a substituted or unsubstituted alkyl, a substituted or unsubstituted aryl, or a substituted or unsubstituted heteromonocyclic or heterobicyclic group, $R^2$ is a hydrogen atom, a substituted or unsubstituted alkyl, a substituted or unsubstituted aryl, a substituted or unsubstituted heteromonocyclic or heterobicyclic group, or —CON($R^6$)$R^7$, $R^6$ is a hydrogen atom, or a substituted or unsubstituted alkyl, $R^7$ is a substituted or unsubstituted aryl, a substituted or unsubstituted heteromonocyclic group, or a substituted or unsubstituted alkyl, or —N($R^6$)$R^7$ may be a cyclic imino group, $Y^1$ is a direct bond, a substituted or unsubstituted alkylene, —CO(CH$_2$)$_n$—, —SO$_2$(CH$_2$)$_n$—, —CONH(CH$_2$)$_n$—, —CSNH(CH$_2$)$_n$—, or —COO(CH$_2$)$_n$—, n is an integer of from 0 to 5, the wavy line means (E)-configuration or (Z)-configuration, $R^3$ is a hydrogen atom, a substituted or unsubstituted aryl, a substituted or unsubstituted heteromonocyclic group, a substituted or unsubstituted heterobicyclic group, or a substituted or unsubstituted cycloalkyl, $Y^2$ is a substituted or unsubstituted alkylene, or an alkenylene, $R^4$ is a hydrogen atom, a substituted or unsubstituted alkanoyl, a substituted or unsubstituted alkyl, —COOR$^8$, —SO$_2$R$^9$, —COR$^{10}$, —CON(R$^{11}$)R$^{12}$, —CSN(R$^{13}$)R$^{14}$, a cycloalkyl, a substituted or unsubstituted aryl, a substituted or unsubstituted heteromonocyclic group, —C(=NH)N(R$^{15}$)R$^{16}$, $R^5$ is a hydrogen atom, or a substituted or unsubstituted alkyl, or —N(R$^4$)R$^5$ may be a cyclic imino group, $R^8$ is a substituted or unsubstituted alkyl, a cycloalkyl, a substituted or unsubstituted aryl, or a substituted or unsubstituted heteromonocyclic group, $R^9$ is a substituted or unsubstituted alkyl, a substituted or unsubstituted aryl, or a substituted or unsubstituted heteromonocyclic group, $R^{10}$ is a cycloalkyl, a substituted or unsubstituted aryl, or a substituted or unsubstituted heteromonocyclic group, $R^{11}$ is a hydrogen atom or an alkyl, $R^{12}$ is a hydrogen atom, a substituted or unsubstituted alkyl, a cycloalkyl, a substituted or unsubstituted aryl, a substituted or unsubstituted arylcarbonyl, or a substituted or unsubstituted heteromonocyclic group, or a-N(R$^{11}$)R$^{12}$ may be a cyclic imino group, $R^{13}$ is a hydrogen atom or an alkyl, $R^{14}$ is a hydrogen atom, a substituted or unsubstituted alkyl, a cycloalkyl, a substituted or unsubstituted aryl, a substituted or unsubstituted arylcarbonyl, or a substituted or unsubstituted heteromonocyclic group, or —N(R$^{13}$)R$^{14}$ may be a cyclic imino group, $R^{15}$ is a hydrogen atom or an alkyl, $R^{16}$ is a hydrogen atom or a substituted or unsubstituted alkyl, or —N(R$^{15}$)R$^{16}$ may be a cyclic imino group, or a pharmaceutically acceptable salt thereof, or a prodrug thereof.

[2] The 5-membered cyclic compound according to the above [1], provided that when $Y^1$ is a direct bond, then —N(R$^4$)R$^5$ is neither an amino, nor a dialkylamino, nor an acetylamino, or a pharmaceutically acceptable salt thereof, or a prodrug thereof.

[3] The 5-membered cyclic compound according to the above [1], which is a compound of the formula:

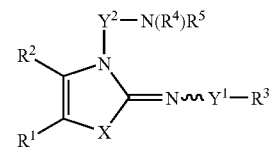

wherein X is an oxygen atom or a sulfur atom, $R^1$ is a hydrogen atom, a substituted or unsubstituted alkyl, a substituted or unsubstituted aryl, or a substituted or unsubstituted heterobicyclic group, $R^2$ is a hydrogen atom, a substituted or unsubstituted alkyl, a substituted or unsubstituted aryl, or a substituted or unsubstituted heterobicyclic group, $Y^1$ is a direct bond, a substituted or unsubstituted alkylene, —CO(CH$_2$)$_n$—, or —SO$_2$(CH$_2$)$_n$— (n is an integer of from 0 to 5), the wavy line means (E)-configuration or (Z)-configuration, $R^3$ is a substituted or unsubstituted aryl, a substituted or unsubstituted 5- or 6-membered heteromonocyclic group, or a substituted or unsubstituted heterobicyclic group, $Y^2$ is a substituted or unsubstituted alkylene, or an alkenylene, $R^4$ is a hydrogen atom, an alkanoyl, an aryl, a substituted or unsubstituted alkyl, an alkylcarbamoyl, an alkoxycarbonyl, an alkyl-aminothiocarbonyl, an alkylsulfonyl, or a substituted or unsubstituted arylsulfonyl, $R^5$ is a hydrogen atom, or a substituted or unsubstituted alkyl, or a pharmaceutically acceptable salt thereof, or a prodrug thereof.

[4] The 5-membered cyclic compound according to the above [1], which is a compound of the formula:

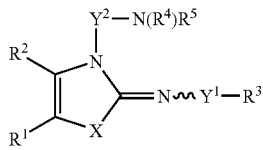

wherein X is an oxygen atom or a sulfur atom, $R^1$ is a hydrogen atom; an alkyl; an alkyl being substituted by a hydroxy, a halogen atom or an amino; an aryl; an aryl which is substituted by one or more groups selected from the group consisting of an alkoxy, a halogen-substituted alkoxy, a hydroxy, a halogen atom, a cyano, an amino, a mono- or di-(alkyl)amino, a 5- or 6-membered cyclic imino group having optionally an oxygen atom or a nitrogen atom as a heteroatom for ring formation, a nitro, an alkyl, an alkyl being substituted by a halogen atom or a hydroxy, a cycloalkyl, a cycloalkyl-substituted alkyl, a methylenedioxy, an ethylenedioxy, a carboxy, an alkoxycarbonyl, a carbamoyl, an alkylcarbamoyl, a di(alkyl)carbamoyl, an alkylthio, an alkylsulfinyl, an alkylsulfonyl, a sulfamoyl, an alkyl-sulfamoyl, a di(alkyl)sulfamoyl, an aryl, and an aryl being substituted by an alkyl, an alkoxy, a halogen atom or a hydroxy; a heterobicyclic group which is formed by condensing a benzene ring with a 5- or 6-membered heterocyclic group containing 1 to 3 heteroatoms selected from a nitrogen atom, an oxygen atom and a sulfur atom; or a heterobicyclic group which is formed by condensing a benzene ring with a 5- or 6-membered heterocyclic group being substituted by an alkyl, an alkoxy, a halogen atom or a hydroxy, and containing 1 to 3 heteroatoms selected from a nitrogen atom, an oxygen atom and a sulfur atom, $R^2$ is a hydrogen atom; an alkyl; an alkyl being substituted by a hydroxy, a halogen atom or an amino; an aryl; an aryl being substituted one or more groups selected from the group consisting of an alkoxy, a halogen-substituted alkoxy, a hydroxy, a halogen atom, a cyano, an amino, a mono- or di-(alkyl)amino, a 5- or 6-membered cyclic imino group having optionally an oxygen atom or a nitrogen atom as a heteroatom for ring formation, a nitro, an alkyl, an alkyl being substituted by a halogen atom or a hydroxy, a cycloalkyl, a cycloalkyl-substituted alkyl, methylenedioxy, ethylenedioxy, carboxy, an alkoxy-carbonyl, carbamoyl, an alkylcarbamoyl, a di(alkyl)carbamoyl, an alkylthio, an alkylsulfinyl, an alkylsulfonyl, a sulfamoyl, an alkyl-sulfamoyl, a di(alkyl)sulfamoyl, an aryl, and an aryl being substituted by an alkyl, an alkoxy, a halogen atom, or a hydroxy group; a heterobicyclic group which is formed by condensing a benzene ring with a 5- or 6-membered heterocyclic group containing 1 to 3 heteroatoms selected from a nitrogen atom, an oxygen atom and a sulfur atom; or a heterobicyclic group which is formed by condensing a benzene ring with a 5- or 6-membered heterocyclic group being substituted by an alkyl, an alkoxy, a halogen atom or a hydroxy group, and containing 1 to 3 heteroatoms selected from a nitrogen atom, an oxygen atom and a sulfur atom, $Y^1$ is a direct bond; a straight chain or branched chain $C_1$-$C_5$ alkylene; a straight chain or branched chain $C_1$-$C_5$ alkylene being substituted by a hydroxy, a halogen atom or an amino; —CO(CH$_2$)$_n$—; —SO$_2$(CH$_2$)$_n$— (n is an integer of from 0 to 5), $R^3$ is an aryl; an aryl being substituted by one or more groups selected from the group consisting of an alkoxy, a halogen-substituted alkoxy, a hydroxy, a halogen atom, a cyano, an amino, a mono- or di-(alkyl)amino, a nitro, an alkyl, an alkyl being substituted by a halogen atom or a hydroxy, a cycloalkyl, a cycloalkyl-substituted alkyl, methylenedioxy, ethylenedioxy, carboxy, an alkoxycarbonyl, a carbamoyl, an alkylcarbamoyl, a di-(alkyl)carbamoyl, an alkylthio, an alkylsulfinyl, an alkylsulfonyl, a sulfamoyl, an alkylsulfamoyl, a di-(alkyl)sulfamoyl, an aryl, and an aryl being substituted by an alkyl, an alkoxy, a halogen atom or a hydroxy; a 5- or 6-membered heteromonocyclic group containing 1 to 3 heteroatoms selected from a nitrogen atom, an oxygen atom and a sulfur atom; a 5- or 6-membered heteromonocyclic group being substituted by an alkyl, an alkoxy, a halogen atom or a hydroxy, and containing 1 to 3 heteroatoms selected from a nitrogen atom, an oxygen atom and a sulfur atom; a heterobicyclic group which is formed by condensing a benzene ring with a 5- or 6-membered heterocyclic group containing 1 to 3 heteroatoms selected from a nitrogen atom, an oxygen atom and a sulfur atom; or a heterobicyclic group which is formed by condensing a benzene ring with a 5- or 6-membered heterocyclic group being substituted by an alkyl, an alkoxy, a halogen atom or a hydroxy and containing 1 to 3 heteroatoms selected from a nitrogen atom, an oxygen atom and a sulfur atom, $Y^2$ is a straight chain or branched chain $C_2$-$C_5$ alkylene; a straight chain or branched chain $C_2$-$C_5$ alkylene being substituted by a hydroxy, an alkoxy, a halogen atom, an amino or an alkanoylamino; or a straight chain or branched chain $C_3$-$C_5$ alkenylene, $R^4$ is a hydrogen atom; an alkanoyl; an aroyl; an alkyl; an alkyl being substituted by a hydroxy, an alkoxy, a halogen atom or an amino: an alkylcarbamoyl; an alkoxycarbonyl; an alkylaminothiocarbonyl; an alkylsulfonyl; an arylsulfonyl; or an alkyl-substituted arylsulfonyl, $R^5$ is a hydrogen; an alkyl; or an alkyl being substituted by a hydroxy, a halogen atom or an amino, or a pharmaceutically acceptable salt thereof, or a prodrug thereof.

[5] The 5-membered cyclic compound according to any one of the above [1] to [4], wherein X is a sulfur atom, or a pharmaceutically acceptable salt thereof, or a prodrug thereof.

[6] The 5-membered cyclic compound according to any one of the above [1] to [5], wherein $R^1$ is a hydrogen atom, or a pharmaceutically acceptable salt thereof, or a prodrug thereof.

[7] The 5-membered cyclic compound according to any one of the above [1] to [6], wherein $R^2$ is a substituted or unsubstituted alkyl, a substituted or unsubstituted aryl, a substituted or unsubstituted heteromonocyclic or heterobicyclic group, —CON($R^6$)$R^7$, or a substituted or unsubstituted heterocyclic carbonyl, or a pharmaceutically acceptable salt thereof, or a prodrug thereof.

[8] The 5-membered cyclic compound according to any one of the above [1] to [6], wherein $R^2$ is a substituted or unsubstituted aryl, or a pharmaceutically acceptable salt thereof, or a prodrug thereof.

[9] The 5-membered cyclic compound according to any one of the above [1] to [8], wherein $Y^1$ is a substituted or unsubstituted alkylene, $-CO(CH_2)_n-$, $-SO_2(CH_2)_n-$, $-CONH(CH_2)_n-$, $-CSNH(CH_2)_n-$, or $-COO(CH_2)_n-$, or a pharmaceutically acceptable salt thereof, or a prodrug thereof.

[10] The 5-membered cyclic compound according to any one of the above [1] to [8], wherein $Y^1$ is a direct bond, $-CO-$, $-SO_2-$, $-CONH-$, or $-COO-$, or a pharmaceutically acceptable salt thereof, or a prodrug thereof.

[11] The 5-membered cyclic compound according to any one of the above [1] to [8], wherein $Y^1$ is a direct bond or a $-CO-$, or a pharmaceutically acceptable salt thereof, or a prodrug thereof.

[12] The 5-membered cyclic compound according to any one of the above [1] to [11], wherein $R^3$ is a substituted or unsubstituted aryl, or a substituted or unsubstituted heteromonocyclic group, or a pharmaceutically acceptable salt thereof, or a prodrug thereof.

[13] The 5-membered cyclic compound according to any one of the above [1] to [12], wherein the wavy line means (Z)-configuration, or a pharmaceutically acceptable salt thereof, or a prodrug thereof.

[14] The 5-membered cyclic compound according to any one of the above [1] to [13], wherein $Y^2$ is ethylene or trimethylene, or a pharmaceutically acceptable salt thereof, or a prodrug thereof.

[15] The 5-membered cyclic compound according to any one of the above [1] to [14], wherein $R^4$ is a substituted or unsubstituted alkanoyl, a substituted or unsubstituted alkyl, a substituted or unsubstituted alkylcarbamoyl, a substituted or unsubstituted alkylaminothiocarbonyl, or a substituted or unsubstituted alkoxycarbonyl, or a pharmaceutically acceptable salt thereof, or a prodrug thereof.

[16] The 5-membered cyclic compound according to any one of the above [1] to [14], wherein $R^4$ is a substituted or unsubstituted alkanoyl, a substituted or unsubstituted alkyl, or a substituted or unsubstituted alkylcarbamoyl, or a pharmaceutically acceptable salt thereof, or a prodrug thereof.

[17] The 5-membered cyclic compound according to any one of the above [1] to [15], wherein $R^5$ is a hydrogen atom, or a pharmaceutically acceptable salt thereof, or a prodrug thereof.

[18] The 5-membered cyclic compound according to the above [1], which is a compound of the formula (2):

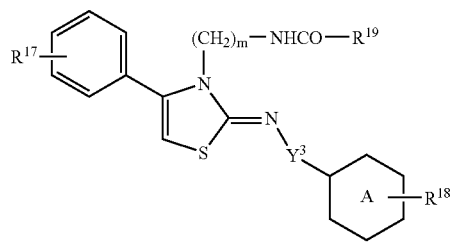

(2)

wherein Ring A is a benzene ring or a pyridine ring, m is 2 or 3, $Y^3$ is a direct bond or a carbonyl, the number of $R^{17}$ is 1 or 2, and $R^{17}$s are independently selected from a halogen atom, a $C_1$-$C_4$ alkoxy, a trifluoromethoxy, a morpholino and a methylenedioxy, the number of $R^{18}$ is 1 or 2, and $R^{18}$s are independently selected from a halogen atom, a $C_1$-$C_4$ alkoxy, a trifluoromethoxy and a hydroxy, $R^{19}$ is a $C_1$-$C_4$ alkyl; a $C_1$-$C_4$ alkyl being substituted by a hydroxy, a $C_1$-$C_4$ alkoxy, a mono- or di-($C_1$-$C_4$ alkyl)amino, a morpholino or a carboxy; a $C_1$-$C_4$ alkylamino; or a $C_1$-$C_4$ alkylamino being substituted by a hydroxy, a $C_1$-$C_4$ alkoxy, a mono- or di-($C_1$-$C_4$ alkyl)amino, a morpholino or a carboxy, or a pharmaceutically acceptable salt thereof, or a prodrug thereof.

[19] The 5-membered cyclic compound according to the above [18], provided that when $Y^3$ is a direct bond, then $R^{19}$ is not a methyl, or a pharmaceutically acceptable salt thereof, or a prodrug thereof.

[20] The 5-membered cyclic compound according to the above [8], wherein Ring A is a benzene ring, (i) $Y^3$ is a direct bond and $R^{19}$ is a $C_1$-$C_4$ alkylamino, or (ii) $Y^3$ is a carbonyl and $R^{19}$ is a $C_1$-$C_4$ alkyl, or a pharmaceutically acceptable salt thereof, or a prodrug thereof.

[21] A medicament, which comprises the 5-membered cyclic compound as set forth in any one of the above [1] to [20], or a pharmaceutically acceptable salt thereof, or a prodrug thereof.

[22] A leukocyte infiltration inhibitor, which comprises the 5-membered cyclic compound as set forth in any one of the above [1] to [20], or a pharmaceutically acceptable salt thereof, or a prodrug thereof.

[23] An agent for treatment of inflammation, which comprises the 5-membered cyclic compound as set forth in any one of the above [1] to [20], or a pharmaceutically acceptable salt thereof, or a prodrug thereof.

[24] An agent for treatment of autoimmune inflammation or allergic inflammation, which comprises the 5-membered cyclic compound as set forth in any one of the above [1] to [20], or a pharmaceutically acceptable salt thereof, or a prodrug thereof.

BEST MODE FOR CARRYING OUT THE INVENTION

Throughout the present specification, the term for each substituent means the following meaning.

The "alkyl" includes, for example, a straight chain or branched chain $C_1$-$C_6$ alkyl group, such as methyl, ethyl, n-propyl, 2-propyl, n-butyl, 2-butyl, 3-methyl-2-propyl, 1,1-dimethylethyl, n-pentyl, n-hexyl, etc.

The substituent of the "substituted alkyl" includes, for example, a hydroxy, a halogen atom, an amino, a mono- or di-(alkyl)amino, a carboxy, an alkoxycarbonyl, an alkoxy, a carbamoyl, a mono- or di-(alkyl)carbamoyl, a cyclic imino group, an alkoxyalkoxy, a hydroxy-alkoxy, a carboxyalkoxy, an alkanoyloxy, an aryloxy, an aryl, an arylcarbonylamino, an arylamino, an arylalkylamino, an alkanoylamino, an alkylthio, a cycloalkyl, an arylalkoxy, an arylalkyl(alkyl)amino, an arylsulfonyl, an alkylsulfonyl, a carbamoylalkoxy, a mono- or di-(alkyl)-carbamoylalkoxy, an arylsulfonylamino, an arylcarbamoylamino, etc. (the alkyl used therein may be substituted by an alkoxy, an alkoxy-carbonyl, a carboxy, a dialkylamino, a hydroxy, and the aryl used herein may be substituted by an alkyl, an alkoxy, a halogen atom, or a hydroxy). The substituted alkyl may have one or more substituents which are the same or different. For example, the substituted alkyl may be an alkyl being substituted by the same or different 1 to 3 groups, preferably by 1 to 2 groups of the above substituents. The especially preferable substituent for the substituted alkyl for $R^4$ is a hydroxy, an alkoxy, a mono- or di-(alkyl)amino, a morpholino, a carboxy, an alkoxyalkoxy, a hydroxyalkoxy, a carboxyalkoxy, etc.

The "alkyl being substituted by a halogen atom or a hydroxy" is a straight chain or branched chain $C_1$-$C_6$ alkyl being substituted by 1 to 3 groups selected from a halogen atom such as fluorine, chlorine, bromine, iodine, etc., and a hydroxy, for example, fluoromethyl, difluoromethyl, trifluoromethyl, chloromethyl, bromomethyl, fluoroethyl, 2,2,2-trifluoroethyl, 3-fluoro-1-propyl, 3-fluoro-2-propyl, 4-fluoro-1-butyl, 4-fluoro-2-butyl, 3-fluoromethyl-2-propyl, 1,1-di(fluoromethyl)ethyl, 5-fluoro-1-pentyl, 6-fluoro-1-hexyl, hydroxymethyl, 2-hydroxyethyl, 1-hydroxyethyl, 2-hydroxy-1-propyl, 2,3-dihydroxy-1-propyl, 4-hydroxy-1-butyl, 5-hydroxy-1-pentyl, 6-hydroxy-1-hexyl, etc.

The "alkoxy" is a straight chain or branched chain $C_1$-$C_6$ alkoxy, for example, methoxy, ethoxy, n-propoxy, 2-propoxy, n-butoxy, 1,1-dimethylethoxy, n-pentyloxy, n-hexyloxy, etc.

The substituent of the "substituted alkoxy" is, for example, the same substituents for the substituted alkyl.

The "halogen-substituted alkoxy" is a straight chain or branched chain $C_1$-$C_6$ alkoxy, which is substituted by 1 to 3 halogen atoms selected from fluorine atom, chlorine atom, bromine atom, etc., for example, fluoromethoxy, difluoromethoxy, trifluoromethoxy, chloromethoxy, bromomethoxy, 2-fluoroethoxy, 3-fluoropropoxy, 4-fluorobutoxy, etc.

The "alkylamino" is, for example, an amino being substituted by a straight chain or branched chain $C_1$-$C_6$ alkyl, such as methylamino, ethylamino, n-propylamino, 2-propylamino, n-butylamino, 2-butylamino, 1-methylpropylamino, 1,1-dimethylethylamino, n-pentylamino, n-hexylamino, etc.

The "dialkylamino" includes, for example, an amino being substituted by 1 to 2 straight chain or branched chain $C_1$-$C_6$ alkyl groups, such as dimethylamino, diethylamino, ethylmethylamino, di-n-propylamino, di-n-butylamino, etc.

The "halogen atom" is fluorine, chlorine, bromine, and iodine, and the preferable halogen atom is fluorine, chlorine, and bromine.

The "cycloalkyl" includes, for example, a $C_3$-$C_8$ cycloalkyl, such as cyclopropyl, cyclobutyl, cyclopentyl, cyclohexyl, cycloheptyl, and cyclooctyl.

The substituent of the "substituted cycloalkyl" is, for example, an alkyl, an alkoxy, a hydroxy, etc.

The "cycloalkylalkyl" includes, for example, a straight chain or branched chain $C_1$-$C_6$ alkyl being substituted by a $C_3$-$C_8$ cycloalkyl, such as cyclopropylmethyl, cyclobutylmethyl, cyclopentylethyl, cyclohexylmethyl, cyclohexylpropyl, etc.

The "alkoxycarbonyl" includes, for example, a straight chain or branched chain $C_1$-$C_6$ alkoxycarbonyl, such as methoxycarbonyl, ethoxycarbonyl, n-propoxycarbonyl, 2-propoxycarbonyl, n-butoxycarbonyl, 2-butoxycarbonyl, 1-methylpropoxycarbonyl, 1,1-dimethylethoxycarbonyl, n-pentyloxycarbonyl, n-hexyloxycarbonyl, etc.

The "alkanoyl" includes, for example, a straight chain or branched chain $C_1$-$C_7$ alkanoyl, such as formyl, acetyl, propanoyl, butanoyl, pentanoyl, pivaloyl, hexanoyl, heptanoyl, etc.

The substituent of the "substituted alkanoyl" is, for example, the substituents for the substituted alkyl, and preferably is a hydroxy, an alkoxy, a cyclic imino group, a carboxy, an alkoxyalkoxy, a carboxyalkoxy, an alkoxycarbonyl, an alkanoyloxy, an aryloxy, an aryl, an aryl-carbonylamino, an arylamino, amino, a mono- or di-(alkyl)amino, an arylalkylamino, an aroylamino, an alkanoylamino, an alkylthio, a halogen atom, etc. Especially preferably substituents are hydroxy, an alkoxy, a dialkylamino, morpholino, carboxy, etc. The "substituted alkanoyl" has 1 to 3 substituents, preferably 1 to 2 substituents selected from these substituents.

The "alkylcarbamoyl" includes, for example, a straight chain or branched chain $C_1$-$C_6$ alkyl-substituted carbamoyl, such as methyl-carbamoyl, ethylcarbamoyl, n-propylcarbamoyl, 2-propylcarbamoyl, n-butylcarbamoyl, 2-butylcarbamoyl, 3-methyl-2-propylcarbamoyl, 1,1-dimethylethylcarbamoyl, n-pentylcarbamoyl, n-hexylcarbamoyl, etc.

The "dialkylcarbamoyl" includes, for example, a carbamoyl being substituted by 1 to 2 straight chain or branched chain $C_1$-$C_6$ alkyl, such as dimethylcarbamoyl, diethylcarbamoyl, ethylmethylcarbamoyl, di-n-propylcarbamoyl, di-n-butylcarbamoyl, etc.

The "alkylthio" includes, for example, a straight chain or branched chain $C_1$-$C_6$ alkylthio, such as methylthio, ethylthio, n-propylthio, 2-propylthio, n-butylthio, 2-butylthio, 1-methylpropylthio, 1,1-dimethylethylthio, n-pentylthio, n-hexylthio, etc.

The "alkylsulfinyl" includes, for example, a straight chain or branched chain $C_1$-$C_6$ alkylsulfinyl, such as methylsulfinyl, ethylsulfinyl, n-propylsulfinyl, 2-propylsulfinyl, n-butylsulfinyl, 2-butylsulfinyl, 1-methylpropylsulfinyl, 1,1-dimethylethylsulfinyl, n-pentylsulfinyl, n-hexylsulfinyl, etc.

The "alkylsulfonyl" includes, for example, a straight chain or branched chain $C_1$-$C_6$ alkylsulfonyl, such as methylsulfonyl, ethylsulfonyl, n-propylsulfonyl, 2-propylsulfonyl, n-butylsulfonyl, 2-butylsulfonyl, 1-methylpropylsulfonyl, 1,1-dimethylethylsulfonyl, n-pentylsulfonyl, n-hexylsulfonyl, etc.

The "alkylsulfamoyl" includes, for example, a straight chain or branched chain $C_1$-$C_6$ alkylsulfamoyl, such as methylsulfamoyl, ethylsulfamoyl, n-propylsulfamoyl, 2-propylsulfamoyl, n-butylsulfamoyl, 2-butylsulfamoyl, 1-methylpropylsulfamoyl, 1,1-dimethylethylsulfamoyl, n-pentylsulfamoyl, n-hexylsulfamoyl, etc.

The "dialkylsulfamoyl" includes, for example, a sulfamoyl being substituted by two straight chain or branched chain $C_1$-$C_6$ alkyl groups, such as dimethylsulfamoyl, diethylsulfamoyl, ethylmethylsulfamoyl, di-n-propylsulfamoyl, di-n-butylsulfamoyl, etc.

The "alkylaminothiocarbonyl" includes, for example, a straight chain or branched chain $C_1$-$C_6$ alkyl-substituted aminothiocarbonyl, such as methylaminothiocarbonyl, ethylaminothiocarbonyl, n-propylaminothiocarbonyl, n-butylaminothiocarbonyl, n-pentylaminothiocarbonyl, n-hexylaminothiocarbonyl, etc.

The "alkylene" includes, for example, a straight chain or branched chain $C_1$-$C_6$ alkylene group, such as methylene, ethylene, trimethylene, tetramethylene, pentamethylene, methylethylene, 2-methyltrimethylene, 2,2-dimethyltrimethylene, hexamethylene, etc. The suitable examples of the alkylene for $Y^2$ is a straight chain or branched chain $C_2$-$C_6$ alkylene, and more preferably, a straight chain or branched chain $C_2$-$C_4$ alkylene, and further preferably ethylene or trimethylene.

The substituents of the "substituted alkylene" is, for example, hydroxy, an alkoxy, a halogen atom, amino, an alkanoylamino, etc., and the "substituted alkylene" may have 1 to 3 substituents, preferably 1 to 2 substituents selected from the above. As an example for the substituted alkylene, 2-hydroxytrimethylene, etc. may be exemplified.

The "alkenylene" includes, for example, a straight chain or branched chain $C_3$-$C_6$ alkenylene, such as propenylene, butenylene, 2-butenylene, pentenylene, 2-pentenylene, 3-pentenylene, etc.

The "aryl" includes, for example, a $C_6$-$C_{10}$ aryl, such as phenyl, naphthyl, etc., and preferably one is phenyl.

The "substituted aryl" includes, for example, an aryl substituted by an alkyl, an alkoxy, a halogen-substituted alkoxy, a hydroxy, a cyclic imino group, a heterocyclic group, a halogen atom, a carboxy, a cyano, an amino, a mono- or di-(alkyl)amino, a nitro, an alkyl being substituted by a halogen atom or a hydroxy, a cycloalkyl, a cycloalkylalkyl, methylenedioxy, ethylenedioxy, an alkoxycarbonyl, carbamoyl, a mono- or di-(alkyl)carbamoyl, an alkylthio, an alkylsulfinyl, an alkylsulfonyl, sulfamoyl, an alkylsulfamoyl, a dialkylsulfamoyl, an aryl, or an aryl substituted by an alkyl, an alkoxy, a halogen atom or hydroxy, etc. The preferable substituents are an alkyl, an alkoxy, a halogen-substituted alkoxy, a hydroxy, a cyclic imino group, a heteromonocyclic group, a halogen atom, an alkyl being substituted by a halogen atom or a hydroxy, methylenedioxy, etc., and especially preferable substituents are an alkyl, an alkoxy, a halogen-substituted alkoxy, a hydroxy, a cyclic imino group, a halogen atom, methylenedioxy, etc. The suitable substituents of the substituted aryl group for $R^1$, $R^2$ and $R^3$ are an alkoxy, a di(alkyl) amino, a halogen-substituted alkoxy, a cyclic imino group, a halogen atom, an alkyl substituted by a halogen atom or hydroxy, methylenedioxy, etc., and more preferable ones are a $C_1$-$C_4$ alkoxy, trifluoromethoxy, a morpholino, a halogen atom, methylenedioxy, etc. These substituted aryl group may have 1 to 3 substituents, preferably 1 to 2 substituents, which are the same or different.

The "aryl substituted by a group selected from an alkyl, an alkoxy, a halogen atom and a hydroxy" includes a $C_6$-$C_{10}$ aryl (e.g., phenyl, naphthyl) substituted by one or more groups, preferably 1 to 3 groups, more preferably 1 to 2 groups, which are the same or different, and selected from a straight chain or branched chain $C_1$-$C_6$ alkyl such as methyl, ethyl, n-propyl, 2-propyl, n-butyl, 2-butyl, 1-methylpropyl, 1,1-dimethylethyl, n-pentyl, n-hexyl, etc., a straight chain or branched chain $C_1$-$C_6$ alkoxy such as methoxy, ethoxy, propoxy, 2-propoxy, n-butoxy, 1,1-dimethylethoxy, n-pentyloxy, n-hexyloxy, etc., a halogen atom such as fluorine, chlorine, bromine, iodine, etc., and hydroxy. Specifically, 4-methylphenyl, 2-methylphenyl, 4-(n-propyl)phenyl, 4-(2-propyl)phenyl, 4-(n-butyl)phenyl, 4-methoxyphenyl, 3,4-dimethoxy-phenyl, 3,4,5-trimethoxyphenyl, 4-ethoxyphenyl, 4-(n-propoxy) phenyl, 4-(n-butoxy)phenyl, 4-bromophenyl, 4-fluorophenyl, 3,4-difluorophenyl, 4-chlorophenyl, 4-hydroxyphenyl, 2-hydroxyphenyl, etc. may be exemplified.

The "cyclic imino group" includes, for example, a 5- or 6-membered cyclic imino group optionally having another oxygen atom or nitrogen atom as a heteroatom for ring formation, such as pyrrolidino, piperidino, morpholino, etc. The cyclic imino group for —N($R^6$)$R^7$ may be a 5- or 6-membered cyclic imino group optionally having another oxygen atom or nitrogen atom as a heteroatom for ring formation which may be condensed with a benzene ring, for example, benzopiperidino, benzopyrrolidinyl, benzomorpholino, etc.

The "heteromonocyclic group" includes a 5- or 6-membered heterocyclic group containing 1 to 3 heteroatoms selected from a nitrogen atom, an oxygen atom, and a sulfur atom, provided that an oxygen atom and a sulfur atom are not simultaneously contained, for example, an aromatic heterocyclic group such as thienyl, furyl, pyrrolyl, pyrazolyl, thiazolyl, isothiazolyl, oxazolyl, isoxazolyl, pyridyl, pyrazinyl, pyrimidinyl, pyridazinyl, etc. and a non-aromatic heterocyclic group such as dioxolanyl, pyranyl, dioxanyl, etc. The heteromonocyclic group is preferably an aromatic heterocyclic group, especially preferably pyridyl.

The "heterobicyclic group" is fused heterocyclic groups, wherein a 5- or 6-membered heterocyclic group containing 1 to 3 heteroatoms selected from a nitrogen atom, an oxygen atom and a sulfur atom (wherein an oxygen atom and a sulfur atom should not be simultaneously contained) and a benzene ring are condensed, for example, benzofuryl, benzothienyl, indolyl, isoindolyl, indazolyl, quinolyl, isoquinolyl, quinazolyl, phthalazinyl, quinoxalinyl, etc.

The substituents of the "substituted heteromonocyclic group" and the "substituted heterobicyclic group" are an alkyl, an alkoxy, a halogen atom, a hydroxy, etc. The substituted heteromonocyclic group may have 1 to 3 substituents, preferably 1 to 2 substituents, which are the same or different.

The "aroyl" includes, for example, a $C_7$-$C_{11}$ aroyl, such as benzoyl, naphthoyl, etc.

The "prodrug" means a compound, which can be hydrolyzed in the living body and converted into the 5-membered cyclic compound of the present invention. The prodrug of the present invention includes any compound, which can be prepared by any conventional method for preparing a prodrug in this field. For example, when the 5-membered cyclic compound of the present invention has a carboxyl group or an amino group being easily hydrolyzed in the living body, then a compound wherein these groups are derived into an ester group or an amido group is a prodrug thereof. When the 5-membered cyclic compound has a carboxyl group, then a compound wherein said carboxyl group is converted into an alkyl such as methyl, ethyl, etc., an alkyloxyalkyl such as methyloxymethyl, ethyloxymethyl, 2-methyloxyethyl, 2-methyloxyethyloxymethyl, etc., an acyloxymethyl such as pivaloyloxymethyl, acetyloxymethyl, cyclohexylacetyloxymethyl, 1-methylcyclohexylcarbonyloxymethyl, etc., an alkoxycarbonylalkyl such as ethyloxycarbonyloxy-1-ethyl, etc., or a cycloalkyloxycarbonylalkyl such as cyclohexyloxycarbonyloxy-1-ethyl, etc. is a prodrug thereof. When the 5-membered cyclic compound has an amino group, then a compound wherein said amino group is converted into an acetamide group is a prodrug thereof.

The 5-membered cyclic compound of the formula (1) of the present invention may be converted into a pharmaceutically acceptable salt thereof. The pharmaceutically acceptable salt includes acid addition salts and base addition salts. The acid addition salt may be, for example, a salt with an inorganic acid such as hydrochloride, hydrobromide, sulfate, etc., a salt with an organic acid such as citrate, oxalate, malate, tartrate, fumarate, maleate, etc., and the base addition salt may be, for example, a salt with an inorganic base such as sodium salt, potassium salt, etc., and a salt with an organic base such as a salt with meglumine or trishydroxymethylaminomethane, etc.

The compounds within the scope of the present invention may occasionally contain molecular asymmetry or a substituent having an asymmetric carbon, and may have an optical isomer. In such cases, the present compound also includes each isomer or a mixture thereof. The present compound and a pharmaceutically acceptable salt thereof may be in the form of a solvate thereof such as hydrate.

The 5-membered cyclic compound of the formula (I) of the present invention may be prepared by the following Processes or a modified method thereof.

Process 1

The compound (1) wherein X is a sulfur atom is prepared by the following process.

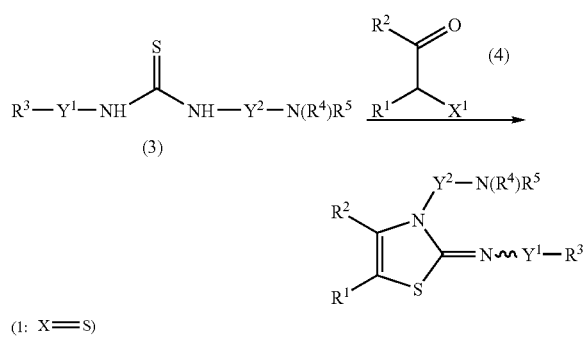

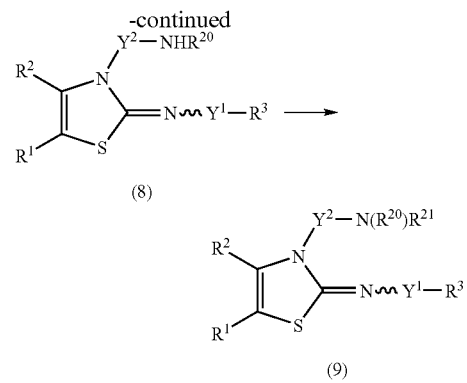

wherein $R^1$, $R^2$, $R^3$, $R^4$, $R^5$, $Y^1$ and $Y^2$ are as defined above, and $X^1$ is a halogen atom such as chlorine atom, bromine atom, etc.

The thiourea compound (3) and the α-haloketone compound (4) are reacted in a solvent in the presence or absence of a base to give the compound (1) wherein X is a sulfur atom. The solvent may be an alcohol (e.g., methanol, ethanol, 2-propanol, etc.), ethers (e.g., diethyl ether, tetrahydrofuran (THF), etc.), halogenated hydrocarbons (e.g., dichloromethane, dichloroethane, chloroform, etc.), aprotic solvents (e.g., dimethylformamide, etc.), aromatic solvents (e.g., toluene, etc.), etc. The base may be an organic amine such as triethylamine, pyridine, 4-dimethylaminopyridine, etc., or an inorganic base such as potassium carbonate, sodium carbonate, etc. The reaction is carried out at a temperature of from room temperature to a boiling point of the solvent.

Process 2

The compound (I) wherein X is a sulfur atom can also be prepared by the following Process. This process is effective for cases wherein a protecting group is necessary in a step of introduction of $R^4$ and $R^5$. The protecting group may be any conventional protecting groups for amino group, and the case wherein a 2-methyl-2-propyloxycarbonyl is used as a protecting group is explained below.

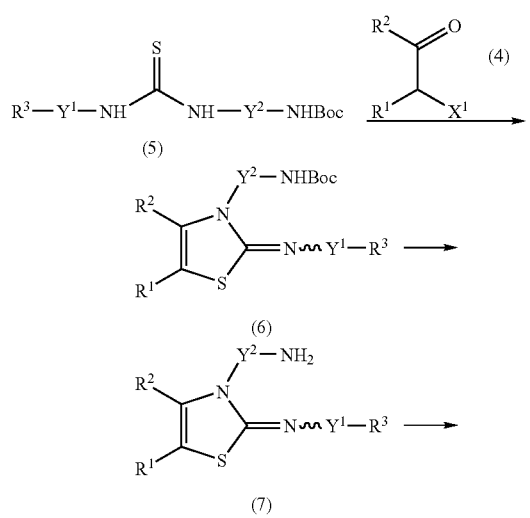

wherein $R^1$, $R^2$, $R^3$, $Y^1$, $Y^2$ and $X^1$ are as defined above; $R^{20}$ is a substituted or unsubstituted alkanoyl, a substituted or unsubstituted alkyl, —$COOR^8$, —$SO_2R^9$, —$COR^{10}$, —$CON(R^{11})R^{12}$, —$CSN(R^{13})R^{14}$, a cycloalkyl, a substituted or unsubstituted aryl, a substituted or unsubstituted heteromonocyclic group, —$C(=NH)N(R^{15})R^{16}$, etc.; $R^{21}$ is a substituted or unsubstituted alkyl, etc.; Boc is a 2-methyl-2-propyloxycarbonyl; $R^8$, $R^9$, $R^{10}$, $R^{11}$, $R^{12}$, $R^{13}$, $R^{14}$, $R^{15}$ and $R^{16}$ are as defined above.

The thiourea compound (5) and the α-haloketone compound (4) are reacted in a solvent in the presence or absence of a base to give the compound (6). The solvent may be alcohols (e.g., methanol, ethanol, 2-propanol, etc.), ethers (e.g., diethyl ether, THF, etc.), halogenated hydrocarbons (e.g., dichloromethane, dichloroethane, chloroform, etc.), aprotic solvents (e.g., dimethylformamide, etc.), aromatic solvents (e.g., toluene, etc.), etc. The base may be organic amines (e.g., triethylamine, pyridine, 4-dimethylaminopyridine, etc.), or organic bases (e.g., potassium carbonate, sodium carbonate, etc). The reaction is carried out at a temperature of from room temperature to a boiling point of the solvent.

Then, the compound (6) is de-protected in the presence of an acid in a solvent to give the compound (7). The acid may be inorganic acids such as hydrochloric acid, etc., or organic acids such as trifluoroacetic acid, etc. The solvent may be ethers (e.g., diethyl ether, THF, dioxane, etc.), halogenated hydrocarbons (e.g., dichloromethane, dichloroethane, chloroform, etc.), etc. The reaction is carried out at a temperature of from 0° C. to a boiling point of the solvent.

The compound (7) is reacted with a corresponding compound such as an alkyl halide, an ester, an acid chloride, an acid anhydride, a chloroformic acid ester, sulfonyl chloride, a sulfonic acid ester, isocyanate, or isothiocyanate, etc. in the presence or absence of a base in a solvent to give the compound (8). Examples of said compound are a substituted or unsubstituted alkanoyl halide, a substituted or unsubstituted aroyl halide, a substituted or unsubstituted alkyl halide, an alkylcarbamoyl halide, a halogenoformic acid alkyl ester, an alkylsulfonyl halide, a substituted or unsubstituted arylsulfonyl halide, an alkylcarboxylic anhydride, an arylcarboxylic anhydride, an alkylcarboxylic acid alkyl ester, an arylcarboxylic acid alkyl ester, an alkylisocyanate, an alkyl thioisocyanate, etc. The solvent may be ethers (e.g., diethyl ether, THF, etc.), halogenated hydrocarbons (e.g., dichloromethane, dichloroethane, chloroform, etc.), aprotic solvents (e.g., dimethylformamide, etc.), or aromatic solvents (e.g., toluene, etc.). The base includes organic amines (e.g., triethylamine, pyridine, 4-dimethyl-aminopyridine, etc.), inorganic bases (e.g., potassium carbonate, sodium carbonate, etc.). The reaction is carried out at a temperature of from room temperature to a boiling point of the solvent.

The compound (8) is further reacted with a compound of the formula: $R^{21}$-$X^2$ ($R^{21}$ is as defined above, and $X^2$ is a halogen atom such as chlorine atom, bromine atom, etc.) in a solvent in the presence of a base to give the compound (9). The solvent may be ethers (e.g., diethyl ether, THF, etc.), halogenated hydrocarbons (e.g., dichloromethane, dichloroethane, chloroform, etc.), aprotic solvents (e.g., dimethylformamide, etc.), aromatic solvents (e.g., toluene, etc.), etc. The base may be an organic amine (e.g., triethylamine, pyridine, 4-dimethylaminopyridine, etc.), an alkali metal carbonate (e.g., potassium carbonate, sodium carbonate, etc.), an alkali metal hydride (e.g., sodium hydride, potassium hydride, etc.), lithium isopropylamide, etc. The reaction is carried out at a temperature of from about 0° C. to a boiling point of the solvent.

In the reaction of the compound (7) and the compound (8), a carboxylic acid may be used as a reactive reagent. In this case, a condensing agent such as N,N'-dicyclohexylcarbodiimide, 1-ethyl-3-(3-dimethylaminopropyl)carbodiimide, etc. may be used as well.

Process 3

The compound (1) wherein X is a sulfur atom may also be prepared by the following Process.

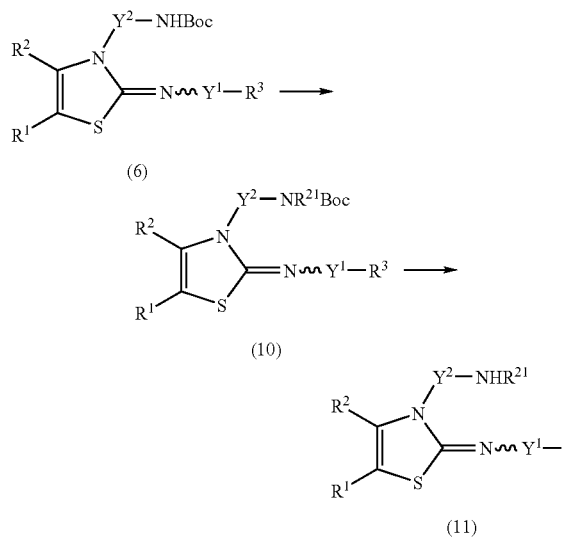

wherein $R^1$, $R^2$, $R^3$, $R^{21}$, $Y^1$, $Y^2$ and Boc are as defined above.

The compound (6) is reacted with a compound of the formula: $R^{21}$-$X^2$ ($R^{21}$ is as defined above, $X^2$ is a halogen atom such as chlorine atom, bromine atom, etc.) in a solvent in the presence of a base to give the compound (10). The solvent may be ethers (e.g., diethyl ether, THF, etc.), halogenated hydrocarbons (e.g., dichloromethane, dichloroethane, chloroform, etc.), aprotic solvents (e.g., dimethylformamide, etc.), aromatic solvents (e.g., toluene, etc.), etc. The base includes an alkali metal hydride such as sodium hydride, potassium hydride, etc., lithium diisopropylamide, etc. The reaction is carried out at a temperature of from room temperature to a boiling point of the solvent.

The compound (10) is subjected to deprotection in a solvent in the presence of an acid to give the compound (11). The acid may be an inorganic acid such as hydrochloric acid, an organic acid such as trifluoroacetic acid, etc. The solvent is, for example, ethers (e.g., diethyl ether, THF, dioxane, etc.), halogenated hydrocarbons (e.g., dichloromethane, dichloroethane, chloroform, etc.). The reaction is carried out at a temperature of from about 0° C. to a boiling point of the solvent.

The starting compounds used in the above Processes 1 to 3 are prepared by the following processes.

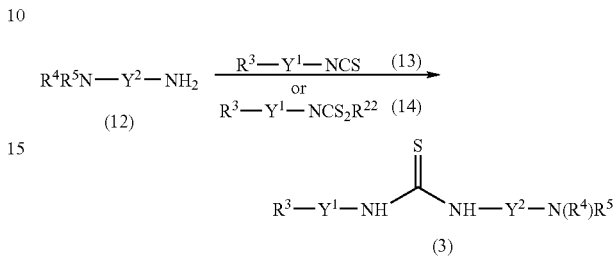

wherein $R^3$, $R^4$, $R^5$, $Y^1$ and $Y^2$ are as defined above, and $R^{22}$ is an alkyl.

The amine compound (12) and the isocyanate compound (13) or the dithiocarbamide acid ester (14) are reacted in a solvent to give the thiourea compound (3). The solvent may be alcohols (e.g., methanol, ethanol, 2-propanol, etc.), ethers (e.g., diethyl ether, THF, etc.), halogenated hydrocarbons (e.g., dichloromethane, dichloroethane, chloroform, etc.), aprotic solvents (e.g., dimethylformamide, etc.), aromatic solvents (e.g., toluene, etc.). The reaction is carried out at a temperature of from room temperature to a boiling point of the solvent.

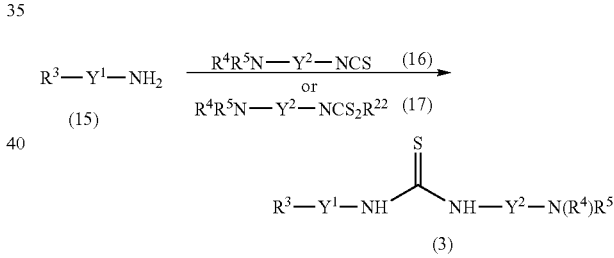

wherein $R^3$, $R^4$, $R^5$, $R^{22}$, $Y^1$ and $Y^2$ are as defined above.

The amine compound (15) and the isocyanate compound (16) or the dithiocarbamide acid ester (17) are reacted in a solvent to give the thiourea compound (3). The solvent may be alcohols (e.g., methanol, ethanol, 2-propanol, etc.), ethers (e.g., diethyl ether, THF, etc.), halogenated hydrocarbons (e.g., dichloromethane, dichloroethane, chloroform, etc.), aprotic solvents (e.g., dimethylformamide, etc.), aromatic solvents (e.g., toluene, etc.), etc. The reaction is carried out at a temperature of from room temperature to a boiling point of the solvent.

The thiourea compound (5) which is protected by 2-methyl-2-propyloxycarbonyl, etc. may be prepared by the following process.

-continued

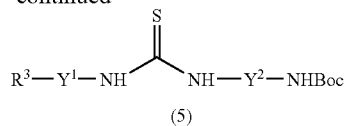

wherein $R^3$, $R^{22}$, $Y^1$, $Y^2$ and Boc are as defined above.

The amine compound (18) and the isocyanate compound (13) or the dithiocarbamide acid ester (14) are reacted in a solvent to give the thiourea compound (5). The solvent may be alcohols (e.g., methanol, ethanol, 2-propanol, etc.), ethers (e.g., diethyl ether, THF, etc.), halogenated hydrocarbons (e.g., dichloromethane, dichloroethane, chloroform, etc.), aprotic solvents (e.g., dimethylformamide, etc.), aromatic solvents (e.g., toluene, etc.), etc. The reaction is carried out at a temperature of from room temperature to a boiling point of the solvent.

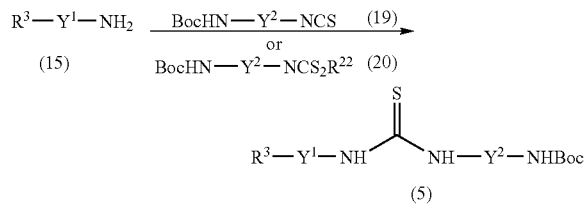

wherein $R^3$, $R^{22}$, $Y^1$, $Y^2$ and Boc are as defined above.

The amine compound (15) and the isocyanate compound (19) or the dithiocarbamide acid ester (20) are reacted in a solvent to give the thiourea compound (5). The solvent may be alcohols (e.g., methanol, ethanol, 2-propanol, etc.), ethers (e.g., diethyl ether, THF, etc.), halogenated hydrocarbons (e.g., dichloromethane, dichloroethane, chloroform, etc.), aprotic solvents (e.g., dimethylformamide, etc.), aromatic solvents (e.g., toluene, etc.), etc. The reaction is carried out at a temperature of from room temperature to a boiling point of the solvent.

The isothiocyanate compounds (13), (16) and (19) are commercially available ones, or can be prepared from a corresponding amino compound, for example, by the method disclosed in the literatures such as Synlett. 1997, 773-774, J. Org. Chem., 1997, 62, 4539-4540, or J. Med. Chem., 1984, 27, 1570-1574. In addition, these compounds are also prepared from a corresponding carboxylic acid, for example, by the method disclosed in the literatures such as Synth. Commun. 1997, 27, 751-756, or Indian, J. Chem., 1998, 1153-1156.

The dithiocarbamide acid ester compounds (14), (17), and (20) are commercially available ones, or can be prepared from a corresponding amino compound, for example, by the method disclosed in the literatures such as J. Chem. Soc., 1956, 1644-1649 or Syn. Commun., 1984, 537-546.

The α-haloketone compound (4) is a commercially available one or can be prepared from a corresponding ketone compound, for example, by the method disclosed in the literatures such as J. Med. Chem., 1987, 1497-1502, Tetrahedoron Lett., 1998, 4987-4990, or Acta Chim. Scand., 1986, B40, 700-702.

Process 4

The compound (1) wherein X is an oxygen atom is prepared by the following Process.

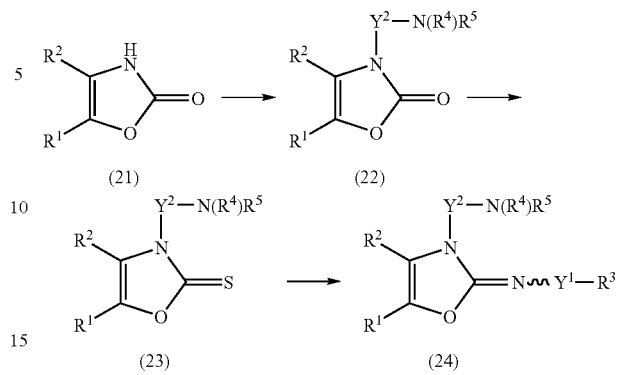

wherein $R^1$, $R^2$, $R^3$, $R^4$, $R^5$, $Y^1$ and $Y^2$ are as defined above.

The compound of the formula (21) is reacted with a compound of the formula: $R^4(R^5)N-Y^2-X^3$ (wherein $R^4$, $R^5$, $Y^2$ are as defined above, $X^3$ is a halogen atom such as a chlorine atom, bromine atom, etc.) in a solvent in the presence of a base to give the compound (22). The solvent may be ethers (e.g., diethyl ether, THF, etc.), halogenated hydrocarbons (e.g., dichloromethane, dichloroethane, chloroform, etc.), aprotic solvents (e.g., dimethylformamide, etc.), aromatic solvents (e.g., toluene, etc.). The base may be an alkali metal hydride (e.g., sodium hydride, potassium hydride, etc.), etc. The reaction is carried out at a temperature of from room temperature to a boiling point of the solvent.

The compound (22) is reacted with a sulfurating reagent such as phosphorus pentaphosphate, etc. to give the compound (23). The solvent may be ethers (e.g., diethyl ether, THF, etc.), halogenated hydrocarbons (e.g., dichloromethane, dichloroethane, chloroform, etc.), aprotic solvents (e.g., dimethylformamide, etc.), aromatic solvents (e.g., toluene, etc.). The reaction is carried out at a temperature of from room temperature to a boiling point of the solvent.

Then, the compound (23) is reacted with a compound of the formula: $R^3-Y^1-NH_2$ ($R^3$ and $Y^1$ are as defined above) in a solvent to give the compound (24). The solvent may be alcohols (e.g., methanol, ethanol, 2-propanol, etc.), ethers (e.g., diethyl ether, THF, etc.), halogenated hydrocarbons (e.g., dichloromethane, dichloroethane, chloroform, etc.), aprotic solvents (e.g., dimethylformamide, etc.), aromatic solvents (e.g., toluene, etc.), etc. The reaction is carried out at a temperature of from room temperature to a boiling point of the solvent.

Process 5

The compound (1) wherein X is a sulfur atom is prepared by the following Process.

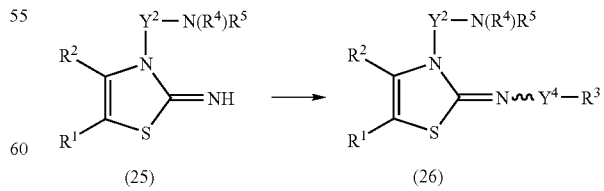

wherein $R^1$, $R^2$, $R^3$, $R^4$, $R^5$ and $Y^2$ are as defined above; $Y^4$ is a substituted or unsubstituted alkylene, $-CO(CH_2)_n-$, $-SO_2(CH_2)_n-$, $-CONH(CH_2)_n-$, or $-CONH(CH_2)_n-$, $-CSNH(CH_2)_n-$, or $-COO(CH_2)_n-$.

The imine compound (25) is reacted with a corresponding alkyl halide, ester, acid chloride, acid anhydride, chloroformic acid ester, sulfonyl chloride, sulfonic acid ester, isocyanate, or isothiocyanate, etc. in the presence or absence of a base in a solvent, or with a carboxylic acid to give the compound (26). The reaction is carried out in a similar manner to in the synthesis of the compound (8).

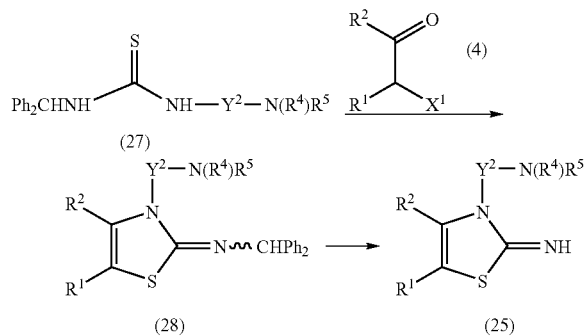

wherein $R^1$, $R^2$, $R^4$, $R^5$, $Y^2$ and $X^1$ are as defined above.

In the above Process, the process for preparing the compound (25), using the thiourea compound (27) being protected by a diphenylmethyl group as a protecting group is exemplified. In a similar manner to in Process 1, the protected thiourea compound (27) and the α-haloketone compound (4) are reacted to give the compound (28). The protecting group of the compound (28) is removed by treating with an acid catalyst in a solvent to give the compound (25). The acid may be inorganic acids (e.g., hydrochloric acid, hydrobromic acid, sulfuric acid, etc.), sulfonic acids such as methanesulfonic acid, etc. The solvent may be ethers (e.g., ether, THF, etc.), alcohols (e.g., methanol, ethanol, 2-propanol, etc.), acetic acid, and water. The reaction is carried out at a temperature of from room temperature to a boiling point of the solvent.

When carrying out the above Process, if necessary, techniques of protection or deprotection may be used. The techniques of protection or deprotection are disclosed in detail in the literature of Greene, et al., (T. W. Greene and P. G. M. Wuts, "Protecting Groups in Organic Synthesis", 1991, JOHN WILEY & SONS, INC.).

In addition, after forming a 5-membered cyclic compound, the function groups thereof may be converted into other functions groups. The conversion reactions can be carried out by a conventional method used in the organic chemistry, and these methods are disclosed in the following texts.

Jikken Kagaku Koza (in Japanese, i.e, Experimental Chemical Lecture), vol. 19-26 (1992, MARUZEN CO., LTD.)

Seimitsu-Yuki-Gosei (in Japanese, i.e., Fine Organic Synthesis) (1993, Nankodo, Co., Ltd.)

Compendium of Organic Synthetic Methods, Vol. 1-9 (John Wiley & Sons)

Comprehensive Organic Synthesis, Vol. 1-9 (1991, Pergamon Press)

Comprehensive Organic Transformations (1989, VCH Publishers)

Survey of Organic Syntheses, Vol. 1-2 (1970, 1977, John Wiley & Sons)

Specifically, ester groups, carboxyl groups, amido groups, hydroxy group, ether groups, etc. can be transformed each other, and halogen atoms can be converted into an amino group, and amino group can be converted into urea group.

The 5-membered cyclic compound (1) of the present invention or an intermediate for preparing the same can be purified by a conventional method. When the 5-membered cyclic compound (1) of the present invention or an intermediate for preparing the same has an isomer, such isomer can be purified likewise, for example, by column chromatography, recrystallization, etc. The solvent for recrystallization may be alcohols (e.g., methanol, ethanol, 2-propanol, etc.), ethers (e.g., diethyl ether, etc.), esters (e.g., ethyl acetate, etc.), aromatic hydrocarbons (e.g., toluene, etc.), ketones (e.g., acetone, etc.), hydrocarbons (e.g., hexane, etc.) or a mixture of these solvents.

An optical isomer can purely be isolated, for example, by optical resolution. Optical resolution is carried out, when the present compound or an intermediate therefor has a basic substituent such as amino group, etc. by treating the present compound or an intermediate therefor with an optically active acid (e.g., monocarboxylic acid such as mandelic acid, N-benzyloxyalanine, lactic acid, dicarboxylic acid such as tartaric acid, o-diisopropylidene tartaric acid, malic acid, etc.), a sulfonic acid such as camphor sulfonic acid, bromocamphorsulfonic acid) in an inert solvent (e.g., alcohols such as methanol, ethanol, 2-propanol, etc., ethers such as diethyl ether, etc., esters such as ethyl acetate, etc., aromatic hydrocarbons such as toluene, etc., acetonitrile, or a mixture thereof) to give a salt thereof. When the present compound or an intermediate therefor has an acidic substituent such as carboxyl group, etc., the present compound or an intermediate therefor forms a salt with an optically active amine (e.g., organic amines such as α-phenethylamine, kinin, quinidine, cinchonidine, cinchonine, strychnine, etc. The temperature for forming a salt in the above optional resolution method may be in the range of from room temperature to a boiling point of the solvent to be used. In order to improve the optical purity of the product, it is desirable to raise the reaction temperature to around the boiling point of the solvent, and before collecting the precipitated salts by filtration, the reaction mixture is cooled, if necessary, to improve the yield. The optically active acid or amine is used in an amount of about 0.5 to about 2.0 equivalents, preferably in an amount of about one equivalent, to 1 equivalent of the substrate. If necessary, the resulting crystals are recrystallized from an inert solvent such as alcohols (e.g., methanol, ethanol, 2-propanol, etc.), ethers (e.g., diethyl ether, etc.), esters (e.g., ethyl acetate, etc.), aromatic hydrocarbons (e.g., toluene, etc.), acetonitrile, or a mixture of these solvents to give an optical salt thereof of a higher purity. Further, if necessary, the resulting salt is treated with an acid or a base in a conventional manner to give a free base.

The 5-membered cyclic compound (1) of the present invention or a salt thereof, or a prodrug thereof is useful as a medicament, and especially exhibits an inhibitory activity against the infiltration of leukocytes such as eosinophils, lymphocytes, etc., and based on this pharmacological activity thereof, it is useful as a remedy for autoimmune inflammation, allergic inflammation, acute inflammation, or other cellular infiltration inflammatory diseases. The autoimmune inflammation includes, for example, rheumatism, multiple sclerosis, inflammatory bowel diseases, type 1 diabetes mellitus, etc. The allergic inflammation includes, for example, bronchial asthma, inflammatory bowel diseases, allergic rhinitis, atopic dermatitis, urticaria, allergic conjunctivitis, etc. Among the bronchial asthma, the present 5-membered cyclic compound, etc. is useful especially for late asthmatic response. The acute inflammation includes, for example, inflammatory pulmonary diseases, etc. The other inflammatory diseases include, for example, hypereosinophilic syndrome, eosinophilic vasculitis, eosinophilic granuloma, rejection after transplantation, metastasis of tumor, etc. When the present compound is used as an antiinflammatory agent, it can be used in combination with a steroid, which is used as a remedy for inflammatory diseases, by which the therapeutic effect thereof can be enhanced, and further, it may be possible that the dosage of a steroid having potent side effects can be reduced or not used at all. When the present compound is used as a remedy for allergic diseases, it can be used in combination with an antiallergic agent (e.g., an inhibitory agent of chemical mediator release, an histamine antagonist, a leukotriene antagonist, a thromboxane antagonist, etc.), and when it is used as a remedy for bronchial asthma, it can be used in combination with a bronchodilator (e.g., xanthines such as theophylline, β-stimulants, etc.), or an anticholinergic agent. When it is used as a remedy for autoimmune diseases such as rheumatoid, it can be used in combination with a nonsteroidal anti-inflammatory agent such as a cyclooxygenase (COX) inhibitor, etc.

The 5-membered cyclic compound of the present invention, or a salt thereof, or a prodrug thereof, can be administered either orally or parenterally. When administered orally, it is administered in a conventional pharmaceutical preparation. When administered parenterally, it can be administered in the form of a pharmaceutical preparation for local administration, an injection, an endermatic agent, etc. The pharmaceutical composition for oral administration or rectal administration includes, for example, capsules, tablets, pills, powders, cachets, suppositories, liquids, etc. The injection preparation includes, for example, aseptic solutions or suspensions, etc. The pharmaceutical preparation for local administration includes, for example, creams, ointments, lotions, percutaneous preparations (e.g., conventional patches, matrixes, etc.).

The present compound can be formulated into a pharmaceutical composition by using a pharmaceutical acceptable excipient or additive by a conventional method. The pharmaceutically acceptable excipient or diluent includes, for example, carriers, binders, flavors, buffers, thickening agents, coloring agents, stabilizers, emulsifiers, dispersing agents, suspending agents, preservatives, etc.

The pharmaceutically acceptable carrier or diluent includes, for example, magnesium carbonate, magnesium stearate, talc, sugar, lactose, pectin, dextrin, starch, gelatin, tragacanth, methyl cellulose, sodium carboxymethyl cellulose, low-melting wax, cacao butter, etc.

Capsules are formulated by enclosing the present compound together with a pharmaceutically acceptable carrier or diluent in capsules. The present compound is enclosed in capsules after mixing with a pharmaceutically acceptable carrier or diluent, or without a pharmaceutically acceptable carrier or diluent. Cachets are formulated likewise.

Powders are formulated with a pharmaceutically acceptable base for powders. The base includes, for example, talc, lactose, starch, etc. Drops are formulated with an aqueous or non-aqueous base and one or more pharmaceutically acceptable diffusing agents, suspending agents, solubilizers, etc.

Liquid preparations for injection include, for example, solutions, suspensions, emulsions, etc. such as aqueous solution, water-propylene glycol solution, etc. Liquid preparation can also be formulated in a solution of polyethylene glycol or/and propylene glycol which may contain water. Liquid preparation for oral administration may be prepared by adding the present compound into water, and further adding thereto coloring agents, flavors, stabilizers, sweetening agents, solubilizers, thickening agents, if necessary. In addition, liquid preparation for oral administration can also be prepared by adding the present compound into water together with a dispersing agent and further added thereto a thickening agent. The thickening agent includes, for example, pharmaceutically acceptable natural or synthesized gum, resin, methyl cellulose, sodium carboxymethyl cellulose, or a conventional suspending agent, etc.

The preparation for local administration includes, for example, the above-mentioned liquid preparations, and creams, aerosols, sprays, powders, lotions, ointments, etc.

The preparation for oral administration is prepared by mixing the present compound with a conventional pharmaceutically acceptable diluent or carrier. The ointments and creams are prepared, for example, by adding a thickening agent and/or gelatinizing agent to an aqueous or oily base, and formulating it. Said base includes, for example, water, liquid paraffin, vegetable oil (e.g., peanut oil, caster oil, etc.), etc. The thickening agent includes, for example, soft paraffin, aluminum stearate, cetostearyl alcohol, propylene glycol, polyethylene glycol, lanoline, hydrogenated lanoline, bees wax, etc.

The lotion may be prepared by adding one or more pharmaceutically acceptable stabilizers, suspending agents, emulsifiers, dispersing agents, thickening agents, coloring agents, flavors, etc. to an aqueous or oily base.

The preparation for local administration further contains, if necessary, antiseptic agents or bacterial growth inhibitors such as methyl hydroxybenzoate, propyl hydroxybenzoate, chlorocresol, benzalkonium chloride, etc.

The present compound also can be administered nasally in the form of a liquid spray, powder or drop.

The dosage and the frequency of administration of the present compounds may vary according to the conditions, ages, weights of the patients and the administration form, etc., but the present compounds can usually be administered orally in a dose of about 1 to about 1000 mg per day in adult, preferably in a dose of about 2 to about 500 mg, especially preferably in a dose of about 5 to about 100 mg per day in adult, once a day, or divided into several dosage units. When the present compound is administered in an injection preparation, the dosage thereof is in the range of about 0.1 to about 300 mg, preferably in the range of about 1 to about 200 mg, once a day, or divided into several dosage units.

EXAMPLES

The present invention is illustrated by the following Examples, but should not be construed to be limited thereto.

Example 1

N-{4-(4-bromophenyl)-3-[3-(dimethylamino)propyl]thiazol-2(3H)-ylidene}aniline

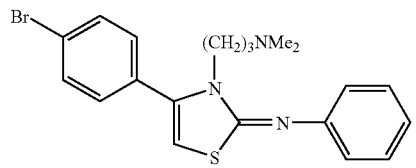

A mixture of N-[3-(dimethylamino)propyl]-N'-phenylthiourea (800 mg) obtained in Reference Example 3 as described below and 2-bromo-4'-bromoacetophenone (1.09 g) in ethanol (30 ml) was heated with reflux under nitrogen atmosphere. Nine hours thereafter, the reaction mixture was concentrated under reduced pressure, and to the residue was added a saturated aqueous sodium hydrogen carbonate solution, and the mixture was extracted with chloroform. The organic layer was washed with a saturated brine, dried over sodium sulfate, and the solvent was evaporated under reduced pressure. The residue was purified by silica gel column chromatography (chloroform: methanol (50:1)), and crystallized from isopropyl alcohol to give the title compound (830 mg)

m.p.: 110-111° C. $^1$H-NMR (CDCl$_3$): δ 1.79 (2H, m), 2.11 (6H, s), 2.52 (2H, t, J=7.0), 3.92 (2H, t, J=7.0), 5.74 (1H, s), 7.02-7.09 (3H, m), 7.26-7.37 (4H, m), 7.58 (2H, d, J=8.4)

Example 2

N-{3-[3-(Dimethylamino)propyl]-5-phenylthiazol-2(3H)-ylidene}aniline

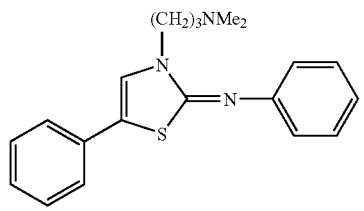

Using N-[3-(dimethylamino)propyl]-N'-phenylthiourea (650 mg) obtained in Reference Example 3 as described below, 2-bromo-2-phenylacetoaldehyde (600 mg) and N,N-dimethylformamide (11 ml), the title compound (497 mg) was obtained in a similar manner to in Example 1.

m.p.: 84-86° C. $^1$H-NMR (CDCl$_3$): δ 2.01 (2H, m), 2.26 (6H, s), 2.37 (2H, t, J=6.8), 3.98 (2H, t, J=6.8), 6.97 (1s, s), 7.03-7.38 (10H, m)

Examples 3 to 7

In a similar manner to in Example 1, various α-bromoketone and thiourea were reacted to give the compounds as listed in Table 1.

TABLE 1

| Ex. | R$^2$ | Y$^1$—R$^3$ | Y$^2$—N(R$^4$)R$^5$ | yield | m.p. ° C. |
|---|---|---|---|---|---|
| 3 | phenyl | phenyl | (CH$_2$)$_3$NMe$_2$ | 86% | 56-58 |
| 4 | 4-methoxyphenyl | phenyl | (CH$_2$)$_3$NMe$_2$ | 100% | 63-65 |
| 5 | 4-bromophenyl | phenyl | (CH$_2$)$_2$NMe$_2$ | 58% | 126-128 |
| 6 | 4-bromophenyl | 2-pyridyl | (CH$_2$)$_3$NMe$_2$ | 41% | 127-128 |
| 7 | 4-bromophenyl | benzoyl | (CH$_2$)$_3$NMe$_2$ | 34% | 100-102 |

Example 8

N-[3-(2-Aminoethyl)-4-(4-bromophenyl)thiazol-2(3H)-ylidene]aniline (1) t-Butyl 2-[4-(4-bromophenyl)-2-(phenylimino)thiazol-3(2H)-yl]ethyl-carbamate

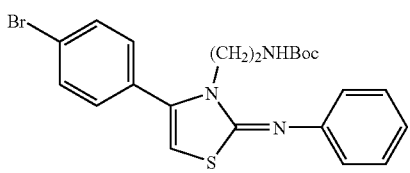

A mixture of t-butyl 2-[(anilinocarbothioyl)amino]ethylcarbamate (1.5 g) obtained in Reference Example 1, 2-bromo-4'-bromoacetophenone (1.55 g), potassium carbonate (772 mg) and N,N-dimethylformamide (38 ml) was heated at 80° C. with stirring under nitrogen atmosphere. Two hours thereafter, the reaction mixture was concentrated under reduced pressure, and to the residue was added a saturated aqueous sodium hydrogen carbonate solution, and the mixture was extracted with chloroform. The organic layer was washed with a saturated brine, dried over sodium sulfate, and the solvent was evaporated under reduced pressure. The residue was purified by silica gel column chromatography [n-hexane: ethyl acetate (9:1)], and crystallized from isopropyl alcohol to give the title compound (2.41 g).

$^1$H-NMR (CDCl$_3$): δ 1.43 (9H, s), 3.38 (2H, m), 3.94 (2H, t, J=5.5), 5.77 (1H, s), 5.91 (1H, m), 7.05-7.12 (3H, m), 7.28-7.38 (4H, m), 7.59 (2H, d, J=8.4)

(2) N-[3-(2-Aminoethyl)-4-(4-bromophenyl)thiazol-2(3H)-ylidene]aniline

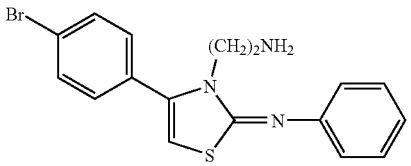

A mixture of t-butyl 2-[4-(4-bromophenyl)-2-(phenylimino)-thiazol-3(2H)-yl]ethylcarbamate (1.5 g), trifluoroacetic acid (10 ml) and water (5 ml) was stirred at room temperature for 2 hours. The reaction mixture was concentrated under reduced pressure, and to the residue was added a saturated aqueous sodium hydrogen carbonate solution, and the mixture was extracted with chloroform. The organic layer was washed with a saturated brine, dried over sodium sulfate, and the solvent was evaporated under reduced pressure. The residue was crystallized from n-hexane to give the title compound (937 mg).

m.p.: 58-61° C. $^1$H-NMR (CDCl$_3$): δ 2.93 (2H, t, J=6.6), 3.87 (2H, t, J=6.6), 5.76 (1H, s), 7.04-7.08 (3H, m), 7.26-7.37 (4H, m), 7.59 (2H, d, J=8.4)

Example 9

N-[3-(3-Aminopropyl)-4-(4-methoxyphenyl)-thiazol-2(3H)-ylidene]aniline (1) t-Butyl 3-[4-(4-methoxyphenyl)-2-(phenylimino)thiazol-3(2H)-yl]-propylcarbamate

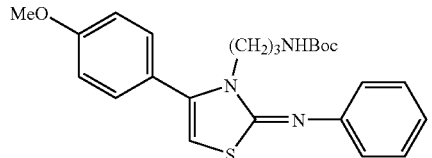

t-Butyl 3-[(anilinocarbothioyl)amino]propylcarbamate (309 mg) obtained in Reference Example 4, 2-bromo-4'-methoxyacetophenone (252 mg), potassium carbonate (339 mg) and ethanol (8 ml) were treated in a similar manner to in Example 8 (1) to give the title compound (429 mg).

$^1$H-NMR (CDCl$_3$): δ 1.41 (9H, s), 1.64 (2H, m), 3.07 (2H, m), 3.86 (3H, s), 3.95 (2H, t, J=6.6), 5.74 (1H, s), 5.87 (1H, m), 6.97-7.37 (9H, m)

(2) N-[3-(3-Aminopropyl)-4-(4-methoxyphenyl)-thiazol-2(3H)-ylidene]-aniline

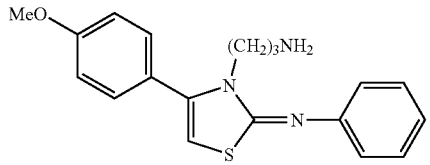

A mixture of t-butyl 3-[4-(4-methoxyphenyl)-2-(phenylimino)-thiazol-3(2H)-yl]propylcarbamate (400 mg) and a 4N solution of hydrogen chloride in dioxane (8 ml) was stirred at room temperature for 2 hours. The solvent was evaporated under reduced pressure, and to the residue was added diethyl ether. The insoluble salt was collected by filtration to give the title compound (379 mg) as hydrochloride.

m.p.: 215-218° C. $^1$H-NMR (CDCl$_3$, free amino compound): δ 1.70 (2H, m), 2.64 (2H, t, J=6.6), 3.85 (3H, s), 3.94(2H, t, J=6.6), 5.70 (1H, s), 6.94-7.10 (5H, m), 7.26-7.36 (4H, m)

Example 10

N-[3-(3-Aminopropyl)-5-methyl-4-phenylthiazol-2(3H)-ylidene]aniline (1) t-Butyl 3-[5-methyl-4-phenyl-2-(phenylimino)thiazol-3(2H)-yl]-propylcarbamate

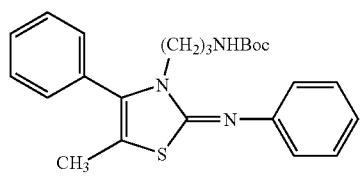

A mixture of t-butyl 3-[(anilinocarbothioyl)amino]propylcarbamate (300 mg) obtained in Reference Example 4, 2-bromo-propiophenone (227 mg) and ethanol (8 ml) was heated with reflux under nitrogen atmosphere. Two hours thereafter, the reaction mixture was concentrated under reduced pressure, and to the residue was added a saturated aqueous sodium hydrogen carbonate solution, and the residue was extracted with chloroform. The organic layer was washed with a saturated brine, and dried over sodium sulfate, and the solvent was evaporated under reduced pressure. The residue was purified by silica gel column chromatography [n-hexane:ethyl acetate (8:2)] to give the title compound (389 mg).

$^1$H-NMR (CDCl$_3$): δ 1.40 (9H, s), 1.54 (2H, m), 1.91 (3H, s), 3.06 (2H, m), 3.84 (2H, t, J=6.4), 6.04 (1H, m), 7.02-7.49 (10H, m)

(2) N-[3-(3-Aminopropyl)-5-methyl-4-phenylthiazol-2(3H)-ylidene]-aniline

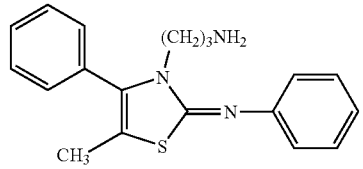

t-Butyl 3-[5-methyl-4-phenyl-2-(phenylimino)thiazol-3(2H)-yl]propylcarbamate (370 mg) and a 4N solution of hydrogen chloride in dioxane (4 ml) were treated in a similar manner to in Example 9 (2) to give the title compound (327 mg) as hydrochloride.

m.p.: 240-243° C.

Example 11

N-[3-(3-Aminopropyl)-4-(1,1'-biphenyl-4-yl)thiazol-2(3H)-ylidene]aniline (1) t-Butyl 3-[4-(1,1'-biphenyl-4-yl)-2-(phenylimino)thiazol-3(2H)-yl]-propylcarbamate

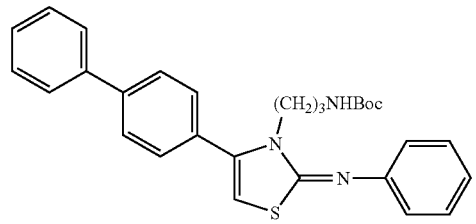

t-Butyl 3-(anilinocarbothioylamino)propylcarbamate (200 mg) obtained in Reference Example 4, 2-bromo-4'-phenylacetophenone (197 mg) and ethanol (4 ml) were treated in a similar manner to in Example 10 (1) to give the title compound (275 mg).

$^1$H-NMR (CDCl$_3$): δ 1.39 (9H, s), 1.69 (2H, m), 3.11 (2H, m), 4.02 (2H, t, J=6.4), 5.84 (1s, s), 5.87 (1H, m), 7.04-7.18 (3H, m), 7.33-7.48 (7H, m), 7.50-7.70(4H, m)

(2) N-[3-(3-Aminopropyl)-4-(1,1'-biphenyl-4-yl)thiazol-2(3H)-ylidene]-aniline

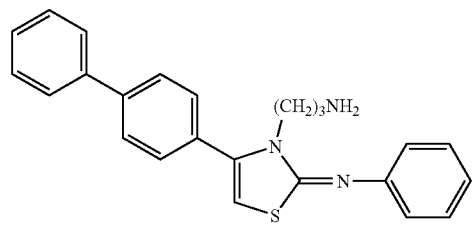

A mixture of t-butyl 3-[4-(1,1'-biphenyl-4-yl)-2-(phenylimino)-thiazol-3(2H)-yl]propylcarbamate (233 mg) and a 4N solution of hydrogen chloride in dioxane (2 ml) was stirred at room temperature for one hour. To the reaction mixture was added water, and the mixture was washed with diethyl ether. The aqueous layer was basified with a saturated aqueous sodium hydrogen carbonate solution, and the mixture was extracted with chloroform. The organic layer was washed with a saturated brine, and dried over sodium sulfate, and the solvent was evaporated under reduced pressure to give the title compound (185 mg).

m.p.: 50-54° C. $^1$H-NMR (CDCl$_3$): δ 1.74 (2H, m), 2.69 (2H, t, J=6.6), 4.02 (2H, t, J=6.6), 5.81 (1H, s), 7.04-7.11 (3H, m), 7.33-7.47 (7H, m), 7.48-7.69 (4H, m)

Examples 12 to 149

Various α-bromoketones and thiourea were reacted in a similar manner to in Examples 8 to 10 or 11 to give the compounds as listed in Tables 2 to 12.

TABLE 2

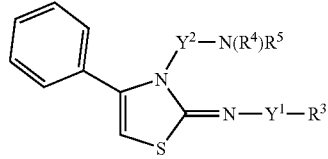

| Ex. | $Y^1-R^3$ | $Y^2-N(R^4)R^5$ | yield | m.p. ° C. |
|---|---|---|---|---|
| 12 | phenyl | (CH$_2$)$_3$NH$_2$ | 68% (hydrochloride) | 251-254 |
| 13 | 2-methoxyphenyl | (CH$_2$)$_3$NH$_2$ | 93% (hydrochloride) | 260-261 |
| 14 | 3-methoxyphenyl | (CH$_2$)$_3$NH$_2$ | 86% (hydrochloride) | 228-231 |

TABLE 2-continued

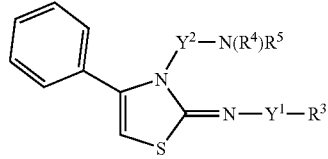

| Ex. | $Y^1-R^3$ | $Y^2-N(R^4)R^5$ | yield | m.p. ° C. |
|---|---|---|---|---|
| 15 | 4-methoxyphenyl | (CH$_2$)$_3$NH$_2$ | 97% (hydrochloride) | 252-254 |
| 16 | 2,5-dimethoxyphenyl | (CH$_2$)$_3$NH$_2$ | 72% (hydrochloride) | 240-244 |
| 17 | 3,5-dimethoxyphenyl | (CH$_2$)$_3$NH$_2$ | 60% (hydrochloride) | 226-228 |
| 18 | 2,4-dimethoxyphenyl | (CH$_2$)$_3$NH$_2$ | 61% (hydrochloride) | 243-246 |
| 19 | 3,4-dimethoxyphenyl | (CH$_2$)$_3$NH$_2$ | 63% (hydrochloride) | 233-236 |
| 20 | 2-chlorophenyl | (CH$_2$)$_3$NH$_2$ | 86% (hydrochloride) | 249-251 |
| 21 | 4-chlorophenyl | (CH$_2$)$_3$NH$_2$ | 69% (hydrochloride) | 255-258 |
| 22 | 4-fluorophenyl | (CH$_2$)$_3$NH$_2$ | 67% (hydrochloride) | 250-252 |
| 23 | 2-pyridyl | (CH$_2$)$_3$NH$_2$ | 35% (hydrochloride) | 208-211 |
| 24 | 3-pyridyl | (CH$_2$)$_3$NH$_2$ | 73% (hydrochloride) | 208-210 |
| 25 | 4-pyridyl | (CH$_2$)$_3$NH$_2$ | 30% (hydrochloride) | 212-216 |
| 26 | phenyl | CH$_2$CH(OH)—CH$_2$NH$_2$ | 69% | oil |
| 27 | phenyl | (CH$_2$)$_2$CH—(OH)CH$_2$NH$_2$ | 84% | oil |
| 28 | benzyl | (CH$_2$)$_3$NH$_2$ | 27% (hydrochloride) | 65-67 |

TABLE 3

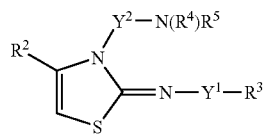

| Ex. | $R^2$ | $Y^1-R^3$ | $Y^2-N(R^4)R^5$ | yield | m.p. ° C. |
|---|---|---|---|---|---|
| 29 | 2-methoxyphenyl | phenyl | (CH$_2$)$_2$NH$_2$ | 100% (hydrochloride) | 170-174 |
| 30 | 2-methoxyphenyl | phenyl | (CH$_2$)$_3$NH$_2$ | 60% (hydrochloride) | 156-162 |
| 31 | 2-methoxyphenyl | 4-methoxyphenyl | (CH$_2$)$_3$NH$_2$ | 96% (hydrochloride) | 222-225 |
| 32 | 3-methoxyphenyl | phenyl | (CH$_2$)$_2$NH$_2$ | 70% (hydrochloride) | 197-200 |
| 33 | 3-methoxyphenyl | phenyl | (CH$_2$)$_3$NH$_2$ | 89% (hydrochloride) | 234-237 |
| 34 | 3-methoxyphenyl | 4-methoxyphenyl | (CH$_2$)$_3$NH$_2$ | 98% (hydrochloride) | 240-241 |
| 35 | 4-methoxyphenyl | phenyl | (CH$_2$)$_2$NH$_2$ | 99% (hydrochloride) | 220-222 |
| 36 | 4-methoxyphenyl | 2-methoxyphenyl | (CH$_2$)$_3$NH$_2$ | 82% (hydrochloride) | 218-220 |
| 37 | 4-methoxyphenyl | 3-methoxyphenyl | (CH$_2$)$_3$NH$_2$ | 80% (hydrochloride) | 223-225 |
| 38 | 4-methoxyphenyl | 4-methoxyphenyl | (CH$_2$)$_3$NH$_2$ | 91% (hydrochloride) | 255-257 |
| 39 | 4-methoxyphenyl | 2,4-dimethoxyphenyl | (CH$_2$)$_3$NH$_2$ | 100% (hydrochloride) | 248-250 |
| 40 | 4-methoxyphenyl | 2,5-dimethoxyphenyl | (CH$_2$)$_3$NH$_2$ | 89% (hydrochloride) | 249-250 |

TABLE 3-continued

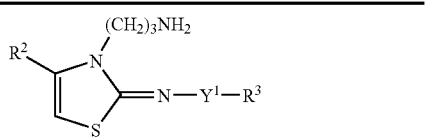

| Ex. | R² | Y¹—R³ | Y²—N(R⁴)R⁵ | yield | m.p. ° C. |
|---|---|---|---|---|---|
| 41 | 4-methoxyphenyl | 3,4,5-trimethoxyphenyl | (CH₂)₃NH₂ | 68% (hydrochloride) | 237-238 |
| 42 | 4-methoxyphenyl | 2-hydroxyphenyl | (CH₂)₃NH₂ | 53% (hydrochloride) | 154-158 |

TABLE 4

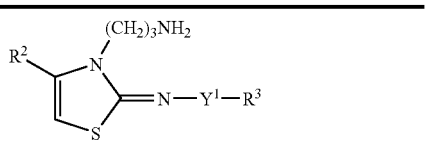

| Ex. | R² | Y¹—R³ | yield | m.p. ° C. |
|---|---|---|---|---|
| 43 | 4-methoxyphenyl | 3-hydroxyphenyl | 86% (hydrochloride) | 170-174 |
| 44 | 4-methoxyphenyl | 4-hydroxyphenyl | 100% (hydrochloride) | 261-262 |
| 45 | 4-methoxyphenyl | 3,4-(methylenedioxy)phenyl | 86% (hydrochloride) | 248-250 |
| 46 | 4-methoxyphenyl | 4-fluorophenyl | 100% (hydrochloride) | 250-256 |
| 47 | 4-methoxyphenyl | 5-methoxy-2-pyridyl | 100% (hydrochloride) | 83-88 |
| 48 | 4-methoxyphenyl | benzyl | 51% (hydrochloride) | oil |
| 49 | 4-methoxyphenyl | phenethyl | 18% (hydrochloride) | 205-208 |
| 50 | 4-methoxyphenyl | 3-phenylpropyl | 8% (hydrochloride) | oil |
| 51 | 4-methoxyphenyl | 4-pyridylmethyl | 41% (hydrochloride) | amorphous |
| 52 | 4-methoxyphenyl | 2-(4-pyridyl)ethyl | 27% (hydrochloride) | 129-132 |
| 53 | 4-(methylthio)phenyl | 4-chloro-2,5-dimethoxyphenyl | 58% (hydrochloride) | 240-241 |
| 54 | 3,4-dimethoxyphenyl | phenyl | 100% (hydrochloride) | 256-258 |
| 55 | 3,4-dimethoxyphenyl | 3-methoxyphenyl | 97% (hydrochloride) | 218-220 |
| 56 | 3,4-dimethoxyphenyl | 4-methoxyphenyl | 100% (hydrochloride) | 246-247 |
| 57 | 3,4-dimethoxyphenyl | 2,4-dimethoxyphenyl | 97% (hydrochloride) | 235-238 |
| 58 | 3,4-dimethoxyphenyl | 3,4-(methylenedioxy)phenyl | 69 (hydrochloride) | 243-245 |
| 59 | 3,4-dimethoxyphenyl | 4-fluorophenyl | 62% (hydrochloride) | 240-244 |

TABLE 5

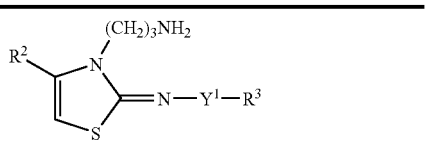

| Ex. | R² | Y¹—R³ | yield | m.p. ° C. |
|---|---|---|---|---|
| 60 | 3,4,5-trimethoxyphenyl | phenyl | 96% (hydrochloride) | 135-139 |
| 61 | 3,4,5-trimethoxyphenyl | 4-methoxyphenyl | 97% (hydrochloride) | 233-235 |
| 62 | 3,4,5-trimethoxyphenyl | 2,4-dimethoxyphenyl | 86% (hydrochloride) | 233-236 |
| 63 | 3,4,5-trimethoxyphenyl | 3,4-(methylenedioxy)phenyl | 87% (hydrochloride) | 230-233 |
| 64 | 3,4,5-trimethoxyphenyl | 4-fluorophenyl | 76% (hydrochloride) | 232-233 |
| 65 | 4-(methanesulfonyl)phenyl | phenyl | 87% (hydrochloride) | 156-160 |
| 66 | 3,4-(methylenedioxy)phenyl | phenyl | 61% (hydrochloride) | 226-228 |
| 67 | 3,4-(methylenedioxy)phenyl | 2-methoxyphenyl | 90% (hydrochloride) | 248-251 |
| 68 | 3,4-(methylenedioxy)phenyl | 3-methoxyphenyl | 100% (hydrochloride) | 247-250 |
| 69 | 3,4-(methylenedioxy)phenyl | 4-methoxyphenyl | 37% (hydrochloride) | 256-259 |

TABLE 6

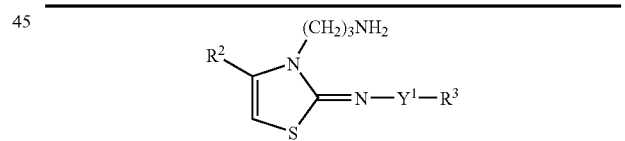

| Ex. | R² | Y¹—R³ | yield | m.p. ° C. |
|---|---|---|---|---|
| 70 | 3,4-(methylenedioxy)phenyl | 2,4-dimethoxyphenyl | 70% (hydrochloride) | 220-224 |
| 71 | 3,4-(methylenedioxy)phenyl | 3,4,5-trimethoxyphenyl | 55% (hydrochloride) | 66-70 |
| 72 | 3,4-(methylenedioxy)phenyl | 2,3-(methylenedioxy)phenyl | 74% (hydrochloride) | 230-232 |
| 73 | 3,4-(methylenedioxy)phenyl | 3,4-(methylenedioxy)phenyl | 62% (hydrochloride) | 242-245 |
| 74 | 3,4-(methylenedioxy)phenyl | 2-methoxy-4,5-(methylenedioxy)phenyl | 100% (hydrochloride) | 248-251 |
| 75 | 3,4-(methylenedioxy)phenyl | 2-methoxy-4-(trifluoromethoxy)phenyl | 69% (hydrochloride) | 237-238 |
| 76 | 3,4-(methylenedioxy)phenyl | 2-(trifluoromethoxy)phenyl | 98% (hydrochloride) | 233-236 |
| 77 | 3,4-(methylenedioxy)phenyl | 4-(trifluoromethoxy)phenyl | 82% (hydrochloride) | 232-234 |

TABLE 6-continued

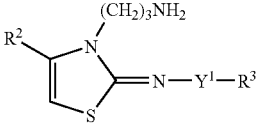

| Ex. | R² | Y¹—R³ | yield | m.p. ° C. |
|---|---|---|---|---|
| 78 | 3,4-(methylene-dioxy)phenyl | 4-chloro-2-methoxyphenyl | 82% (hydrochloride) | 254-256 |
| 79 | 3,4-(methylene-dioxy)phenyl | 4-chloro-2,5-dimethoxyphenyl | 93% (hydrochloride) | 235-237 |

TABLE 7

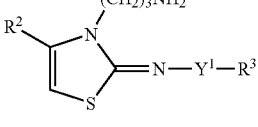

| Ex. | R² | Y¹—R³ | yield | m.p. ° C. |
|---|---|---|---|---|
| 80 | 3,4-(methylene-dioxy)phenyl | 2,4-dichloro-6-methoxyphenyl | 76% (hydrochloride) | 172-176 |
| 81 | 3,4-(methylene-dioxy)phenyl | 4-chloro-2,6-dimethoxyphenyl | 98% (hydrochloride) | 174-178 |
| 82 | 3,4-(methylene-dioxy)phenyl | 4-chloro-2-methoxy-5-methylphenyl | 89% (hydrochloride) | 210-213 |
| 83 | 3,4-(methylene-dioxy)phenyl | 4-nitro-2-methoxyphenyl | 70% (hydrochloride) | 226-228 |
| 84 | 3,4-(methylene-dioxy)phenyl | 4-methylphenyl | 84% (hydrochloride) | 252-253 |
| 85 | 3,4-(methylene-dioxy)phenyl | 4-(trifluoromethyl)-phenyl | 56% (hydrochloride) | 209-212 |
| 86 | 3,4-(methylene-dioxy)phenyl | 2-bromo-4-(trifluoromethoxy)-phenyl | 80% (hydrochloride) | 154-159 |
| 87 | 3,4-(methylene-dioxy)phenyl | 4-bromo-2-(trifluoromethoxy)-phenyl | 12% (hydrochloride) | 244-246 |
| 88 | 3,4-(methylene-dioxy)phenyl | 4-fluorophenyl | 74% (hydrochloride) | 225-226 |
| 89 | 3,4-(methylene-dioxy)phenyl | 3,4-difluoro-phenyl | 35% (hydrochloride) | 216-218 |

TABLE 8

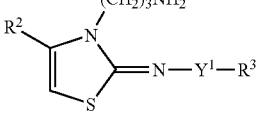

| Ex. | R² | Y¹—R³ | yield | m.p. ° C. |
|---|---|---|---|---|
| 90 | 3,4-(methylene-dioxy)phenyl | 2,4-difluoro-phenyl | 45% (hydrochloride) | 244-246 |
| 91 | 3,4-(methylene-dioxy)phenyl | 2,4,6-trifluoro-phenyl | 100% (hydrochloride) | 232-234 |
| 92 | 3,4-(methylene-dioxy)phenyl | 4-fluoro-2-nitrophenyl | 72% (hydrochloride) | 225-229 |
| 93 | 3,4-(methylene-dioxy)phenyl | 2,4-dichloro-phenyl | 91% (hydrochloride) | 166-173 |
| 94 | 3,4-(methylene-dioxy)phenyl | 5-isoquinolyl | 86% (hydrochloride) | 255-259 |
| 95 | 3,4-(methylene-dioxy)phenyl | 8-quinolyl | 78% (hydrochloride) | 182-184 |

TABLE 8-continued

| Ex. | R² | Y¹—R³ | yield | m.p. ° C. |
|---|---|---|---|---|
| 96 | 4-(trifluoromethoxy)phenyl | 2-methoxy-4-(trifluoromethoxy)phenyl | 82% (hydrochloride) | 137-139 |
| 97 | 4-(trifluoromethoxy)phenyl | 2-methoxy-4-nitrophenyl | 53% (hydrochloride) | 100-104 |
| 98 | 4-(trifluoromethoxy)phenyl | 4-chloro-2,5-dimethoxyphenyl | 59% (hydrochloride) | 84-88 |
| 99 | 4-(methanesulfonyl)phenyl | 4-methoxyphenyl | 59% (hydrochloride) | 243-245 |

TABLE 9

| Ex. | R² | Y¹—R³ | yield | m.p. ° C. |
|---|---|---|---|---|
| 100 | 4-fluorophenyl | phenyl | 73% (hydrochloride) | 234-237 |
| 101 | 4-fluorophenyl | 3-methoxyphenyl | 93% (hydrochloride) | 227-230 |
| 102 | 4-fluorophenyl | 4-methoxyphenyl | 59% (hydrochloride) | 252-254 |
| 103 | 4-fluorophenyl | 2,4-dimethoxyphenyl | 100% (hydrochloride) | 108-112 |
| 104 | 4-fluorophenyl | 3,4,5-trimethoxyphenyl | 90% (hydrochloride) | amorphous |
| 105 | 4-fluorophenyl | 2-methoxy-4,5-(methylenedioxy)phenyl | 60% (hydrochloride) | 243-244 |
| 106 | 4-fluorophenyl | 4-chloro-2-methoxyphenyl | 100% (hydrochloride) | 199-202 |
| 107 | 4-fluorophenyl | 4-chloro-2-methoxy-5-methylphenyl | 51% (hydrochloride) | 228-230 |
| 108 | 4-fluorophenyl | 4-chloro-2,5-dimethoxyphenyl | 86% (hydrochloride) | 221-223 |
| 109 | 4-fluorophenyl | 4-nitro-2-methoxy-phenyl | 60% (hydrochloride) | 68-73 |
| 110 | 4-fluorophenyl | 2-(trifluoromethoxy)-phenyl | 100% (hydrochloride) | 238-241 |
| 111 | 4-fluorophenyl | 4-(trifluoromethoxy)-phenyl | 68% (hydrochloride) | 226-228 |

TABLE 10

| Ex. | R² | Y¹—R³ | yield | m.p. ° C. |
|---|---|---|---|---|
| 112 | 4-fluorophenyl | 4-methylphenyl | 70% (hydrochloride) | 254-256 |

TABLE 10-continued

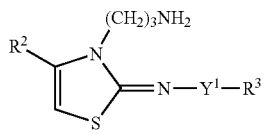

| Ex. | R² | Y¹—R³ | yield | m.p. ° C. |
|---|---|---|---|---|
| 113 | 4-fluorophenyl | 4-(trifluoromethyl)-phenyl | 15% (hydrochloride) | 218-219 |
| 114 | 4-fluorophenyl | 2-fluorophenyl | 64% (hydrochloride) | 244-246 |
| 115 | 4-fluorophenyl | 3-fluorophenyl | 68% (hydrochloride) | 235-237 |
| 116 | 4-fluorophenyl | 4-fluorophenyl | 57% (hydrochloride) | 241-244 |
| 117 | 4-fluorophenyl | 2,4,6-trifluorophenyl | 100% (hydrochloride) | 256-259 |
| 118 | 4-fluorophenyl | 3,4-difluorophenyl | 27% (hydrochloride) | 228-230 |
| 119 | 4-fluorophenyl | 2,4-difluorophenyl | 81% (hydrochloride) | 235-237 |
| 120 | 4-fluorophenyl | 4-fluoro-2-nitrophenyl | 61% (hydrochloride) | 184-190 |
| 121 | 4-fluorophenyl | 2,4-dichlorophenyl | 97% (hydrochloride) | 232-234 |
| 122 | 4-fluorophenyl | 2-pyridyl | 91% | oil |
| 123 | 4-chlorophenyl | phenyl | 91% (hydrochloride) | 230-232 |
| 124 | 4-chlorophenyl | 2-pyridyl | 89% | 82-85 |
| 125 | 4-chlorophenyl | 5-methoxy-2-pyridyl | 84% | 145-148 |
| 126 | 4-chlorophenyl | 5-methyl-2-pyridyl | 83% | 125-127 |

TABLE 11

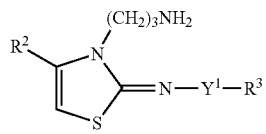

| Ex. | R² | Y¹—R³ | yield | m.p. ° C. |
|---|---|---|---|---|
| 127 | 4-chlorophenyl | phenethyl | 29% (hydrochloride) | 189-189 |
| 128 | 4-chlorophenyl | 3-phenylpropyl | 36% | oil |
| 129 | 4-chlorophenyl | 3-pyridylmethyl | 47% (hydrochloride) | 86-90 |
| 130 | 4-chlorophenyl | 4-pyridylmethyl | 61% | oil |
| 131 | 3,4-dichlorophenyl | phenyl | 70% (hydrochloride) | 195-197 |
| 132 | 4-bromophenyl | phenyl | 53% (hydrochloride) | 241-242 |
| 133 | 4-nitrophenyl | phenyl | 90% | 222-224 |
| 134 | 4-bromophenyl | benzenesulfonyl | 45% (hydrochloride) | 125-130 |
| 135 | 4-(methoxycarbonyl)phenyl | phenyl | 95% (hydrochloride) | 161-165 |
| 136 | 2-naphthyl | phenyl | 89% | oil |
| 137 | 4-hydroxyphenyl | phenyl | 56% (hydrochloride) | 250-252 |
| 138 | 4-(methylthio)phenyl | phenyl | 99% (hydrochloride) | 190-193 |
| 139 | 4-(methylthio)phenyl | 4-methoxyphenyl | 89% (hydrochloride) | 250-252 |
| 140 | 4-(methylthio)phenyl | 2,4-dimethoxyphenyl | 98% (hydrochloride) | 244-246 |
| 141 | 4-(methylthio)phenyl | 2,5-dimethoxyphenyl | 92% (hydrochloride) | 238-241 |

TABLE 12

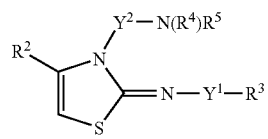

| Ex. | R² | Y¹—R³ | Y²—N(R⁴)R⁵ | yield | m.p. ° C. |
|---|---|---|---|---|---|
| 142 | 3,4-dimethoxyphenyl | phenyl | (CH₂)₂NH₂ | 100% (hydrochloride) | 231-233 |
| 143 | 3,4-(methylenedioxy)phenyl | phenyl | (CH₂)₂NH₂ | 76% | 210-211 |
| 144 | 4-fluorophenyl | phenyl | (CH₂)₂NH₂ | 100% (hydrochloride) | 224-236 |
| 145 | 4-(methanesulfonyl)phenyl | phenyl | (CH₂)₂NH₂ | 84% (hydrochloride) | 220-222 |
| 146 | 4-bromophenyl | phenyl | (CH₂)₄NH₂ | 77% | 127-129 |
| 147 | 4-bromophenyl | 2-pyridyl | (CH₂)₄NH₂ | 67% | 93-95 |
| 148 | 4-bromophenyl | 3-pyridyl | (CH₂)₄NH₂ | 82% | amorphous |
| 149 | 4-bromophenyl | phenyl | (CH₂)₅NH₂ | 95% | oil |

Example 150

N-{4-(4-Bromophenyl)-3-[(3-methylamino)propyl]thiazol-2(3H)-ylidene}-aniline (1) t-Butyl 3-[4-(4-bromophenyl)-2-(phenylimino)thiazol-3(2H)-yl]-propylcarbamate

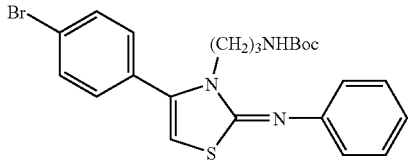

t-Butyl 3-(anilinocarbothioylamino)propylcarbamate (3 g) obtained in Reference Example 4, 2-bromo-4'-bromoacetophenone (2.97 g), potassium carbonate (2.01 g), and N,N-dimethylformamide (75 ml) were treated in a similar manner to in Example 8 (1) to give the title compound (2.90 g).

$^1$H-NMR (CDCl$_3$): δ 1.41 (9H, s), 1.65 (2H, m), 3.08 (2H, m), 3.93 (2H, t, J=6.6), 5.73 (1H, m), 5.79 (1H, s), 7.04-7.14 (3H, m), 7.24-7.37 (4H, m), 7.60 (2H, d, J=8.4)

(2) t-Butyl 3-[4-(4-bromophenyl)-2-(phenylimino)thiazol-3(2H)-yl]-propyl(methyl)carbamate

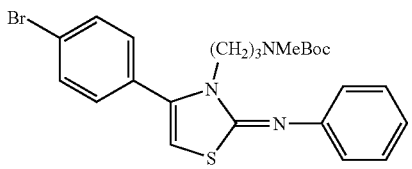

t-Butyl 3-[4-(4-bromophenyl)-2-(phenylimino)thiazol-3(2H)-yl]-propylcarbamate (250 mg) was dissolved in N,N-dimethylformamide (2 ml), and thereto was added sodium hydride (26 mg, 60% dispersion in oil) under nitrogen atmosphere in an ice bath, and the mixture was stirred for 15 minutes. To the reaction mixture was added methyl iodide (41 µl), and the mixture was warmed to room temperature, and stirred for 6 hours. Water was added to the reaction mixture, and the mixture was extracted with diethyl ether. The organic layer was washed with a saturated brine, dried over sodium sulfate, and the solvent was evaporated under reduced pressure. The residue was purified by silica gel column chromatography [n-hexane:ethyl acetate (10:1)] to give the title compound (249 mg) as colorless oil.

$^1$H-NMR (CDCl$_3$): δ 1.40 (9H, s), 1.86 (2H, m), 2.72 (3H, s), 3.16 (2H, m), 3.81 (2H, t, J=7.5), 5.76 (1H, s), 7.03-7.08 (3H, m), 7.25 (2H, d, J=8.4), 7.34 (2H, m), 7.59 (2H, d, J=8.4)

(3) N-{4-(4-Bromophenyl)-3-[3-(methylamino)propyl]thiazol-2(3H)-ylidene}aniline

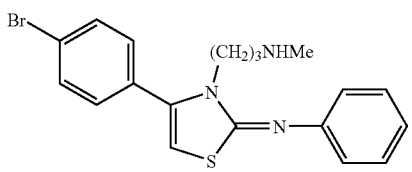

t-Butyl 3-[4-(4-bromophenyl)-2-(phenylimino)thiazol-3(2H)-yl]-propyl(methyl)carbamate (200 mg) were treated in a similar manner to in Example 8 (2) to give the title compound (149 mg).

m.p.: 143-148° C. $^1$H-NMR (CDCl$_3$): δ 1.84 (2H, m), 2.38 (3H, s), 2.61 (2H, t, J=6.8), 3.92 (2H, t, J=6.8), 5.80 (1H, s), 7.05-7.10 (3H, m), 7.26 (2H, d, J=8.4), 7.36 (2H, m), 7.60 (2H, d, J=8.4)

Example 151

N-{4-(4-Bromophenyl)-3-[4-(methylamino)butyl]thiazol-2(3H)-ylidene}-aniline (1) t-Butyl 4-[4-(4-bromophenyl)-2-(phenylimino)thiazol-3(2H)-yl]butyl-carbamate

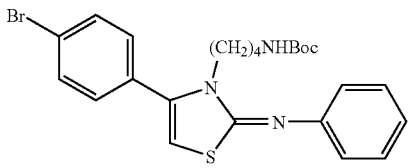

t-Butyl 4-(anilinocarbothioylamino)butylcarbamate (1.5 g) obtained in Reference Example 21, 2-bromo-4'-bromoacetophene (1.42 g), potassium carbonate (962 mg) and N,N-dimethylformamide (35 ml) were treated in a similar manner to in Example 8 (1) to give the title compound (2.1 g) as amorphous.

$^1$H-NMR (CDCl$_3$): δ 1.36-1.40 (11H, m), 1.67 (2H, m), 3.09 (2H, m), 3.80 (2H, t, J=7.5), 4.90 (1H, m), 5.75 (1H, s), 7.03-7.09 (3H, m), 7.25 (2H, d, J=8.4), 7.34 (2H, m), 7.59 (2H, d, J=8.4)

(2) t-Butyl 4-[4-(4-bromophenyl)-2-(phenylimino)thiazol-3(2H)-yl]butyl-(methyl)carbamate

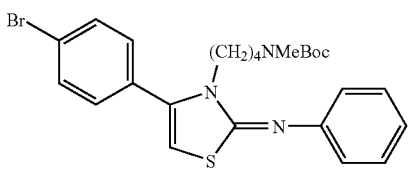

t-Butyl 4-[4-(4-bromophenyl)-2-(phenylimino)thiazol-3(2H)-yl]-butylcarbamate (250 mg) were treated in a similar manner to in Example 150 (2) to give the title compound (205 mg) as colorless oil.

$^1$H-NMR (CDCl$_3$): δ 1.29-1.50 (11H, m), 1.59 (2H, m), 2.77 (3H, s), 3.11 (2H, m), 3.84 (2H, t, J=6.8), 5.75 (1H, s), 7.03-7.07 (3H, m), 7.25 (2H, d, J=8.4), 7.35 (2H, m), 7.59 (2H, d, J=8.4)

(3) N-{4-(4-Bromophenyl)-3-[4-(methylamino)butyl]thiazol-2(3H)-ylidene}aniline

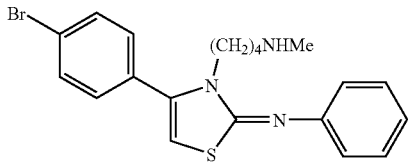

The compound (205 mg) obtained in the above (2) was treated in a similar manner to in Example 8 (2) to give the title compound (158 mg).

m.p.: 56-57° C. $^1$H-NMR (CDCl$_3$): δ 1.46 (2H, m), 1.70 (2H, m), 2.37 (3H, s), 2.56 (2H, t, J=7.0), 3.82 (2H, t, J=7.5), 5.76 (1H, s), 7.05-7.09 (3H, m), 7.26 (2H, d, J=8.4), 7.35 (2H, m), 7.59 (2H, d, J=8.4)

Example 152

N-{4-(4-Methoxyphenyl)-3-[3-(methylamino)propyl]thiazol-2(3H)-ylidene}aniline (1) 3-[4-(4-Methoxyphenyl)-2-(phenylimino)thiazol-3(2H)-yl]propyl-(methyl)carbamate

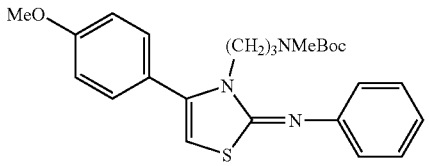

t-Butyl 3-[4-(4-methoxyphenyl)-2-(phenylimino)thiazol-3(2H)-yl]propylcarbamate (1.4 g) obtained in Example 9 (1) was treated in a similar manner to in Example 150 (2) to give the title compound (740 mg) as colorless oil.

$^1$H-NMR (CDCl$_3$): δ 1.39 (9H, s), 1.86 (2H, m), 2.71 (3H, s), 3.14 (2H, m), 3.82 (2H, t, J=7.5), 3.86 (3H, s), 5.69 (1H, s), 6.96 (2H, d, J=8.8), 7.04-7.09 (3H, m), 7.26-7.37 (4H, m)

(2) N-{4-(4-Methoxyphenyl)-3-[3-(methylamino)propyl]thiazol-2(3H)-ylidene}aniline

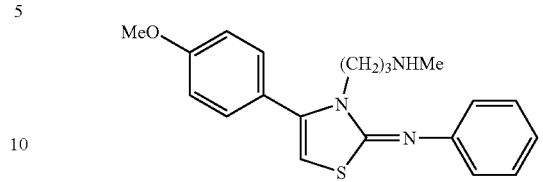

The compound (74 mg) obtained in the above (1) was treated in a similar manner to in Example 9 (2) to give the title compound (750 mg) as hydrochloride.

m.p.: 143-146° C. $^1$H-NMR (CDCl$_3$, free compound): δ 1.77 (2H, m), 2.32 (3H, s), 2.48 (2H, t, J=6.8), 3.86 (3H, s), 3.92 (2H, t, J=7.0), 5.69 (1H, s), 6.96 (2H, d, J=8.8), 7.02-7.09 (3H, m), 7.26-7.37 (4H, m)

Example 153

N-{3-[4-(4-Bromophenyl)-2-phenyliminothiazol-3(2H)-yl]propyl}-acetamide

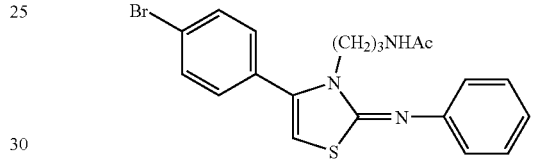

N-[3-(3-Aminopropyl)-4-(4-bromophenyl)-thiazol-2(3H)-ylidene]-aniline hydrochloride (730 mg) obtained in Example 132 and triethyl-amine (0.77 ml) were dissolved in N,N-dimethylformamide (5 ml), and thereto were added dropwise acetic anhydride in an ice bath under nitrogen atmosphere. The mixture was stirred at the same temperature for 2 hours, and thereto was added a saturated aqueous sodium hydrogen carbonate solution, and then the mixture was extracted with ethyl acetate. The organic layer was washed with a saturated brine, dried over sodium sulfate, and the solvent was evaporated under reduced pressure. The residue was crystallized from isopropyl alcohol to give the title compound (580 mg).

m.p.: 155-157° C. $^1$H-NMR (CDCl$_3$): δ 1.66 (2H, m), 1.86 (3H, s), 3.24 (2H, m), 3.90 (2H, t, J=6.4), 5.81 (1H, s), 7.05-7.12 (3H, m), 7.12-7.40 (5H, m), 7.61 (2H, d, J=8.4)

Examples 154 to 167

Various amino compounds and acetic anhydride were reacted in a similar manner to in Example 153 to give the amide compounds as listed in Table 13.

TABLE 13

| Ex. | $R^2$ | $Y^1$-$R^3$ | $Y^2$—N($R^4$)$R^5$ | yield | m.p. °C. |
|---|---|---|---|---|---|
| 154 | 4-methoxyphenyl | phenyl | (CH$_2$)$_2$NHAc | 88% | 97-98 |
| 155 | 4-methoxyphenyl | phenyl | (CH$_2$)$_3$NHAc | 72% | 143-145 |
| 156 | 4-methoxyphenyl | 4-methoxy- | (CH$_2$)$_3$NHAc | 79% | 137-138 |

TABLE 13-continued

| Ex. | $R^2$ | $Y^1$-$R^3$ | $Y^2$—$N(R^4)R^5$ | yield | m.p. ° C. |
|---|---|---|---|---|---|
| 157 | 4-methoxyphenyl | phenyl 2,4-dimethoxy-phenyl | $(CH_2)_3NHAc$ | 79% | 138-139 |
| 158 | 4-methoxyphenyl | 2,5-dimethoxy-phenyl | $(CH_2)_3NHAc$ | 100% | oil |
| 159 | 4-methoxyphenyl | 3,4,5-tri-methoxyphenyl | $(CH_2)_3NHAc$ | 84% | 138-140 |
| 160 | 4-methoxyphenyl | 5-methoxy-2-pyridyl | $(CH_2)_3NHAc$ | 50% | 144-146 |
| 161 | 3,4-dimethoxy-phenyl | 4-methoxy-phenyl | $(CH_2)_3NHAc$ | 81% | 87-90 |
| 162 | 3,4,5-trimethoxy-phenyl | 4-methoxy-phenyl | $(CH_2)_3NHAc$ | 86% | 143-145 |
| 163 | 4-methoxyphenyl | 4-pyridyl-methyl | $(CH_2)_3NHAc$ | 28% | 118-123 |
| 164 | 3,4-(methylene-dioxy)phenyl | 2-methoxy-phenyl | $(CH_2)_3NHAc$ | 79% | 166-169 |
| 165 | 4-fluorophenyl | 2-fluorophenyl | $(CH_2)_3NHAc$ | 85% | 159-160 |
| 166 | 4-fluorophenyl | 3-fluorophenyl | $(CH_2)_3NHAc$ | 81% | 140-141 |
| 167 | 4-fluorophenyl | 4-fluorophenyl | $(CH_2)_3NHAc$ | 89% | 157-158 |

Example 168

2({3-[4-(4-Bromophenyl)-2-(phenylimino)-thiazol-3 (2H)-yl]propyl}-amino)-2-oxoethyl acetate

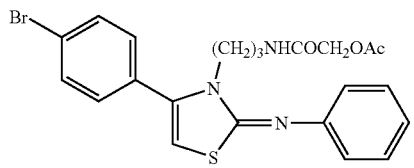

The amino compound (1.21 g) obtained in Example 132 and triethylamine (800 mg) were suspended in tetrahydrofuran (15 ml), and thereto was added dropwise acetoxyacetyl chloride (466 mg) at room temperature under nitrogen atmosphere. The mixture was stirred at the same temperature for 30 minutes, and thereto was added a saturated aqueous sodium hydrogen carbonate solution, and the mixture was extracted with ethyl acetate. The organic layer was washed with a saturated brine, dried over sodium sulfate, and the solvent was evaporated under reduced pressure. The residue was purified by silica gel column chromatography [chloroform:methanol (97:3)] to give the title compound (1.1 g).

m.p.: 156-159° C. $^1$H-NMR (CDCl$_3$): δ 1.56 (2H, m), 1.64 (3H, s), 3.35 (2H, m), 3.90 (2H, t, J=6.1), 4.46 (2H, s), 5.79 (1H, s), 7.00-7.10 (3H, m), 7.24 (2H, d, J=8.4), 7.34 (2H, m), 7.58 (2H, d, J=8.4), 8.01 (1H, t, J=5.9)

Example 169

N-{3-[4-(4-Bromophenyl)-2-(phenylimino)-thiazol-3 (2H)-yl]propyl}-2-hydroxyacetamide

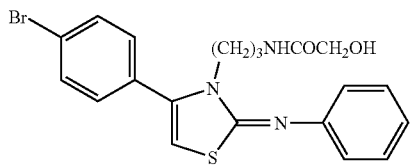

A mixture of the compound (1.1 g) obtained in the above Example 168, a 5% aqueous sodium hydroxide solution (2 ml) and methanol (15 ml) was stirred at room temperature for 30 minutes. The reaction mixture was concentrated under reduced pressure, and to the residue was added water, and the mixture was extracted with chloroform. The organic layer was washed with a saturated brine, dried over sodium sulfate, and the solvent was evaporated under reduced pressure. The residue was purified by silica gel column chromatography [chloroform:methanol (99:1)] to give the title compound (923 mg).

m.p.: 185-186° C. $^1$H-NMR (CDCl$_3$): δ 1.70 (2H, m), 2.52 (1H, m), 3.32 (2H, m), 3.88-3.95 (4H, m), 5.81 (1H, s), 7.04-7.12 (3H, m), 7.26 (2H, d, J=8.4), 7.34 (2H, m), 7.61 (2H, d, J=8.4), 7.68 (1H, m)

Example 170

2-Hydroxy-N-{3-[4-(4-methoxyphenyl)-2-(phenylimino)-thiazol-3(2H)-yl]propyl}acetamide

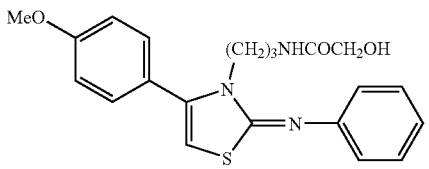

N-[3-(3-Aminopropyl)-4-(4-methoxyphenyl)-thiazol-2(3H)-ylidene]aniline hydrochloride (1.2 g) obtained in Example 9 was treated in a similar manner to in Example 168 and Example 169 to give the title compound (1.1 g) as oil.

$^1$H-NMR (CDCl$_3$): δ 1.69 (2H, m), 2.74 (1H, t, J=5.5), 3.31 (2H, m), 3.87 (3H, s), 3.89-3.94 (4H, m), 5.75 (1H, s), 6.98 (2H, d, J=8.8), 7.05-7.11 (3H, m), 7.26-7.38 (4H, m), 7.74 (1H, m)

Example 171

N-{3-[4-(4-Bromophenyl)-2-phenyliminothiazol-3(2H)-yl]propyl}-methanesulfonamide

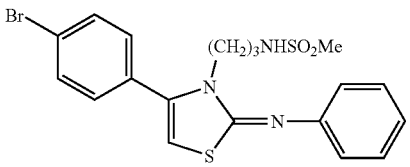

The amino compound (1.21 g) obtained in Example 132 and triethylamine (800 mg) were suspended in tetrahydrofuran (15 ml), and thereto was added dropwise methanesulfonyl chloride (391 mg) at room temperature under nitrogen atmosphere. The mixture was stirred at the same temperature for 30 minutes, and thereto was added a saturated aqueous sodium hydrogen carbonate solution, and then the mixture was extracted with ethyl acetate. The organic layer was washed with a saturated brine, dried over sodium sulfate, and the solvent was evaporated under reduced pressure. The residue was purified by silica gel column chromatography [chloroform:methanol (97:3)] to give the title compound (1.04 g).

m.p.: 128-134° C. $^1$H-NMR (CDCl$_3$): δ 1.69 (2H, m), 2.77 (3H, s), 3.13 (2H, m), 3.96 (2H, t, J=6.0), 5.84 (1H, s), 6.66 (1H, m), 7.06-7.13 (3H, m), 7.24 (2H, d, J=8.2), 7.36 (2H, m), 7.61 (2H, d, J=8.2)

Examples 172 to 174

The amino compound obtained in Example 132 or Example 9 and methanesulfonyl chloride or p-toluenesulfonyl chloride were reacted in a similar manner to in Example 171 to give the sulfonamide compounds as listed in Table 14.

TABLE 14

![structure]

| Ex. | R$^2$ | Y$^2$—N(R$^4$)R$^5$ | yield | m.p. ° C. |
|---|---|---|---|---|
| 172 | 4-methoxyphenyl | (CH$_2$)$_3$NHSO$_2$Me | 43% | 179-181 |
| 173 | 4-methoxyphenyl | (CH$_2$)$_3$NHTs | 46% | 128-130 |
| 174 | 4-bromophenyl | (CH$_2$)$_3$NHTs | 95% | 137-141 |

Ts: tosyl group

Example 175

Methyl 3-[4-(4-bromophenyl)-2-(phenylimino)thiazol-3(2H)-yl]propyl-carbamate

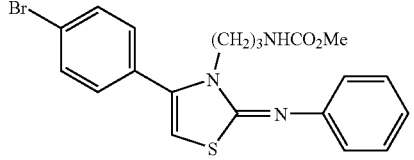

The amino compound (1.21 g) obtained in Example 132 and triethylamine (800 mg) were suspended in tetrahydrofuran (15 ml), and thereto was added dropwise methyl chloroformate (322 mg) at room temperature under nitrogen atmosphere. The mixture was stirred at the same temperature for 30 minutes, and to the reaction mixture was added a saturated aqueous sodium hydrogen carbonate solution, and the mixture was extracted with ethyl acetate. The organic layer was washed with a saturated brine, dried over sodium sulfate, and the solvent was evaporated under reduced pressure. The residue was purified by silica gel column chromatography [chloroform:methanol (95:5)] to give the title compound (1.05 g).

m.p: 132-134° C. $^1$H-NMR (CDCl$_3$): δ 1.62 (2H, m), 3.13 (2H, m), 3.60 (3H, s), 3.90 (2H, t, J=6.4), 5.77 (1H, s), 6.02 (1H, m), 7.03-7.10 (3H, m), 7.21-7.37 (4H, m), 7.56 (2H, d, J=8.4)

Example 176

Methyl 3-[4-(4-methoxyphenyl)-2-(phenylimino)thiazol-3(2H)-yl]propyl-carbamate

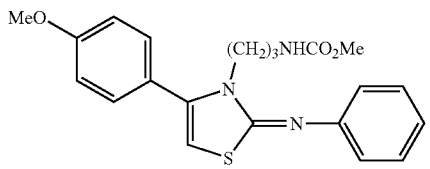

The amino compound (1.2 g) obtained by the method of Example 9 was treated in a similar manner to in Example 175 to give the title compound (698 mg).

m.p.: 106-108° C. $^1$H-NMR (CDCl$_3$): δ 1.61 (2H, m), 3.16 (2H, m), 3.61 (3H, s), 3.86 (3H, s), 3.93 (2H, t, J=6.3), 5.73 (1H, s), 6.11 (1H, m), 6.97 (2H, d, J=8.6), 7.04-7.12 (3H, m), 7.26-7.38 (4H, m)

Example 177

N-{3-[2-(2-Methoxyphenyl)-4-(3,4-methylenedioxyphenyl)iminothiazol-3(2H)-yl]propyl}-N'-ethylurea

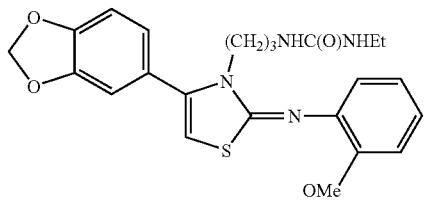

The amino compound (200 mg) obtained in Example 67 and triethylamine (0.13 ml) were dissolved in N,N-dimethylformamide (4 ml), and thereto was added dropwise ethyl isocyanate (38 μl) in an ice bath under nitrogen atmosphere. The mixture was stirred at the same temperature for 1.5 hour, and thereto was added a saturated aqueous sodium hydrogen carbonate solution, and the mixture was extracted with ethyl acetate. The organic layer was washed with a saturated brine, dried over sodium sulfate, and the solvent was evaporated under reduced pressure. The residue was crystallized from diethyl ether to give the title compound (147 mg).

m.p.: 134-136° C. $^1$H-NMR (CDCl$_3$): δ 1.02 (3H, t, J=7.2), 1.54 (2H, m), 3.09-3.16 (4H, m), 3.84 (3H, s), 4.04 (2H, t, J=6.1), 4.29 (1H, m), 5.75 (1H, s), 6.05 (2H, s), 6.44 (1H, m), 6.83-6.86 (3H, m), 6.99-7.26 (4H, m)

Examples 178 to 183

The amino compounds obtained by the method of Example 9, Example 79 or Example 108 and ethyl isocyanate or ethyl isothiocyanate were reacted in a similar manner to in Example 177 to give the urea compounds and the thiourea compounds as listed in Table 15.

Example 184

(1) t-Butyl 3-[4-(4-nitrophenyl)-2-(phenylimino)thiazol-3(2H)-yl]propyl-carbamate

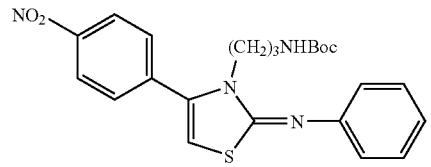

A mixture of t-butyl 3-(anilinocarbothioylamino)propyl-carbamate (6.2 g) obtained in Reference Example 4, 2-bromo-4'-nitroacetophenone (4.9 g) and ethanol (50 ml) was heated with reflux under nitrogen atmosphere. One hour thereafter, the reaction mixture was allowed to cool, and the precipitated crystals were collected by filtration to give the title compound (8.84 g) as hydrobromide.

(2) t-Butyl 3-[4-(4-aminophenyl)-2-(phenylimino)thiazol-3(2H)-yl]propyl-carbamate

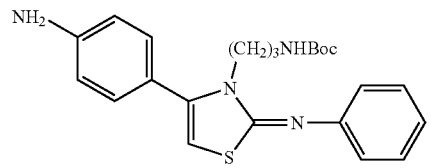

A mixture of the compound (1 g) obtained in the above (1), 10% palladium on active carbon (200 mg) and methanol (50 ml) was subjected to hydrogenation at room temperature under atmospheric pressure. Three hours thereafter, the reac-

TABLE 15

| Ex. | R$^2$ | Y$^1$—R$^3$ | Y$^2$—N(R$^4$)R$^5$ | yield | m.p. ° C. |
|---|---|---|---|---|---|
| 178 | 4-methoxyphenyl | phenyl | (CH$_2$)$_3$NH—C(O)NHEt | 83% | 126-132 |
| 179 | 3,4-(methylenedioxy)phenyl | 4-chloro-2,5-dimethoxyphenyl | (CH$_2$)$_3$NH—C(O)NHEt | 70% | 155-160 |
| 180 | 4-fluorophenyl | 4-chloro-2,5-dimethoxyphenyl | (CH$_2$)$_3$NHC—(O)NHEt | 62% | 152-156 |
| 181 | 4-methoxyphenyl | phenyl | (CH$_2$)$_3$NHC—(S)NHEt | 100% | 180-183 |
| 182 | 3,4-(methylenedioxy)phenyl | 4-chloro-2,5-dimethoxyphenyl | (CH$_2$)$_3$NHC—(S)NHEt | 82% | 175-177 |
| 183 | 4-fluorophenyl | 4-chloro-2,5-dimethoxyphenyl | (CH$_2$)$_3$NHC—(S)NHEt | 76% | 185-186 | tion mixture was filtered through cerite, and the filtrate was evaporated under reduced pressure. To the residue was added a saturated aqueous sodium hydrogen carbonate solution, and the mixture was extracted with ethyl acetate. The organic layer was washed with a saturated brine, dried over sodium sulfate, and the solvent was evaporated under reduced pressure. The residue was purified by silica gel column chromatography [chloroform:methanol (98:2)] to give the title compound (640 mg).

¹H-NMR (CDCl₃): δ 1.40 (9H, s), 1.63 (2H, m), 3.06 (2H, m), 3.86 (2H, brs), 3.94 (2H, t, J=6.6), 5.70 (1H, s), 5.96 (1H, m), 6.71 (2H, d, J=8.6), 7.02-7.36 (7H, m)

(3) 4-[4-(Aminophenyl)-3-(3-aminopropyl)-thiazol-2-ylidene]aniline

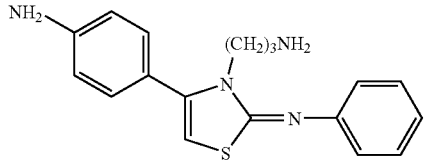

The compound (640 mg) obtained in the above (2) was reacted in a similar manner to in Example 9 (2) to give the title compound (550 mg) as hydrochloride.

m.p.: 254-257° C.

Example 185

(1) Methyl 4-{3-[3-(t-butoxycarbonyl)amino]propyl-2-(phenylimino)-2,3-dihydrothiazol-4-yl}benzoate

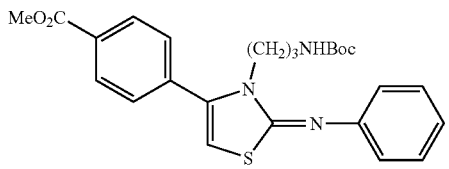

t-Butyl 3-(anilinocarbothioylamino)propylcarbamate (6.19 g) obtained in Reference Example 4, 2-bromo-4'-(methoxycarbonyl)acetophenone (5.14 g) and methanol (51 ml) were treated in a similar manner to in Example 10 (1) to give the title compound (8.84 g).

¹H-NMR (CDCl₃): δ 1.40 (9H, s), 1.62-1.66 (2H, m), 3.08 (2H, m), 3.96-4.00 (5H, m), 5.71 (1H, m), 5.87 (1H, s), 7.05-7.38 (5H, m), 7.47 (2H, d, J=8.3), 8.13 (2H, d, J=8.3)

(2) 4-{3-[3-(t-Butoxycarbonyl)amino]propyl-2-(phenylimino)-2,3-dihydrothiazol-4-yl}benzoic acid

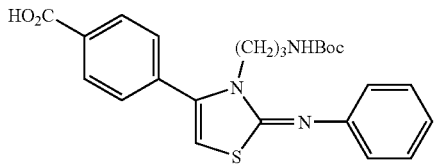

A mixture of the compound (4.68 g) obtained in the above (1), a 1N aqueous sodium hydroxide solution (15 ml) and methanol (30 ml) was heated under reflux for 2 hours. The reaction mixture was concentrated under reduced pressure, and to the residue was added a 10% aqueous citric acid solution, and the precipitated solid was collected by filtration to give the title compound (3.85 g).

(3) 4-[3-(3-Aminopropyl)-2-(phenylimino)-2,3-dihydrothiazol-4-yl]-benzoic acid

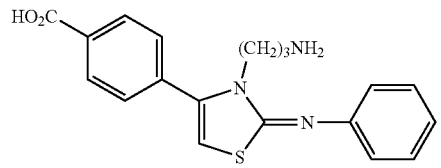

The compound (300 mg) obtained in the above (2) was treated in a similar manner to in Example 9 (2) to give, the title compound (250 mg) as hydrochloride.

m.p.: 248-252° C.

In the following Examples, the identification of the structure was carried out by NMR and LC/MS.

The apparatus for LC/MS and the conditions therefor are as follows.

API 150EX (manufactured by PE SCIEX),

Ionization: ESI,

Voltage: 40 eV

Column: Mightysil RP-18 GP (manufactured by KANTO KAGAKU),

Flow rate: 3.5 ml/min,

Wave length for detection: 220 nm

Analysis condition: (Solution A: 0.05% aqueous trifluoroacetic acid solution; Solution B: 0.035% solution of trifluoroacetic acid in acetonitrile), Method A:

0.0 min (concentration of Solution B: 10%)→0.5 min (concentration of Solution B: 10%)→4.2 min (concentration of Solution B: 99%)

Method B:

0.0 min (concentration of Solution B: 40%)→0.5 min (concentration of Solution B: 40%)→4.2 min (concentration of Solution B: 99%)

Examples 186 to 207

Various α-bromoketones and thiourea were treated in a similar manner to in Example 10 or 11 to give the compounds as listed in Table 16.

TABLE 16

| Ex. No. | Structure | Exact MS | m/z | Method for analysis | Retention Time (min) |
|---|---|---|---|---|---|
| 186 | 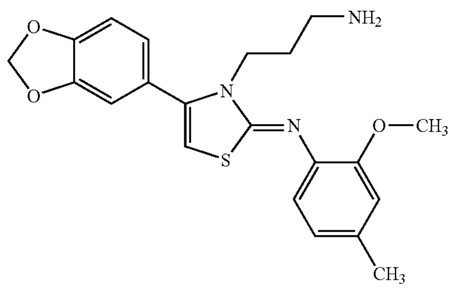 | 397 | 398 | A | 2.97 |
| 187 | 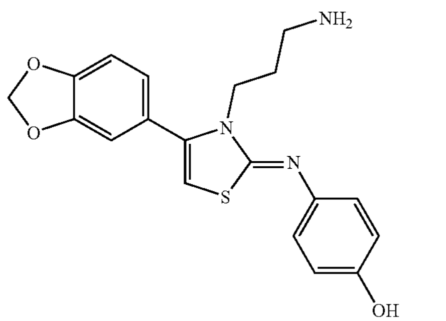 | 369 | 370 | A | 2.55 |
| 188 | 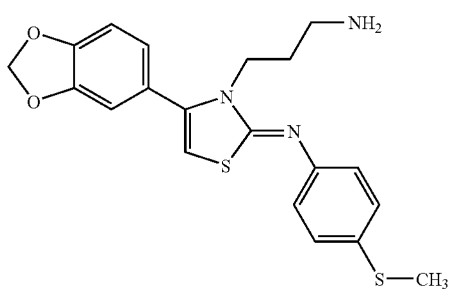 | 399 | 400 | A | 3.04 |
| 189 | 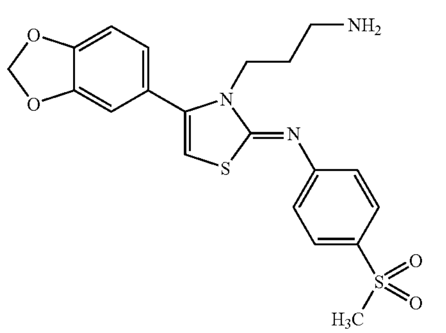 | 431 | 432 | A | 3.04 |

TABLE 16-continued

| Ex. No. | Structure | Exact MS | m/z | Method for analysis | Retention Time (min) |
|---|---|---|---|---|---|
| 190 | 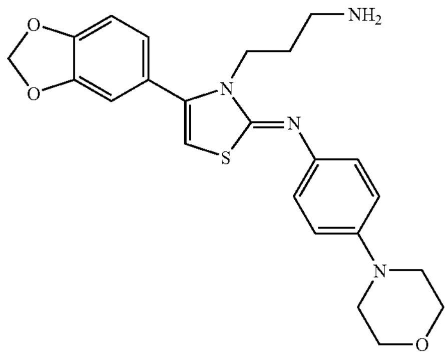 | 438 | 439 | A | 2.79 |
| 191 | 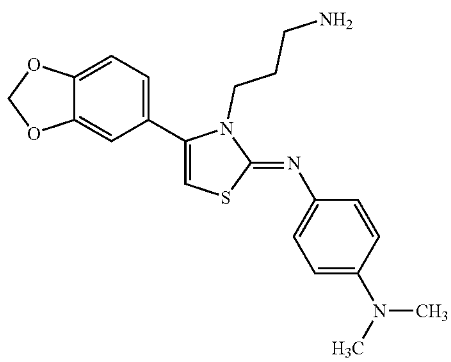 | 396 | 397 | A | 2.70 |
| 192 | 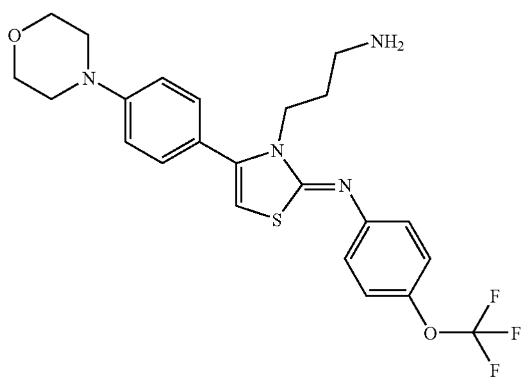 | 478 | 479 | A | 3.35 |
| 193 | 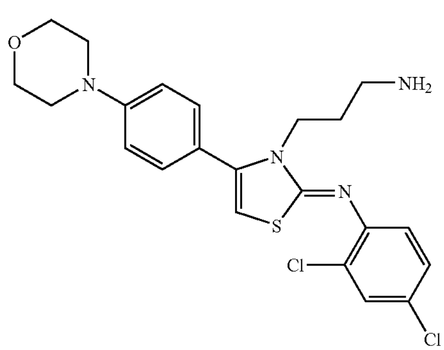 | 462 | 463 | A | 3.70 |

TABLE 16-continued

| Ex. No. | Structure | Exact MS | m/z | Method for analysis | Retention Time (min) |
|---|---|---|---|---|---|
| 194 | 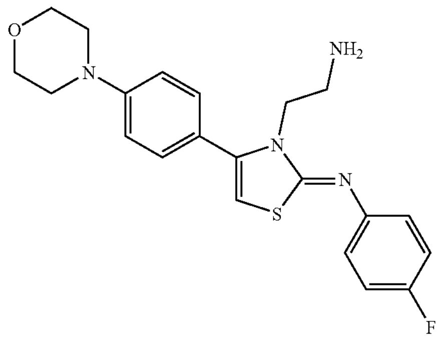 | 398 | 399 | A | 3.08 |
| 195 | 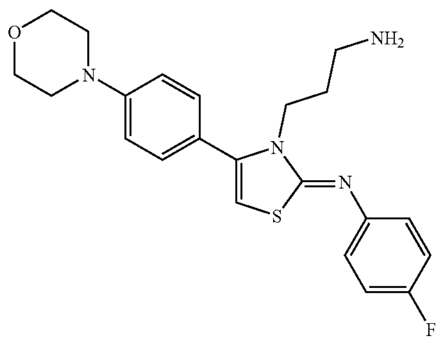 | 412 | 413 | A | 2.88 |
| 196 | 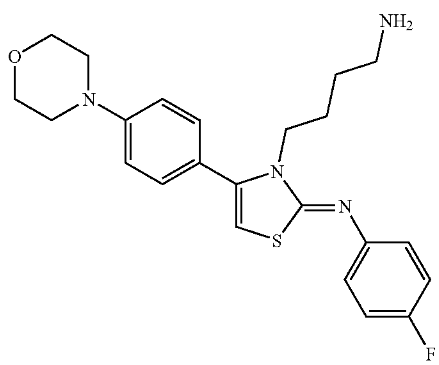 | 426 | 427 | A | 2.90 |
| 197 | 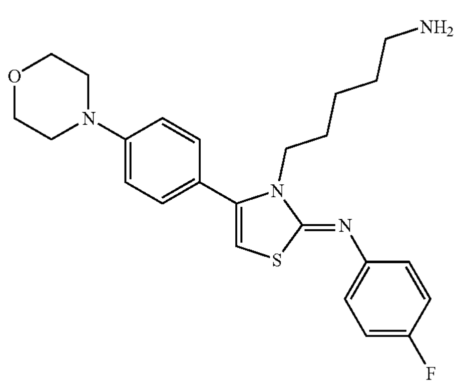 | 440 | 441 | A | 2.94 |

TABLE 16-continued

| Ex. No. | Structure | Exact MS | m/z | Method for analysis | Retention Time (min) |
|---|---|---|---|---|---|
| 198 | 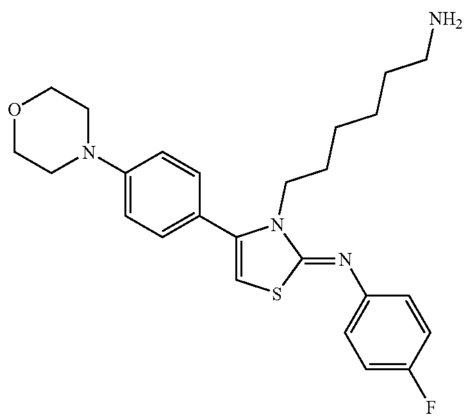 | 454 | 455 | A | 3.02 |
| 199 | 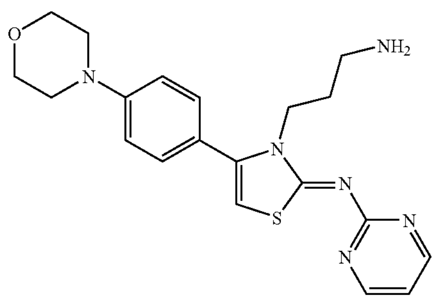 | 396 | 397 | A | 3.16 |
| 200 | 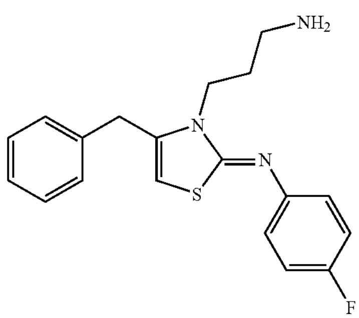 | 341 | 342 | A | 2.96 |
| 201 | 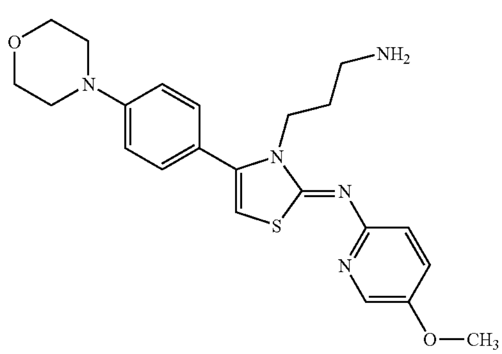 | 425 | 426 | A | 2.90 |

TABLE 16-continued
| Ex. No. | Structure | Exact MS | m/z | Method for analysis | Retention Time (min) |
|---|---|---|---|---|---|
| 202 | 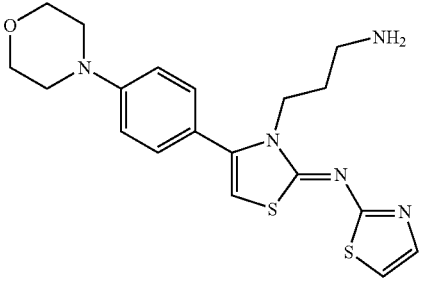 | 401 | 402 | A | 2.68 |
| 203 | 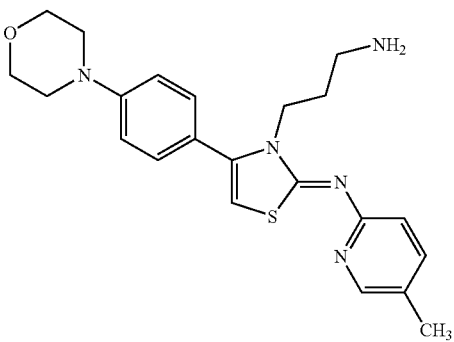 | 409 | 410 | A | 2.84 |
| 204 | 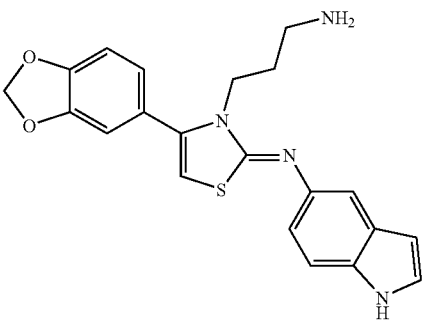 | 392 | 393 | A | 2.87 |
| 205 | 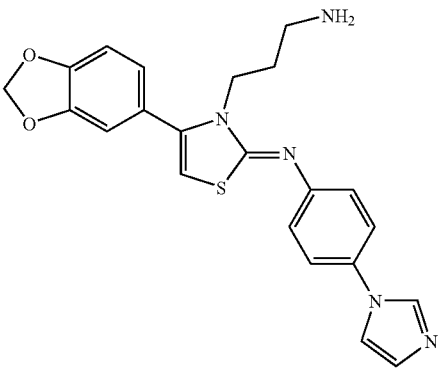 | 419 | 420 | A | 2.49 |

TABLE 16-continued

| Ex. No. | Structure | Exact MS | m/z | Method for analysis | Retention Time (min) |
|---|---|---|---|---|---|
| 206 | 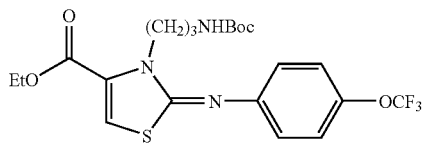 | 359 | 360 | A | 3.04 |
| 207 | 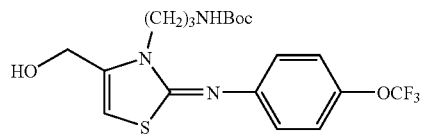 | 371 | 372 | A | 3.01 |

Example 208

N-[3-(3-Aminopropyl)-4-[(benzyloxy)methyl]thiazol-2(3H)-ylidene]-4-(trifluoromethoxy)aniline (1) Ethyl 3-{3-[(tert-butoxycarbonyl)amino]propyl}-2-{[4-(trifluoro-methoxy)phenyl]imino}-2,3-dihydrothiazol-4-carboxylate t-Butyl 3-{[4-(trifluoromethoxy)anilinocarbothioyl]amino}propyl-carbamate (10.0 g) obtained in Reference Example 40, ethyl 2-bromo-pyruvate (3.29 ml) and ethanol (50 ml) were treated in a similar manner to in Example 10 (1), and purified by silica gel column chromatography [n-hexane:ethyl acetate (5:1)] to give the title compound (7.71 g) as a white solid.

(2) tert-Butyl 3-[4-(hydroxymethyl)-2-{[4-(trifluoromethoxy)phenyl]-imino}thiazol-3(2H)-yl]propyl-carbamate Lithium aluminum hydride (1.0 g) was suspended in tetrahydrofuran (200 ml), and thereto was added dropwise a solution of the compound (3.0 g) obtained in the above (2) in tetrahydrofuran (100 ml) in an ice bath under nitrogen atmosphere. One hour thereafter, water was added to the reaction mixture, and the excess lithium aluminum hydride was decomposed, and thereto was added a 10N aqueous sodium hydroxide solution. The resulting slurry was dried over sodium sulfate, and the filtrate was evaporated under reduced pressure to give the title compound (2.61 g).

(3) tert-Butyl 3-[4-[(benzyloxy)methyl]-2-{[4-(trifluoromethoxy)phenyl]-imino}thiazol-3(2H)-yl]propylcarbamate

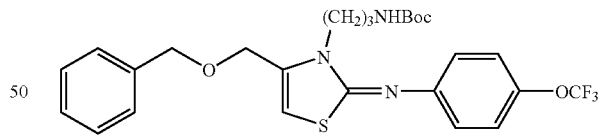

The compound (313 mg) obtained in the above (2) was dissolved in N,N-dimethylformamide (3 ml), and thereto was added sodium hydride (56 mg, 60% dispersion in oil) in an ice bath under nitrogen atmosphere, and the mixture was stirred for 30 minutes. To the reaction mixture was added benzyl bromide (179 mg), and the mixture was warmed to room temperature, and then stirred for one hour. The reaction mixture was poured into a 10% aqueous citric acid solution under ice-cooling, and the mixture was extracted with chloroform. The organic layer was washed with a saturated brine, dried over sodium sulfate, and the solvent was evaporated under reduced pressure. The residue was purified by silica gel column chromatography [n-hexane:ethyl acetate (5:1)] to give the title compound (137 mg) as oil.

(4) N-[3-(3-Aminopropyl)-4-[(benzyloxy)methyl]
thiazol-2(3H)-ylidene]-4-(trifluoromethoxy)aniline

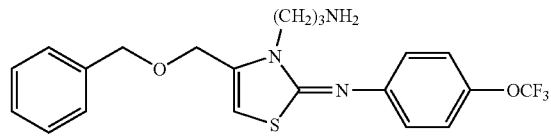

The compound (137 mg) obtained in the above (3) was treated in a similar manner to in Example 9 (2) to give the title compound (133 mg) as hydrochloride.

LC/MS: 438 (MH$^+$), retention time; 3.52 min (Condition A)

Example 209

N-[3-(3-Aminopropyl)-4-{[(4-chlorobenzyl)oxy]methyl}thiazol-2(3H)-ylidene]-4-(trifluoromethoxy)aniline

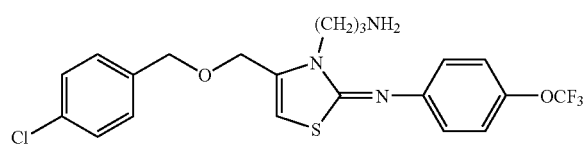

The compound (313 mg) obtained in Example 208 (2) and 4-chlorobenzyl bromide (216 mg) were treated in a similar manner to in Example 208 (3), (4) to give the title compound (152 mg) as hydrochloride.

LC/MS: m/z=472 (MH$^+$), retention time: 3.72 min (Condition A)

Example 210

N-[3-(3-Aminopropyl)-4-[(benzyloxy)methyl]thiazol-2(3H)-ylidene]-5-methoxy-2-pyridinamine (1) tert-Butyl 3-[4-(hydroxymethyl)-2-[(5-methoxy-2-pyridyl)imino]-thiazol-3(2H)-yl]propylcarbamate

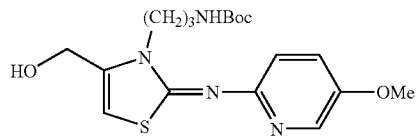

t-Butyl 3-[(5-methoxy-2-pyridylaminocarbothioyl)amino]propyl-carbamate (10.0 g) obtained in Reference Example 62 was treated in a similar manner to in Example 208 (1), (2) to give the title compound (4 g) as pale yellow solid.

(2) N-[3-(3-Aminopropyl)-4-[(benzyloxy)methyl]
thiazol-2(3H)-ylidene]-5-methoxy-2-pyridinamine

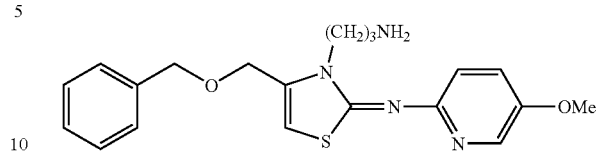

The compound (283 mg) obtained in the above (1) was treated in a similar manner to in Example 208 (3), (4) to give the title compound (128 mg) as hydrochloride.

LC/MS: m/z=385 (MH$^+$), retention time: 2.99 min (Condition A)

Example 211

N-[3-(3-Aminopropyl)-4-{[(4-chlorobenzyl)oxy]methyl}thiazol-2(3H)-ylidene]-5-methoxy-2-pyridinamine

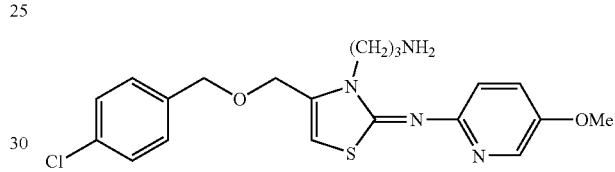

The compound (276 mg) obtained in Example 210 (1) was treated in a similar manner to in Example 208 (3), (4) to give the title compound (92 mg) as hydrochloride.

LC/MS: m/z 419 (MH$^+$), retention time: 3.21 min (Condition A)

Example 212

N-[3-(3-Aminopropyl)-4-{[(4-chlorobenzyl)(methyl)amino]methyl}thiazol-2(3H)-ylidene]-4-(trifluoromethoxy)aniline (1) tert-Butyl 3-[4-{[(4-chlorobenzyl)(methyl)amino]methyl}-2-{[4-(trifluoromethoxy)phenyl]imino}thiazol-3(2H)-yl]propylcarbamate

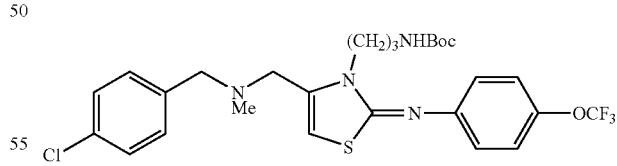

The compound (300 mg) obtained in Example 208 (2) and triethylamine (101 mg) were dissolved in tetrahydrofuran (30 ml), and thereto was added dropwise methanesulfonyl chloride (115 mg) under ice-cooling. The mixture was stirred at the same temperature for 1.5 hour, and thereto was further added N-methyl-4-chlorobenzylamine (1.04 g), and the mixture was further stirred for one hour. Water was added to the reaction mixture, and the mixture was extracted with ethyl acetate. The organic layer was washed with a saturated brine, dried over sodium sulfate, and the solvent was evaporated (2) N-[3-(3-Aminopropyl)-4-{[(4-chlorobenzyl)(methyl)amino]methyl}-thiazol-2(3H)-ylidene]-4-(trifluoromethoxy)aniline

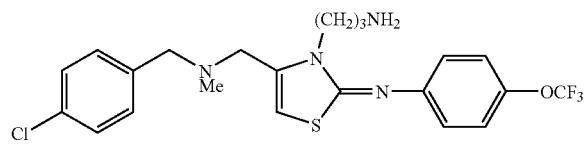

The compound (80 mg) obtained in the above (1) was treated in a similar manner to in Example 9 (2) to give the title compound (83 mg) as hydrochloride.
LC/MS: m/z=485 (MH$^+$), retention time: 3.43 min (Condition A)

Example 213

N-[3-(3-Aminopropyl)-4-{[(4-chlorobenzyl)(methyl)amino]methyl}thiazol-2(3H)-ylidene]-5-methoxy-2-pyridinamine

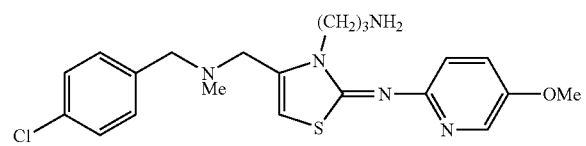

The compound (200 mg) obtained in Example 210 (1) was treated in a similar manner to in Example 212 to give the title compound (145 mg) as hydrochloride.
LC/MS: m/z=432 (MH$^+$), retention time: 2.83 min (Condition A)

Example 214

N-Methyl-N'-{2-[2-[(4-fluorophenyl)imino]-4-[4-(morpholino)phenyl]-thiazol-3(2H)-yl]ethyl}urea

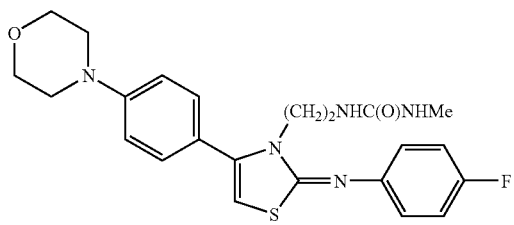

The amino compound (25 g, hydrochloride) obtained in Example 194, methyl isocyanate (3.1 g) and triethylamine (50 ml) were reacted in a similar manner to in Example 177, and crystallized from methanol to give the title compound (12.93 g).
m.p.: 191-194° C. $^1$H-NMR (CDCl$_3$): δ 2.66 (3H, d, J=4.7), 3.24 (4H, t, J=4.8), 3.43 (2H, m), 3.86-3.89 (6H, m), 5.10-5.60 (2H, m), 5.73 (1H, s), 6.95 (2H, d, J=8.8), 7.03-7.05 (4H, m), 7.27 (2H, dd, J=1.9, J=8.2).

Example 215

Ethyl N-{3-[2-[(4-chloro-2-methoxyphenyl)imino]-4-(4-fluorophenyl)-thiazol-3(2H)-yl]propyl}glycinate

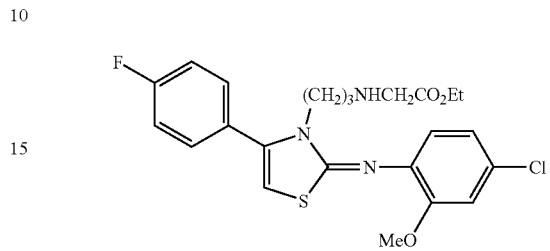

The compound (25 g, free amino compound) obtained in Example 106, and triethylamine (9.78 ml) were dissolved in tetrahydrofuran (250 ml), and thereto was added dropwise a solution of ethyl bromoacetate (7.21 ml) in tetrahydrofuran (60 ml) under ice-cooling over a period of 40 minutes. Then, the mixture was stirred at room temperature overnight, and thereto was added water, and the mixture was extracted with ethyl acetate. The organic layer was washed with a saturated brine, dried over sodium sulfate, and the solvent was evaporated under reduced pressure. The residue was purified by silica gel column chromatography [chloroform: methanol (30:1)] to give the title compound (24.7 g) as oil.
$^1$H-NMR (CDCl$_3$): δ 1.23 (3H, t, J=7.2), 1.77 (2H, m), 2.54 (2H, t, J=6.8), 3.26 (2H, s), 3.83 (3H, s), 3.94 (2H, t, J=7.2), 4.13 (2H, q, J=7.2), 5.75 (1H, s), 6.90-6.98 (3H, m), 7.14 (2H, dd, J=8.4, J=8.6), 7.37 (2H, dd, J=5.3, J=8.6) LC/MS: m/z=478 (MH$^+$), retention time: 3.61 min (Condition A)

Example 216

Ethyl N-{3-[2-[(4-chloro-2-methoxyphenylimino)]-4-(4-fluoro-phenyl)-thiazol-3 (2H)-yl]propyl}-β-alaninate

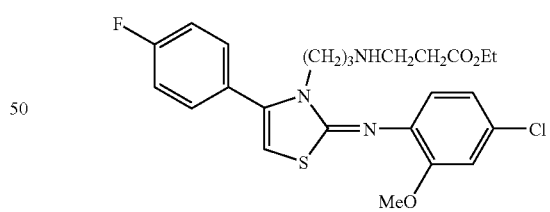

The compound (1.74 g, free amino compound) obtained in Example 106 was dissolved in ethanol (10 ml), and thereto was added a solution of ethyl acrylate (0.48 ml) in ethanol (30 ml) under ice-cooling over a period of 15 minutes. Then, the mixture was stirred at room temperature overnight, and water was added to the reaction mixture, and the mixture was extracted with ethyl acetate. The organic layer was washed with a saturated brine, dried over sodium sulfate, and the solvent was evaporated under reduced pressure. The residue was purified by silica gel column chromatography [chloroform:methanol (30:1)] to give the title compound (1.87 g) as oil.

¹H-NMR (CDCl₃): δ 1.23 (3H, t, J=7.2), 1.77 (2H, m), 2.40 (2H, t, J=6.8), 2.57 (2H, t, J=6.8), 2.77 (2H, t, J=6.8), 3.83 (3H, s), 3.93 (2H, t, J=7.2), 4.09 (2H, q, J=7.2), 5.76 (1H, s), 6.90-6.97 (3H, m), 7.14 (2H, dd, J=8.6, J=8.6), 7.36 (2H, dd, J=5.3, J=8.6). LC/MS: m/z=492 (MH⁺), retention time: 3.60 min (Condition A)

Example 217

N-{3-[4-(4-Fluorophenyl)-2-[(4-fluorophenyl)imino] thiazol-3(2H)-yl]-propyl}guanidine (1) N,N''-di-tert-Butoxycarbonyl-N'-{3-[4-(4-fluorophenyl)-2-[(4-fluoro-phenyl)imino]thiazol-3(2H)-yl]propyl}guanidine

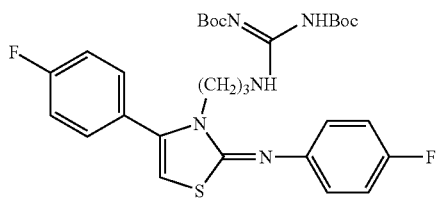

The compound (837 mg, free amino compound) obtained in Example 116 was dissolved in ethanol (10 ml), and thereto was added 1,3-bis(tert-butoxycarbonyl)-2-methylisothiourea (639 mg) at room temperature under nitrogen atmosphere, and the mixture was stirred for 7 hours. The reaction mixture was concentrated under reduced pressure, and the residue was purified by silica gel column chromatography [n-hexane:ethyl acetate (5:1)] to give the title compound (1.12 g).

(2) N-{3- [4-(4-Fluorophenyl)-2-[(4-fluorophenyl) imino]thiazol-3(2H)-yl]-propyl}guanidine

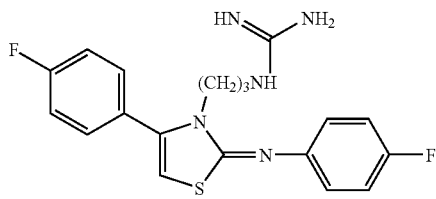

The compound (1.12 g) obtained in the above (1) was treated in a similar manner to in Example 9 (2) to give the title compound (905 mg) as hydrochloride.

LC/MS: m/z=388 (MH⁺), retention time: 2.81 min (Condition A)

Example 218

N-{3-[2 -[(4-Fluorophenyl)imino]-4-[4-(morpholino) phenyl]thiazol-3(2H)-yl]propyl}-4-morpholinecarboximidamide (1) tert-Butyl 3-[2-[(4-fluorophenyl)imino]-4-[4-(morpholino)phenyl]-thiazol-3(2H)-yl]propyl[imino (morpholino)methyl]carbamate

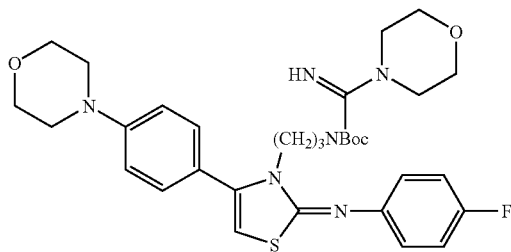

The compound (522 mg, hydrochloride) obtained in Example 195 was suspended in tetrahydrofuran (30 ml), and thereto was added 1-(1H-1,2,3-benzotriazol-1-yl)-1-morpholinomethaneimine (1.16 g), which was synthesized by the method of Katritzky, A. R. (cf., J. Org. Chem., 2000, 65, 8080-8082) at room temperature under nitrogen atmosphere, and the mixture was stirred overnight. To the reaction mixture was added a 10% aqueous sodium carbonate solution, and the mixture was extracted with chloroform. The organic layer was washed with a saturated brine, dried over sodium sulfate, and the solvent was evaporated under reduce pressure. The residue was dissolved in tetrahydrofuran (30 ml), and thereto was added di-t-butyl dicarbonate (240 mg) at room temperature under nitrogen atmosphere, and the mixture was stirred at room temperature for 6 hours. The reaction mixture was concentrated under reduced pressure, and the residue was purified by silica gel column chromatography [chloroform:methanol (95:5)] to give the title compound (540 mg) as amorphous.

(2) N-{3-[2-[(4-Fluorophenyl)imino]-4-[4-(morpholino)phenyl]thiazol-3(2H)-yl]propyl}-4-morpholinecarboximidamide

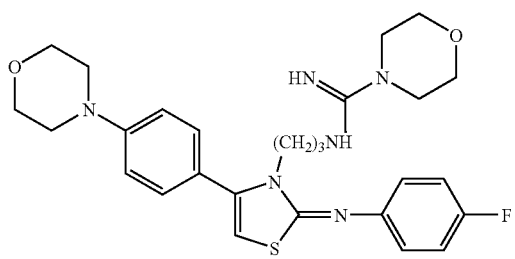

The compound (535 mg) obtained in the above (1) was treated in a similar manner to in Example 9 (2) to give the title compound (467 mg) as hydrochloride.

LC/MS: m/z=525 (MH⁺), retention time: 2.98 min (Condition A)

Example 219

N-{3-[4-(1,3-benzodioxol-5-yl)-2-{[4-(trifluoromethoxy)phenyl]imino}-thiazol-3(2H)-yl]propyl}-2-hydroxyacetamide

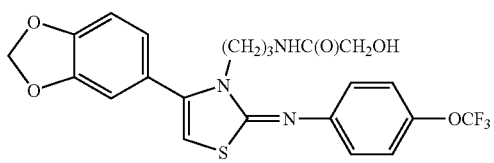

To a mixture of the compound (600 mg, free amino compound) obtained in Example 77, 2-hydroxyacetic acid (156 mg), 1-hydroxy-benzotriazole monohydrate (315 mg) and N,N-dimethylformamide (10 ml) was added 1-ethyl-3-(3-dimethylaminopropyl)carbodiimide hydrochloride (394 mg), and the mixture was stirred at room temperature overnight. To the reaction mixture was added water, and the mixture was extracted with ethyl acetate. The organic layer was washed with a saturated brine, dried over sodium sulfate, and the solvent was evaporated under reduced pressure. The residue was crystallized from isopropyl alcohol to give the title compound (458 mg).

$^1$H-NMR (DMSO-$d_6$): δ 1.67 (2H, m), 3.00 (2H, m), 3.71 (2H, d, J=5.7), 3.81 (2H, t, J=7.9), 5.41 (1H, t, J=5.7), 6.11 (2H, s), 6.18 (1H, s), 6.93 (1H, d, J=8.1), 7.01-7.11 (4H, m), 7.30 (2H, d, J=8.4), 7.71 (1H, m) LC/MS: m/z=496 (MH$^+$), retention time: 3.49 min (Condition A)

Example 220

N'-{3-[2-[(4-Fluorophenyl)imino]-4-[4-(morpholino)phenyl]thiazol-3(2H)-yl]propyl}-N,N-dimethylurea

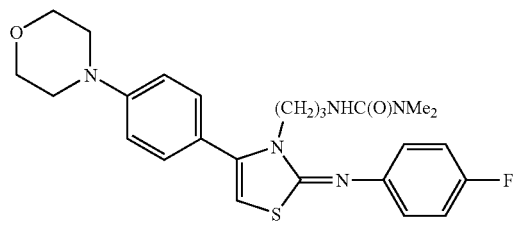

The title compound was synthesized by combinatorial chemistry technique. That is, to a solution of the compound obtained in Example 195 (free amino compound) in tetrahydrofuran (45.3 μmol/ml) (1 ml) were added a solution of triethylamine in tetrahydrofuran (118 μmol/ml) (500 μl) and a solution of N,N-dimethylcarbamoyl chloride in tetrahydrofuran (58.9 μmol/ml) (1 ml), and the mixture was stirred at room temperature for 6 hours. To the reaction mixture was added Tris-Amine resin (manufactured by Argonaut) (about 10 mg) and isocyanate resin (manufactured by Argonaut) (about 20 mg), and the mixture was stirred at room temperature overnight. The reaction mixture was filtered, and the filter cake was washed twice with chloroform (1 ml), and the filtrate was washed with a saturated aqueous sodium hydrogen carbonate solution (2 ml), and then further washed twice with water (2 ml). The organic layer was passed through a filter containing magnesium sulfate, and the filter was washed twice with chloroform (1 ml), and the filtrate was concentrated to give the title compound (18 mg).

LC/MS: m/z=484 (MH$^+$), retention time: 3.29 min (Condition A)

Example 221

N-butyl-N'-{3-[2-[(4-fluorophenyl)imino]-4-[4-(morpholino)phenyl]-thiazol-3(2H)-yl]propyl}urea

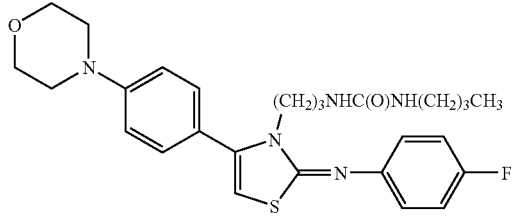

The title compound was synthesized by combinatorial chemistry technique. That is, to a solution of the compound (free amino compound) obtained in Example 195 in tetrahydrofuran (45.3 μmol/ml) (1 ml) was added a solution of n-butyl isocyanate in tetrahydrofuran (58.9 μmol/ml) (1 ml), and the mixture was stirred at room temperature for 6 hours. To the reaction mixture were added Tris-amine resin (manufactured by Argonaut) (about 10 mg) and isocyanate resin (manufactured by Argonaut) (about 20 mg), and the mixture was stirred at room temperature overnight. The reaction mixture was filtered, and the filter cake was washed twice with chloroform (1 ml), and the filtrate was washed with a saturated aqueous sodium hydrogen carbonate solution (2 ml), then washed twice with water (2 ml). The organic layer was passed through the filter containing magnesium sulfate, and the filter was washed twice with chloroform (1 ml), and the filtrate was concentrated to give the title compound (22 mg).

LC/MS: m/z=512 (MH$^+$), retention time: 3.649 min (Condition A)

Example 222

N-{3-[2-[(4-Fluorophenyl)imino]-4-[4-(morpholino)phenyl]thiazol-3(2H)-yl]propyl}benzamide

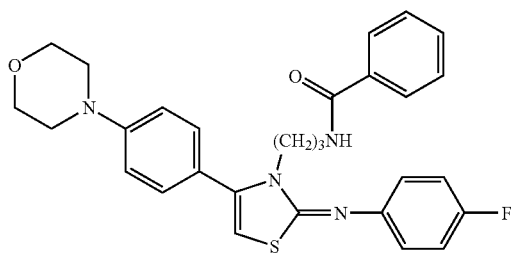

The title compound was synthesized by combinatorial chemistry technique. That is, to a solution of the compound (free amino compound) obtained in Example 195 in tetrahydrofuran (45.3 μmol/ml) (1 ml) were added benzoic acid in tetrahydrofuran (58.9 μmol/ml) (1 ml), a solution of 1-hydroxybenzotriazole monohydrate in tetrahydrofuran (118 μmol/ml) (500 μl), and a suspension of 1-ethyl- 3-(3-dimethylaminopropyl)carbodiimide hydrochloride in tetrahydrofuran (118 μmol/ml) (500 μl), and the mixture was stirred at room temperature overnight. To the reaction mixture was added chloroform (2.5 ml), and the mixture was washed with a saturated aqueous sodium hydrogen carbonate solution (2 ml), then washed twice with water (2 ml). The organic layer was passed through the filter containing magnesium sulfate, and the filter was washed twice with chloroform (1 ml), and the filtrate was concentrated to give the title compound (23 mg).

LC/MS: m/z=517 (MH$^+$), retention time: 3.55 min (Condition A)

Examples 223 to 312

The corresponding amino compounds were treated to give the following compounds as listed in Table 17.

TABLE 17

| Ex. No. | Structure | Exact MS | m/z | Method for analysis | Retention time (min) | Ref. Ex. |
| --- | --- | --- | --- | --- | --- | --- |
| 223 | 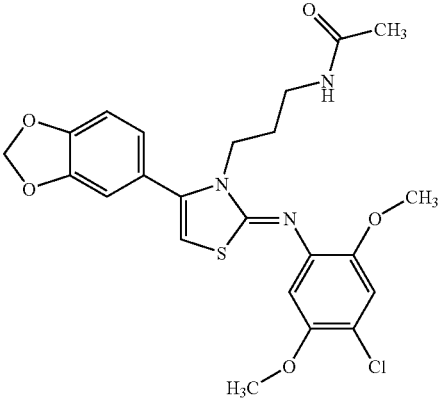 | 489 | 490 | A | 3.40 | 153 |
| 224 | 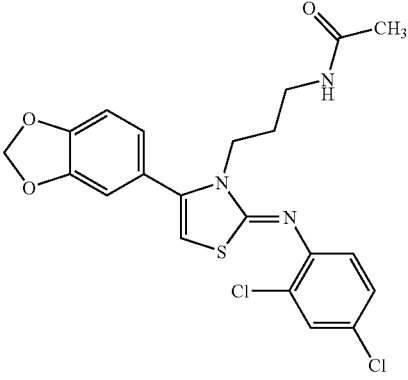 | 463 | 464 | A | 4.02 | 153 |
| 225 | 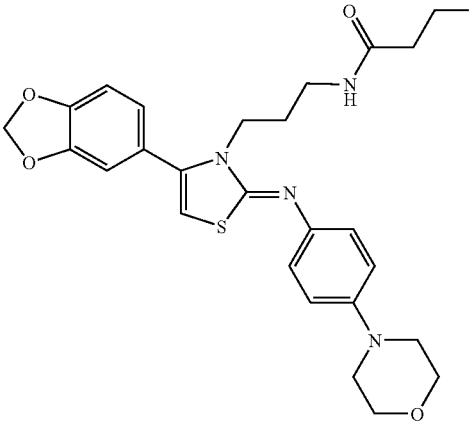 | 508 | 509 | A | 3.31 | 168 |

TABLE 17-continued
| Ex. No. | Structure | Exact MS | m/z | Method for analysis | Retention time (min) | Ref. Ex. |
|---|---|---|---|---|---|---|
| 226 | 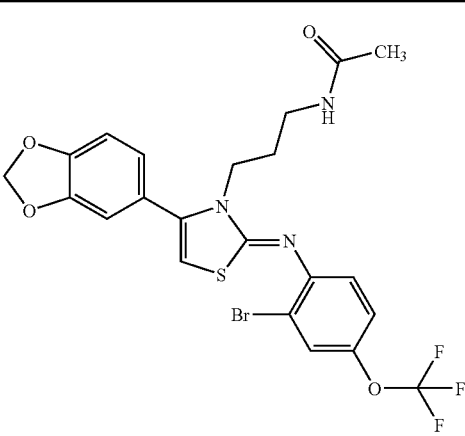 | 558 | 559 | B | 2.73 | 153 |
| 227 | 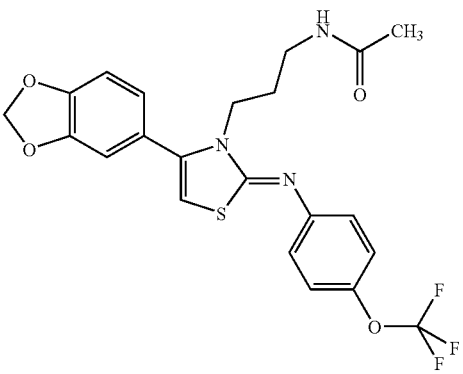 | 479 | 480 | A | 3.56 | 153 |
| 228 | 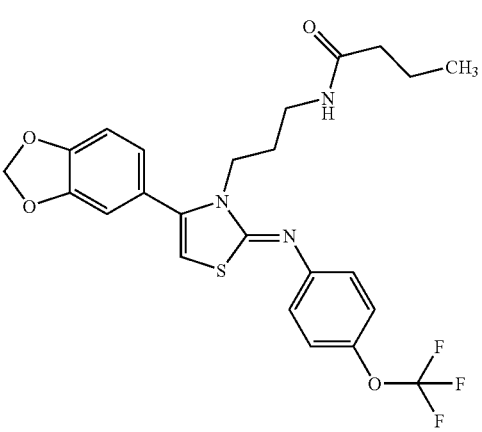 | 507 | 508 | A | 3.83 | 168 |

TABLE 17-continued
| Ex. No. | Structure | Exact MS | m/z | Method for analysis | Retention time (min) | Ref. Ex. |
|---|---|---|---|---|---|---|
| 229 | 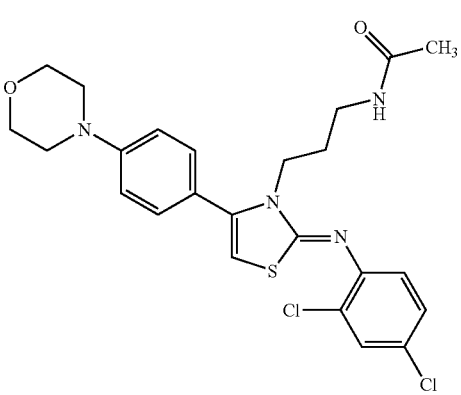 | 504 | 505 | A | 3.91 | 153 |
| 230 | 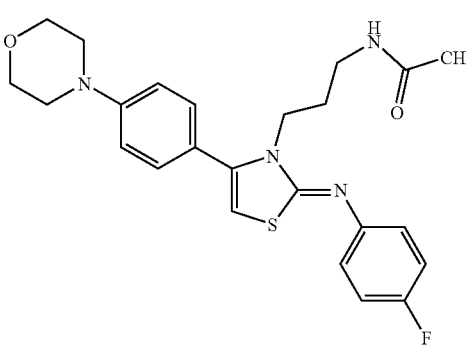 | 454 | 455 | A | 3.18 | 222 |
| 231 | 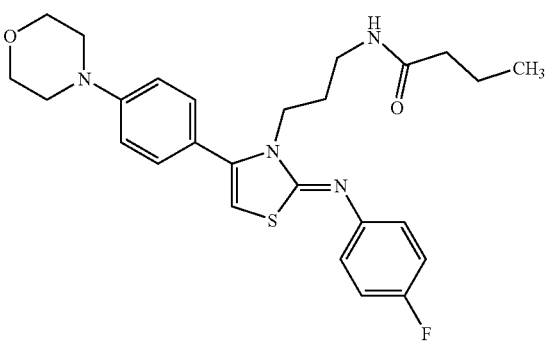 | 482 | 483 | A | 3.52 | 222 |
| 232 | 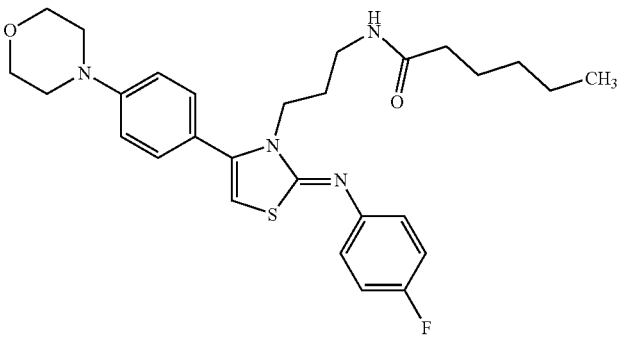 | 510 | 511 | A | 3.75 | 222 |

TABLE 17-continued
| Ex. No. | Structure | Exact MS | m/z | Method for analysis | Retention time (min) | Ref. Ex. |
|---|---|---|---|---|---|---|
| 233 | 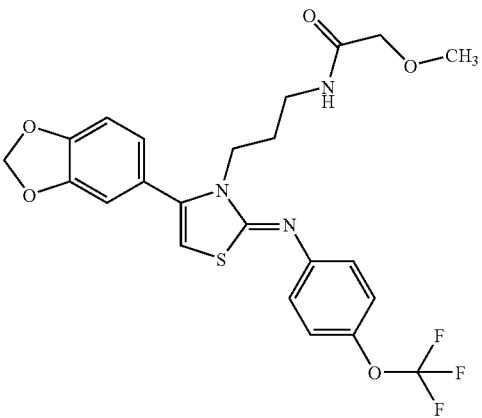 | 509 | 510 | A | 3.70 | 168 |
| 234 | 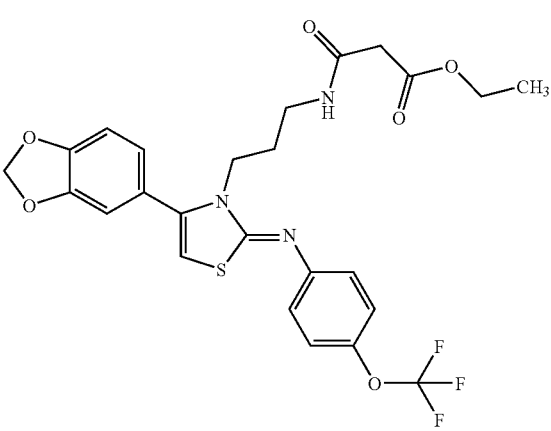 | 551 | 552 | A | 3.82 | 168 |
| 235 | 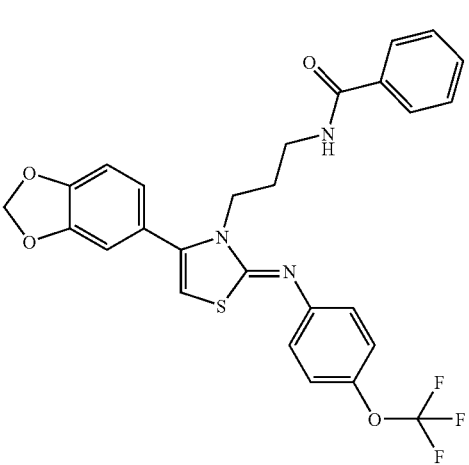 | 541 | 542 | A | 3.95 | 168 |

TABLE 17-continued

| Ex. No. | Structure | Exact MS | m/z | Method for analysis | Retention time (min) | Ref. Ex. |
|---|---|---|---|---|---|---|
| 236 | 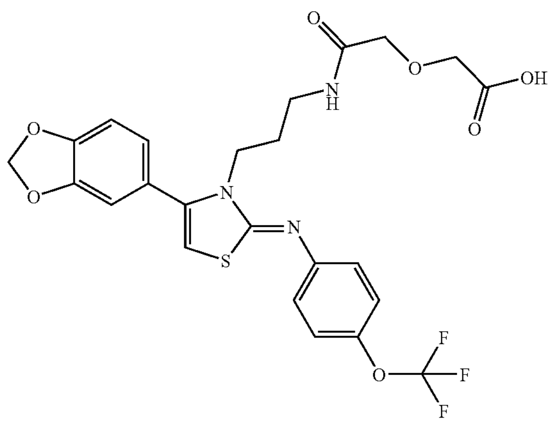 | 553 | 554 | A | 3.54 | 153 |
| 237 | 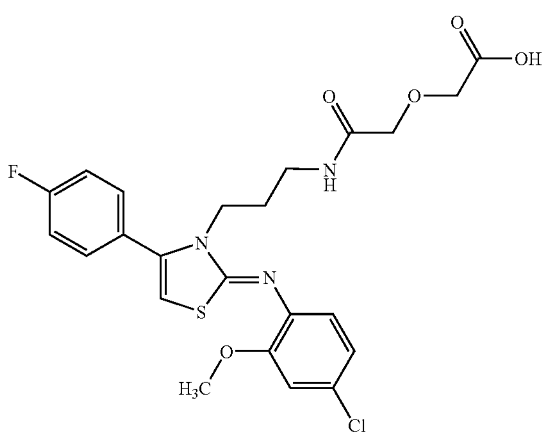 | 507 | 508 | A | 3.34 | 153 |
| 238 | 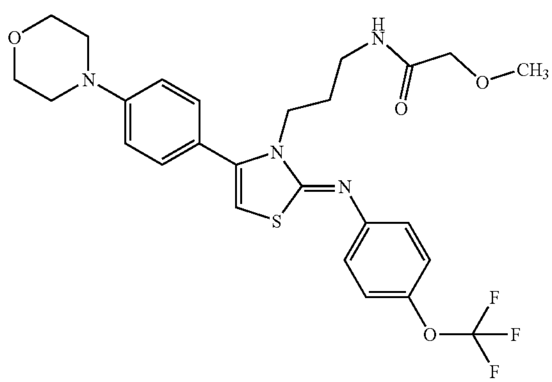 | 550 | 551 | A | 3.67 | 168 |

TABLE 17-continued

| Ex. No. | Structure | Exact MS | m/z | Method for analysis | Retention time (min) | Ref. Ex. |
|---|---|---|---|---|---|---|
| 239 | 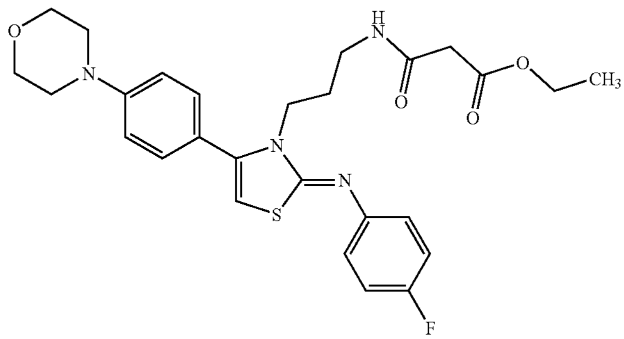 | 526 | 527 | A | 3.41 | 220 |
| 240 | 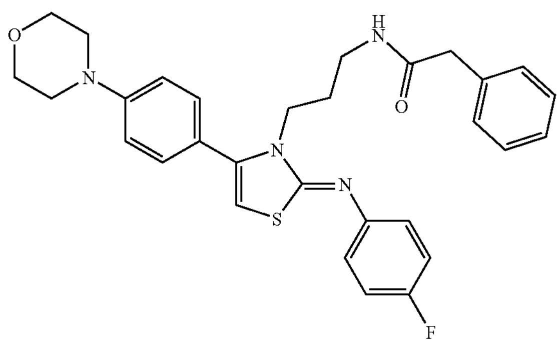 | 530 | 531 | A | 3.66 | 220 |
| 241 | 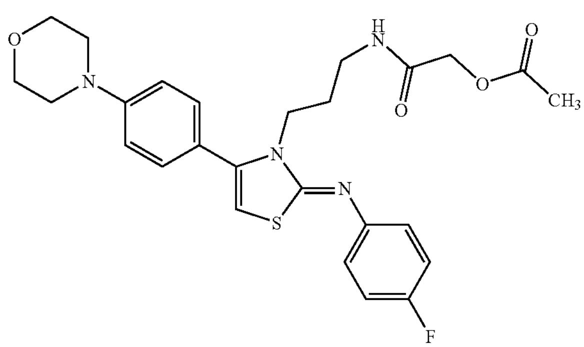 | 512 | 513 | A | 3.30 | 220 |
| 242 | 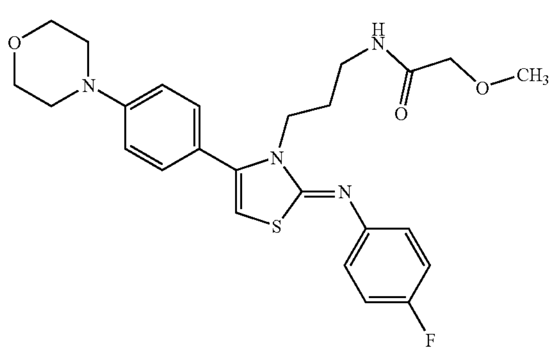 | 484 | 485 | A | 3.27 | 222 |

TABLE 17-continued
| Ex. No. | Structure | Exact MS | m/z | Method for analysis | Retention time (min) | Ref. Ex. |
|---|---|---|---|---|---|---|
| 243 | 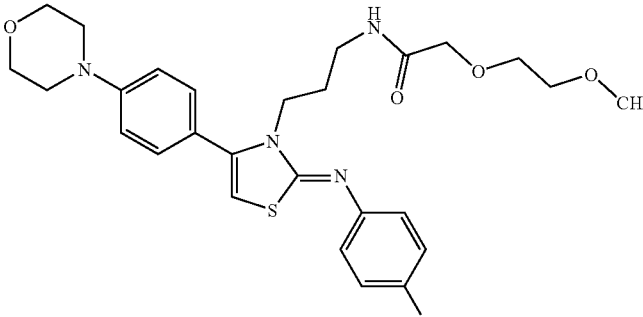 | 528 | 529 | A | 3.30 | 222 |
| 244 | 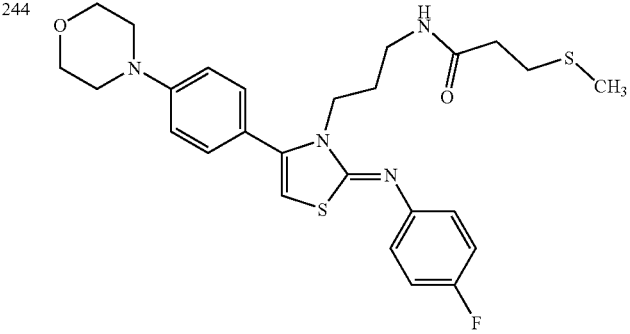 | 514 | 515 | A | 3.51 | 222 |
| 245 | 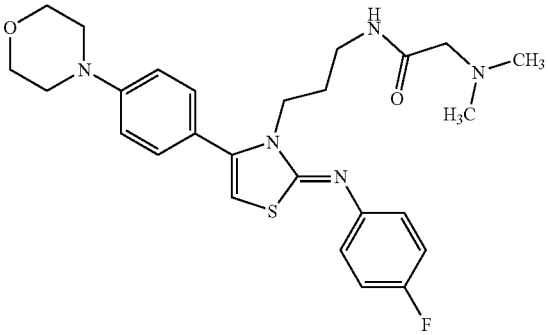 | 497 | 498 | A | 2.95 | 222 |
| 246 | 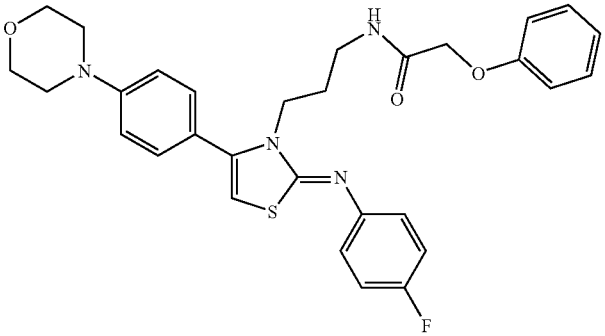 | 546 | 547 | A | 3.68 | 222 |

TABLE 17-continued

| Ex. No. | Structure | Exact MS | m/z | Method for analysis | Retention time (min) | Ref. Ex. |
|---|---|---|---|---|---|---|
| 247 | 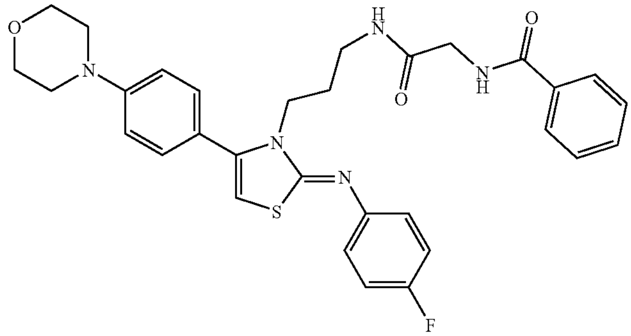 | 573 | 574 | A | 3.46 | 222 |
| 248 | 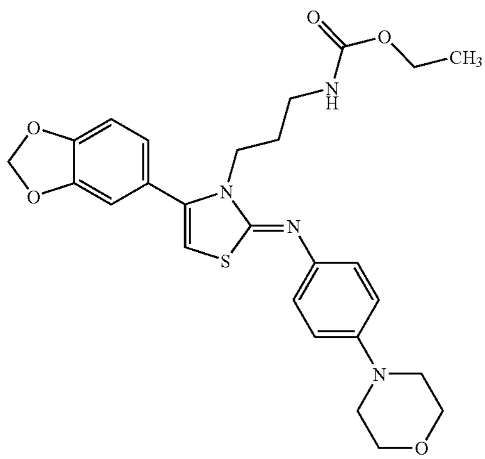 | 510 | 511 | A | 3.40 | 175 |
| 249 | 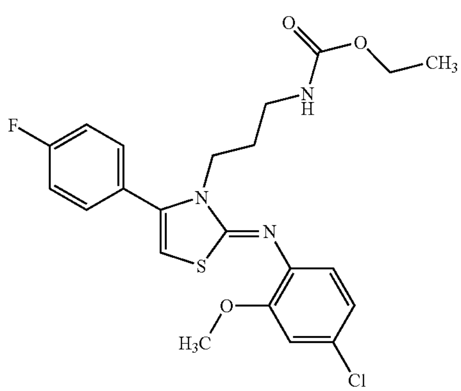 | 463 | 464 | A | 3.75 | 175 |
| 250 | 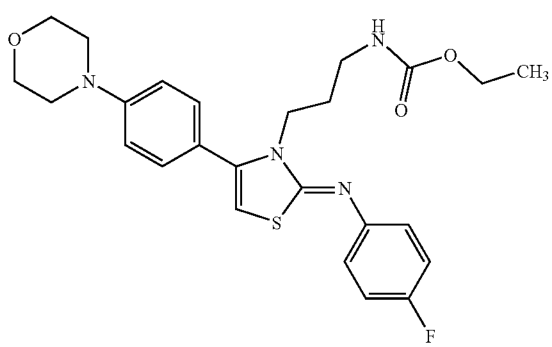 | 484 | 485 | A | 3.52 | 220 |

TABLE 17-continued
| Ex. No. | Structure | Exact MS | m/z | Method for analysis | Retention time (min) | Ref. Ex. |
|---|---|---|---|---|---|---|
| 251 | 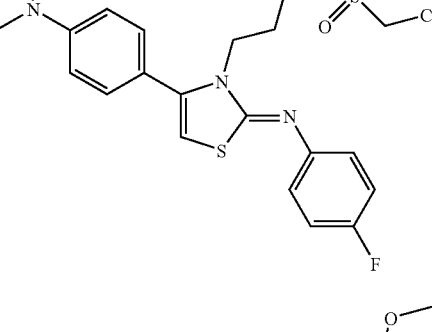 | 504 | 505 | A | 3.38 | 220 |
| 252 | 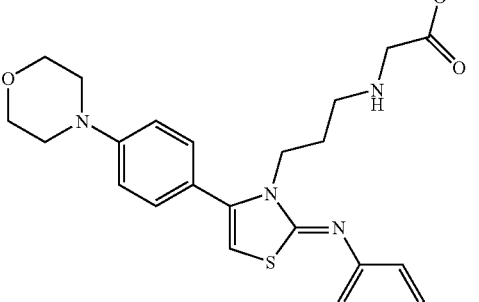 | 498 | 499 | A | 3.14 | 215 |
| 253 | 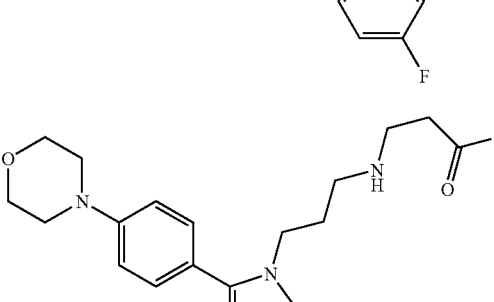 | 512 | 513 | A | 3.16 | 216 |
| 254 | 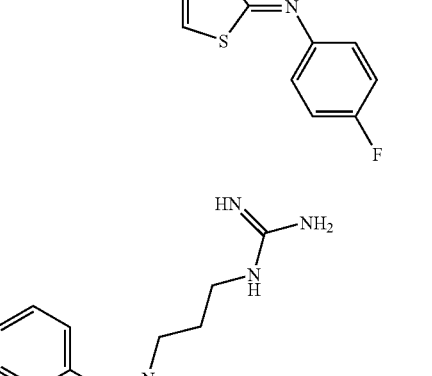 | 433 | 434 | A | 3.10 | 217 |

TABLE 17-continued

| Ex. No. | Structure | Exact MS | m/z | Method for analysis | Retention time (min) | Ref. Ex. |
|---|---|---|---|---|---|---|
| 255 | 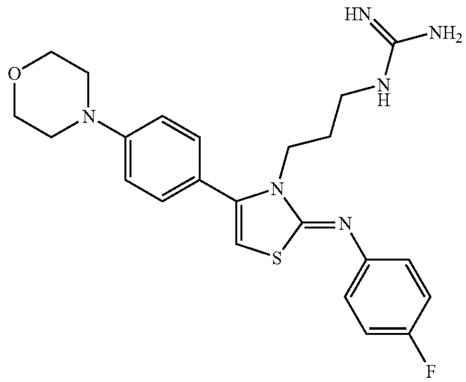 | 454 | 455 | A | 2.90 | 217 |
| 256 | 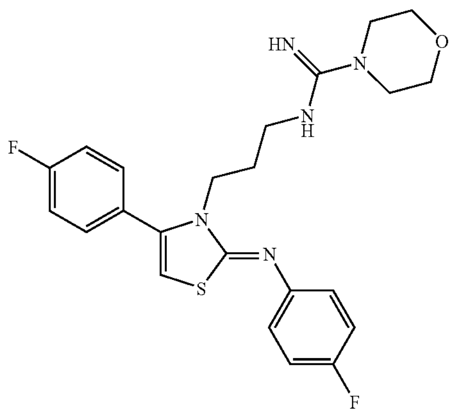 | 457 | 458 | A | 2.94 | 218 |
| 257 | 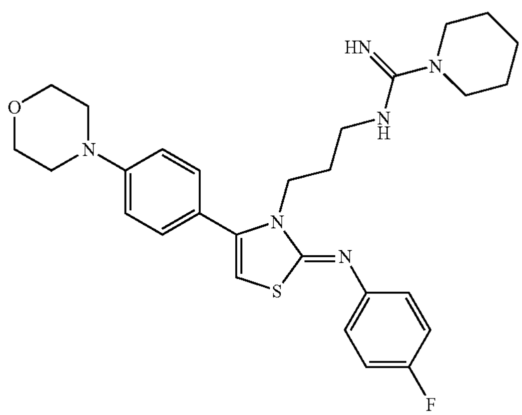 | 522 | 523 | A | 3.13 | 218 |
| 258 | 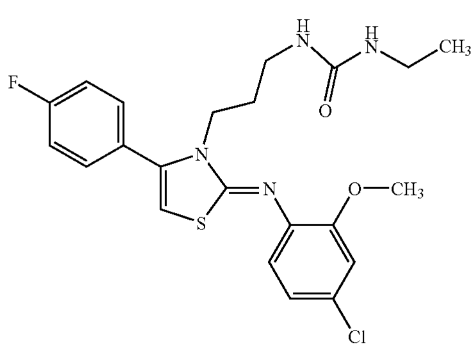 | 462 | 463 | A | 3.49 | 177 |

TABLE 17-continued

| Ex. No. | Structure | Exact MS | m/z | Method for analysis | Retention time (min) | Ref. Ex. |
|---|---|---|---|---|---|---|
| 259 | 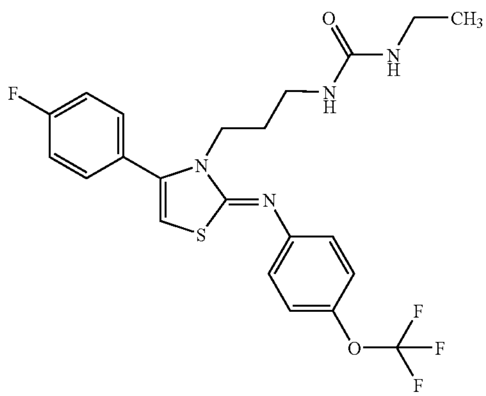 | 482 | 483 | A | 3.69 | 177 |
| 260 | 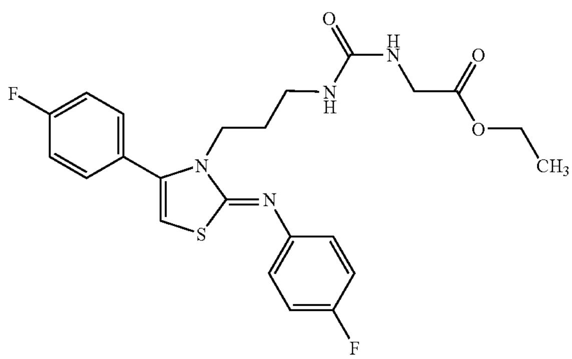 | 474 | 475 | A | 3.39 | 177 |
| 261 | 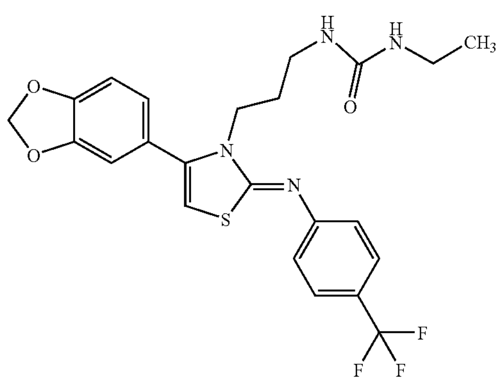 | 492 | 493 | A | 3.74 | 177 |
| 262 | 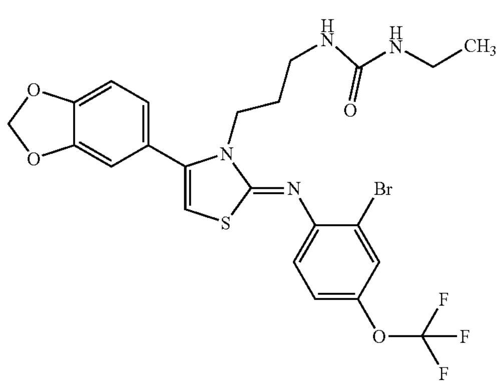 | 586 | 587 | B | 2.81 | 177 |

TABLE 17-continued

| Ex. No. | Structure | Exact MS | m/z | Method for analysis | Retention time (min) | Ref. Ex. |
|---|---|---|---|---|---|---|
| 263 | 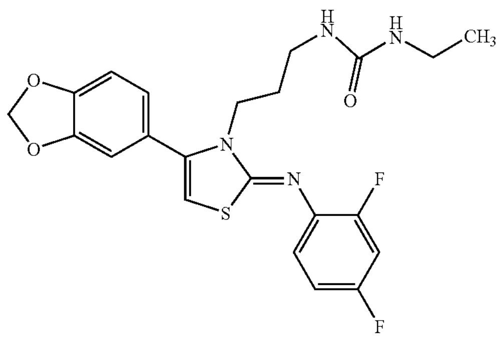 | 460 | 461 | A | 3.42 | 177 |
| 264 | 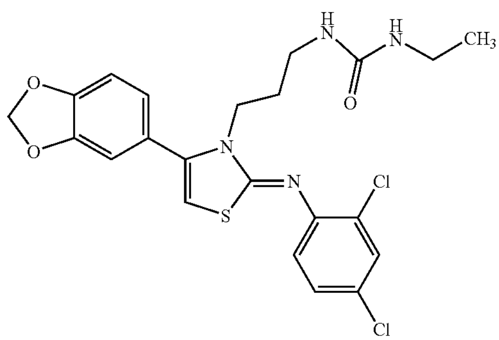 | 492 | 493 | A | 4.02 | 177 |
| 265 | 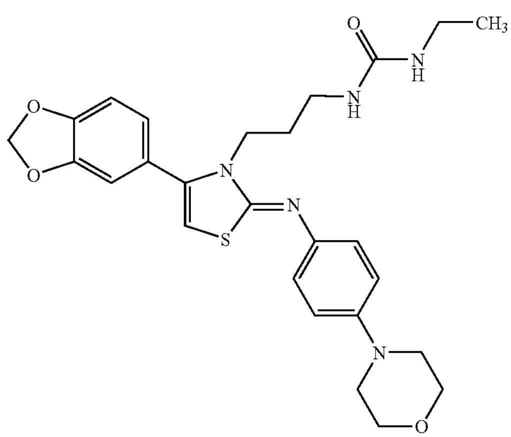 | 509 | 510 | A | 3.21 | 177 |
| 266 | 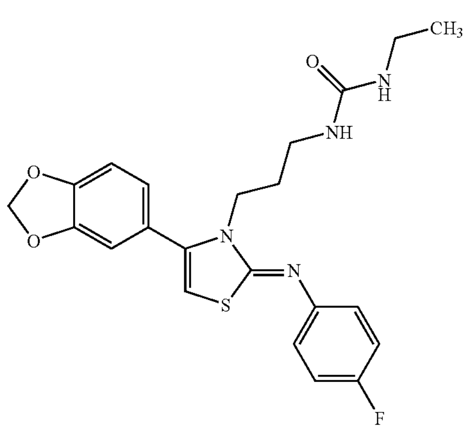 | 442 | 443 | A | 3.26 | 177 |

TABLE 17-continued

| Ex. No. | Structure | Exact MS | m/z | Method for analysis | Retention time (min) | Ref. Ex. |
|---|---|---|---|---|---|---|
| 267 | 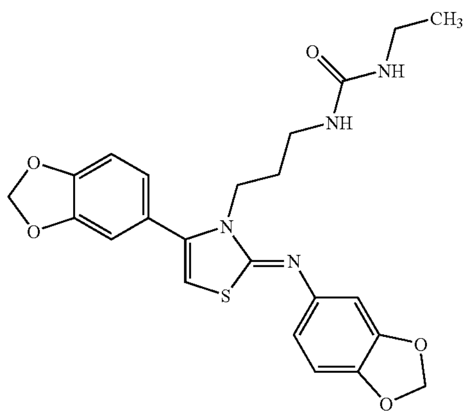 | 468 | 469 | A | 3.24 | 177 |
| 268 | 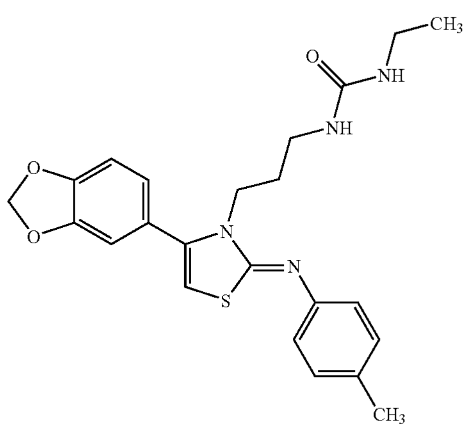 | 438 | 439 | A | 3.39 | 177 |
| 269 | 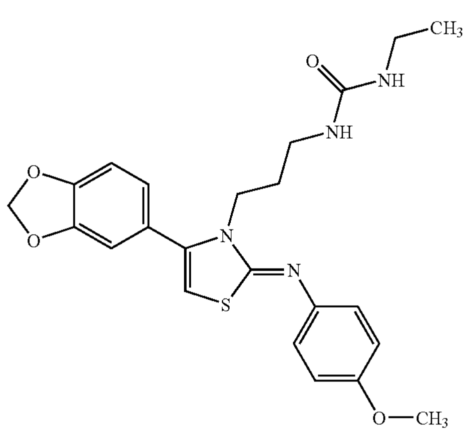 | 454 | 455 | A | 3.27 | 177 |

TABLE 17-continued

| Ex. No. | Structure | Exact MS | m/z | Method for analysis | Retention time (min) | Ref. Ex. |
|---|---|---|---|---|---|---|
| 270 | 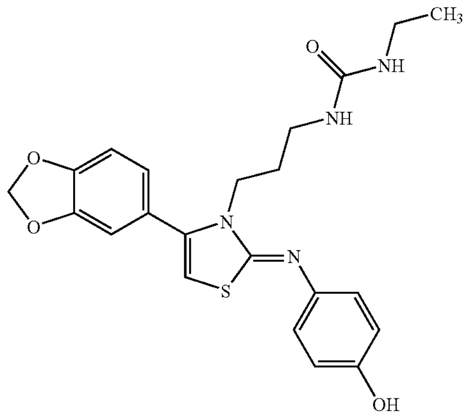 | 440 | 441 | A | 3.00 | 177 |
| 271 | 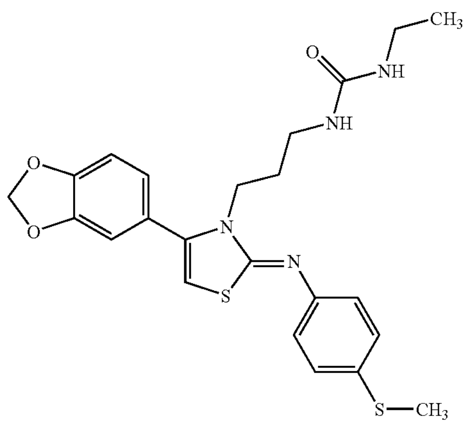 | 470 | 471 | A | 3.46 | 177 |
| 272 | 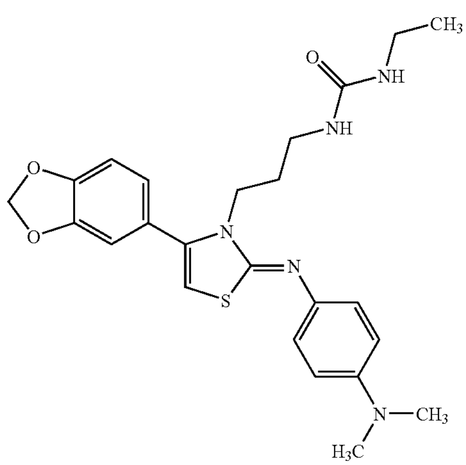 | 467 | 468 | A | 3.04 | 177 |

TABLE 17-continued
| Ex. No. | Structure | Exact MS | m/z | Method for analysis | Retention time (min) | Ref. Ex. |
|---|---|---|---|---|---|---|
| 273 | 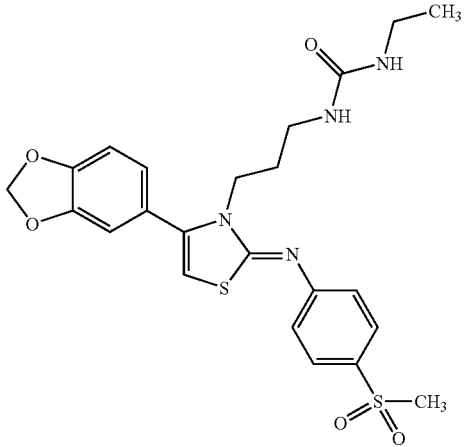 | 502 | 503 | A | 3.14 | 177 |
| 274 | 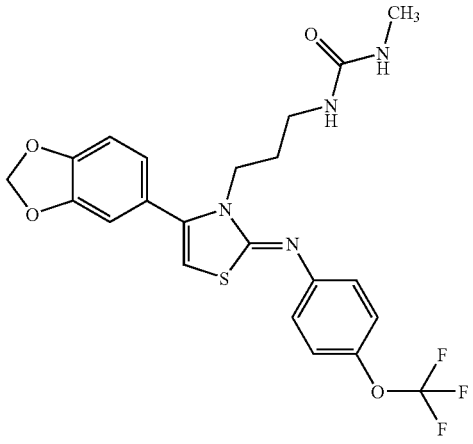 | 494 | 495 | A | 3.56 | 177 |
| 275 | 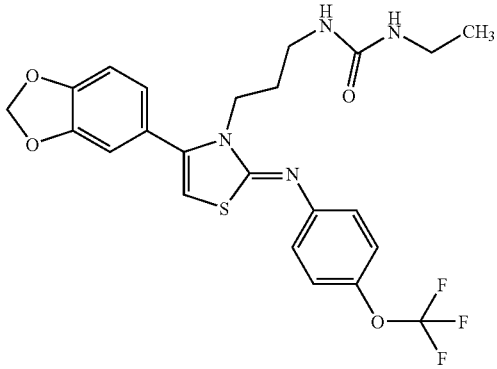 | 508 | 509 | A | 3.69 | 177 |

TABLE 17-continued

| Ex. No. | Structure | Exact MS | m/z | Method for analysis | Retention time (min) | Ref. Ex. |
|---|---|---|---|---|---|---|
| 276 | 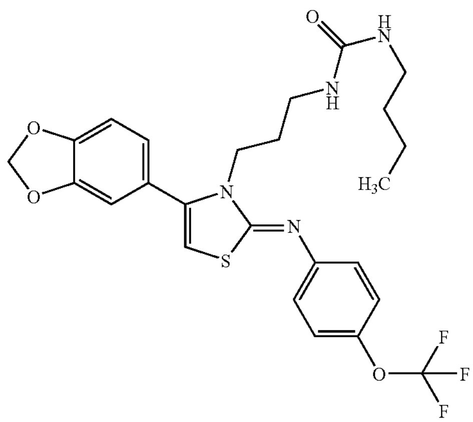 | 536 | 537 | A | 3.96 | 177 |
| 277 | 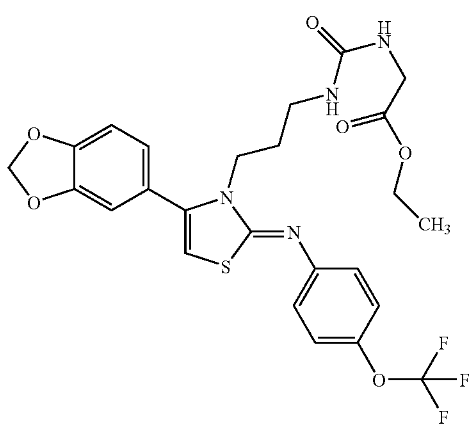 | 566 | 567 | A | 3.76 | 177 |
| 278 | 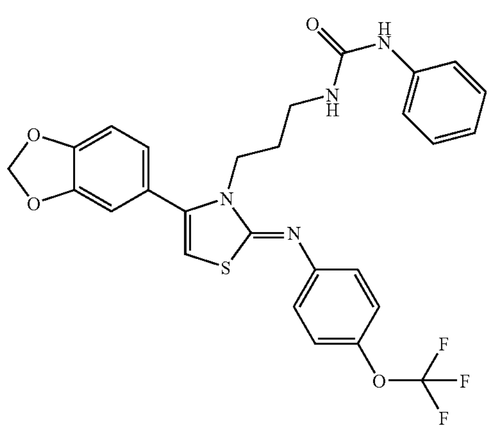 | 556 | 557 | A | 3.98 | 177 |

TABLE 17-continued
| Ex. No. | Structure | Exact MS | m/z | Method for analysis | Retention time (min) | Ref. Ex. |
|---|---|---|---|---|---|---|
| 279 | 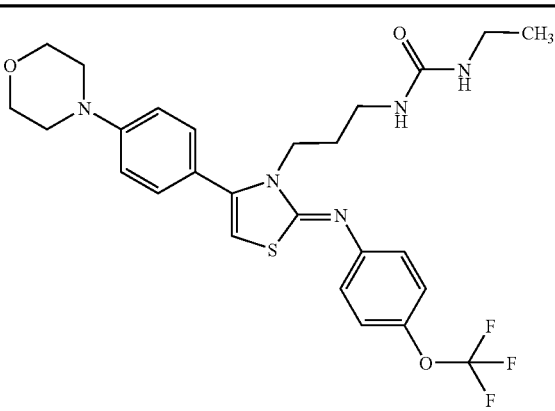 | 549 | 550 | A | 3.69 | 177 |
| 280 | 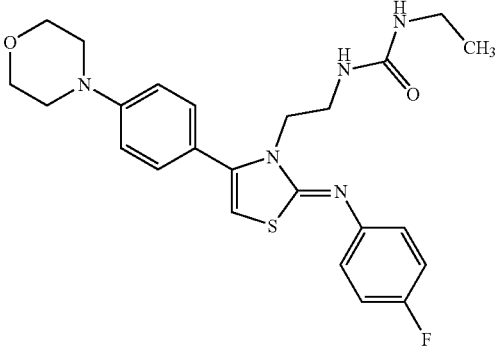 | 469 | 470 | A | 3.33 | 177 |
| 281 | 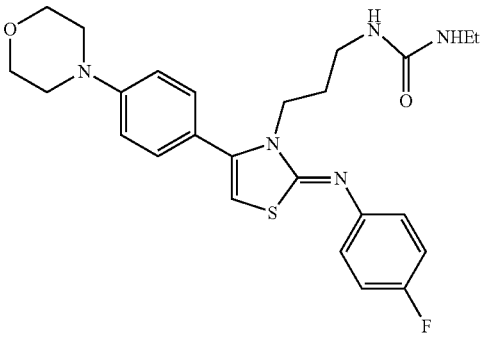 | 483 | 484 | A | 3.29 | 177 |
| 282 | 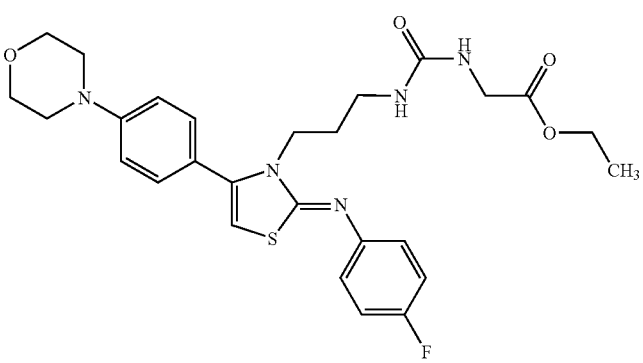 | 541 | 542 | A | 3.40 | 177 |

TABLE 17-continued

| Ex. No. | Structure | Exact MS | m/z | Method for analysis | Retention time (min) | Ref. Ex. |
|---|---|---|---|---|---|---|
| 283 | 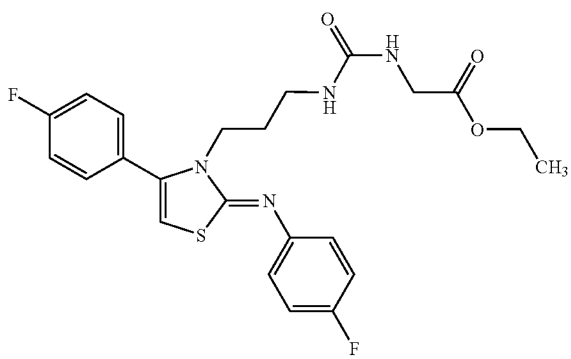 | 474 | 475 | A | 3.39 | 177 |
| 284 | 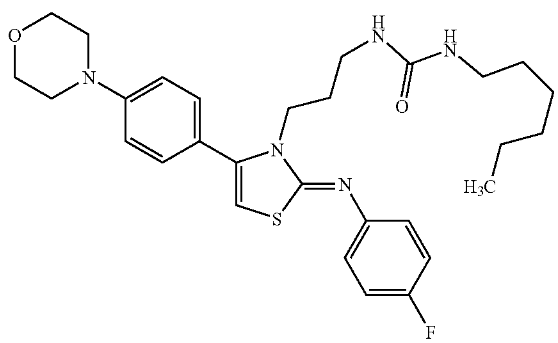 | 539 | 540 | A | 3.98 | 221 |
| 285 | 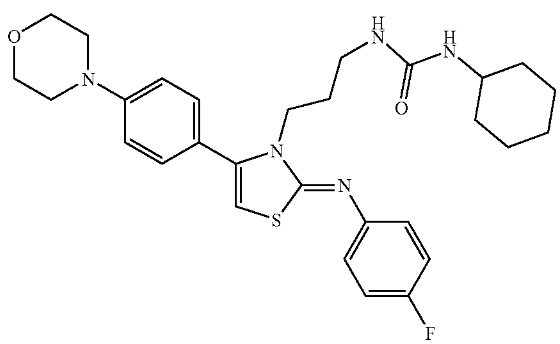 | 537 | 538 | A | 3.79 | 221 |
| 286 | 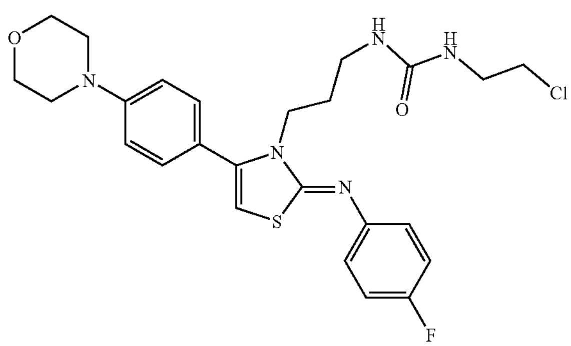 | 517 | 518 | A | 3.47 | 221 |

TABLE 17-continued

| Ex. No. | Structure | Exact MS | m/z | Method for analysis | Retention time (min) | Ref. Ex. |
|---|---|---|---|---|---|---|
| 287 | 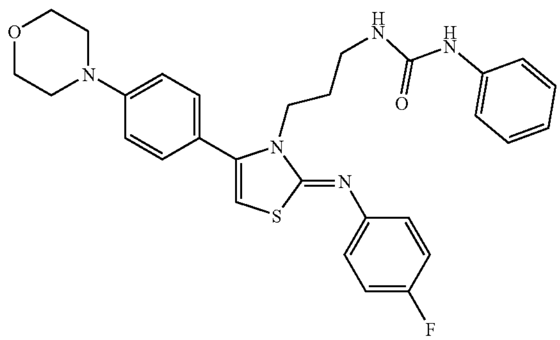 | 531 | 532 | A | 3.68 | 221 |
| 288 | 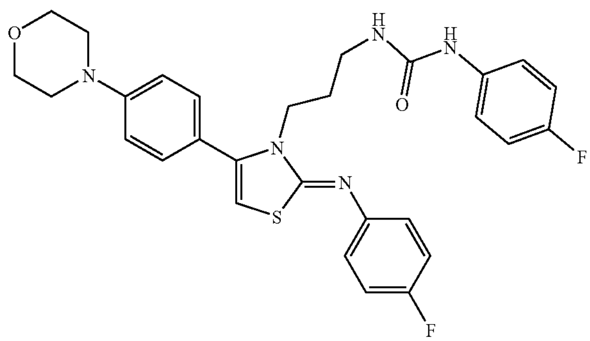 | 549 | 550 | A | 3.73 | 221 |
| 289 | 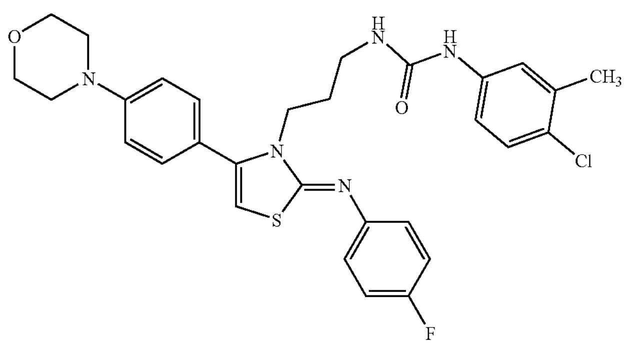 | 579 | 580 | A | 3.99 | 221 |
| 290 | 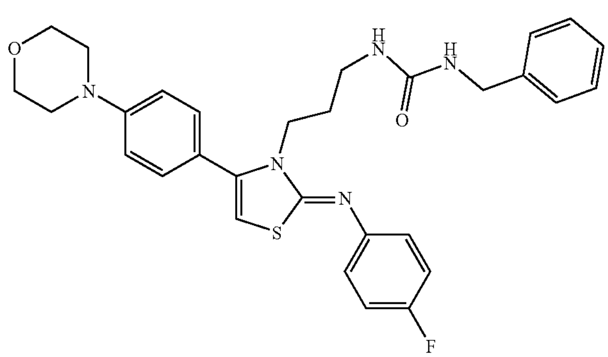 | 545 | 546 | A | 3.70 | 221 |

TABLE 17-continued

| Ex. No. | Structure | Exact MS | m/z | Method for analysis | Retention time (min) | Ref. Ex. |
|---|---|---|---|---|---|---|
| 291 | 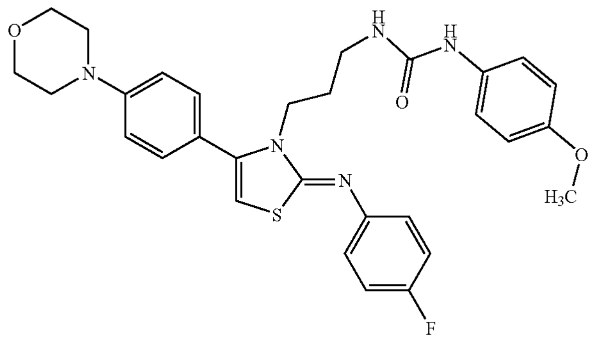 | 561 | 562 | A | 3.60 | 221 |
| 292 | 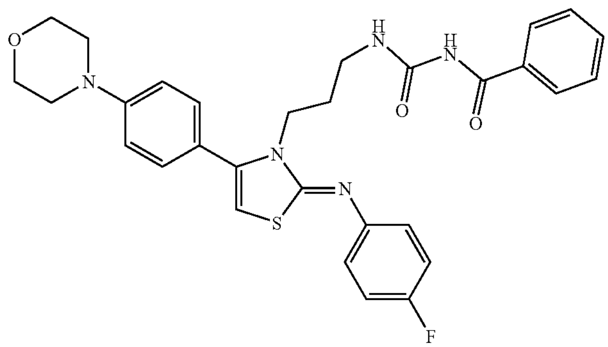 | 559 | 560 | A | 3.62 | 221 |
| 293 | 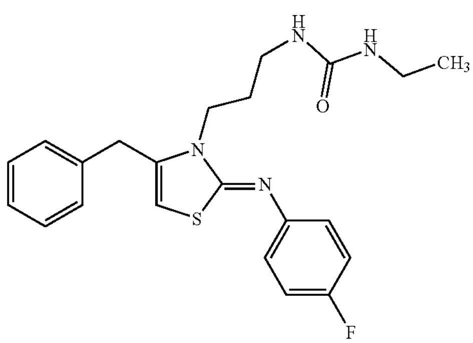 | 412 | 413 | A | 3.40 | 221 |
| 294 | 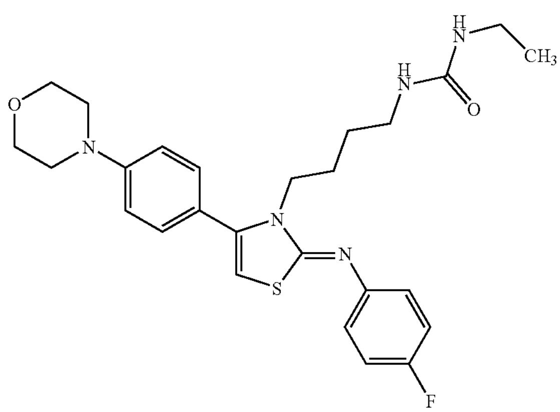 | 497 | 498 | A | 3.42 | 221 |

TABLE 17-continued

| Ex. No. | Structure | Exact MS | m/z | Method for analysis | Retention time (min) | Ref. Ex. |
|---|---|---|---|---|---|---|
| 295 | 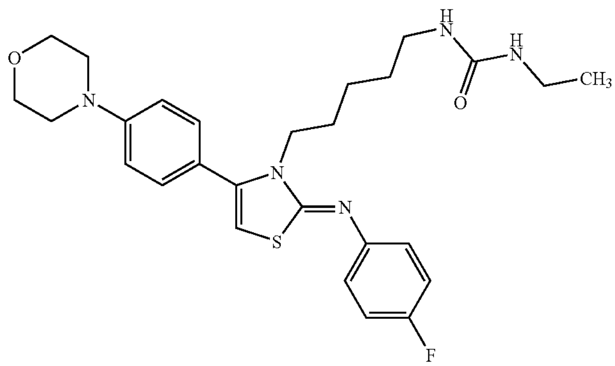 | 511 | 512 | A | 3.38 | 221 |
| 296 | 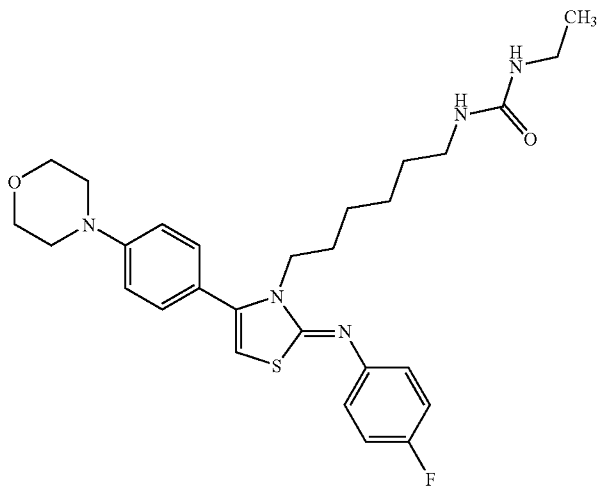 | 525 | 526 | A | 3.45 | 221 |
| 297 | 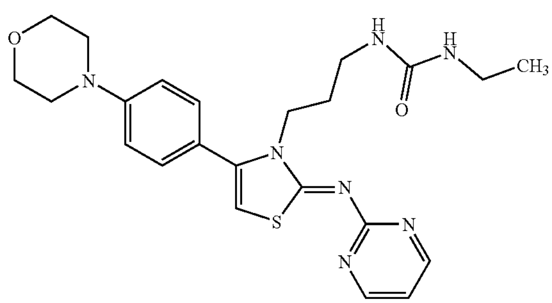 | 467 | 468 | A | 3.13 | 221 |
| 298 | 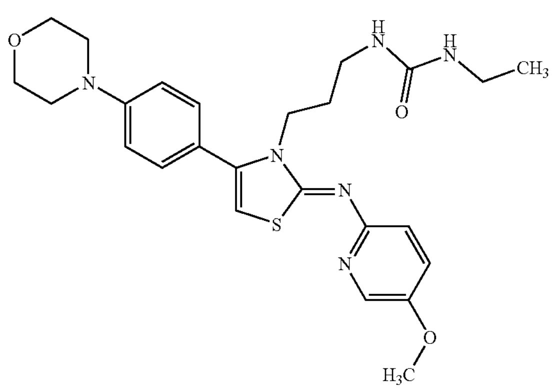 | 496 | 497 | A | 3.40 | 221 |

TABLE 17-continued

| Ex. No. | Structure | Exact MS | m/z | Method for analysis | Retention time (min) | Ref. Ex. |
|---|---|---|---|---|---|---|
| 299 | 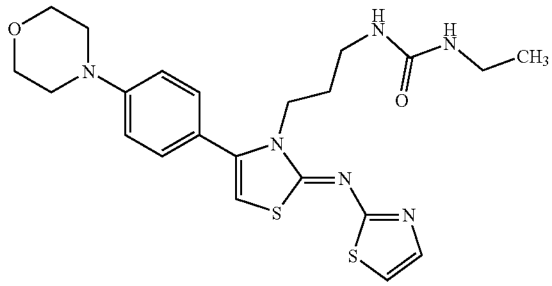 | 472 | 473 | A | 3.08 | 221 |
| 300 | 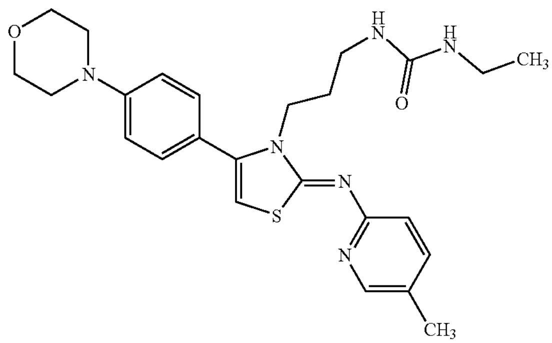 | 480 | 481 | A | 3.37 | 221 |
| 301 | 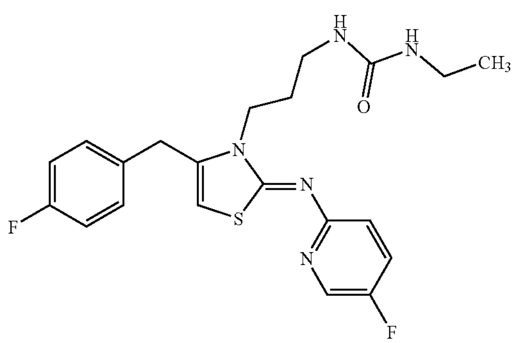 | 430 | 431 | A | 3.43 | 221 |
| 302 | 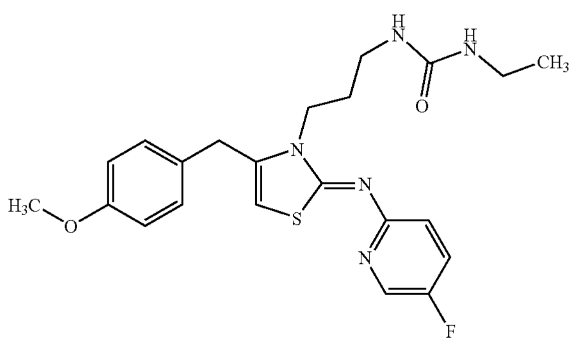 | 442 | 443 | A | 3.43 | 221 |

TABLE 17-continued

| Ex. No. | Structure | Exact MS | m/z | Method for analysis | Retention time (min) | Ref. Ex. |
|---|---|---|---|---|---|---|
| 303 | 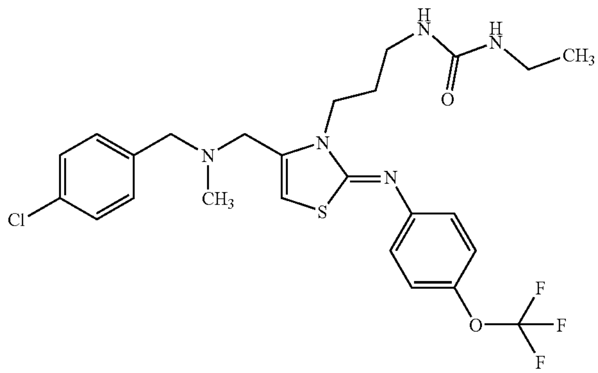 | 555 | 556 | A | 3.80 | 221 |
| 304 | 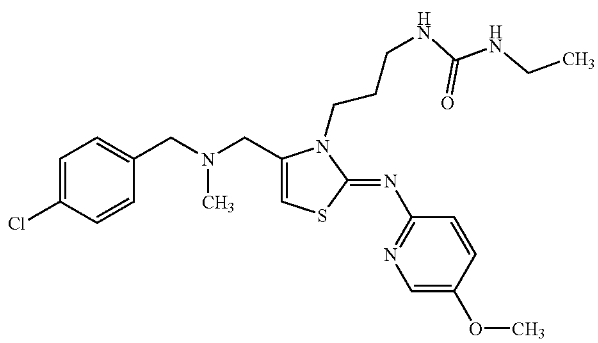 | 502 | 503 | A | 3.25 | 221 |
| 305 | 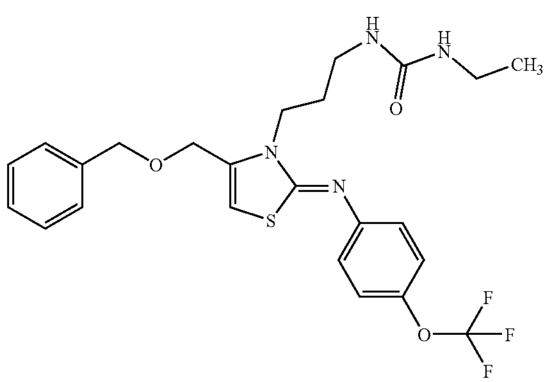 | 508 | 509 | A | 3.85 | 221 |
| 306 | 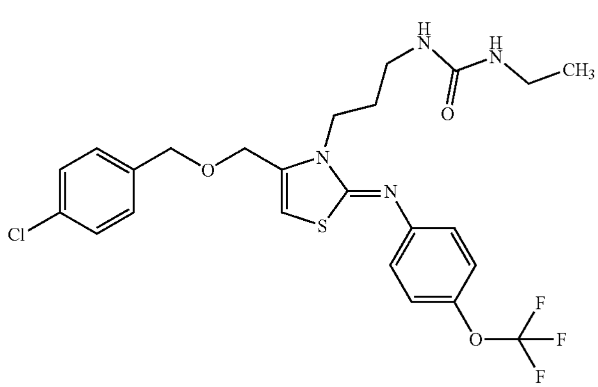 | 542 | 543 | A | 3.99 | 221 |

TABLE 17-continued

| Ex. No. | Structure | Exact MS | m/z | Method for analysis | Retention time (min) | Ref. Ex. |
|---|---|---|---|---|---|---|
| 307 | 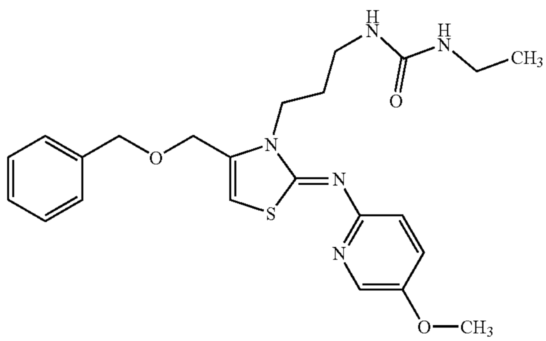 | 455 | 456 | A | 3.54 | 221 |
| 308 | 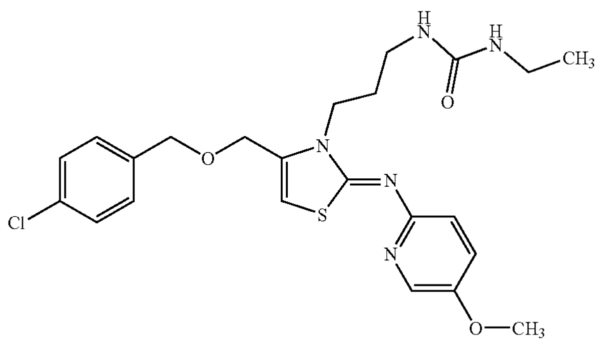 | 489 | 490 | A | 3.74 | 221 |
| 309 | 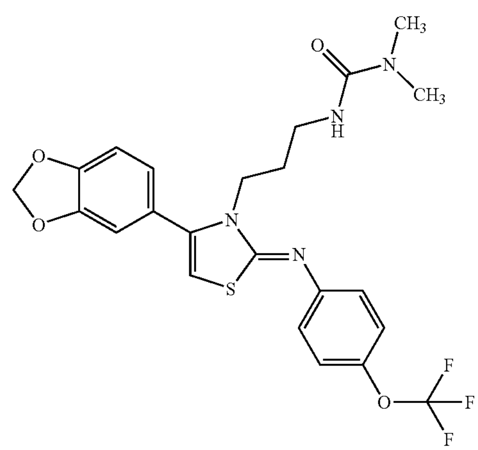 | 508 | 509 | A | 3.64 | 175 |
| 310 | 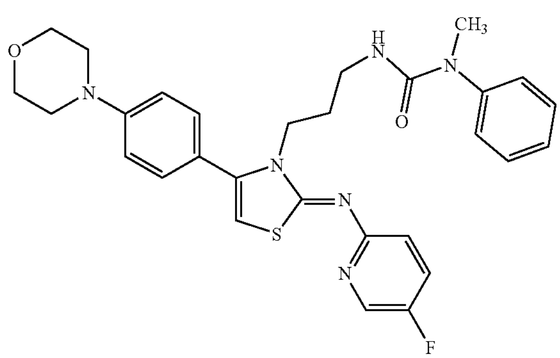 | 545 | 546 | A | 3.58 | 220 |

TABLE 17-continued
| Ex. No. | Structure | Exact MS | m/z | Method for analysis | Retention time (min) | Ref. Ex. |
|---|---|---|---|---|---|---|
| 311 | 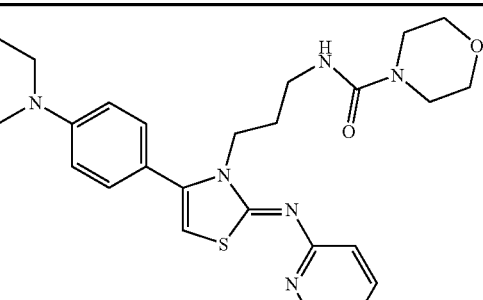 | 525 | 526 | A | 3.27 | 220 |
| 312 | 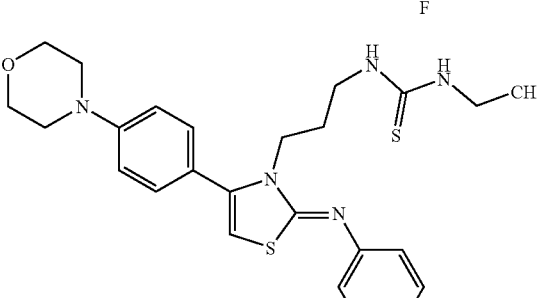 | 499 | 500 | A | 3.46 | 221 |
Examples 313 to 319
The corresponding amino compounds being protected with a Boc were treated in a similar manner to in Example 150 to give the compounds as listed in Table 18.
TABLE 18
| Ex No. | Structure | Exact MS | m/z | Method for analysis | Retention Time (min) |
|---|---|---|---|---|---|
| 313 | 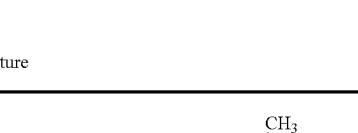 | 405 | 406 | A | 3.24 |

TABLE 18-continued

| Ex No. | Structure | Exact MS | m/z | Method for analysis | Retention Time (min) |
|---|---|---|---|---|---|
| 314 | 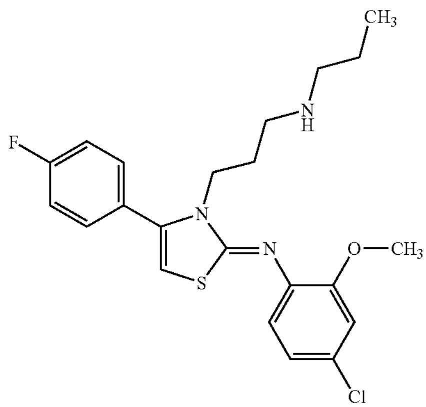 | 433 | 434 | A | 3.49 |
| 315 | 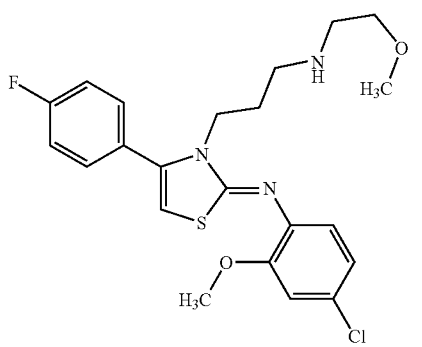 | 449 | 450 | A | 3.41 |
| 316 | 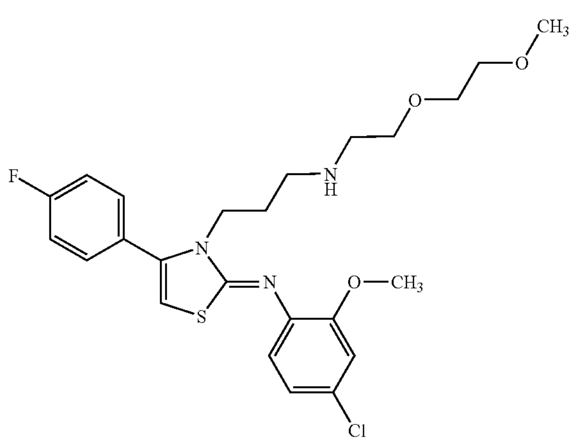 | 493 | 494 | A | 3.42 |

TABLE 18-continued

| Ex No. | Structure | Exact MS | m/z | Method for analysis | Retention Time (min) |
|---|---|---|---|---|---|
| 317 | 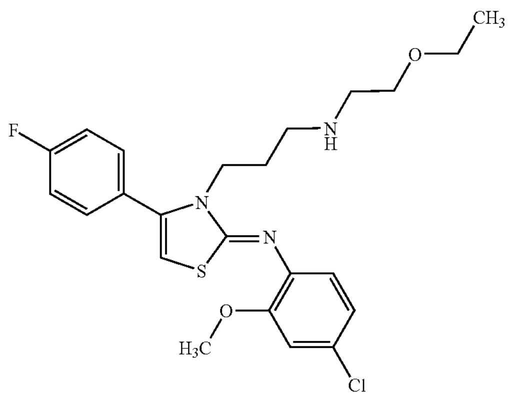 | 463 | 464 | A | 3.55 |
| 318 | 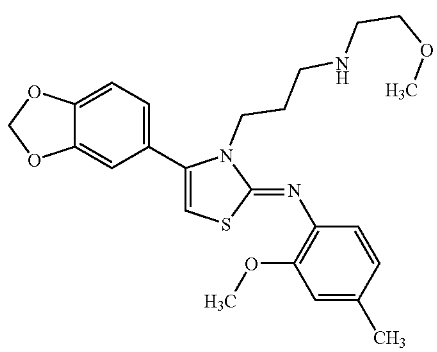 | 455 | 456 | A | 3.07 |
| 319 | 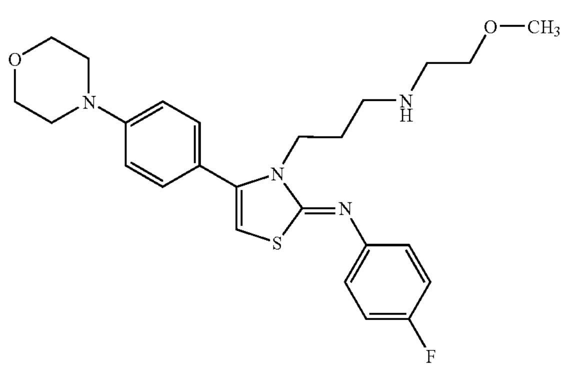 | 470 | 471 | A | 3.02 |

Example 320

4-Chloro-N-[4-(4-fluorophenyl)-3-{3-[(2,2,2-trifluoroethyl)amino]propyl}-thiazol-2(3H)-ylidene]-2-methoxyaniline

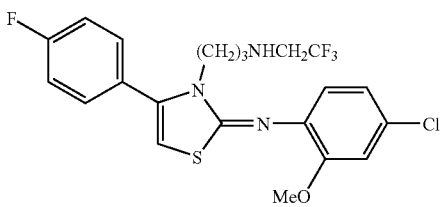

To a mixture of the compound (1.0 g, free amino compound) obtained in Example 106, triethylamine (0.72 ml) and tetrahydrofuran (5 ml) was added 2,2,2-trifluoroethyl trifluoromethanesulfonate (592 mg), and the mixture was refluxed under nitrogen atmosphere for 2 hours. To the reaction mixture was added water, and the mixture was extracted with ethyl acetate. The organic layer was washed with a saturated brine, dried over sodium sulfate, and the solvent was evaporated under reduced pressure. The residue was purified by silica gel column chromatography [n-hexane:ethyl acetate (85:15)] to give the title compound (800 mg) as oil.

$^1$H-NMR (CDCl$_3$): δ 1.72 (2H, m), 2.64 (2H, t, J=6.6), 3.04 (2H, q, J=9.5), 3.82 (3H, s), 3.95 (2H, t, J=6.8), 5.77 (1H, s), 6.90-6.98 (3H, m), 7.15 (2H, dd, J=8.8, J=8.6), 7.36 (2H, dd, J=5.3, J=8.8). LC/MS: m/z=474 (MH$^+$), retention time: 3.68 min (Condition A)

Example 321

2-({3-[2-[(4-Chloro-2-methoxyphenyl)imino]-4-(4-fluorophenyl)thiazol-3(2H)-yl]propyl}amino)ethanol (1) Ethyl N-(tert-butoxycarbonyl)-N-{3-[2-[(4-chloro-2-methoxyphenyl)-imino]-4-(4-fluorophenyl)thiazol-3(2H)-yl]propyl}glycinate

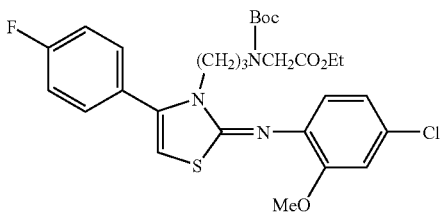

To a solution of the compound (24.6 g) obtained in Example 215 in tetrahydrofuran (150 ml) was added di-t-butyl dicarbonate (11.26 g), and the mixture was stirred at room temperature for 2 hours. The reaction mixture was concentrated under reduced pressure to give the title compound (27.7 g) as oil.

(2) tert-Butyl 3-[2-[(4-chloro-2-methoxyphenyl)imino]-4-(4-fluoro-phenyl)thiazol-3(2H)-yl]propyl (2-hydroxyethyl)carbamate

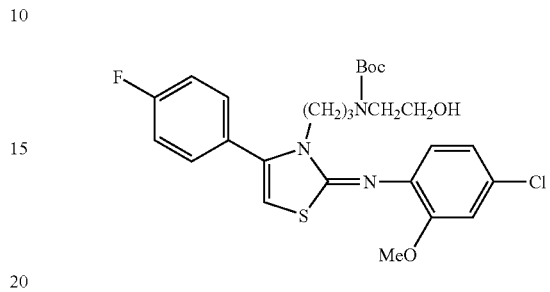

To a solution of the compound (3 g) obtained in the above (1) in tetrahydrofuran (20 ml) was added lithium borohydride (170 mg), and the mixture was stirred at room temperature overnight. To the reaction mixture was added water, and the mixture was extracted with ethyl acetate. The organic layer was washed with a saturated brine, dried over sodium sulfate, and the solvent was evaporated under reduced pressure. The residue was purified by silica gel column chromatography [n-hexane:ethyl acetate (1:1)] to give the title compound (2.14 g) as amorphous.

(3) 2-({3-[2-[(4-Chloro-2-methoxyphenyl)imino]-4-(4-fluorophenyl)-thiazol-3(2H)-yl]propyl}amino)ethanol

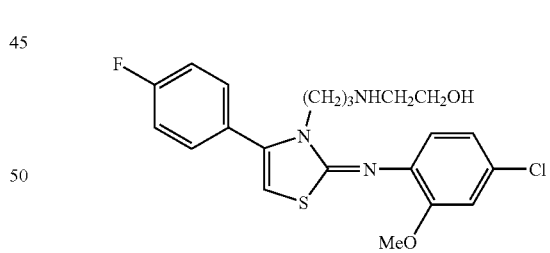

The compound (850 mg) obtained in the above (2) was treated in a similar manner to in Example 9 (2) to give the title compound (758 mg) as hydrochloride.

$^1$H-NMR (DMSO-d$_6$): δ 2.02 (2H, m), 2.89 (4H, m), 3.63 (2H, t, J=5.3), 3.89 (3H, s), 4.20 (2H, m), 6.93 (1H, s), 7.16 (1H, dd, J=2.2, J=8.4), 7.35-7.44 (4H, m), 7.67 (2H, dd, J=8.6, J=5.3), 9.10 (2H, brs). LC/MS: m/z=436 (MH$^+$), retention time: 3.18 min (Condition A)

Example 322

3-({3-[2-[(4-Chloro-2-methoxyphenyl)imino]-4-(4-fluorophenyl)thiazol-3(2H)-yl]propyl}amino)-1-propanol (1) Ethyl N-(tert-butoxycarbonyl)-N-{3-[2-[(4-chloro-2-methoxyphenyl)-imino]-4-(4-fluorophenyl)thiazol-3(2H)-yl]propyl}-β-alaninate

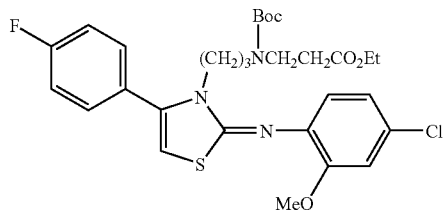

The amino compound (1.87 g) obtained in Example 216 was treated in a similar manner to in Example 321 (1) to give the title compound (2.16 g) as oil.

(2) 3-({3-[2-[(4-Chloro-2-methoxyphenyl)imino]-4-(4-fluorophenyl)-thiazol-3(2H)-yl]propyl}amino)-1-propanol

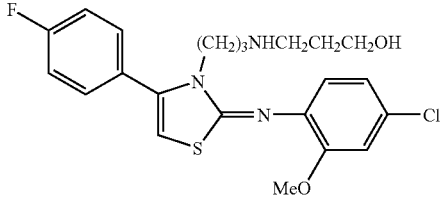

The compound (1.3 g) obtained in the above (1) was treated in a similar manner to in Example 321 (2), (3) to give the title compound (889 mg) as hydrochloride.

LC/MS: m/z=450 (MH$^+$), retention time: 3.21 min (Condition A)

Examples 323 to 326

The corresponding ester compounds were treated in a similar manner to in Example 321 (2) to give the compounds as listed in Table 19.

TABLE 19

| Ex No. | Structure | Exact MS | m/z | Method for analysis | Retention Time (min) |
|---|---|---|---|---|---|
| 323 | 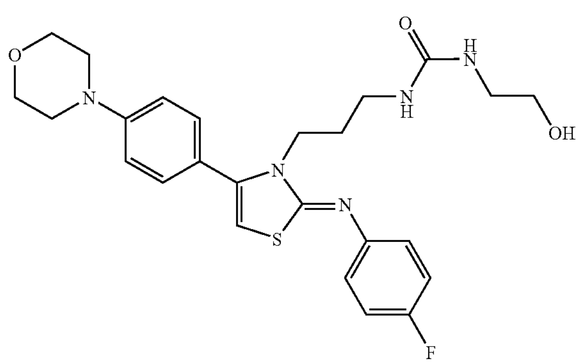 | 499 | 500 | A | 3.10 |
| 324 | 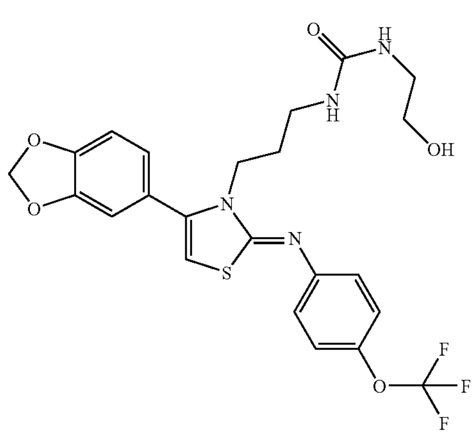 | 524 | 525 | A | 3.45 |

TABLE 19-continued

| Ex No. | Structure | Exact MS | m/z | Method for analysis | Retention Time (min) |
|---|---|---|---|---|---|
| 325 | 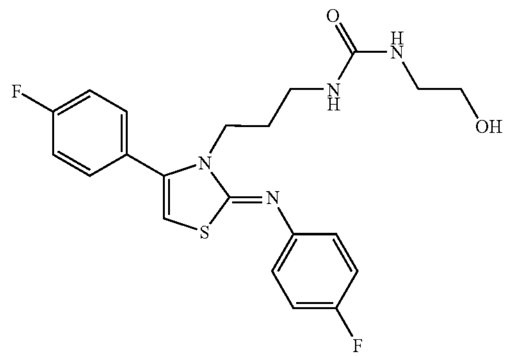 | 432 | 433 | A | 3.01 |
| 326 | 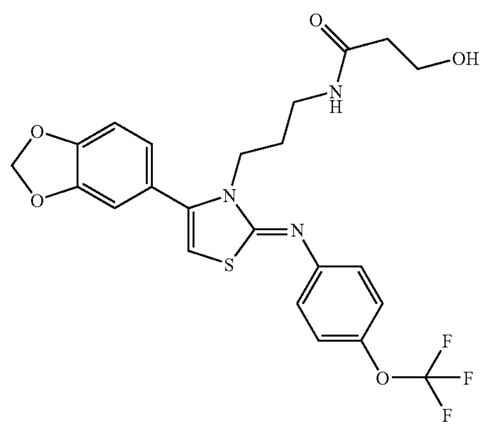 | 509 | 510 | A | 3.46 |

Example 327

N-{3-[2-[(4-Chloro-2-methoxyphenyl)imino]-4-(4-fluorophenyl)thiazol-3(2H)-yl]propyl}glycine (1) N-(tert-Butoxycarbonyl)-N-{3-[2-[(4-chloro-2-methoxyphenyl)imino]-4-(4-fluorophenyl)thiazol-3(2H)-yl]propyl}glycine

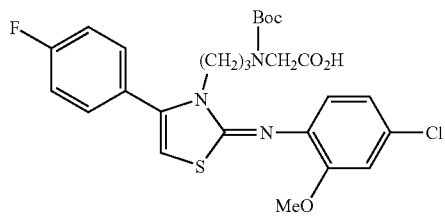

To a solution of the compound (3 g) obtained in Example 321 (1) in ethanol (5 ml) was added dropwise a 4N aqueous sodium hydroxide solution (5 ml), and the mixture was stirred at room temperature for 4 hours. To the reaction mixture was added water, and the mixture was acidified with a 10% aqueous citric acid solution, and extracted with ethyl acetate. The organic layer was washed with a saturated brine, dried over sodium sulfate, and the solvent was evaporated under reduced pressure to give the title compound (2.92 g) as foam.

(2) N-{3-[2-[(4-Chloro-2-methoxyphenyl)imino]-4-(4-fluorophenyl)-thiazol-3(2H)-yl]propyl}glycine

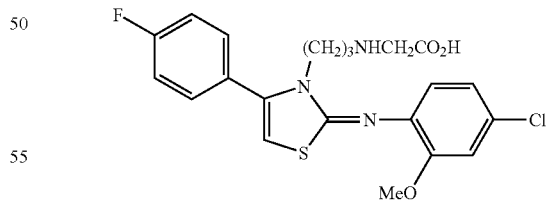

The compound (665 mg) obtained in the above (1) was treated in a similar manner to in Example 9 (2) to give the title compound (577 mg) as hydrochloride.

LC/MS: m/z=450 (MH$^+$), retention time: 3.20 min (Condition A).

Example 328

N-{3-[2-[(4-Chloro-2-methoxyphenyl)imino]-4-(4-fluorophenyl)thiazol-3(2H)-yl]propyl}-β-alanine (1) N-(tert-Butoxycarbonyl)-N-{3-[2-[(4-chloro-2-methoxyphenyl)imino]-4-(4-fluorophenyl)thiazol-3(2H)-yl]propyl}-β-alanine

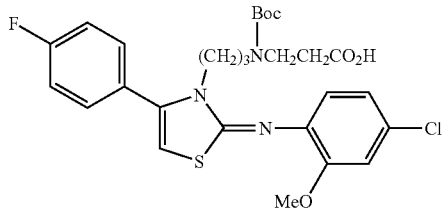

The ester compound (850 mg) obtained in Example 322 (1) was treated in a similar manner to in Example 327 (1) to give the title compound (715 mg) as foam.

(2) N-{3-[2-[(4-Chloro-2-methoxyphenyl)imino]-4-(4-fluorophenyl)-thiazol-3(2H)-yl]propyl}-β-alanine

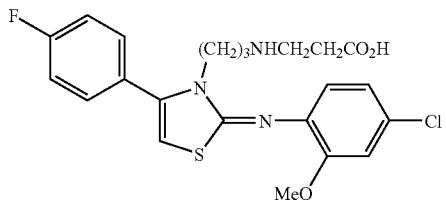

The compound (700 mg) obtained in the above (1) was treated in a similar manner to in Example 9 (2) to give the title compound (588 mg) as hydrochloride.

LC/MS: m/z=464 (MH$^+$), retention time: 3.26 min (Condition A).

Example 329

N-{3-[2-[(4-Fluorophenyl)imino]-4-[4-(morpholino)phenyl]thiazol-3(2H)-yl]propyl}glycine (1) Ethyl N-(tert-butoxycarbonyl)-N-{3-[2-[(4-fluorophenyl)imino]-4-[4-(morpholino)phenyl]thiazol-3(2H)-yl]propyl}glycinate

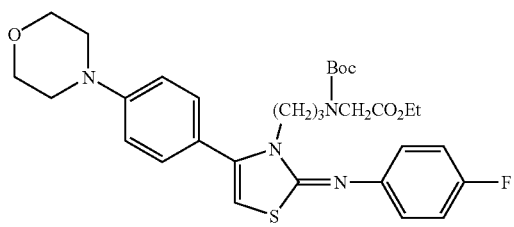

The amino compound (3.3 g) obtained in Example 252 was treated in a similar manner to in Example 321 (1) to give the title compound (4.1 g) as oil.

(2) N-(tert-Butoxycarbonyl)-N-{3-[2-[(4-fluorophenyl)imino]-4-[4-(morpholino)phenyl]-1,3-thiazol-3(2H)-yl]propyl}glycine

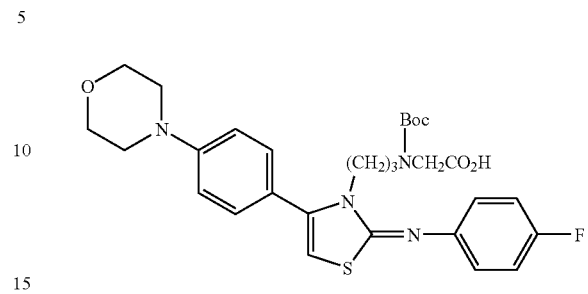

The compound (4.1 g) obtained in the above (1) were treated in a similar manner to in Example 327 (1) to give the title compound (3.0 g) as foam.

(3) N-{3-[2-[(4-Fluorophenyl)imino]-4-[4-(morpholino)phenyl]thiazol-3(2H)-yl]propyl}glycine

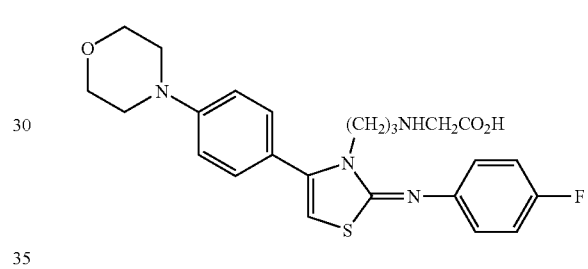

The compound (30 mg) obtained in the above (2) was treated in a similar manner to in Example 9 (2) to give the title compound (31 mg) as hydrochloride.

LC/MS: m/z=471 (MH$^+$), retention time: 2.92 min (Condition A)

Example 330

N-{3-[2-[(4-Fluorophenyl)imino]-4-[4-(morpholino)phenyl]-1,3-thiazol-3(2H)-yl]propyl}-β-alanine (1) Ethyl N-(tert-butoxycarbonyl)-N-{3-[-2-[(4-fluorophenyl)imino]-4-[4-(morpholino)phenyl]thiazol-3(2H)-yl]propyl}-β-alanate

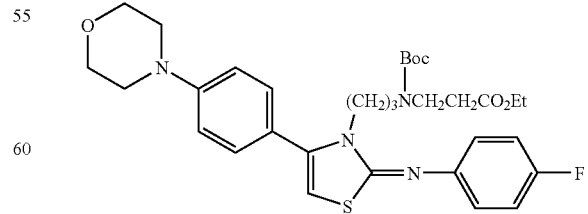

The amino compound (900 mg) obtained in Example 253 was treated in a similar manner to in Example 321 (1) to give the title compound (1.08 g) as oil.

(2) N-(tert-Butoxycarbonyl)-N-{3-[(2-[(4-fluorophenyl)imino]-4-[4-(morpholino)phenyl]thiazol-3(2H)-yl)propyl]-β-alanine

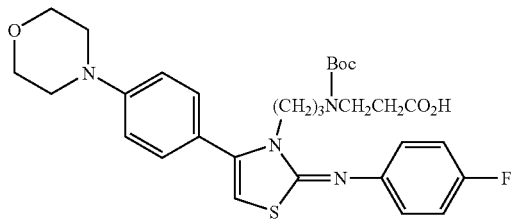

The compound (1.08 g) obtained in the above (1) was treated in a similar manner to in Example 327 (1) to give the title compound (800 mg) as foam.

(3) N-{3-[2-[(4-Fluorophenyl)imino]-4-[4-(morpholino)phenyl]-1,3-thiazol-3(2H)-yl]propyl}-β-alanine

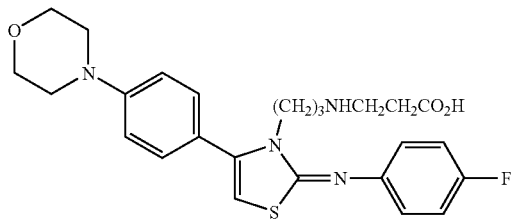

The compound (300 mg) obtained in the above (2) was treated in a similar manner to in Example 9 (2) to give the title compound (310 mg) as hydrochloride.

LC/MS: m/z=485 (MH$^+$), retention time: 3.13 min (Condition A)

Example 331

N-[({3-[4-(1,3-Benzodioxol-5-yl)-2-{[4-(trifluoromethoxy)phenyl]imino}-thiazol-3(2H)-yl]propyl}amino)carbonyl]glycine

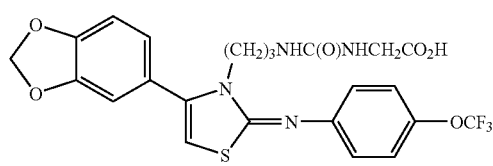

The compound (800 mg) obtained in Example 277 was treated in a similar manner to in Example 327 (1), and crystallized from ethyl acetate to give the title compound (726 mg).

LC/MS: m/z=539 (MH$^+$), retention time: 3.50 min (Condition A)

Example 332

3-({3-[4-(1,3-Benzodioxol-5-yl)-2-{[4-(trifluoromethoxy)phenyl]imino}-thiazol-3(2H)-yl]propyl}amino)-3-oxopropanoic acid

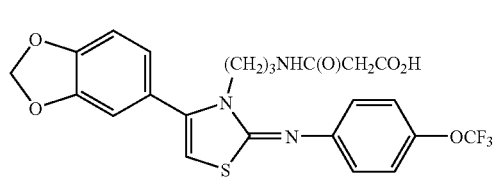

The compound (800 mg) obtained in Example 234 was treated in a similar manner to in Example 327 (1), and crystallized from ethyl acetate to give the title compound (726 mg).

LC/MS: m/z=524 (MH$^+$), retention time: 3.55 min (Condition A)

Example 333

[2-({3-[2-[(4-Chloro-2-methoxyphenyl)imino]-4-(4-fluorophenyl)thiazol-3(2H)-yl]propyl}amino)ethoxy]acetic acid (1) Ethyl [2-((tert-butoxycarbonyl){3-[2-[(4-chloro-2-methoxyphenyl)-imino]-4-(4-fluorophenyl)thiazol-3(2H)-yl]propyl}amino)ethoxy]acetate

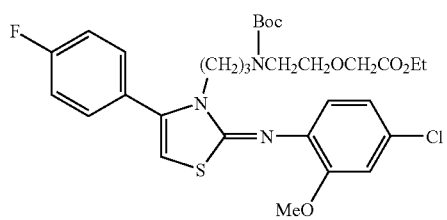

The compound (1.1 g) obtained in Example 321 (2) was dissolved in tetrahydrofuran (20 ml), and thereto was added portionwise sodium hydride (410 mg, 60% dispersion in oil) in several portions under nitrogen atmosphere in an ice bath, and the mixture was stirred for 30 minutes. To the reaction mixture was added ethyl bromoacetate (0.45 ml), and the mixture was warmed to room temperature, and then stirred for 6 hours. The reaction mixture was poured into a 5% aqueous citric acid solution under ice-cooling, and the mixture was extracted with ethyl acetate. The organic layer was washed with a saturated brine, dried over sodium sulfate, and the solvent was evaporated under reduced pressure. The residue was purified by silica gel column chromatography [n-hexane:ethyl acetate (8:2)] to give the title compound (980 mg) as colorless oil.

(2) [2-((tert-Butoxycarbonyl){3-[2-[(4-chloro-2-methoxyphenyl)imino]-4-(4-fluorophenyl)thiazol-3(2H)-yl]propyl}amino)ethoxy]acetic acid

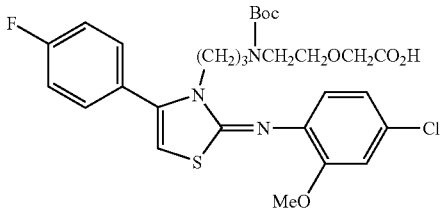

The compound (950 mg) obtained in the above (1) was treated in a similar manner to in Example 327 (1) to give the title compound (762 mg) as foam.

(3) [2-({3-[2-[(4-Chloro-2-methoxyphenyl)imino]-4-(4-fluorophenyl)-thiazol-3(2H)-yl]propyl}amino)ethoxy]acetic acid

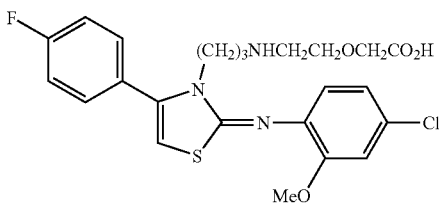

The compound (750 mg) obtained in the above (2) was treated in a similar manner to in Example 9 (2) to give the title compound (579 mg) as hydrochloride.
LC/MS: m/z=494 (MH$^+$), retention time: 3.27 min (Condition A)

Example 334

N$^2$-{3-[2-[(4-Chloro-2-methoxyphenyl)imino]-4-(4-fluorophenyl)thiazol-3(2H)-yl]propyl}-N$^1$-ethylglycinamide (1) N$^2$-(tert-Butoxycarbonyl)-N$^2$-{3-[2-[(4-chloro-2-methoxyphenyl)-imino]-4-(4-fluorophenyl)thiazol-3(2H)-yl]propyl}-N$^1$-ethylglycinamide

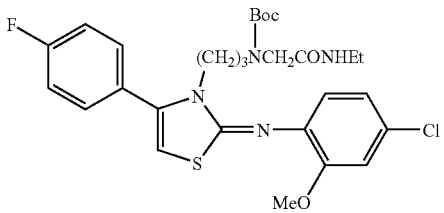

To a mixture of the carboxylic acid compound (1.0 g) obtained in Example 327 (1), ethylamine hydrochloride (297 mg), 1-hydroxybenzo-triazole monohydrate (418 mg), 1-ethyl-3-(3-dimethylaminopropyl)-carbodiimide hydrochloride (394 mg) and N,N-dimethylformamide (7 ml) was added dropwise N,N-diisopropylethylamine (1.27 ml), and the mixture was stirred overnight. To the reaction mixture was added water, and the mixture was extracted with ethyl acetate. The organic layer was washed with a saturated brine, dried over sodium sulfate, and the solvent was evaporated under reduced pressure. The residue was purified by silica gel column chromatography [n-hexane:ethyl acetate (1:1)] to give the title compound (929 mg) as foam.

(2) N$^2$-{3-[2-[(4-chloro-2-methoxyphenyl)imino]-4-(4-fluorophenyl)-thiazol-3(2H)-yl]propyl}-N$^1$-ethylglycinamide

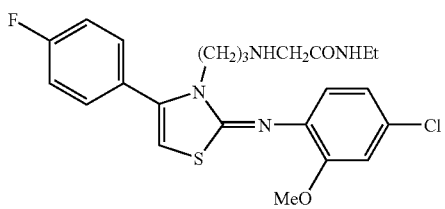

The compound (900 mg) obtained in the above (1) was treated in a similar manner to in Example 9 (2) to give the title compound (850 mg) as hydrochloride.
LC/MS: m/z=477 (MH$^+$), retention time: 3.36 min (Condition A)

Example 335

N$^1$-ethyl-N$^2$-{3-[2-[(4-fluorophenyl)imino]-4-[4-(morpholino)phenyl]-thiazol-3(2H)-yl]propyl}glycinamide

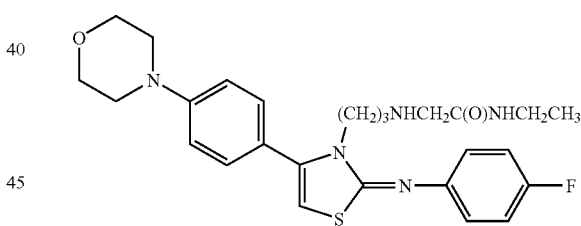

The title compound was synthesized by combinatorial chemistry technique. That is, to a solution of the compound obtained in Example 329 (2) in dichloromethane (43.8 μmol/ml) (1 ml) were added a solution of ethylamine hydrochloride in N,N-dimethylformamide (35.0 μmol/ml) (1 ml), a solution of diisopropylethylamine (35.0 μmol/ml) (1 ml) and a suspension of carbodiimide resin in dichloromethane (79.2 mg/ml, manufactured by Argonaut) (1 ml), and the mixture was stirred at room temperature overnight. The reaction mixture was filtered, and the filter cake was washed twice with dichloromethane (1 ml), and the filtrate was washed with a saturated aqueous sodium hydrogen carbonate solution (2 ml), and then washed twice with water (2 ml). The organic layer was passed through a filter containing magnesium sulfate, and the filter was washed twice with dichloromethane (1 ml), and the filtrate was concentrated. To the residue was added a 90% trifluoroacetic acid (2 ml), and the mixture was stirred at room temperature for 2 hours, and concentrated. The residue was dissolved in dichloromethane (2 ml), and excess amount of ion-exchange resin (Dowex 1-X8, OH-type) was added thereto, and the mixture was stirred at room temperature for 1 hour. The reaction mixture was filtered, and the filter cake was washed twice with dichloromethane (1 ml), and the filtrate was concentrated to give the title compound (6 mg).

LC/MS: m/z=498 (MH$^+$), retention time: 3.01 min (Condition A)

Examples 336 to 347

The corresponding carboxylic acid compounds and various amines were reacted in a similar manner to in Example 334 or Example 335 to give the compounds as listed in Table 20.

TABLE 20

| Ex No. | Structure | Exact MS | m/z | Method for analysis | Retention Time (min) |
|---|---|---|---|---|---|
| 336 | 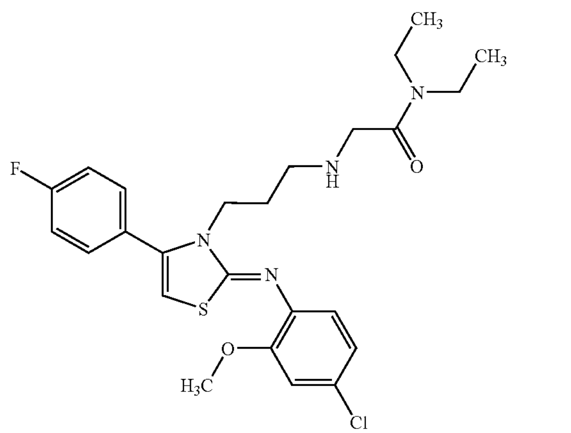 | 504 | 505 | A | 3.59 |
| 337 | 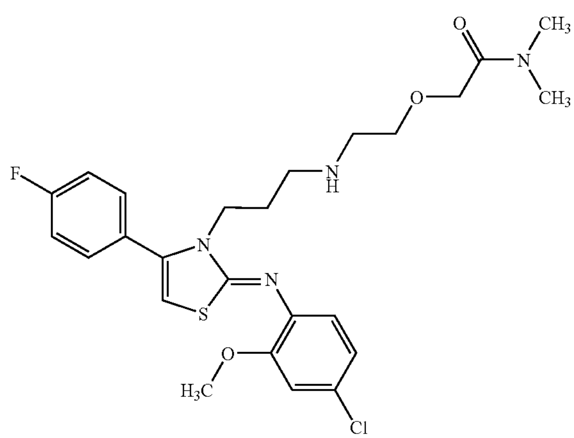 | 520 | 521 | A | 3.33 |
| 338 | 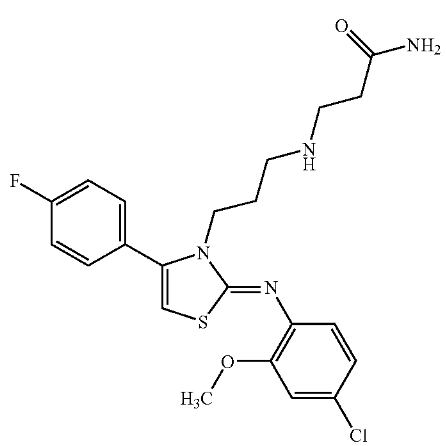 | 462 | 463 | A | 3.14 |

TABLE 20-continued

| Ex No. | Structure | Exact MS | m/z | Method for analysis | Retention Time (min) |
|---|---|---|---|---|---|
| 339 | 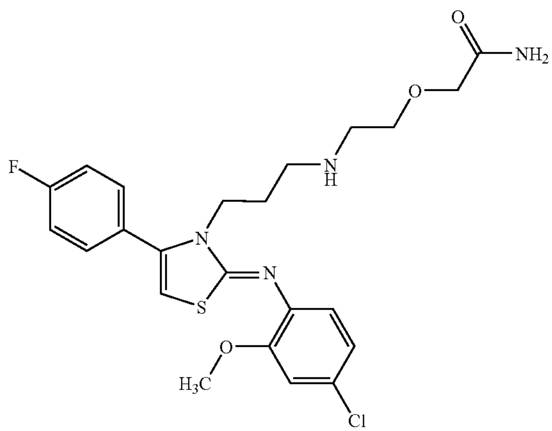 | 492 | 493 | A | 3.18 |
| 340 | 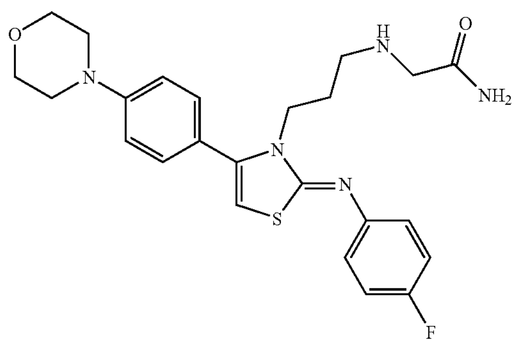 | 469 | 470 | A | 2.89 |
| 341 | 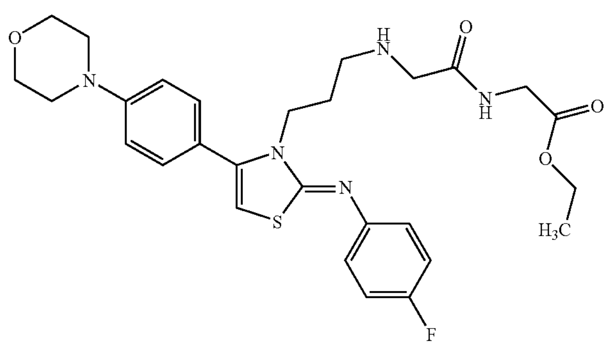 | 555 | 556 | A | 3.11 |
| 342 | 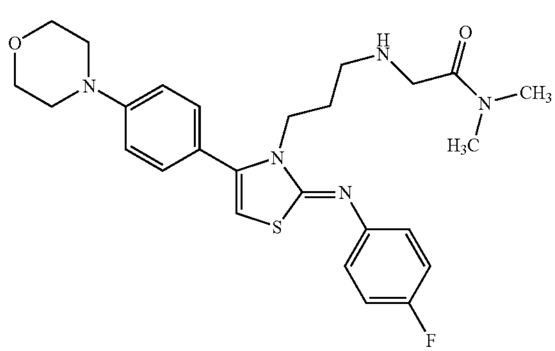 | 497 | 498 | A | 2.98 |

TABLE 20-continued
| Ex No. | Structure | Exact MS | m/z | Method for analysis | Retention Time (min) |
|---|---|---|---|---|---|
| 343 | 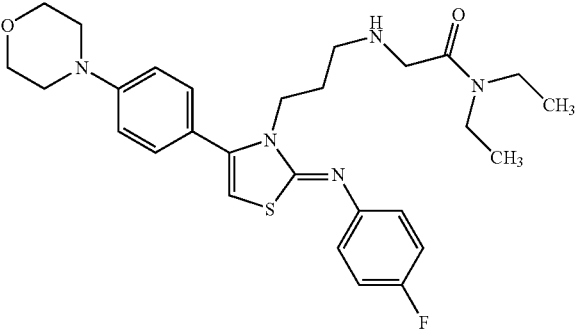 | 525 | 526 | A | 3.18 |
| 344 | 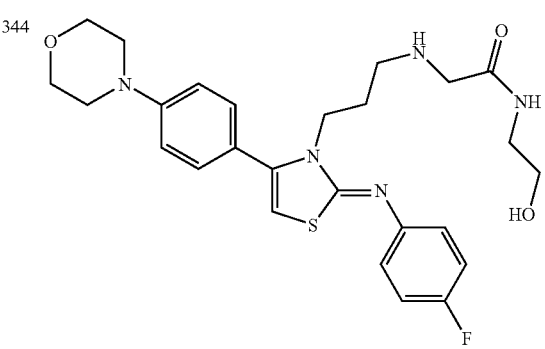 | 513 | 514 | A | 2.90 |
| 345 | 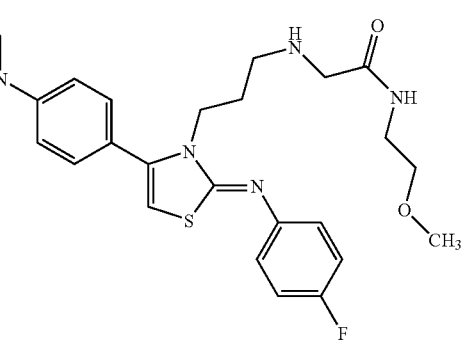 | 527 | 528 | A | 2.99 |
| 346 | 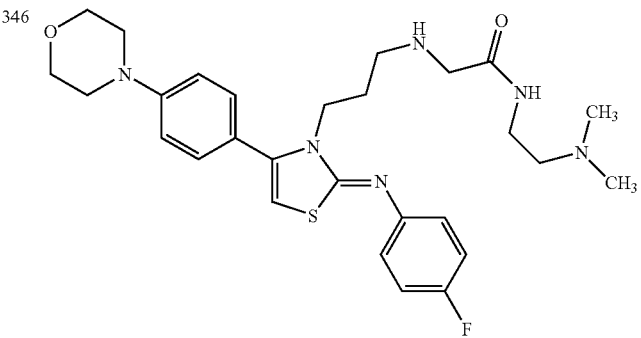 | 540 | 541 | A | 2.83 |

TABLE 20-continued

| Ex No. | Structure | Exact MS | m/z | Method for analysis | Retention Time (min) |
|---|---|---|---|---|---|
| 347 | 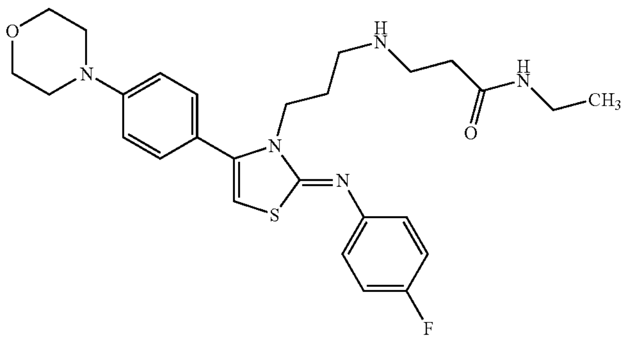 | 511 | 512 | A | 3.02 |

Example 348

4-Nitrophenyl 3-[2-[(4-fluorophenyl)imino]-4-[4-(morpholino)phenyl]-thiazol-3(2H)-yl]propylcarbamate

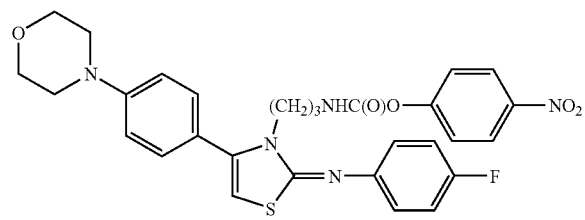

The compound (3.0 g, hydrochloride) obtained in Example 195 was suspended in tetrahydrofuran (36 ml), and thereto was added dropwise diisopropylethylamine (5 ml) in an ice bath under nitrogen atmosphere, and the mixture was stirred for 30 minutes. To the reaction mixture was added 4-nitrophenyl chloroformate (1.19 g), and the mixture was stirred for 3.5 hours. To the reaction mixture was added a saturated aqueous sodium hydrogen carbonate solution, and the mixture was extracted with ethyl acetate. The organic layer was washed with a saturated brine, dried over sodium sulfate, and the solvent was evaporated under reduced pressure. The residue was crystallized from a mixture of n-hexane and ethyl acetate to give the title compound (2.57 g).

$^1$H-NMR (CDCl$_3$): δ 1.72 (2H, m), 3.23-3.30 (6H, m), 3.88 (4H, t, J=4.9), 3.99 (2H, t, J=6.2), 5.78 (1H, s), 6.96 (2H, d, J=8.8), 7.02-7.10 (4H, m), 7.22-7.29 (5H, m), 8.21 (2H, dd, J=7.1, J=2.0).

Example 349

N-[2-(Dimethylamino)ethyl]-N'-{3-[2-[(4-fluorophenyl)imino]-4-[4-(morpholino)phenyl]thiazol-3(2H)-yl]propyl}urea

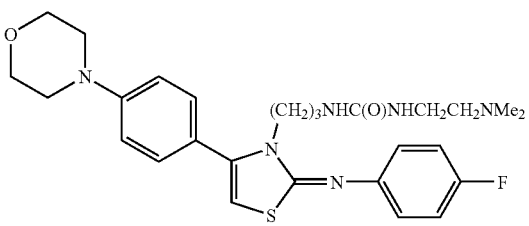

The compound (108 mg) obtained in Example 348 was dissolved in dichloromethane (3 ml), and thereto was added N,N-dimethyl-ethylenediamine (33 mg) at room temperature under nitrogen atmosphere, and the mixture was stirred for one hour. To the reaction mixture was added 1% aqueous sodium hydroxide solution, and the mixture was extracted with chloroform. The organic layer was washed with a saturated brine, dried over sodium sulfate, and the solvent was evaporated under reduced pressure to give the title compound (84 mg) as pale yellow solid.

$^1$H-NMR (CDCl$_3$): δ 1.66 (2H, m), 2.13 (6H, s), 2.22 (2H, t, J=7.2), 3.09-3.19 (4H, m), 3.24 (4H, t, J=4.8), 3.87-3.94 (6H, m), 4.68 (1H, t, J=4.9), 5.71 (1H, s), 5.94 (1H, m), 6.94 (2H, d, J=8.8), 6.98-7.06 (4H, m), 7.26 (2H, dd, J=7.0, J=1.9).

LC/MS: m/z=527 (MH$^+$), retention time: 2.94 min (Condition A)

Examples 350 to 355

The compounds as listed in Table 21 were obtained in a similar manner to in Example 348, 349.

TABLE 21

| Ex No. | Structure | Exact MS | m/z | Method for analysis | Retention Time (min) |
|---|---|---|---|---|---|
| 350 | 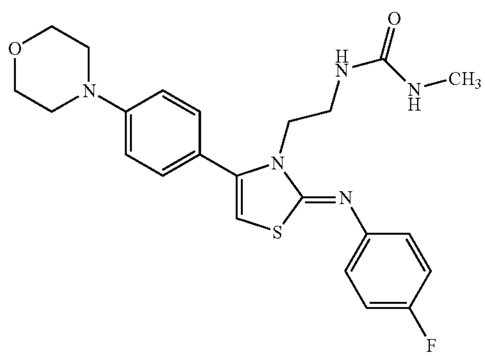 | 455 | 456 | A | 3.17 |
| 351 | 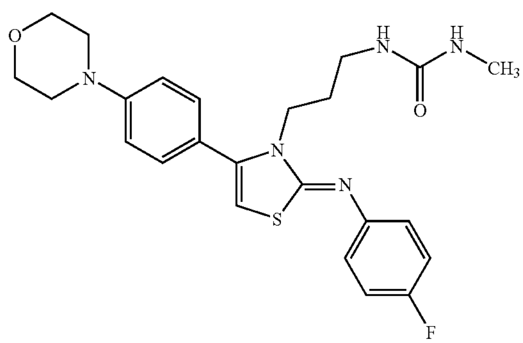 | 469 | 470 | A | 3.16 |
| 352 | 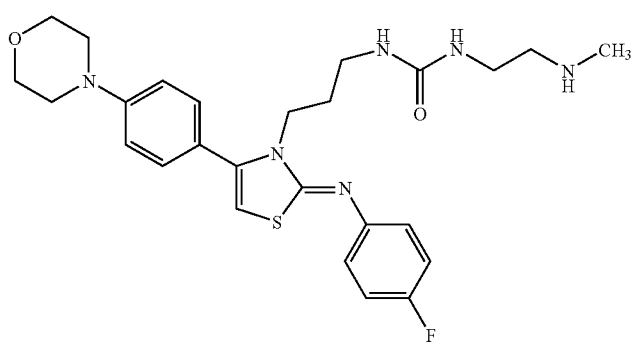 | 512 | 513 | A | 2.92 |
| 353 | 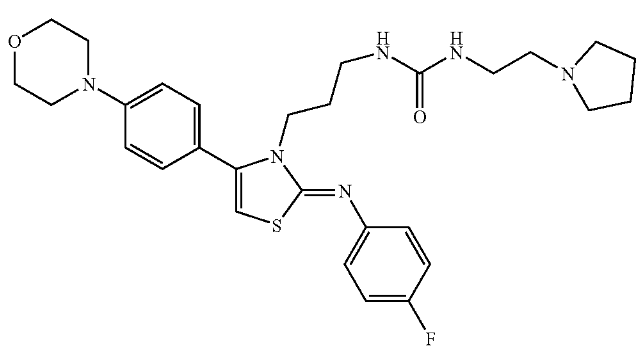 | 552 | 553 | A | 2.96 |

TABLE 21-continued

| Ex No. | Structure | Exact MS | m/z | Method for analysis | Retention Time (min) |
|---|---|---|---|---|---|
| 354 | 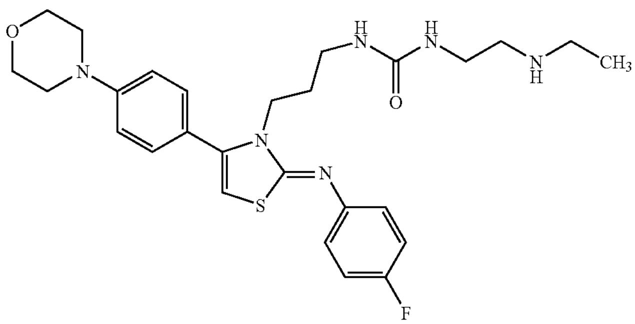 | 526 | 527 | A | 2.99 |
| 355 | 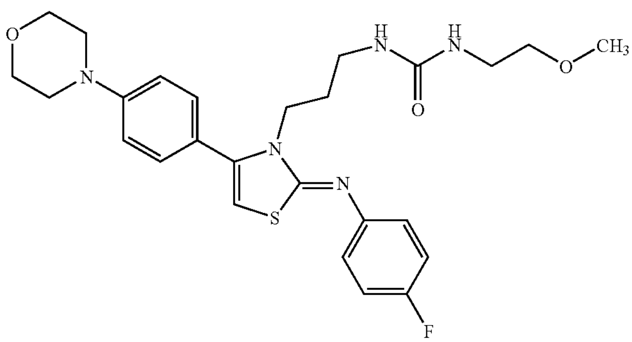 | 513 | 514 | A | 3.26 |

Example 356

2-Bromo-N-{3-[2-[(4-fluorophenyl)imino]-4-[4-(morpholino)phenyl]-thiazol-3(2H)-yl]propyl}acetamide

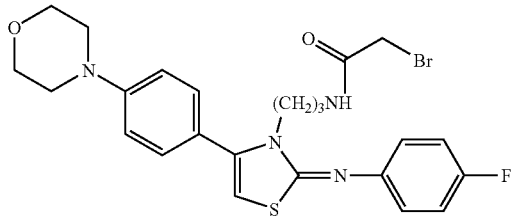

The compound (2.0g, hydrochloride) obtained in Example 195 and bromoacetyl chloride (663 mg) were treated in a similar manner to in Example 168 to give the title compound (1.2 g) was obtained as amorphous.

Example 357

N-{3-[2-[(4-Fluorophenyl)imino]-4-[4-(morpholino)phenyl]thiazol-3(2H)-yl]propyl}-2-(1-pyrrolidinyl)acetamide

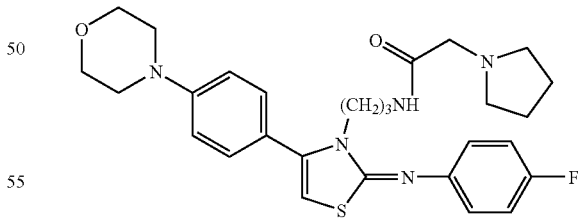

A mixture of the compound (200 mg) obtained in Example 356, pyrrolidine (0.32 ml) and N,N-dimethylformamide (2 ml) was stirred at room temperature for 8 hours. To the reaction mixture was added a saturated aqueous sodium hydrogen carbonate solution, and the mixture was extracted with ethyl acetate. The organic layer was washed with a saturated brine, dried over sodium sulfate, and the solvent was evaporated under reduced pressure. The residue was purified by silica gel column chromatography [chloroform:methanol (97:3)] to give the title compound (123 mg) as oil.

¹H-NMR (CDCl₃): δ 1.56-1.60 (4H, m), 1.70 (2H, m), 2.48 (4H, t, J=5.3), 3.07 (2H, s), 3.15-3.30 (6H, m), 3.86-3.92 (6H, m), 5.69 (1H, s), 6.92-7.06 (6H, m), 7.25 (2H, d, J=7.7), 7.85 (1H, t, J=6.1).

LC/MS: m/z=524 (MH⁺), retention time: 2.95 min (Condition A)

Examples 358 to 361

The compound obtained in Example 356 and various amines were reacted in a similar manner to in Example 357 to give the compounds as listed in Table 22.

TABLE 22

| Ex No. | Structure | Exact MS | m/z | Method for analysis | Retention Time (min) |
|---|---|---|---|---|---|
| 358 | 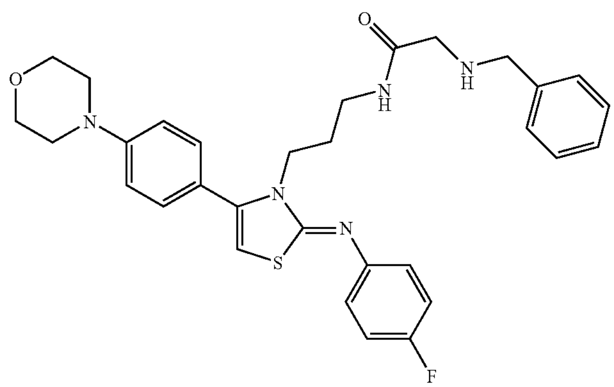 | 559 | 560 | A | 3.14 |
| 359 | 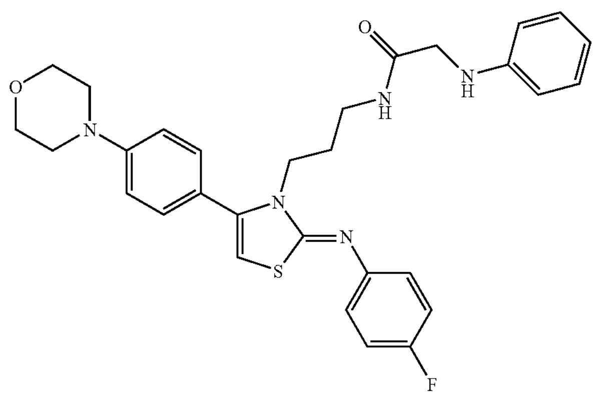 | 545 | 546 | A | 3.63 |
| 360 | 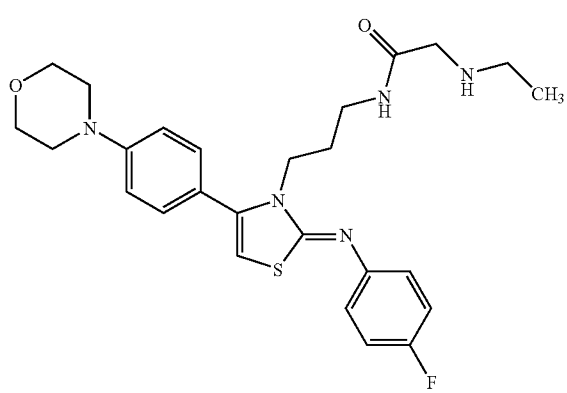 | 497 | 498 | A | 2.92 |

TABLE 22-continued

| Ex No. | Structure | Exact MS | m/z | Method for analysis | Retention Time (min) |
|---|---|---|---|---|---|
| 361 | 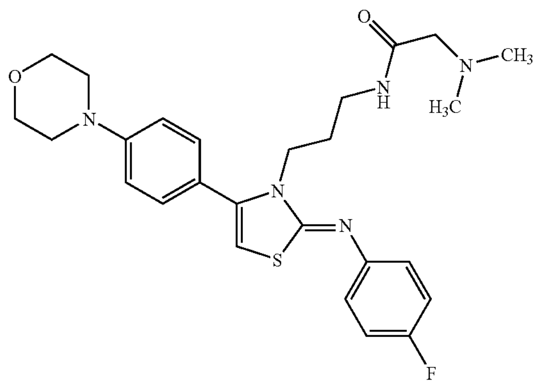 | 497 | 498 | A | 2.92 |

Example 362

3-[2-[(2,4-Dimethoxybenzyl)imino]-4-[4-(trifluoromethoxy)phenyl]-1,3-thiazol-3(2H)-yl]-1-propanamine

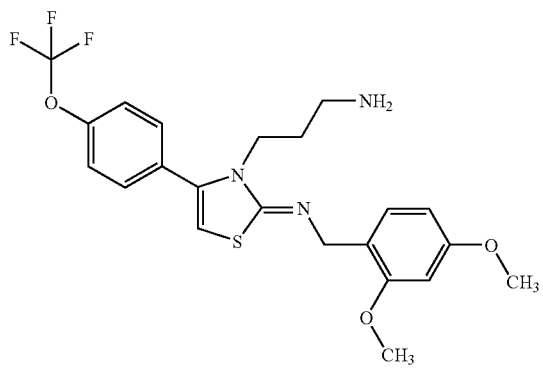

A solution of thiourea (3.40 g) obtained in Reference Example 90 and 4-(trifluoromethoxy)phenacyl bromide (2.76 g) in ethanol (90 ml) was stirred at room temperature for 22 hours, and the solvent was evaporated under reduced pressure, and thereto was added a saturated aqueous sodium hydrogen carbonate solution, and the mixture was extracted with ethyl acetate. The organic layer was washed with a saturated brine, dried over sodium sulfate, and the solvent was evaporated under reduced pressure. The residue was purified by silica gel column chromatography [n-hexane:ethyl acetate (4:1)] to give a cyclized compound (1.32 g). To the resulting cyclized compound (1.20 g) was added a 4N solution of hydrogen chloride in dioxane (12 ml), and the mixture was stirred at room temperature for 0.5 hour. Ether was added to the mixture, and the precipitates were collected by filtration to give the title compound (0.87 g) as hydrochloride.

$^1$H-NMR (DMSO-$d_6$): δ 1.86 (2H, m), 2.74 (2H, m), 3.78 (3H, s), 3.87 (3H, s), 4.15 (2H, t, J=7.2), 4.52 (2H, d, J=5.0), 6.57 (1H, dd, J=2.4, J=8.4), 6.64 (1H, d, J=2.4), 7.09 (1H, s), 7.36 (1H, d, J=8.4), 7.55 (2H, d, J=8.6), 7.71 (2H, d, J=8.6), 8.96 (3H, brs), 11.13 (1H, m).

LC/MS: m/z=468 (MH$^+$), retention time: 3.18 min (Condition A)

Examples 363 to 372

The compounds as listed in Table 23 were obtained in a similar manner to in Example 362 or 373.

TABLE 23

| Ex. No. | Structure | Exact MS | m/z | Method for analysis | Retention time (min) | Ref. Ex. |
|---|---|---|---|---|---|---|
| 363 | 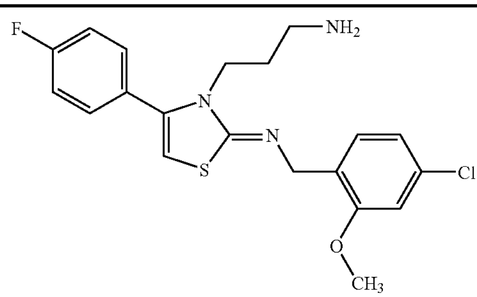 | 405 | 406 | A | 3.05 | 362 |

TABLE 23-continued

| Ex. No. | Structure | Exact MS | m/z | Method for analysis | Retention time (min) | Ref. Ex. |
|---|---|---|---|---|---|---|
| 364 | 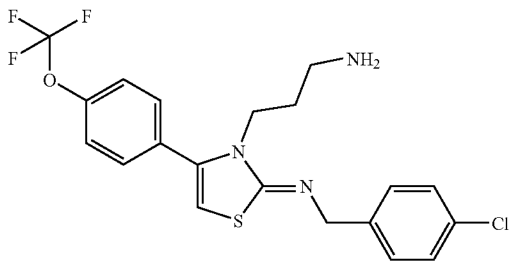 | 441 | 442 | A | 3.25 | 362 |
| 365 | 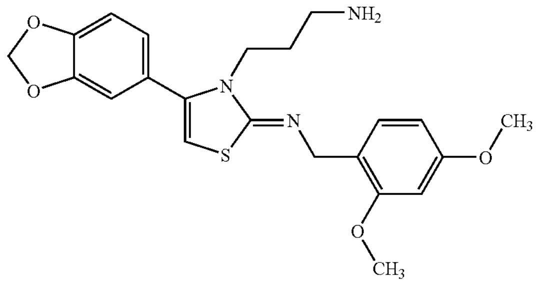 | 427 | 428 | A | 2.94 | 362 |
| 366 | 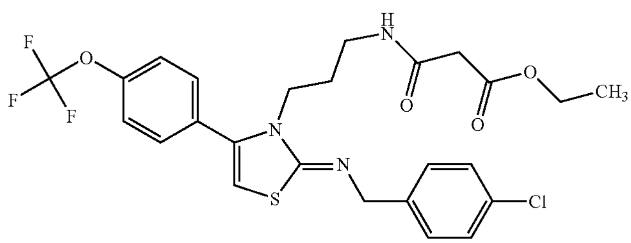 | 555 | 556 | A | 3.92 | 373 |
| 367 | 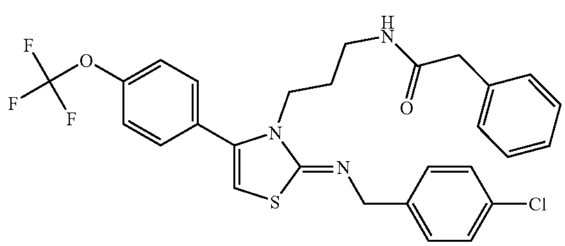 | 559 | 560 | A | 4.08 | 373 |
| 368 | 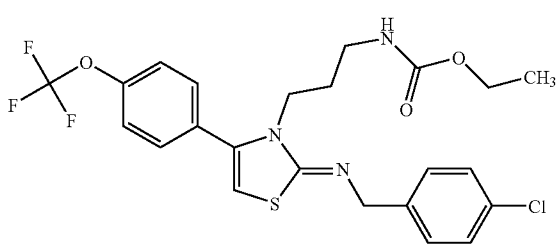 | 513 | 514 | A | 3.97 | 373 |
| 369 | 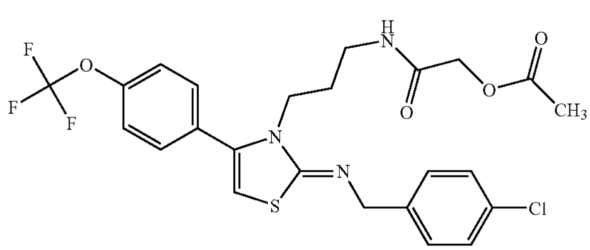 | 541 | 542 | A | 3.78 | 373 |

TABLE 23-continued

| Ex. No. | Structure | Exact MS | m/z | Method for analysis | Retention time (min) | Ref. Ex. |
|---|---|---|---|---|---|---|
| 370 | 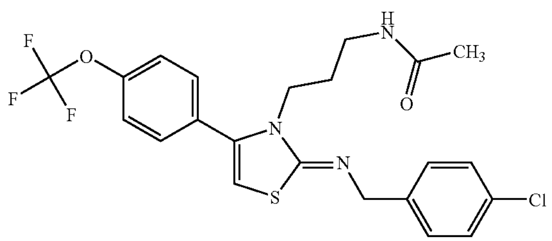 | 483 | 484 | A | 3.68 | 373 |
| 371 | 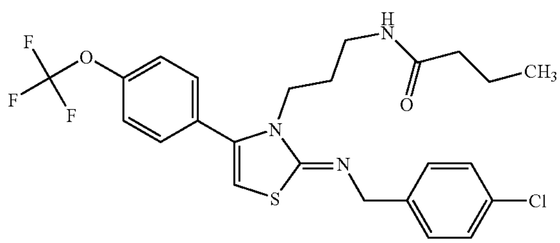 | 511 | 512 | A | 3.91 | 373 |
| 372 | 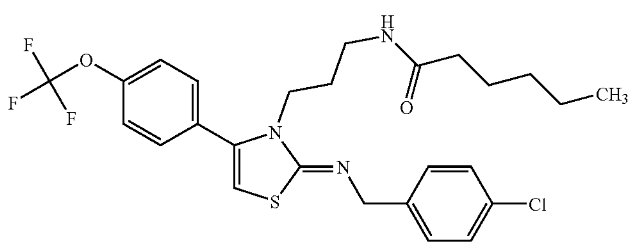 | 539 | 540 | A | 4.19 | 373 |

Example 373

N-{3-[2-[(2,4-dimethoxybenzyl)imino]-4-[4-(trifluoromethoxy)phenyl]-1,3-thiazol-3(2H)-yl]propyl}acetamide

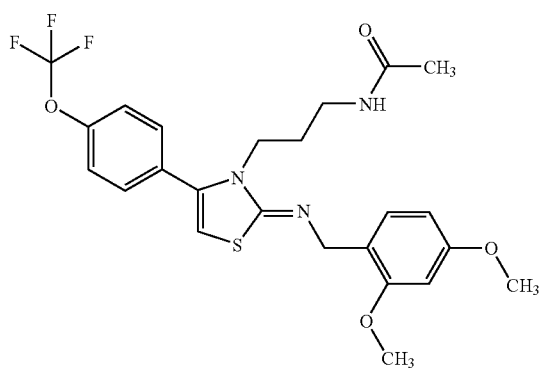

To a mixture of the compound (250 mg, hydrochloride) obtained in Example 362, triethylamine (0.22 ml) and tetrahydrofuran (3 ml) was added acetic anhydride (48 μl) under ice-cooling, and the mixture was stirred for 2 hours. To the reaction mixture was added water, and the mixture was extracted with ethyl acetate. The organic layer was washed with a saturated brine, dried over sodium sulfate, and the solvent was evaporated under reduced pressure. The residue was purified by silica gel column chromatography [2% methanol-chloroform] to give the title compound (230 mg).

$^1$H-NMR (CDCl$_3$): δ 1.48 (2H, m), 1.53 (3H, s), 3.12 (2H, m), 3.78-3.83 (8H, m), 4.21 (2H, s), 5.84 (1H, s), 6.46-6.48 (2H, m), 7.27-7.40 (6H, m).

LC/MS: m/z=510 (MH$^+$), retention time: 3.59 min (Condition A)

Examples 374 to 381

The compounds as listed in Table 24 were obtained in a similar manner to in Example 373 or 382.

TABLE 24

| Ex. No. | Structure | Exact MS | m/z | Method for analysis | Retention time (min) | Ref. Ex. |
|---|---|---|---|---|---|---|
| 374 | 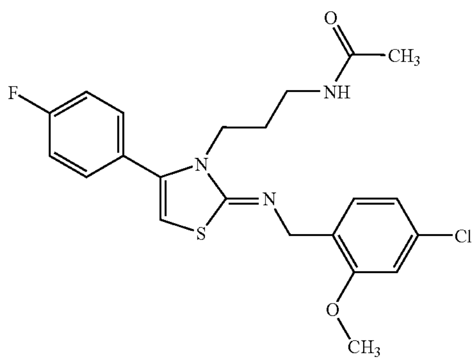 | 447 | 448 | A | 3.44 | 373 |
| 375 | 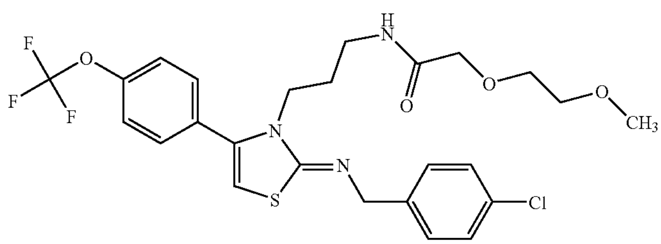 | 557 | 558 | A | 3.8 | 382 |
| 376 | 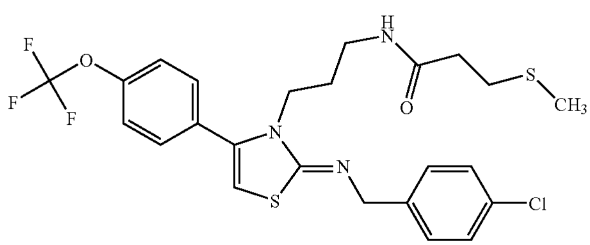 | 543 | 544 | A | 3.92 | 382 |
| 377 | 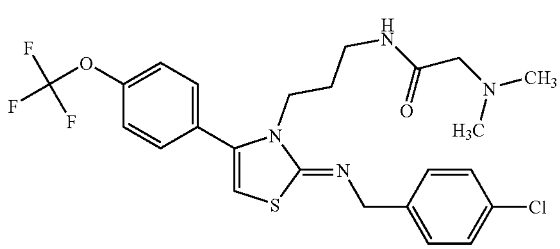 | 526 | 527 | A | 3.29 | 382 |
| 378 | 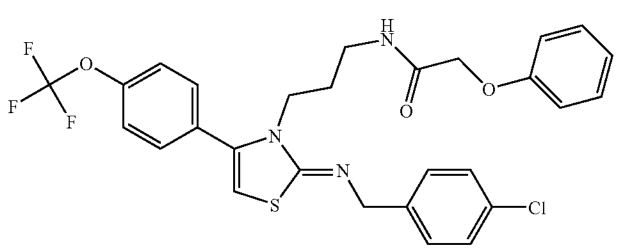 | 575 | 576 | A | 3.96 | 382 |

TABLE 24-continued

| Ex. No. | Structure | Exact MS | m/z | Method for analysis | Retention time (min) | Ref. Ex. |
|---|---|---|---|---|---|---|
| 379 | 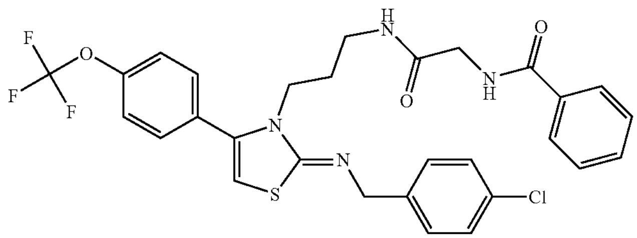 | 602 | 603 | A | 3.93 | 382 |
| 380 | 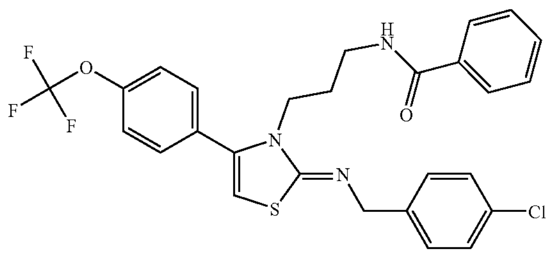 | 545 | 546 | A | 4.03 | 382 |
| 381 | 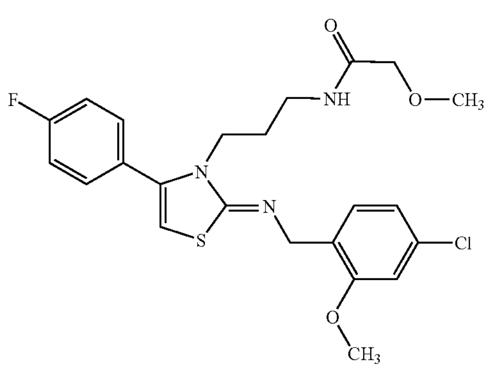 | 477 | 478 | A | 3.54 | 373 |

Example 382

N-{3-[2-[(4-Chlorobenzyl)imino]-4-[4-(trifluoromethoxy)phenyl]-1,3-thiazol-3(2H)-yl]propyl}-2-methoxyacetamide

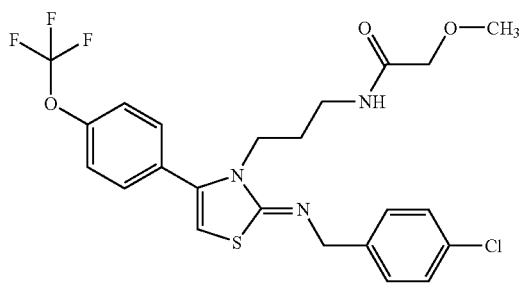

The title compound was synthesized by combinatorial chemistry technique. That is, to a solution of the compound obtained in Example 364 (free amino compound) in tetrahydrofuran (45.3 μmol/l) (1 ml) was added a solution of methoxy acetate in tetrahydrofuran (58.9 μmol/ml) (1 ml), a solution of 1-hydroxybenzotriazole monohydrate in tetrahydrofuran (118 μmol/ml) (500 μl) and a suspension of 1-ethyl-3-(3-dimethylaminopropyl)carbodiimide hydrochloride in tetrahydrofuran (118 μmol/ml) (500 μl), and the mixture was stirred at room temperature overnight. To the reaction mixture was added chloroform (2.5 ml), and the mixture was washed with a saturated aqueous sodium hydrogen carbonate solution (2 ml), and then further washed twice with water (2 ml). The organic layer was passed through a filter containing magnesium sulfate, and the filter was washed twice with chloroform (1 ml), and the filtrate was concentrated to give the title compound.

LC/MS: m/z=514 (MH$^+$), retention time: 3.76 min (Condition A)

Example 383

N-{3-[2-[(2,4-Dimethoxybenzyl)imino]-4-[4-(trifluoromethoxy)phenyl]-1,3-thiazol-3(2H)-yl]propyl}-2-methoxyacetamide

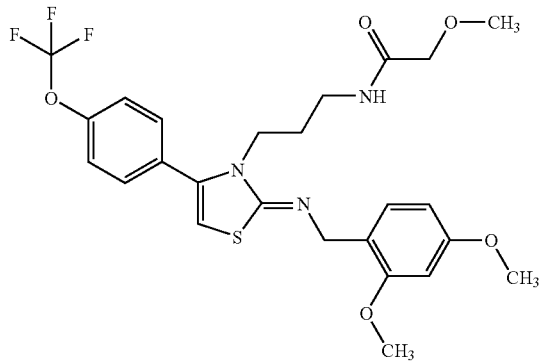

The compound (960 mg, hydrochloride) obtained in Example 362 and 2-methoxyacetyl chloride (0.2 ml) were treated in a similar manner to in Example 373 to give the title compound (260 mg).

$^1$H-NMR (CDCl$_3$): δ 1.64 (2H, m), 3.16-3.26 (5H, m), 3.70 (2H, s), 3.76-3.89 (8H, m), 4.29 (2H, s), 5.79 (1H, s), 6.46-6.50 (2H, m), 7.26-7.33 (4H, m), 7.39 (1H, d, J=8.8), 7.48 (1H, m).

LC/MS: m/z=540 (MH$^+$), retention time: 3.69 min (Condition A)

Example 384

N-{3-[2-[(4-Chlorobenzyl)imino]-4-[4-(trifluoromethoxy)phenyl]-1,3-thiazol-3(2H)-yl]propyl}-2-(1-pyrrolidinyl)acetamide

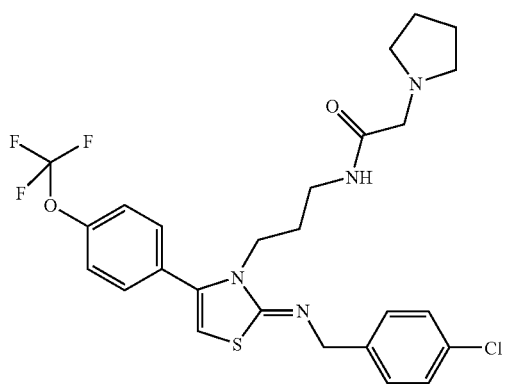

To a mixture of the compound (100 mg, hydrochloride) obtained in Example 364, triethylamine (108 μl) and tetrahydrofuran (2 ml) was added 2-bromoacetyl chloride (30 mg) under ice-cooling, and the mixture was stirred for one hour. To the reaction mixture was added water, and the mixture was extracted with ethyl acetate. The organic layer was washed with a saturated brine, dried over sodium sulfate, and the solvent was evaporated under reduced pressure. The residue was purified by silica gel column chromatography [n-hexane: ethyl acetate (1:1)] to give a reaction intermediate (82 mg). To a mixture of the obtained reaction intermediate (80 mg), triethylamine (20 μl) and tetrahydrofuran (5 ml) was added pyrrolidine (0.119 ml), and the mixture was stirred for one hour. Water was added to the reaction mixture, and the mixture was extracted with ethyl acetate. The organic layer was washed with a saturated brine, dried over sodium sulfate, and the solvent was evaporated under reduced pressure. The residue was purified by silica gel column chromatography [3% methanol in chloroform], and the product was subjected to hydrogen chloride to give the title compound (56 mg) as hydrochloride.

LC/MS: m/z=553 (MH$^+$), retention time: 3.33 min (Condition A)

Examples 385 to 401

The compounds as listed in Table 25 were obtained in a similar manner to in Example 384 or 402.

TABLE 25

| Ex. No. | Structure | Exact MS | m/z | Method for analysis | Retention time (min) | Ref. Ex. |
|---|---|---|---|---|---|---|
| 385 | 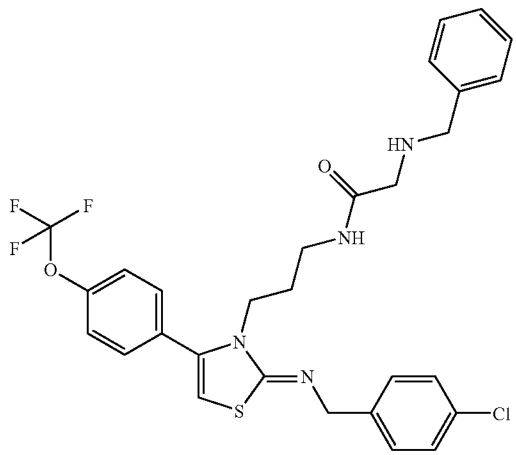 | 588 | 589 | A | 3.48 | 384 |
| 386 | 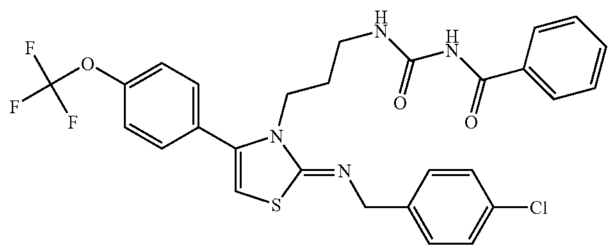 | 588 | 589 | A | 4.11 | 402 |
| 387 | 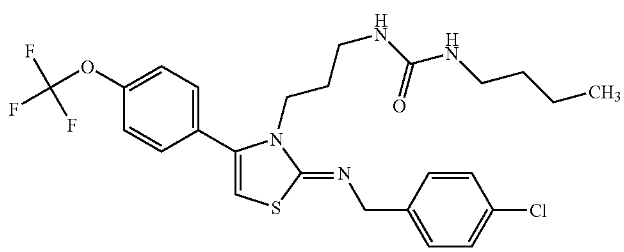 | 540 | 541 | A | 4.06 | 402 |
| 388 | 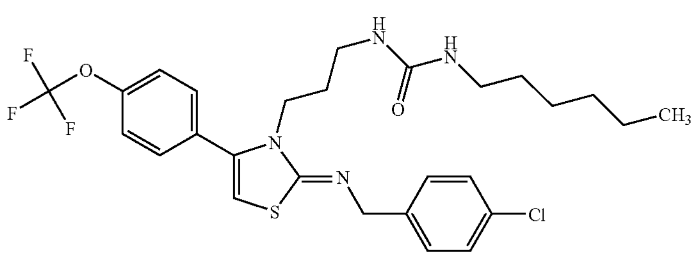 | 568 | 569 | B | 2.94 | 402 |
| 389 | 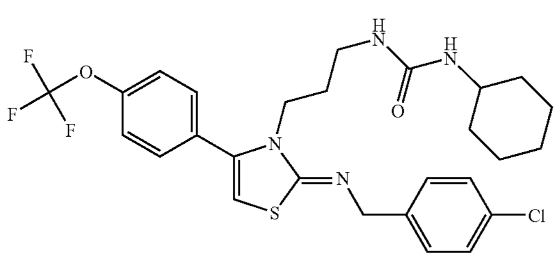 | 566 | 567 | A | 4.18 | 402 |

TABLE 25-continued

| Ex. No. | Structure | Exact MS | m/z | Method for analysis | Retention time (min) | Ref. Ex. |
|---|---|---|---|---|---|---|
| 390 | 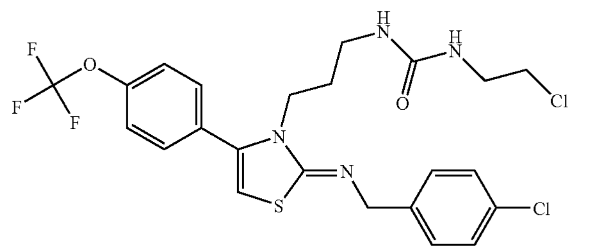 | 546 | 547 | A | 3.95 | 402 |
| 391 | 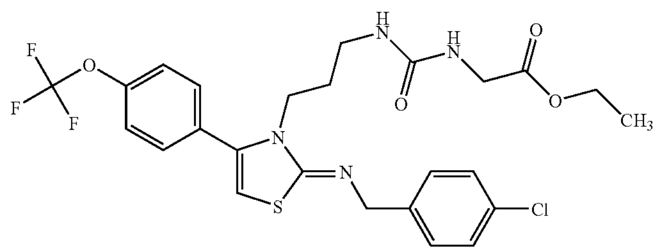 | 570 | 571 | A | 3.88 | 402 |
| 392 | 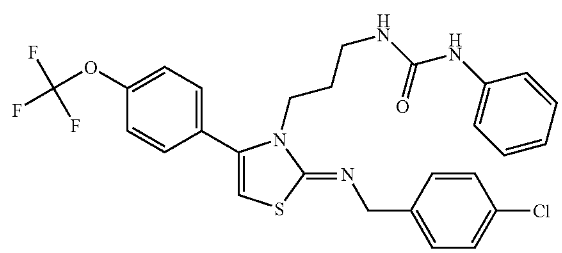 | 560 | 561 | A | 4.09 | 402 |
| 393 | 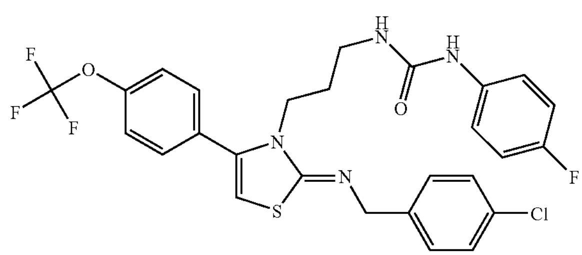 | 578 | 579 | A | 4.13 | 402 |
| 394 | 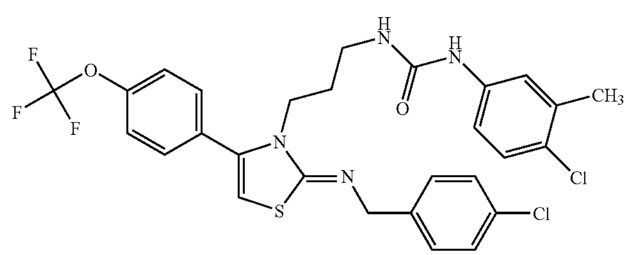 | 608 | 609 | B | 3.06 | 402 |
| 395 | 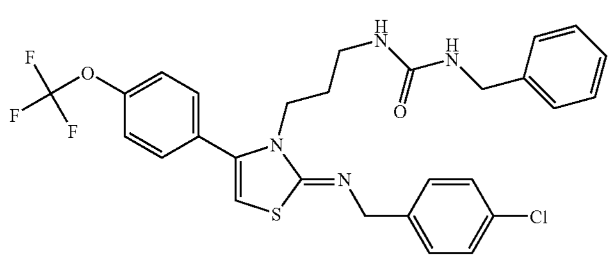 | 574 | 575 | A | 4.1 | 402 |

TABLE 25-continued

| Ex. No. | Structure | Exact MS | m/z | Method for analysis | Retention time (min) | Ref. Ex. |
|---|---|---|---|---|---|---|
| 396 | 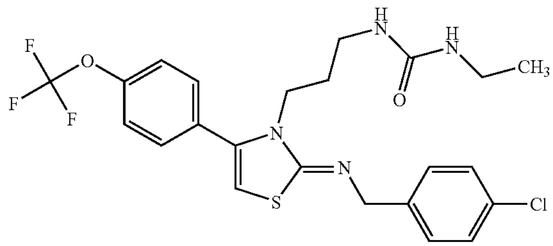 | 528 | 529 | A | 3.93 | 402 |
| 397 | 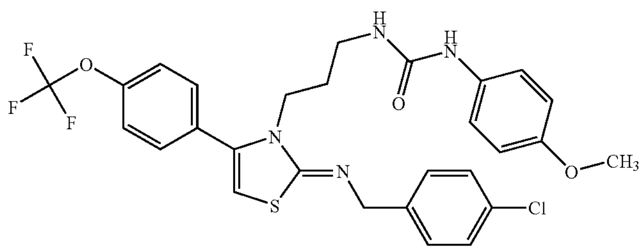 | 590 | 591 | A | 4.01 | 402 |
| 398 | 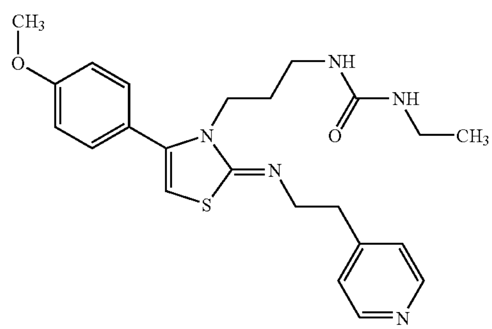 | 439 | 440 | A | 2.46 | 402 |
| 399 | 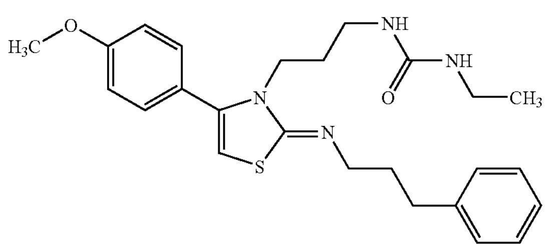 | 452 | 453 | A | 3.59 | 402 |
| 400 | 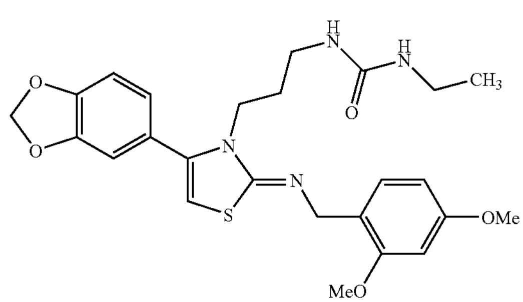 | 499 | 500 | A | 3.41 | 402 |

TABLE 25-continued

| Ex. No. | Structure | Exact MS | m/z | Method for analysis | Retention time (min) | Ref. Ex. |
|---|---|---|---|---|---|---|
| 401 | 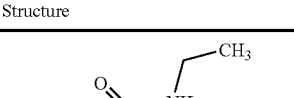 | 425 | 426 | A | 2.20 | 402 |

Example 402

N-{3-[2-[(4-Chloro-2-methoxybenzyl)imino]-4-(4-fluorophenyl)-1,3-thiazol-3(2H)-yl]propyl}-N'-ethylurea

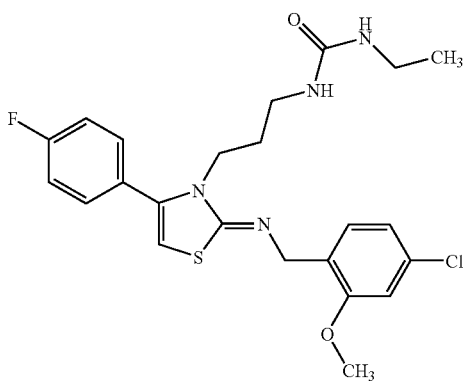

To a solution of the compound (800 mg, free amine) obtained in Example 363 in tetrahydrofuran (5 ml) was added ethyl isocyanate (0.16 ml), and the mixture was stirred for 2 hours. The solvent was evaporated under reduced pressure, and to the residue was added isopropyl alcohol, and the precipitates were collected by filtration to give the title compound (453 mg).

$^1$H-NMR (CDCl$_3$): δ 0.94 (3H, t, J=7.2), 1.43 (2H, m), 2.93-3.06 (4H, m), 3.33(1H, m), 3.81 (2H, t, J=6.2), 3.85 (3H, s), 4.18 (2H, s), 5.82 (1H, s), 6.06 (1H, m), 6.91 (1H, s), 6.97 (1H, d, J=8.1), 7.13 (2H, dd, J=8.6, J=8.4), 7.33 (2H, dd, J=8.6, J=5.3), 7.44 (1H, d, J=8.1). LC/MS: m/z=477 (MH$^+$), retention time: 3.60 min (Condition A)

Examples 403 to 408

The compounds as listed in Table 26 were obtained in a similar manner to in Example 373, 402 or 409.

TABLE 26

| Ex. No. | Structure | Exact MS | m/z | Method for analysis | Retention time (min) | Ref. Ex. |
|---|---|---|---|---|---|---|
| 403 | 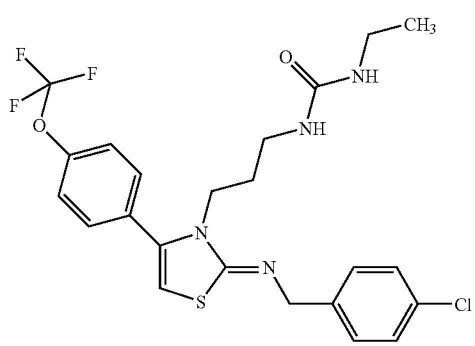 | 513 | 514 | A | 3.79 | 402 |

TABLE 26-continued

| Ex. No. | Structure | Exact MS | m/z | Method for analysis | Retention time (min) | Ref. Ex. |
|---|---|---|---|---|---|---|
| 404 | 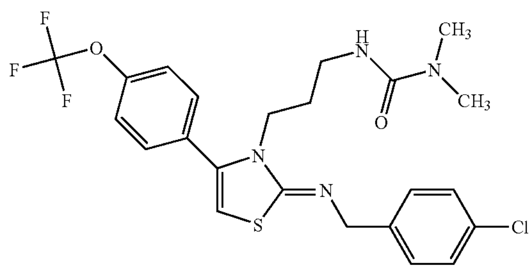 | 513 | 514 | A | 3.79 | 373 |
| 405 | 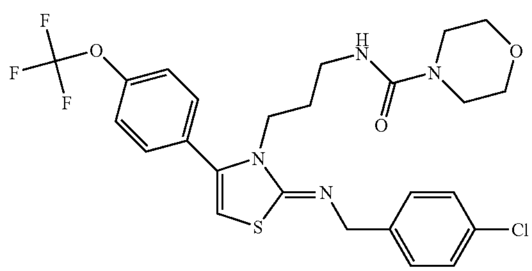 | 554 | 555 | A | 3.73 | 373 |
| 406 | 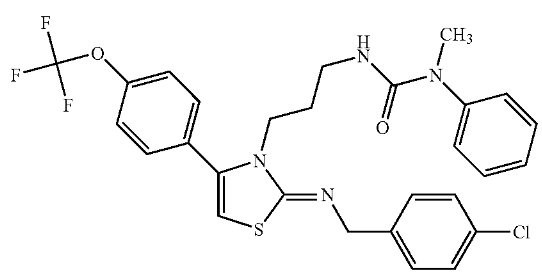 | 574 | 575 | A | 4.12 | 373 |
| 407 | 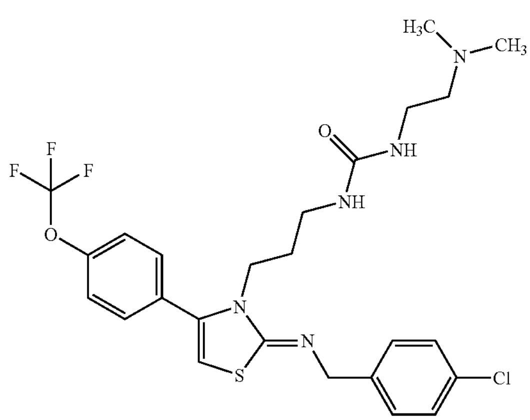 | 555 | 556 | A | 3.29 | 409 |

TABLE 26-continued

| Ex. No. | Structure | Exact MS | m/z | Method for analysis | Retention time (min) | Ref. Ex. |
|---|---|---|---|---|---|---|
| 408 | 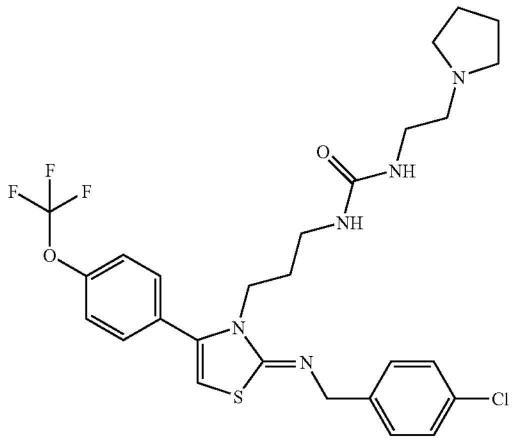 | 581 | 582 | A | 3.33 | 409 |

Example 409

N-{3-[2-[(4-Chlorobenzyl)imino]-4-[4-(trifluoromethoxy)phenyl]-1,3-thiazol-3(2H)-yl]propyl}-N'-(2-methoxyethyl)urea

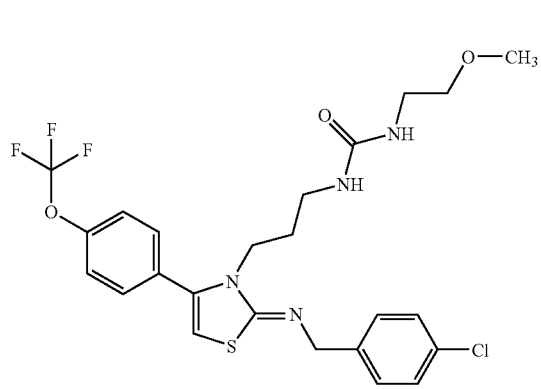

To a mixture of the compound (1.54 g, hydrochloride) obtained in Example 364, diisopropylethylamine (1.94 g) and tetrahydrofuran (30 ml) was added 4-nitrophenyl chloroformate (1.21 g) under ice-cooling, and the mixture was stirred for 2 hours. To the reaction mixture was added a saturated aqueous sodium hydrogen carbonate solution, and the mixture was extracted with ethyl acetate. The organic layer was washed with a saturated brine, dried over sodium sulfate, and the solvent was evaporated under reduced pressure to give a reaction intermediate (1.73 g). To a solution of the resulting reaction intermediate (100 mg) in dichloromethane (5 ml) was added 2-methoxyethylamine (25 mg), and the mixture was stirred for 2 hours. To the reaction mixture was added a 5% aqueous sodium hydroxide solution, and the mixture was extracted with dichloromethane. The organic layer was washed with a saturated brine, dried over sodium sulfate, and the solvent was evaporated under reduced pressure. To the residue was added a mixture of n-hexane and ethyl acetate (1:1), and the precipitates were collected by filtration to give the title compound (60 mg).

LC/MS: m/z=543 (MH$^+$), retention time: 3.73 min (Condition A)

Example 410

{3-[2-[(4-Chlorobenzyl)imino]-4-[4-(trifluoromethoxy)phenyl]-1,3-thiazol-3(2H)-yl]propyl}-(2-hydroxyethyl)urea

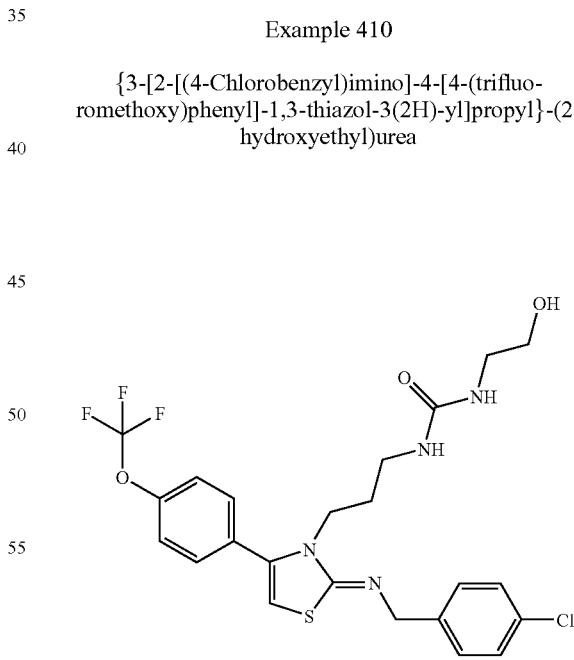

The title compound was obtained in a similar manner to in Example 409.

LC/MS: m/z=529 (MH$^+$), retention time: 3.56 min (Condition A)

Example 411

3-[2-[(4-Chloro-2-methoxybenzyl)imino]-4-(4-fluorophenyl)-1,3-thiazol-3(2H)-yl]-(2-methoxyethyl)-1-propanamine

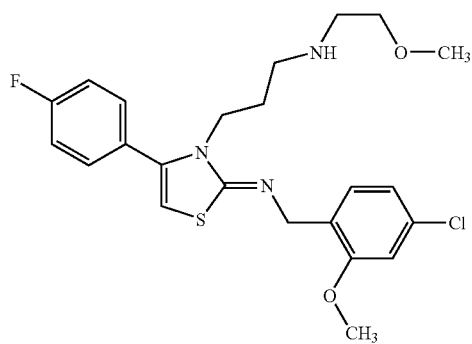

The compound obtained in Example 363 was protected with Boc by a conventional method, and a mixture of the resulting product (1.00 g), sodium hydride (0.24 g) and dimethylformamide (5 ml) was stirred for 0.5 hour, and thereto was added 2-methoxyethyl bromide, and the mixture was stirred for 6 hours. To the reaction mixture was added a 10% aqueous citric acid solution, and the mixture was extracted with ethyl acetate. The organic layer was washed with a saturated brine, dried over sodium sulfate, and the solvent was evaporated under reduced pressure. The residue was purified by silica gel column chromatography [chloroform:ethyl acetate (4:1)], and a 4N solution of hydrogen chloride in dioxane (2 ml) was added thereto, and the mixture was stirred at room temperature for 3 hours. The solvent was evaporated under reduced pressure, and to the residue was added aqueous ammonia, and the mixture was extracted with chloroform. The organic layer was washed with a saturated brine, dried over sodium sulfate, and the solvent was evaporated under reduced pressure to give the title compound (185 mg).

$^1$H-NMR (CDCl$_3$): δ 1.73 (2H, m), 2.49 (2H, t, J=6.8), 2.61 (2H, t, J=5.1), 3.28 (3H, s), 3.35 (2H, t, J=5.1), 3.82-3.86 (5H, m), 4.26 (2H, s), 5.75 (1H, s), 6.85 (1H, d, J=1.8), 6.93 (1H, dd, J=1.8, J=8.1), 7.12 (2H, dd, J=8.6, J=8.4), 7.35 (2H, dd, J=8.6, J=5.3), 7.46 (1H, d, J=8.1). LC/MS: m/z=465 (MH$^+$), retention time: 3.13 min (Condition A)

Examples 412 to 416

The compounds as listed in Table 27 were obtained in a similar manner to in Example 411.

TABLE 27

| Ex. No. | Structure | Exact MS | m/z | Method for analysis | Retention time (min) | Ref. Ex. |
|---|---|---|---|---|---|---|
| 412 | 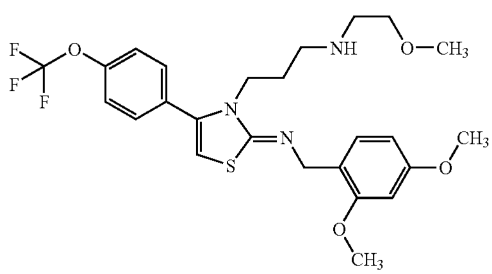 | 525 | 526 | A | 3.27 | 411 |
| 413 | 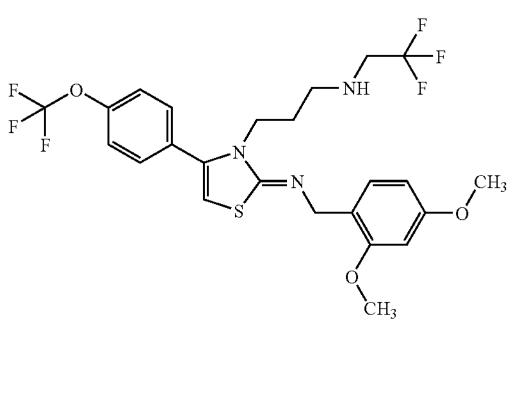 | 549 | 550 | A | 3.73 | 411 |

TABLE 27-continued

| Ex. No. | Structure | Exact MS | m/z | Method for analysis | Retention time (min) | Ref. Ex. |
|---|---|---|---|---|---|---|
| 414 | 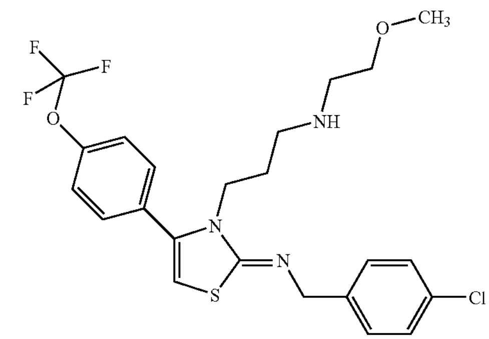 | 499 | | | | 411 |
| 415 | 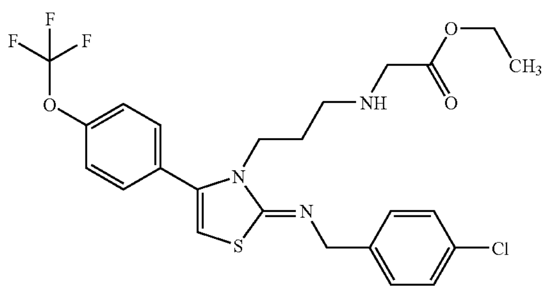 | 527 | 528 | A | 3.42 | 411 |
| 416 | 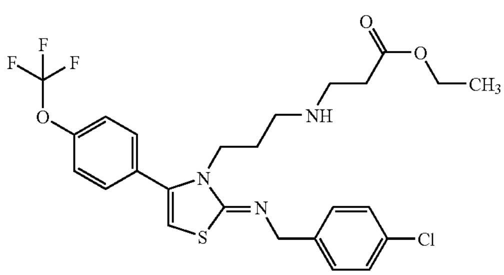 | 541 | 542 | A | 3.46 | 411 |

Example 417

N²-{3-[2-[(4-Chlorobenzyl)imino]-4-[4-(trifluoromethoxy)phenyl]-1,3-thiazol-3(2H)-yl]propyl}-N¹-ethylglycinamide

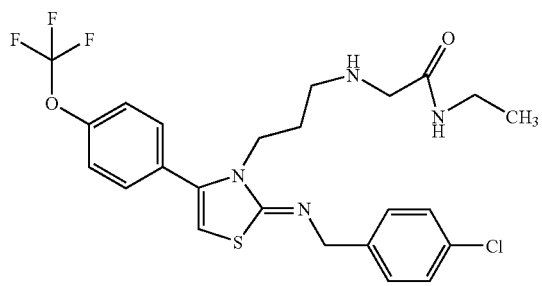

The title compound was synthesized by combinatorial chemistry technique. That is, the compound obtained in Example 427 was protected with a Boc by a conventional method, and to a solution of the resulting product in dichloromethane (43.8 μmol/ml) were added a solution of ethylamine hydrochloride in N,N-dimethylformamide (35.0 μmol/ml) (1 ml), a solution of diisopropylethylamine in dichloromethane (35.0 μmol/ml) (1 ml) and a suspension of carbodiimide resin in dichloromethane (79.2 mg/ml, manufactured by Argonaut) (1 ml), and the mixture was stirred at room temperature overnight. The reaction mixture was filtered, and the filter cake was washed twice with dichloromethane (1 ml), and the filtrate was washed twice with a saturated aqueous sodium hydrogen carbonate solution (2 ml), then washed twice with water (2 ml). The organic layer was passed through a filter containing magnesium sulfate, and the filter was washed twice with dichloromethane (1 ml), and the filtrate was concentrated. To the residue was added a 90% trifluoroacetic acid (2 ml), and the mixture was stirred at room temperature for 2 hours, and the mixture was concentrated. The residue was dissolved in dichloromethane (2 ml), and an excess amount of ion-exchange resin (Dowex 1-X8, OH-type) was added thereto, and the mixture was stirred at room temperature for one hour. The reaction mixture was filtered, and the filter cake was washed twice with dichloromethane (1 ml), and the filtrate was concentrated to give the title compound.

LC/MS: m/z=527 (MH⁺), retention time: 3.34 min (Condition A)

Examples 418 to 426

The compounds as listed in Table 28 were obtained in a similar manner to in Example 417 or 427.

TABLE 28

| Ex. No. | Structure | Exact MS | m/z | Method for analysis | Retention time (min) | Ref. Ex. |
| --- | --- | --- | --- | --- | --- | --- |
| 418 | 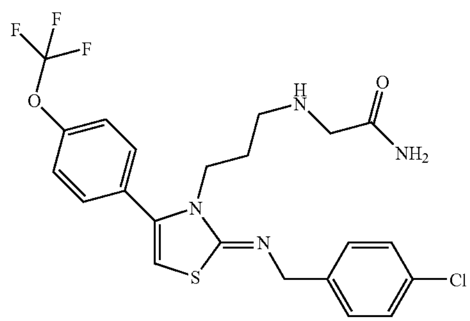 | 498 | 499 | A | 3.25 | 417 |
| 419 | 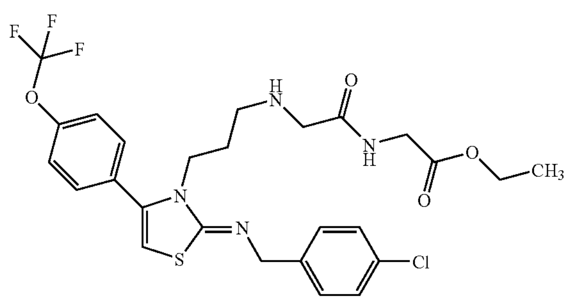 | 584 | 585 | A | 3.40 | 417 |
| 420 | 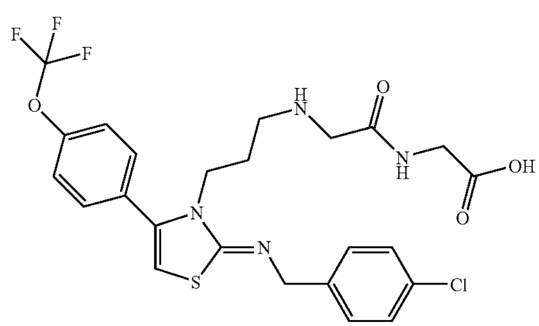 | 556 | 557 | A | 3.25 | 427 |
| 421 | 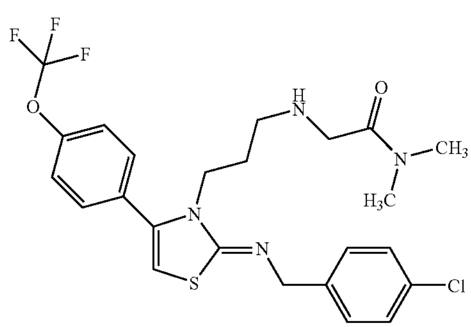 | 526 | 527 | A | 3.33 | 417 |

TABLE 28-continued

| Ex. No. | Structure | Exact MS | m/z | Method for analysis | Retention time (min) | Ref. Ex. |
|---|---|---|---|---|---|---|
| 422 | 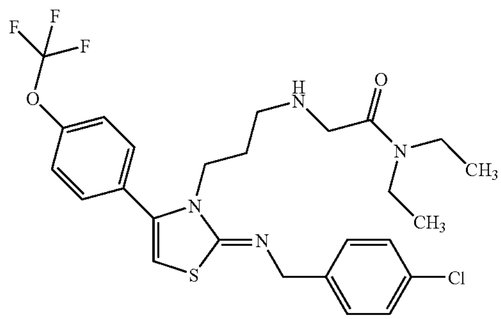 | 554 | 555 | A | 3.44 | 417 |
| 423 | 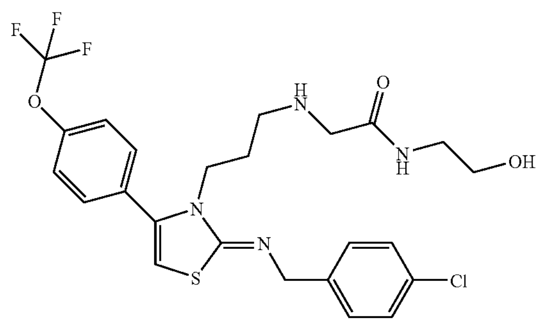 | 542 | 543 | A | 3.23 | 417 |
| 424 | 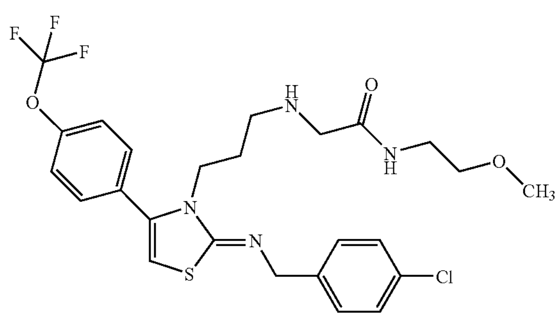 | 556 | 557 | A | 3.30 | 417 |
| 425 | 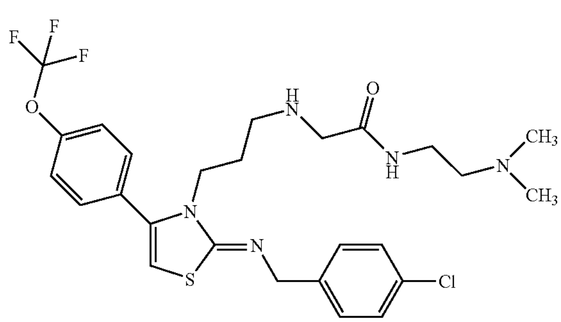 | 569 | 570 | A | 3.12 | 417 |

TABLE 28-continued

| Ex. No. | Structure | Exact MS | m/z | Method for analysis | Retention time (min) | Ref. Ex. |
|---|---|---|---|---|---|---|
| 426 | 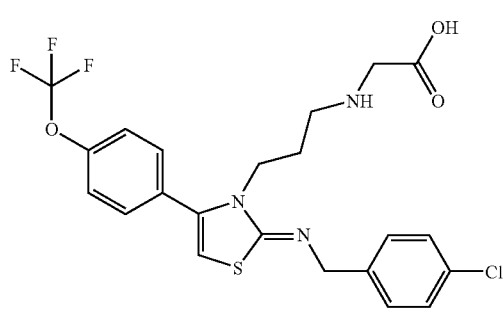 | 540 | 541 | A | 3.35 | 417 |

Example 427

N-{3-[2-[(4-Chlorobenzyl)imino]-4-[4-(trifluoromethoxy)phenyl]-1,3-thiazol-3(2H)-yl]propyl}glycine The compound obtained in Example 415 was protected with a Boc by a conventional method, and a mixture of the resulting compound (1.23 g), a 2N aqueous sodium hydroxide solution (6 ml), and ethanol (6 ml) was stirred for 2 hours, and the solvent was evaporated under reduced pressure. To the residue was added a 10% aqueous citric acid solution, and the mixture was extracted with ethyl acetate. The organic layer was washed with a saturated brine, dried over sodium sulfate, and the solvent was evaporated under reduced pressure. To the residue was added a 4N solution of hydrogen chloride in dioxane (2 ml), and the mixture was stirred at room temperature for 3 hours. To the mixture was added ether, and the precipitates were collected by filtration to give the title compound (148 mg) as hydrochloride.

LC/MS: m/z=500 (MH$^+$), retention time: 3.31 min (Condition A)

Example 428

The following compound was obtained in a similar manner to in Example 427.

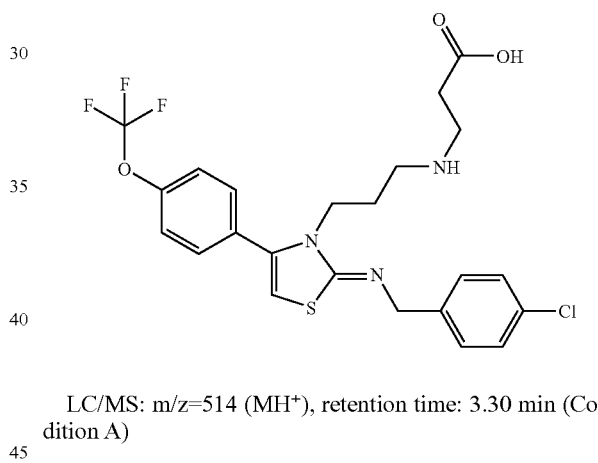

LC/MS: m/z=514 (MH$^+$), retention time: 3.30 min (Condition A)

Example 429

N'-{3-[2-[(4-Chloro-2-methoxybenzyl)imino]-4-(4-fluorophenyl)-1,3-thiazol-3(2H)-yl]propyl}guanidine

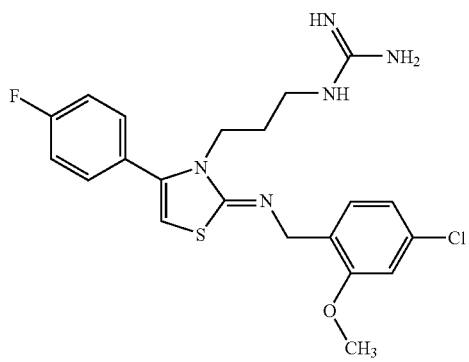

A mixture of the compound (800 mg, free amine) obtained in Example 363, 1,3-bis(tert-butoxycarbonyl)-2-methyl-isothiourea (576 mg) and tetrahydrofuran (5 ml) was refluxed for 3 hours, and the solvent was evaporated under reduced pressure. The residue was purified by silica gel column chromatography [n-hexane:ethyl acetate (4:1)) to give the reaction intermediate (529 mg). To the resulting reaction intermediate (1000 mg) was added a 4N solution of hydrochloric acid in dioxane (20 ml), and the mixture was stirred at room temperature for 4 hours, and the solvent was evaporated under reduced pressure. To the residue was added aqueous ammonia, and the mixture was extracted with chloroform. The organic layer was washed with a saturated brine, dried over sodium sulfate, and the solvent was evaporated under reduced pressure. The residue was purified by silica gel column chromatography [10% methanol in chloroform] to give the title compound (278 mg).

LC/MS: m/z=448 (MH$^+$), retention time: 3.08 min (Condition A)

Example 430

N'-{3-[2-[(4-Chlorobenzyl)imino]-4-[4-(trifluoromethoxy)phenyl]-1,3-thiazol-3(2H)-yl]propyl}ethanesulfonamide

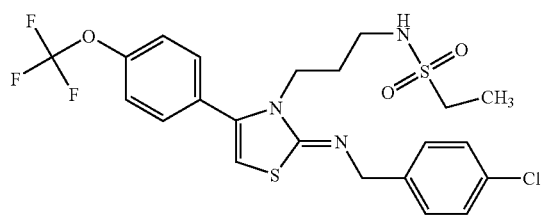

The title compound was synthesized by combinatorial chemistry technique. That is, to a solution of the compound (free amino compound) obtained in Example 364 in tetrahydrofuran (45.3 μmol/ml) (1 ml) were added a solution of triethylamine in tetrahydrofuran (118 μmol/ml) (500 μl) and a solution of ethanesulfonyl chloride in tetrahydrofuran (58.9 μmol/ml) (1 ml), and the mixture was stirred at room temperature for 6 hours. To the reaction mixture was added Tris-Amine resin (manufactured by Argonaut) (about 10 mg) and isocyanate resin (manufactured by Argonaut) (about 20 mg), and the mixture was stirred at room temperature overnight. The reaction mixture was filtered, and the filter cake was washed twice with chloroform (1 ml), and the filtrate was washed with a saturated aqueous sodium hydrogen carbonate solution (2 ml), and then further washed twice with water (2 ml). The organic layer was passed through a filter containing magnesium sulfate, and the filter was washed twice with chloroform (1 ml), and the filtrate was concentrated to give the title compound.

LC/MS: m/z=534 (MH$^+$), retention time: 3.88 min (Condition A)

Example 431

3-(3-Aminopropyl)-N-(4-chlorophenyl)-2-[(2,4-dimethoxybenzoyl)imino]-2,3-dihydro-1,3-thiazol-4-carboxamide 3-({3-[4-(1,3-Benzodioxol-5-yl)-2-{[4-(trifluo4-dimethoxyphenyl)-imino]-2,3-dihydro-1,3-thiazol-4-carboxylic acid

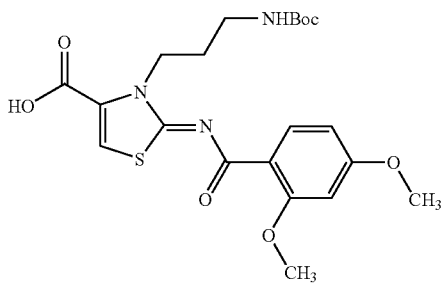

A mixture of the thiourea (5.00 g) obtained in Reference Example 71, ethyl 2-bromopyruvate (1.74 ml) and ethanol (130 ml) was heated with stirring at 60° C., and further subjected to protection with Boc by a conventional method. The resulting ester compound (2.46 g) was subjected to hydrolysis by a conventional method to give the title compound.

(2) 3-(3-Aminopropyl)-N-(4-chlorophenyl)-2-[(2,4-dimethoxybenzoyl)-imino]-2,3-dihydro-1,3-thiazol-4-carboxamide

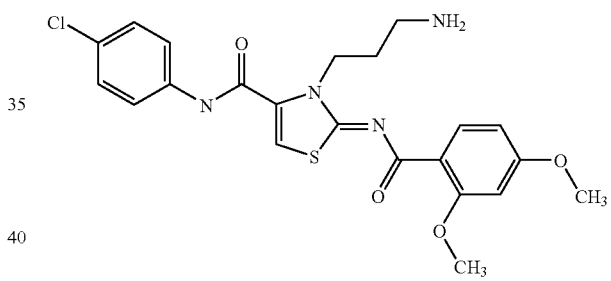

The title compound was synthesized by combinatorial chemistry technique. That is, to a solution of the compound obtained in the above (1) in dichloromethane (45.8 μmol/ml) were added a solution of 4-chlorophenylamine in dichloromethane (35.0 μmol/ml) (1 ml), a solution of diisopropylethylamine in dichloromethane (35.0 μmol/ml) (1 ml), and a suspension of carbodiimide resin in dichloromethane (79.2 mg/ml, manufactured by Argonaut) (1 ml), and the mixture was stirred at room temperature overnight. The reaction mixture was filtered, and the filter cake was washed twice with dichloromethane (1 ml), and the filtrate was washed with a saturated aqueous sodium hydrogen carbonate solution (2 ml), and then further washed twice with water (2 ml). The organic layer was passed through a filter containing magnesium sulfate, and the filter was washed twice with chloroform (1 ml), and the filtrate was concentrated. To the residue was added a 90% trifluoroacetic acid (2 ml), and the mixture was stirred at room temperature for 2 hours, and then the mixture was concentrated to give the title compound as fluoroacetate.

LC/MS: m/z=475 (MH$^+$), retention time: 3.40 min (Condition A)

Examples 432 to 445

The compounds as listed in Table 29 were obtained in a similar manner to in Example 431, 362 or 373.

TABLE 29

| Ex. No. | Structure | Exact MS | m/z | Method for analysis | Retention time (min) | Ref. Ex. |
|---|---|---|---|---|---|---|
| 432 | 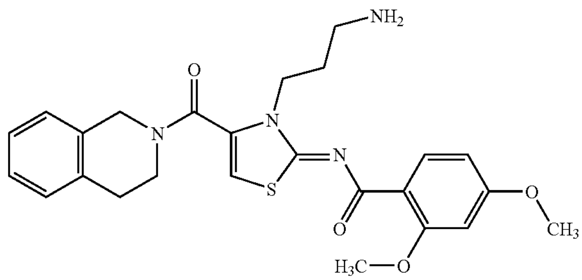 | 481 | 482 | A | 3.31 | 431 |
| 433 | 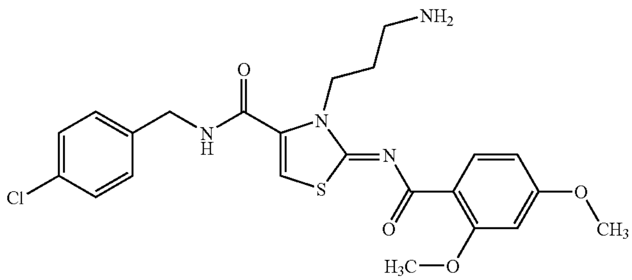 | 488 | 489 | A | 3.37 | 431 |
| 434 | 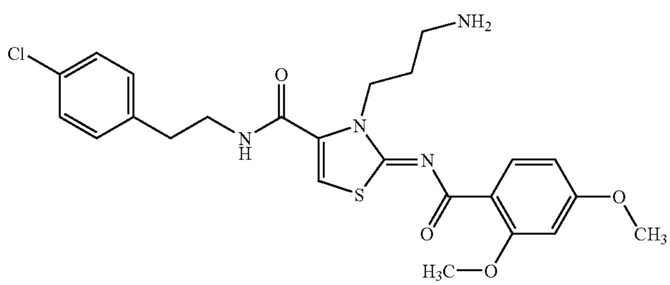 | 502 | 503 | A | 3.45 | 431 |
| 435 | 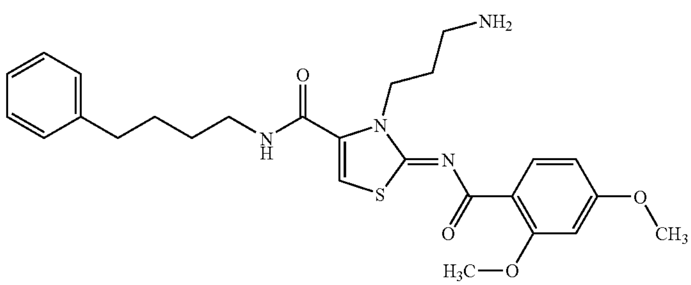 | 497 | 498 | A | 3.56 | 431 |
| 436 | 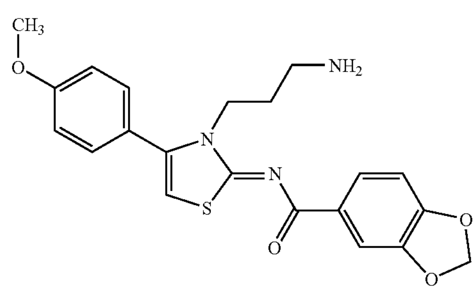 | 411 | 412 | A | 3.36 | 362 |

TABLE 29-continued

| Ex. No. | Structure | Exact MS | m/z | Method for analysis | Retention time (min) | Ref. Ex. |
|---|---|---|---|---|---|---|
| 437 | 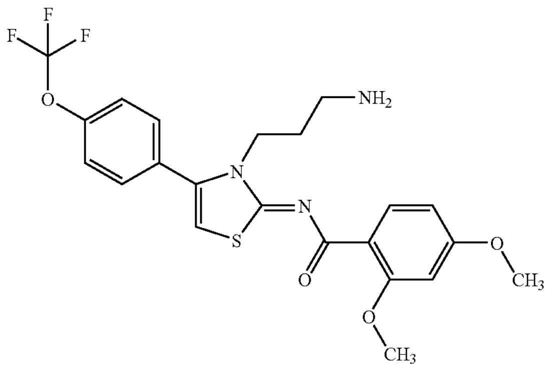 | 481 | 482 | A | 3.52 | 362 |
| 438 | 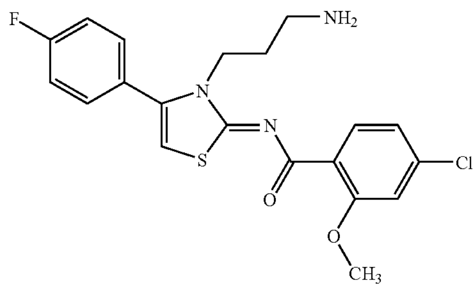 | 419 | 420 | A | 3.36 | 362 |
| 439 | 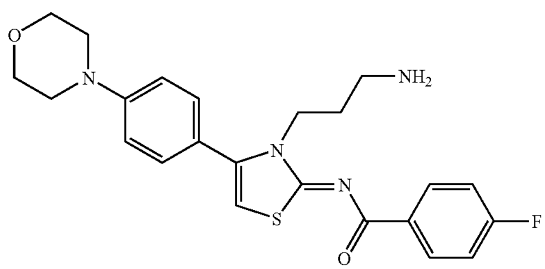 | 441 | 442 | A | 3.36 | 362 |
| 440 | 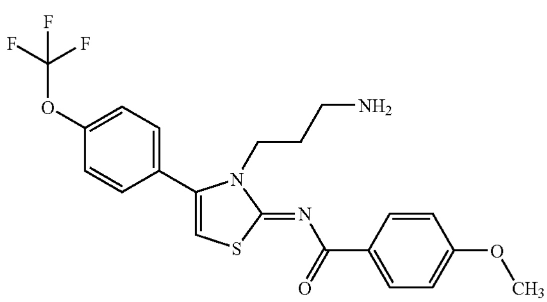 | 451 | 452 | A | 3.66 | 362 |
| 441 | 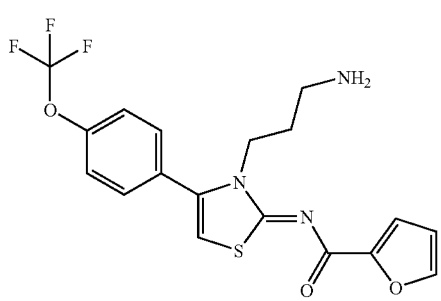 | 411 | 412 | A | 3.43 | 362 |

TABLE 29-continued

| Ex. No. | Structure | Exact MS | m/z | Method for analysis | Retention time (min) | Ref. Ex. |
|---|---|---|---|---|---|---|
| 442 | 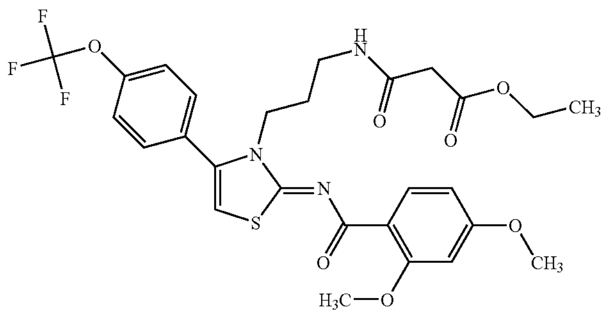 | 595 | 596 | A | 4.04 | 373 |
| 443 | 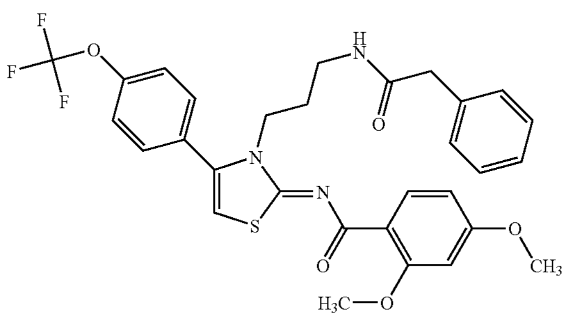 | 599 | 600 | B | 2.6 | 373 |
| 444 | 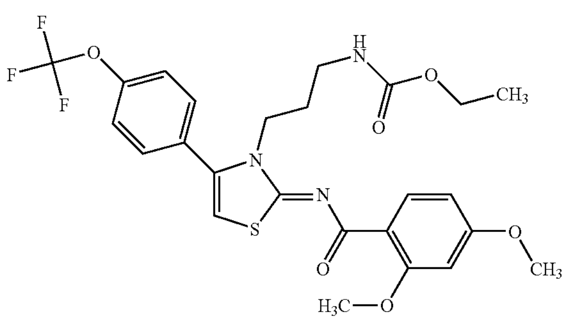 | 553 | 554 | A | 4.15 | 373 |
| 445 | 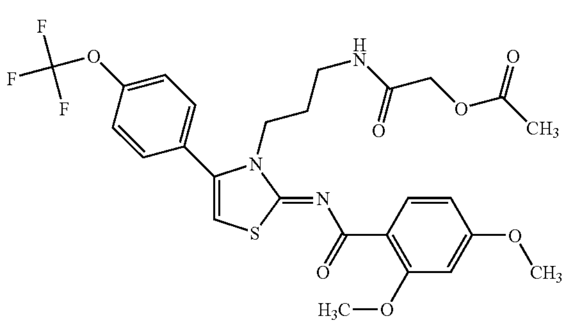 | 581 | 582 | A | 3.85 | 373 |

Example 446

N-[3-[3-(Acetoamino)propyl]-4-[4-(trifluoromethoxy)phenyl]-1,3-thiazol-2(3H)-ylidene]-2,4-dimethoxybenzamide

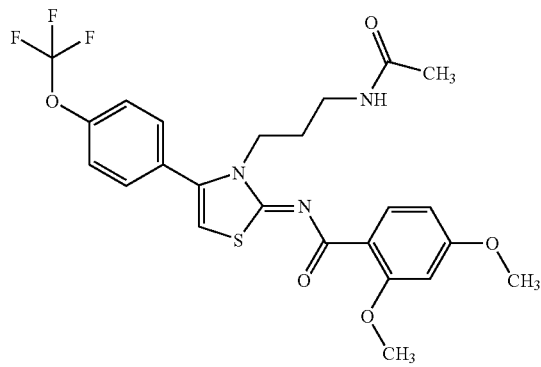

A mixture of thiourea (1.00 g) obtained in Reference Example 80, 2-bromo-4'-(trifluoromethoxy)acetophenone (0.87 g) and isopropanol (10 ml) was stirred at 70° C. for one hour, and the mixture was allowed to cool, and the resulting solid (1.32 g) was collected by filtration. To the resulting solid (3.00 g) was added a 25% solution of hydrobromic acid in acetic acid (9 ml), and the mixture was stirred for 4 hours. The solvent was evaporated under reduced pressure, and the residue was diluted with acetone, and the resulting solid (1.88 g) was collected by filtration. A mixture of the solid thus obtained (1.00 g), triethylamine (0.70 ml), 2,4-dimethoxybenzoyl chloride (0.50 g) and tetrahydrofuran (7 ml) was stirred under ice-cooling for 0.5 hour. To the mixture was added water, and the mixture was extracted with ethyl acetate. The organic layer was washed with a saturated brine, dried over sodium sulfate, and the solvent was evaporated under reduced pressure, and then the residue was crystallized from toluene to give the title compound (0.93 g).

m.p.: 131-132° C. $^1$H-NMR (CDCl$_3$): δ 1.61-1.65 (5H, m), 3.07 (2H, m), 3.86 (3H, s), 3.93 (3H, s), 4.33 (2H, t, J=6.2), 6.54-6.57 (3H, m), 6.79 (1H, m), 7.35 (2H, d, J=8.1), 7.43-7.46 (2H, m), 8.11 (1H, dd, J=7.0, J=2.0). LC/MS: m/z=524 (MH$^+$), retention time: 3.72 min (Condition A)

Examples 447 to 472

The compounds as listed in Table 30 were obtained in a similar manner to in Example 373, 446 or 431.

TABLE 30

| Ex. No. | Structure | Exact MS | m/z | Method for analysis | Retention time (min) | Ref. Ex. |
|---------|-----------|----------|-----|---------------------|----------------------|----------|
| 447 | 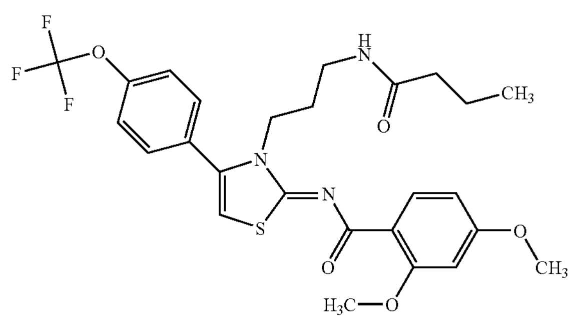 | 551 | 552 | A | 4 | 373 |
| 448 | 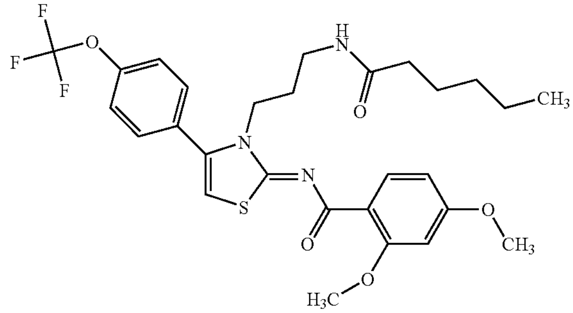 | 579 | 580 | B | 2.85 | 373 |

TABLE 30-continued

| Ex. No. | Structure | Exact MS | m/z | Method for analysis | Retention time (min) | Ref. Ex. |
|---|---|---|---|---|---|---|
| 449 | 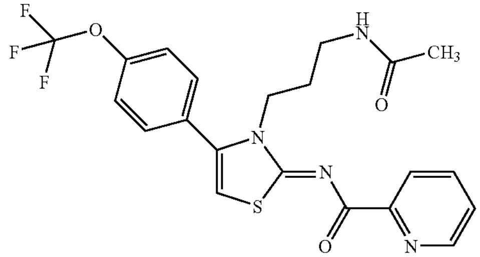 | 464 | 465 | A | 3.32 | 446 |
| 450 | 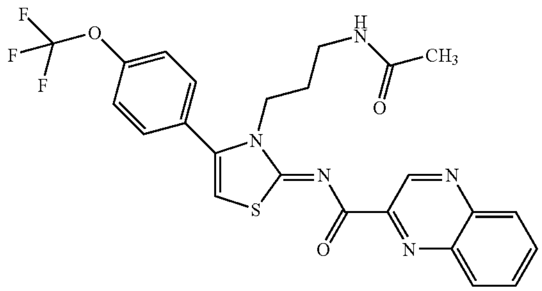 | 515 | 516 | A | 4.01 | 446 |
| 451 | 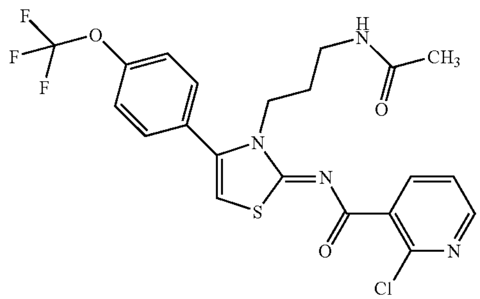 | 498 | 499 | A | 4.00 | 446 |
| 452 | 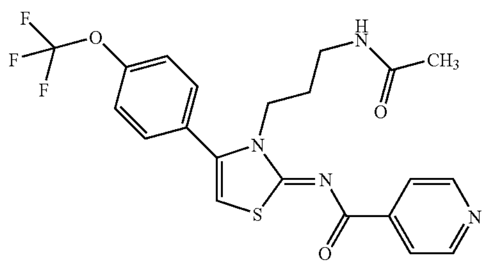 | 463 | 465 | A | 3.36 | 446 |
| 453 | 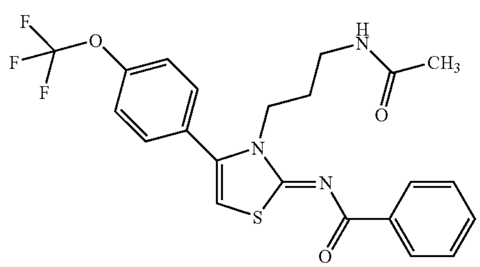 | 462 | 464 | B | 2.64 | 446 |

TABLE 30-continued
| Ex. No. | Structure | Exact MS | m/z | Method for analysis | Retention time (min) | Ref. Ex. |
|---|---|---|---|---|---|---|
| 454 | 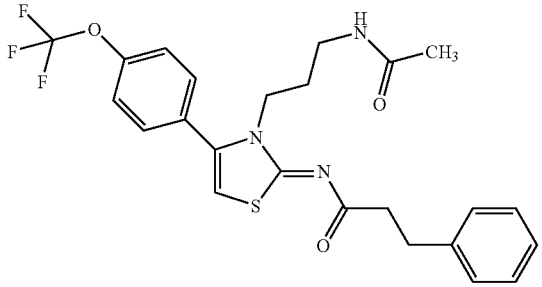 | 491 | 492 | A | 4.09 | 446 |
| 455 | 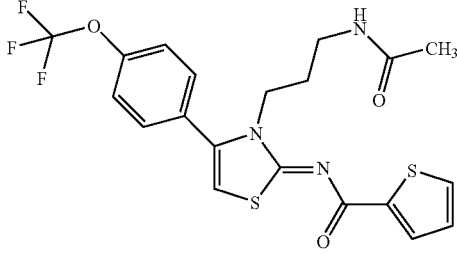 | 469 | 470 | B | 2.35 | 446 |
| 456 | 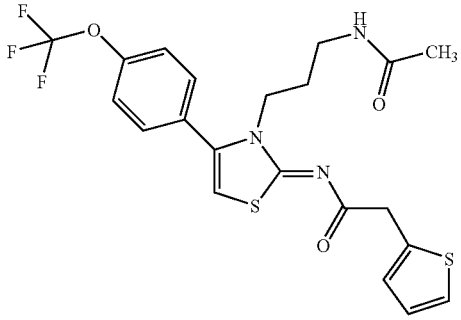 | 483 | 484 | B | 2.06 | 446 |
| 457 | 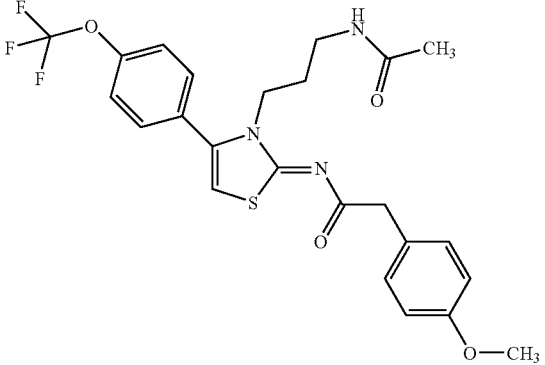 | 507 | 508 | A | 4.05 | 446 |

TABLE 30-continued

| Ex. No. | Structure | Exact MS | m/z | Method for analysis | Retention time (min) | Ref. Ex. |
|---|---|---|---|---|---|---|
| 458 | 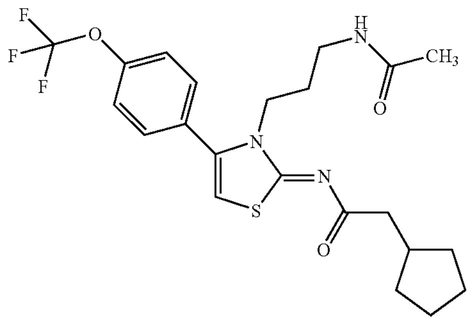 | 469 | 470 | A | 4.02 | 446 |
| 459 | 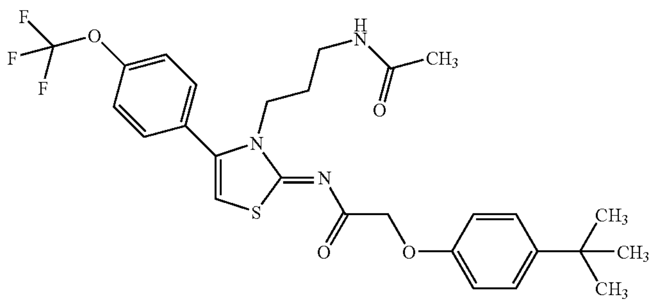 | 549 | 550 | B | 3.75 | 446 |
| 460 | 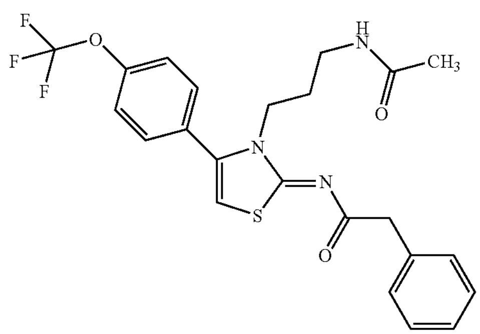 | 477 | 478 | A | 4.09 | 446 |
| 461 | 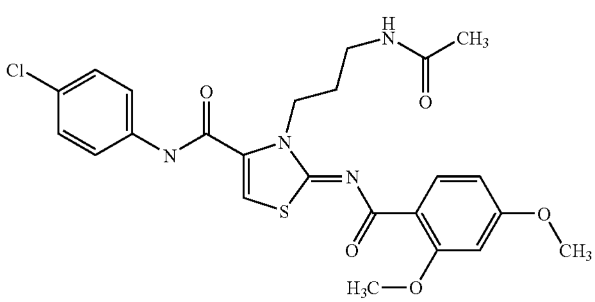 | 516 | 517 | A | 3.84 | 431 |
| 462 | 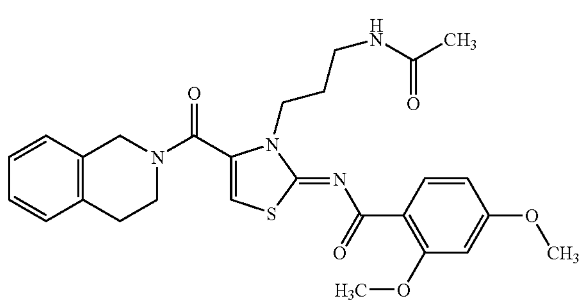 | 522 | 523 | A | 3.61 | 431 |

TABLE 30-continued

| Ex. No. | Structure | Exact MS | m/z | Method for analysis | Retention time (min) | Ref. Ex. |
|---|---|---|---|---|---|---|
| 463 | 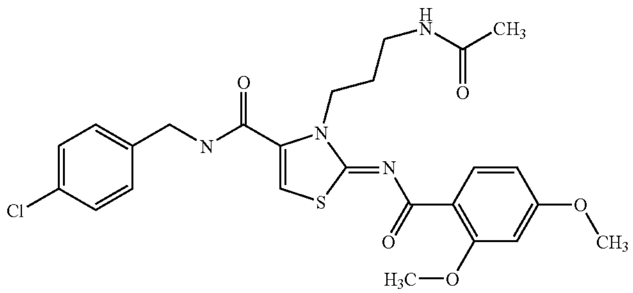 | 530 | 531 | A | 3.73 | 431 |
| 464 | 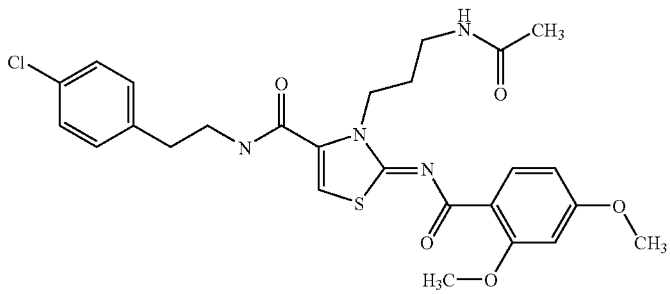 | 544 | 545 | A | 3.8 | 431 |
| 465 | 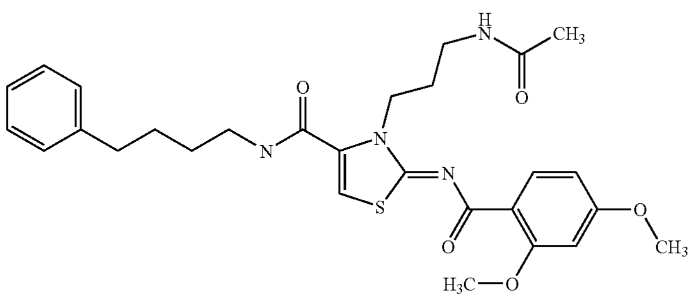 | 538 | 540 | A | 3.89 | 431 |
| 466 | 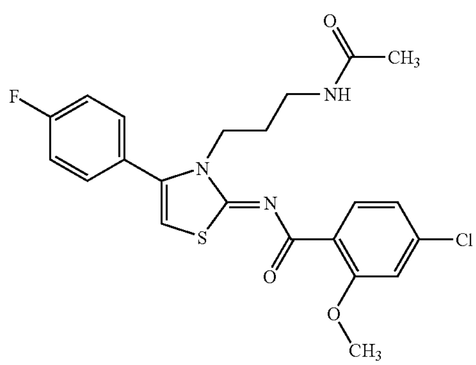 | 461 | 462 | A | 3.83 | 373 |
| 467 | 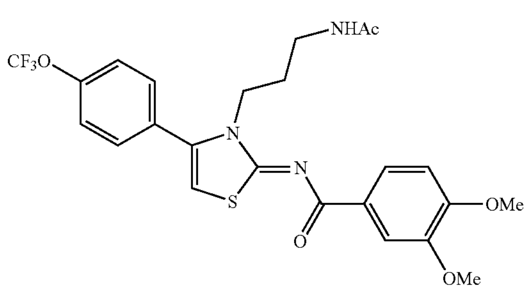 | 523 | 524 | A | 4.16 | 446 |

TABLE 30-continued

| Ex. No. | Structure | Exact MS | m/z | Method for analysis | Retention time (min) | Ref. Ex. |
|---|---|---|---|---|---|---|
| 468 | 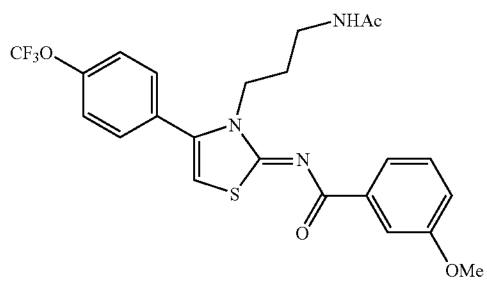 | 493 | 494 | B | 2.78 | 446 |
| 469 | 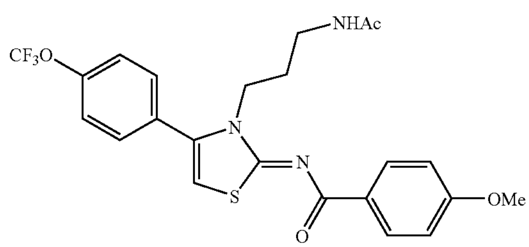 | 493 | 494 | B | 2.67 | 446 |
| 470 | 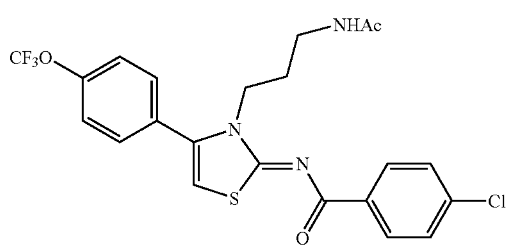 | 497 | 498 | B | 3.34 | 446 |
| 471 | 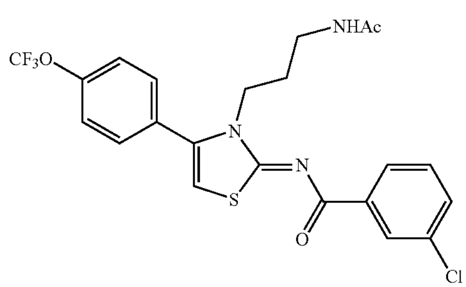 | 497 | 498 | B | 3.36 | 446 |
| 472 | 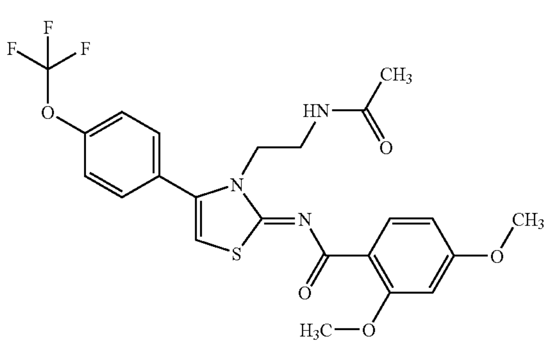 | 509 | 510 | A | 3.77 | 373 |

Example 473

N-[3-[3-(Acetylamino)propyl]-4-({[(4-methylphenyl)sulfonyl]amino}-methyl)thiazol-2(3H)-ylidene]-2,4-dimethoxybenzamide

(1) Ethyl 3-[3-(acetylamino)propyl]-2-[(2,4-dimethoxybenzoyl)imino]-2,3-dihydrothiazol-4-carboxylate

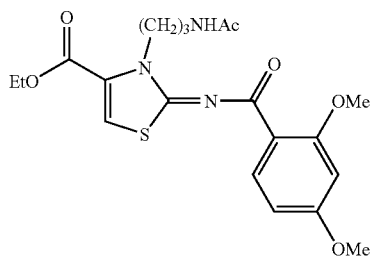

A mixture of the thiourea (24.64 g) obtained in Reference Example 93, ethyl bromopyruvate (10 ml) and ethanol (700 ml) was heated with stirring at 70° C. under nitrogen atmosphere. Five hours thereafter, the reaction mixture was concentrated under reduced pressure, and the residue was crystallized from ethyl acetate to give the title compound (29.36 g) as hydrobromide.

(2) N-[3-[3-(Acetylamino)propyl]-4-(hydroxymethyl)thiazol-2(3H)-ylidene]-2,4-dimethoxybenzamide

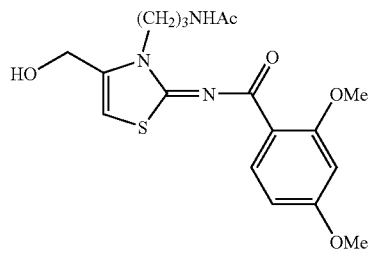

To a solution of the ester compound (10 g) which was prepared by converting the hydrobromide obtained in the above (1) into a free compound in tetrahydrofuran (300 ml) was added lithium borohydride (2.0 g), and the mixture was stirred at room temperature overnight under nitrogen atmosphere. To the reaction mixture was added a 10% aqueous citric acid solution under ice-cooling, and the excess lithium borohydride was decomposed, and the mixture was extracted with chloroform. The organic layer was washed with a saturated brine, dried over sodium sulfate, and the solvent was evaporated under reduced pressure to give the title compound (8.3 g).

(3) N-[3-[3-(Acetylamino)propyl]-4-(azidomethyl)thiazol-2(3H)-ylidene]-2,4-dimethoxybenzamide

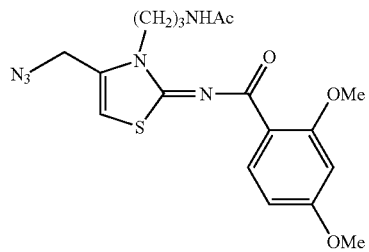

The compound (3.45 g) obtained in the above (2) and triethylamine (976 mg) were dissolved in DMF (35 ml), and thereto was added dropwise methanesulfonyl chloride (0.75 ml) under ice-cooling. The mixture was stirred at the same temperature for 2 hours, and thereto was added sodium azide (627 mg), and the mixture was further stirred for 2 hours. Water was added to the reaction mixture, and the mixture was extracted with ethyl acetate. The organic layer was washed with a saturated brine, dried over sodium sulfate, and the solvent was evaporated under reduced pressure. The residue was purified by silica gel column chromatography [chloroform:methanol (98:2)] to give the title compound (3.48 g) as oil.

(4) N-[3-[3-(Acetylamino)propyl]-4-(aminoethyl)thiazol-2(3H)-ylidene]-2,4-dimethoxybenzamide

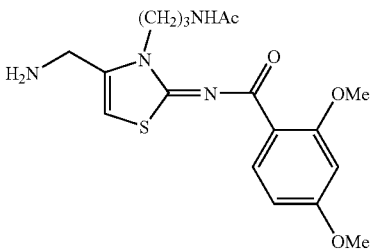

To a solution of the compound (2.3 g) obtained in the above (3) in ethanol (46 ml) was added a 10% palladium on carbon catalyst (230 mg), and the mixture was subjected to hydrogenation under atmospheric pressure. Four hours thereafter, the reaction mixture was filtered through cerite, and the filtrate was concentrated under reduced pressure. The residue was dissolved in a 10% aqueous citric acid solution, and the mixture was washed with chloroform. The aqueous layer was basified with aqueous ammonia, and the mixture was extracted with chloroform. The organic layer was washed with a saturated brine, dried over sodium sulfate, and the solvent was evaporated under reduced pressure to give the title compound (3.48 g) as oil.

5) N-[3-[3-(Acetylamino)propyl]-4-({[(4-methylphenyl)sulfonyl]amino}-methyl)thiazol-2(3H)-ylidene]-2,4-dimethoxybenzamide

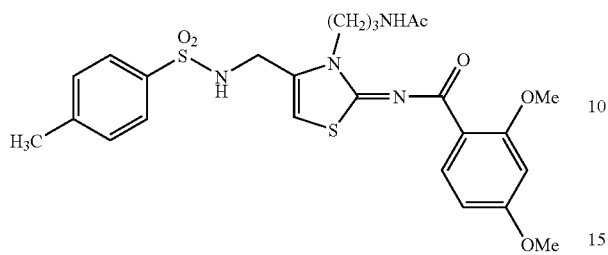

The compound (200 mg) obtained in the above (4) and triethylamine (100 mg) were dissolved in tetrahydrofuran (5 ml), and thereto was added p-toluenesulfonyl chloride (117 mg) at room temperature under nitrogen atmosphere. Two hours thereafter, to the reaction mixture was added a 10% aqueous citric acid solution, and the mixture was extracted with chloroform. The organic layer was washed with a saturated brine, dried over sodium sulfate, and the solvent was evaporated under reduced pressure. The residue was purified by silica gel column chromatography [chloroform:methanol (97:32)] to give the title compound (240 mg) as amorphous.

LC/MS: m/z=547 (MH$^+$), retention time: 3.43 min (Condition A)

Examples 474 to 542

The compounds as listed in Table 31 were obtained in a similar manner to in Example 321, 373, 382, 402, 409, 411, 427, 417, 429, 430 or 446.

TABLE 31

| Ex. No. | Structure | Exact MS | m/z | Method for analysis | Retention time (min) | Ref. Ex. |
|---------|-----------|----------|-----|---------------------|----------------------|----------|
| 474 | 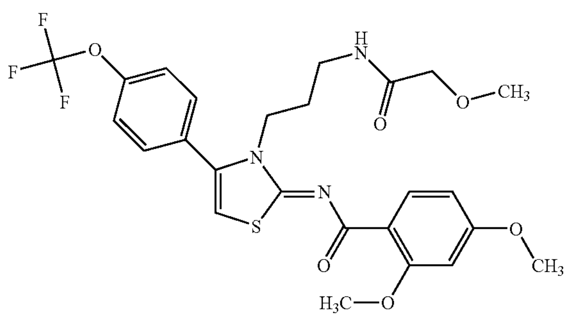 | 553 | 554 | A | 3.84 | 382 |
| 475 | 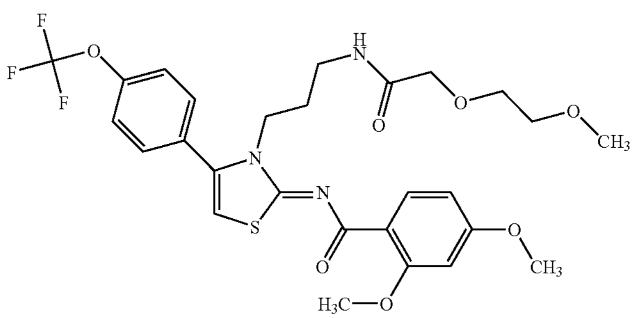 | 597 | 598 | A | 3.85 | 382 |
| 476 | 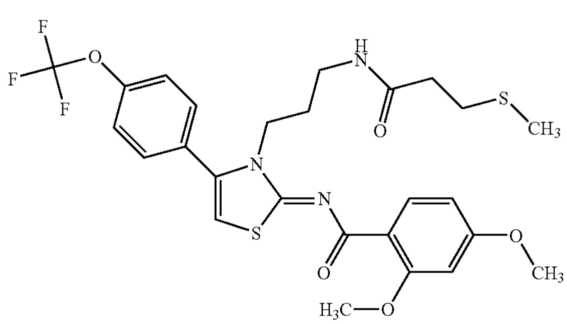 | 583 | 584 | A | 4.03 | 382 |

TABLE 31-continued

| Ex. No. | Structure | Exact MS | m/z | Method for analysis | Retention time (min) | Ref. Ex. |
|---|---|---|---|---|---|---|
| 477 | 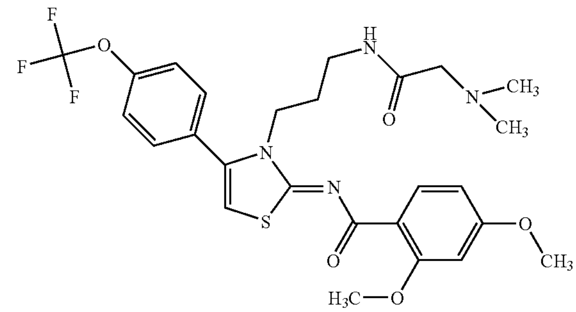 | 566 | 567 | A | 3.43 | 382 |
| 478 | 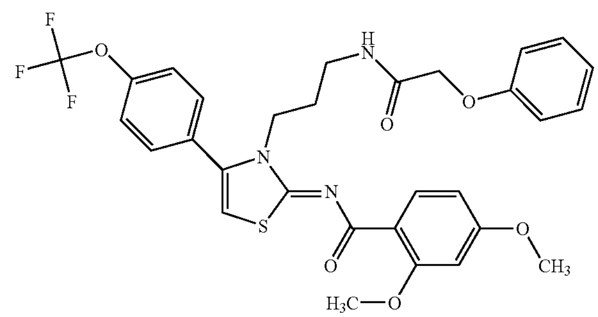 | 615 | 616 | B | 2.78 | 382 |
| 479 | 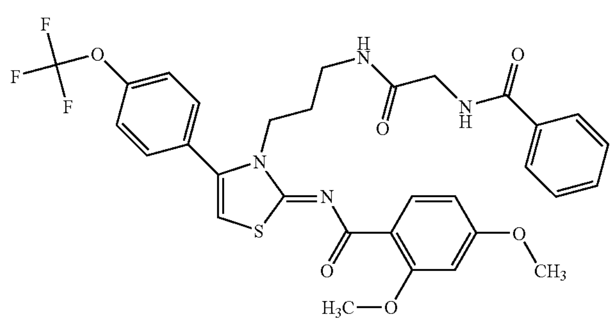 | 642 | 643 | A | 3.96 | 382 |
| 480 | 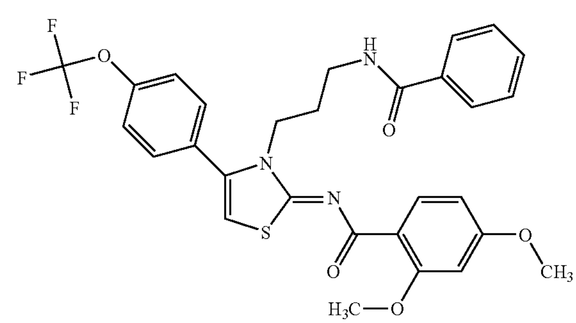 | 585 | 586 | A | 4.17 | 382 |

TABLE 31-continued
| Ex. No. | Structure | Exact MS | m/z | Method for analysis | Retention time (min) | Ref. Ex. |
|---|---|---|---|---|---|---|
| 481 | 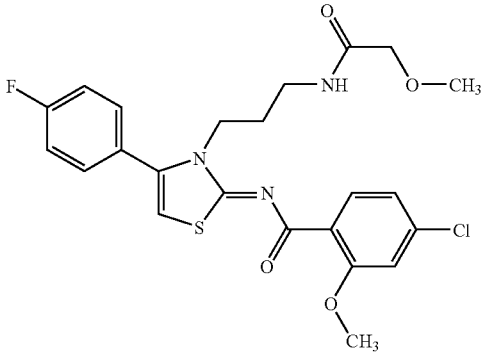 | 492 | 493 | A | 3.99 | 373 |
| 482 | 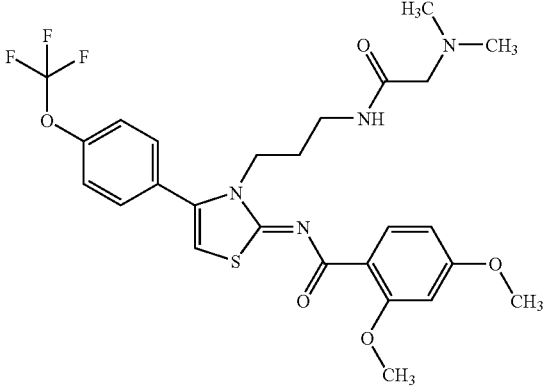 | 566 | 567 | A | 3.39 | 382 |
| 483 | 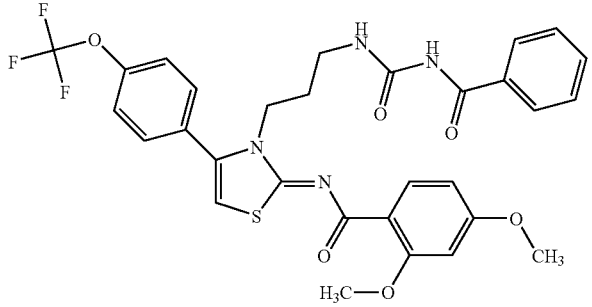 | 628 | 629 | A | 4.18 | 402 |
| 484 | 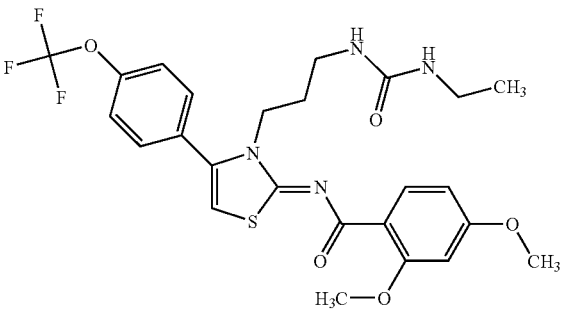 | 552 | 553 | A | 3.75 | 402 |

TABLE 31-continued

| Ex. No. | Structure | Exact MS | m/z | Method for analysis | Retention time (min) | Ref. Ex. |
|---|---|---|---|---|---|---|
| 485 | 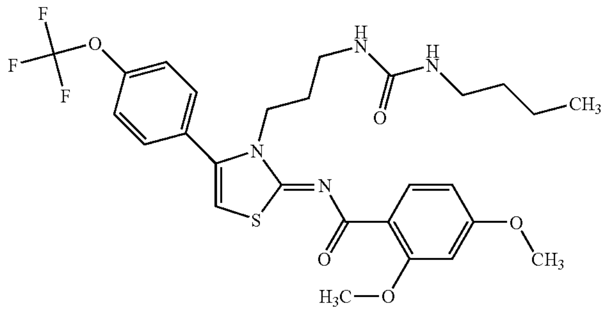 | 580 | 581 | A | 4.05 | 402 |
| 486 | 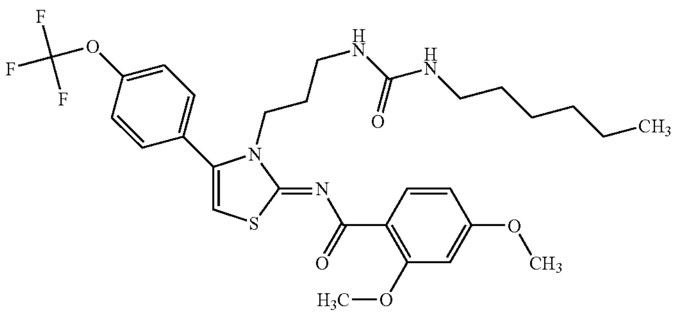 | 608 | 609 | B | 2.85 | 402 |
| 487 | 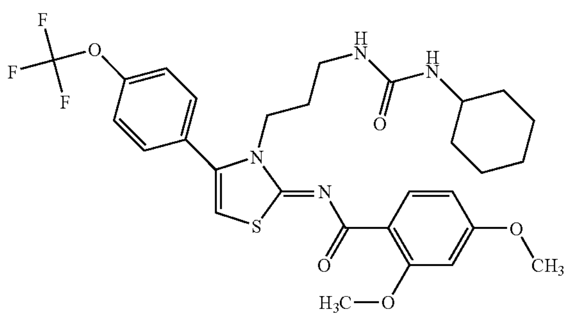 | 606 | 607 | B | 2.49 | 402 |
| 488 | 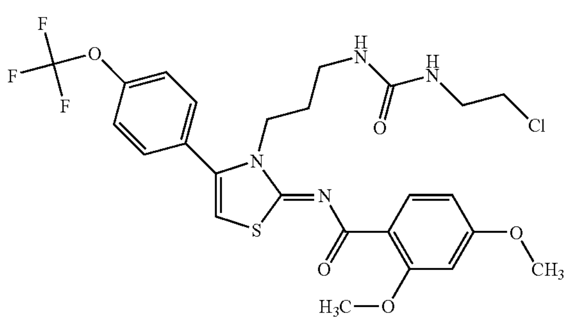 | 586 | 587 | A | 3.89 | 402 |

TABLE 31-continued

| Ex. No. | Structure | Exact MS | m/z | Method for analysis | Retention time (min) | Ref. Ex. |
|---|---|---|---|---|---|---|
| 489 | 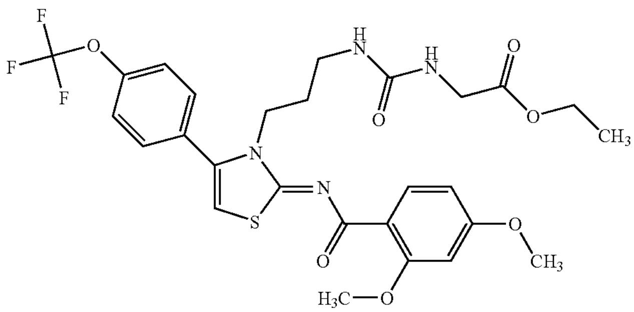 | 610 | 611 | A | 3.84 | 402 |
| 490 | 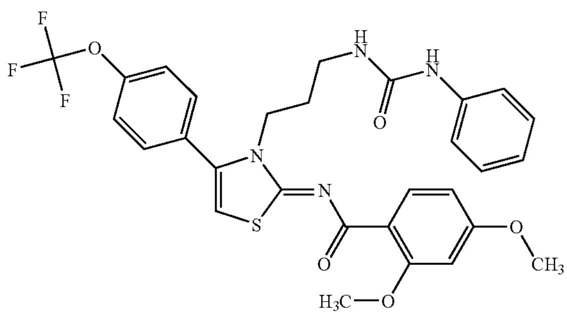 | 600 | 601 | A | 4.16 | 402 |
| 491 | 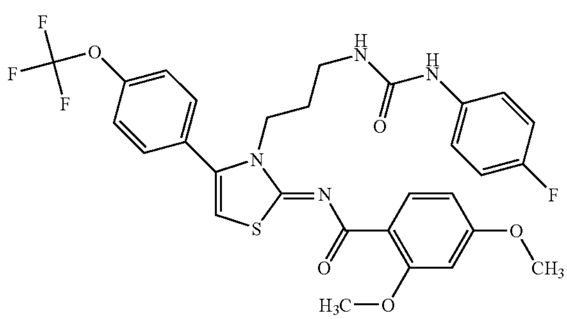 | 618 | 619 | A | 4.16 | 402 |
| 492 | 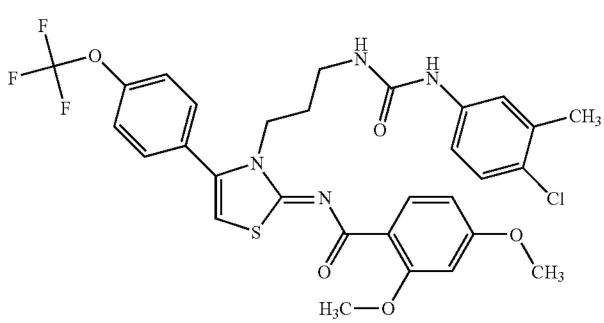 | 648 | 649 | B | 3.14 | 402 |

TABLE 31-continued

| Ex. No. | Structure | Exact MS | m/z | Method for analysis | Retention time (min) | Ref. Ex. |
|---|---|---|---|---|---|---|
| 493 | 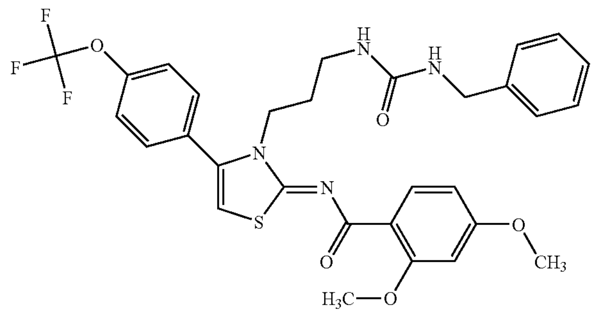 | 614 | 615 | A | 4.11 | 402 |
| 494 | 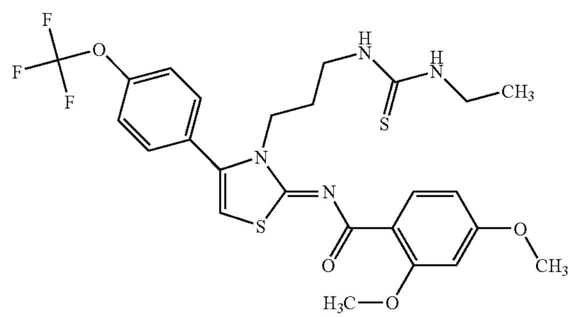 | 568 | 569 | A | 4.05 | 402 |
| 495 | 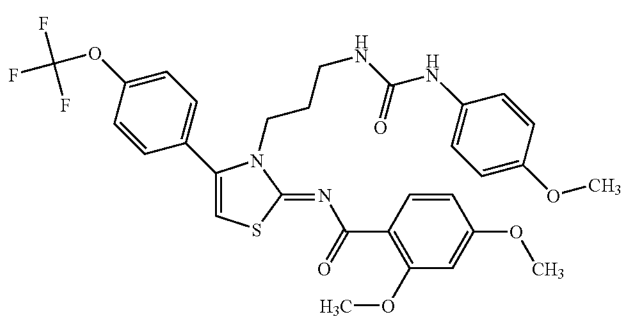 | 630 | 631 | A | 4.05 | 402 |
| 496 | 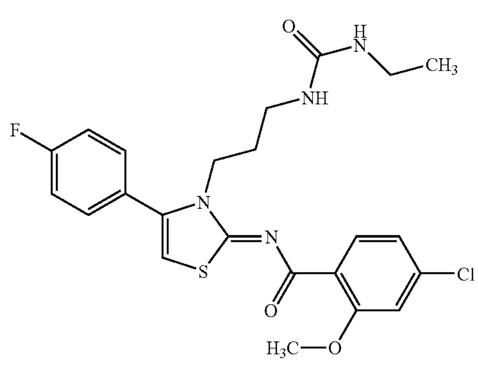 | 490 | 491 | A | 3.86 | 402 |

TABLE 31-continued

| Ex. No. | Structure | Exact MS | m/z | Method for analysis | Retention time (min) | Ref. Ex. |
|---|---|---|---|---|---|---|
| 497 | 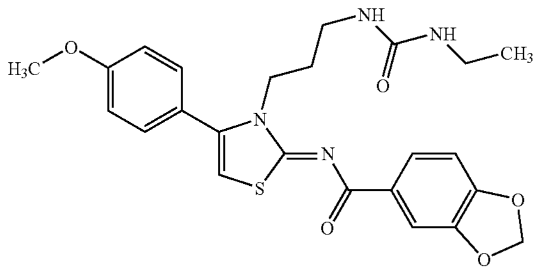 | 482 | 483 | A | 4.00 | 402 |
| 498 | 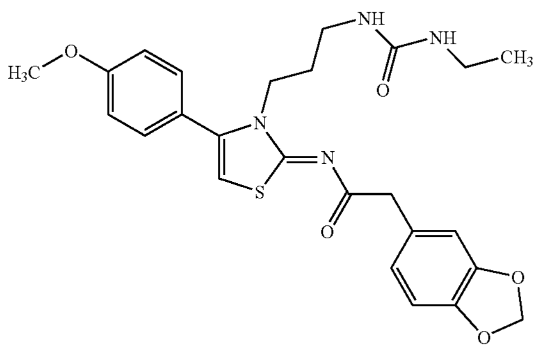 | 496 | 497 | A | 3.63 | 402 |
| 499 | 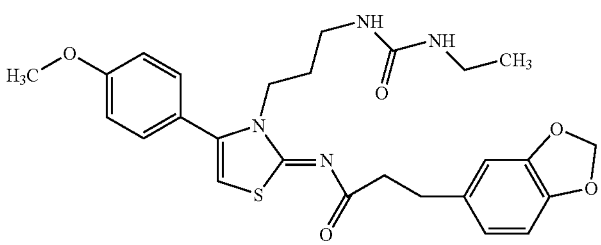 | 510 | 511 | A | 4.13 | 402 |
| 500 | 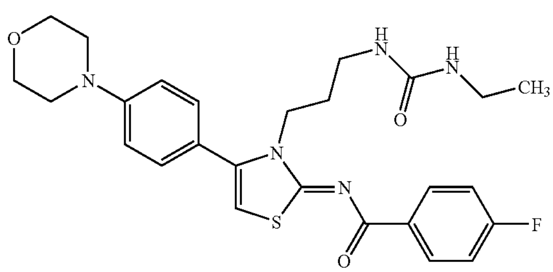 | 511 | 512 | A | 4.01 | 402 |
| 501 | 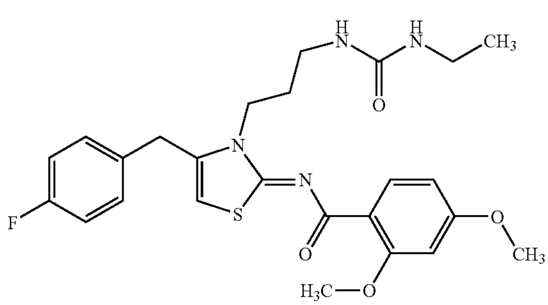 | 500 | 501 | A | 3.53 | 402 |

TABLE 31-continued

| Ex. No. | Structure | Exact MS | m/z | Method for analysis | Retention time (min) | Ref. Ex. |
|---|---|---|---|---|---|---|
| 502 | 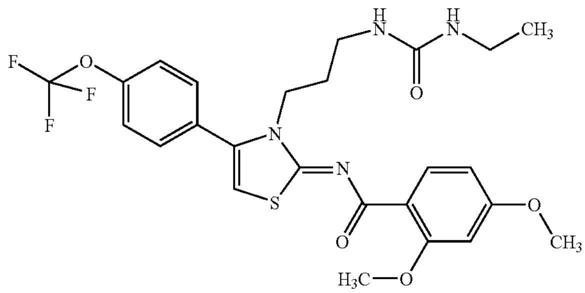 | 522 | 523 | B | 2.87 | 402 |
| 503 | 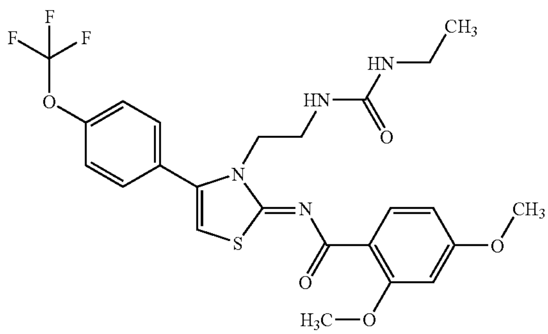 | 538 | 539 | A | 3.76 | 402 |
| 504 | 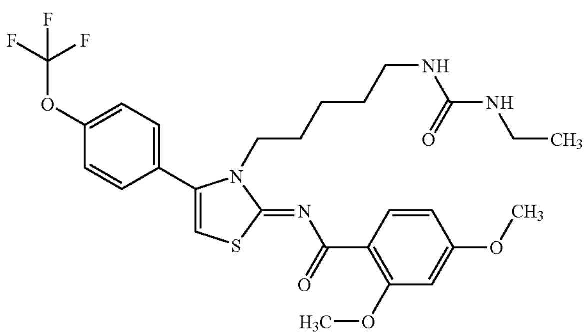 | 580 | 581 | A | 3.84 | 402 |
| 505 | 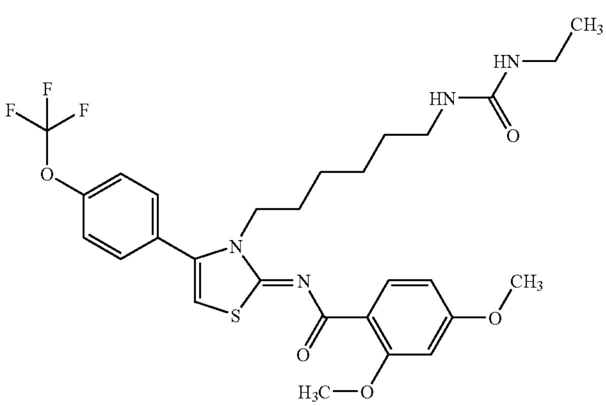 | 594 | 595 | A | 3.91 | 402 |

TABLE 31-continued

| Ex. No. | Structure | Exact MS | m/z | Method for analysis | Retention time (min) | Ref. Ex. |
|---|---|---|---|---|---|---|
| 506 | 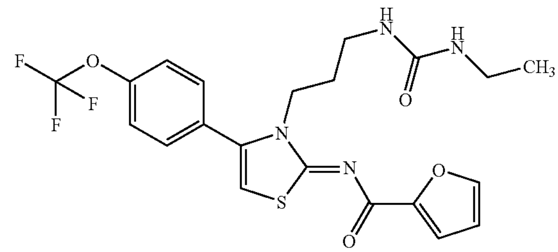 | 482 | 483 | A | 4.10 | 402 |
| 507 | 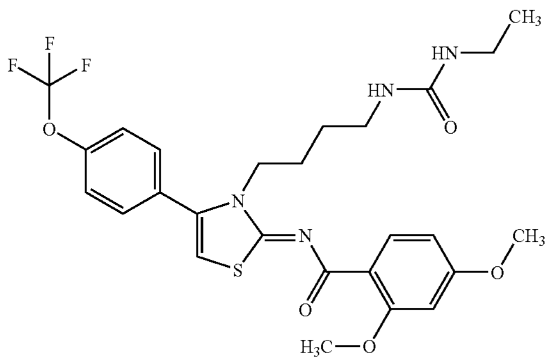 | 566 | 567 | A | 3.78 | 402 |
| 508 | 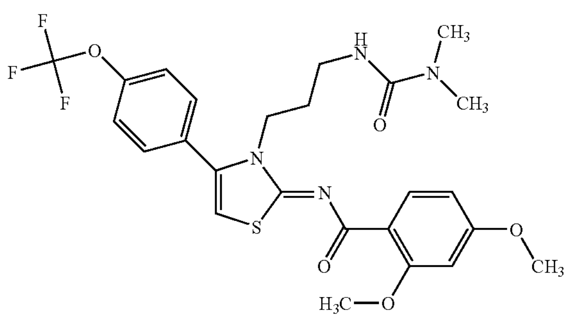 | 552 | 553 | A | 3.72 | 373 |
| 509 | 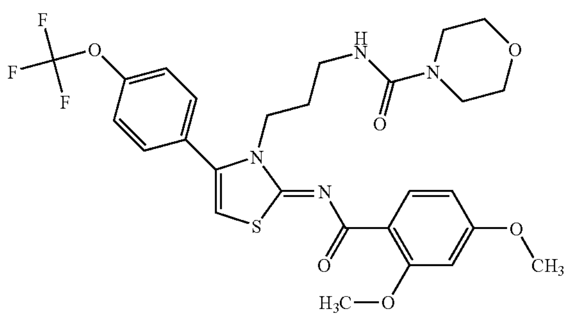 | 594 | 595 | A | 3.71 | 373 |
| 510 | 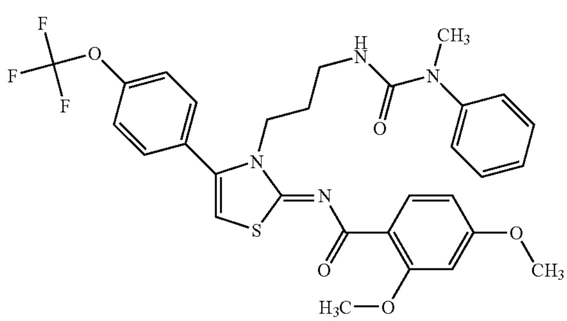 | 614 | 615 | A | 4.14 | 373 |

TABLE 31-continued

| Ex. No. | Structure | Exact MS | m/z | Method for analysis | Retention time (min) | Ref. Ex. |
|---|---|---|---|---|---|---|
| 511 | 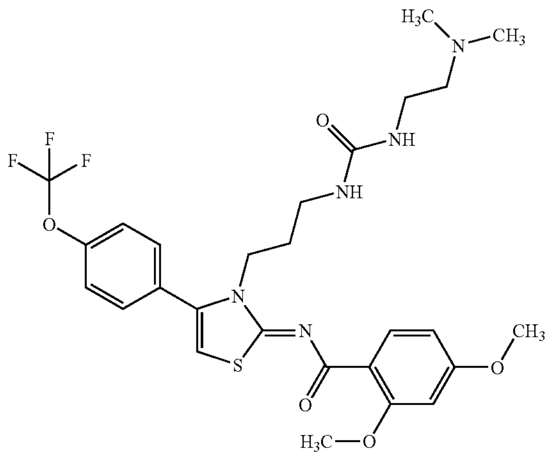 | 595 | 596 | A | 3.29 | 409 |
| 512 | 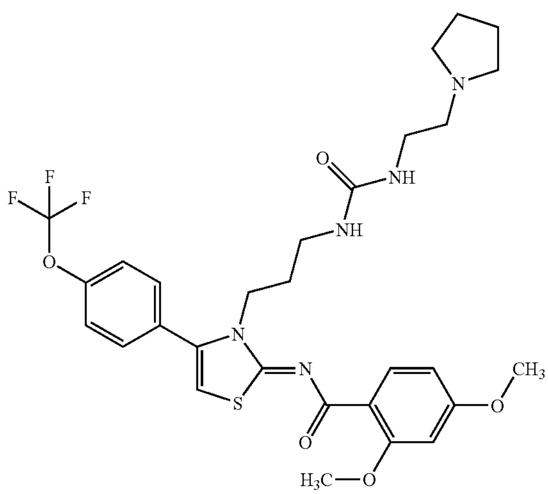 | 621 | 622 | A | 3.35 | 409 |
| 513 | 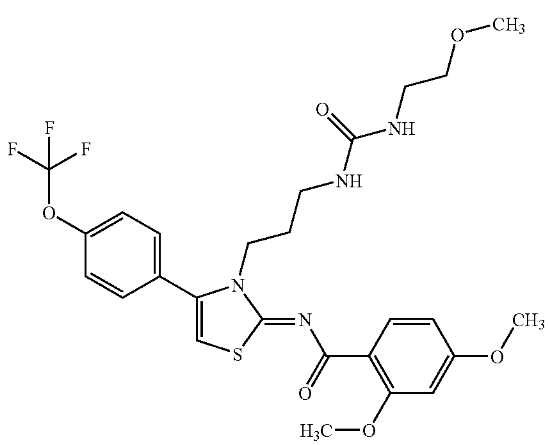 | 582 | 583 | A | 3.70 | 409 |

TABLE 31-continued

| Ex. No. | Structure | Exact MS | m/z | Method for analysis | Retention time (min) | Ref. Ex. |
|---|---|---|---|---|---|---|
| 514 | 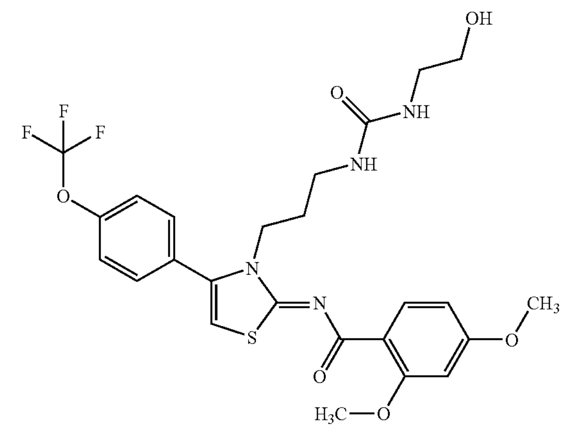 | 569 | 570 | A | 3.50 | 409 |
| 515 | 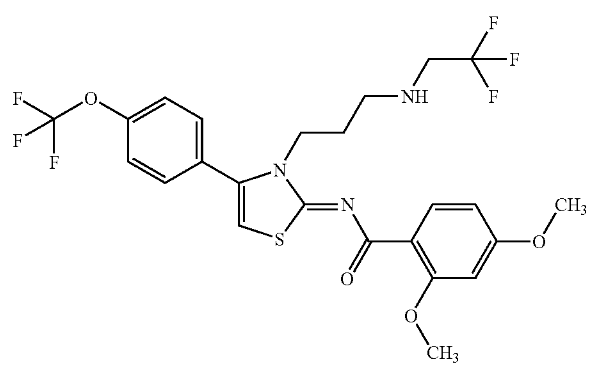 | 563 | 564 | A | 3.87 | 411 |
| 516 | 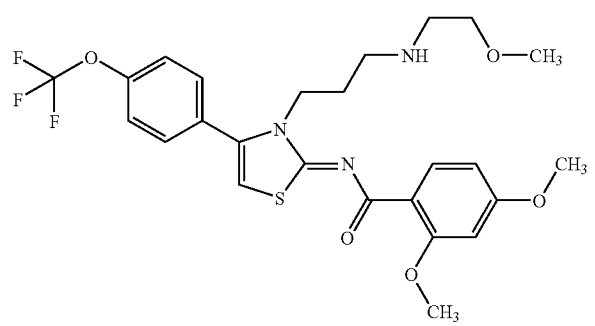 | 539 | 540 | A | 3.63 | 411 |
| 517 | 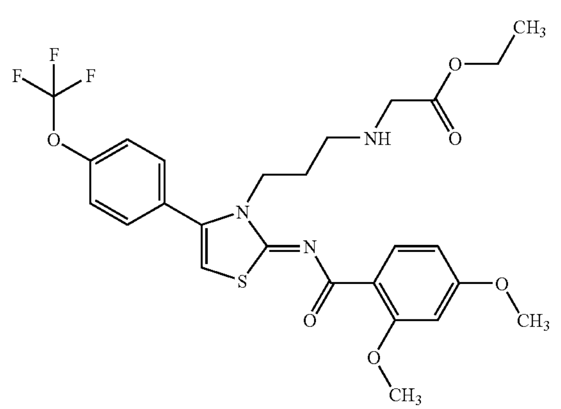 | 567 | 568 | A | 3.75 | 411 |

TABLE 31-continued

| Ex. No. | Structure | Exact MS | m/z | Method for analysis | Retention time (min) | Ref. Ex. |
|---|---|---|---|---|---|---|
| 518 | 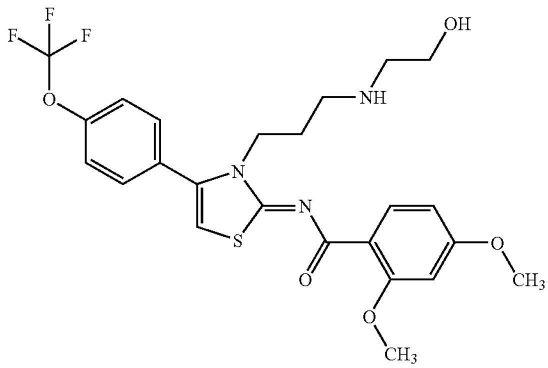 | 525 | 526 | A | 3.48 | 321 |
| 519 | 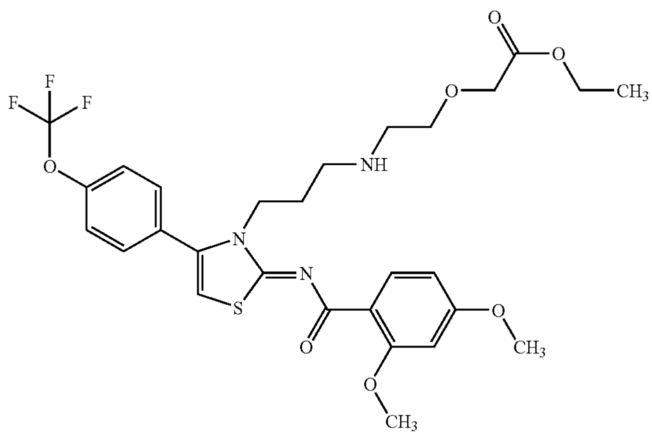 | 611 | 612 | A | 3.83 | 411 |
| 520 | 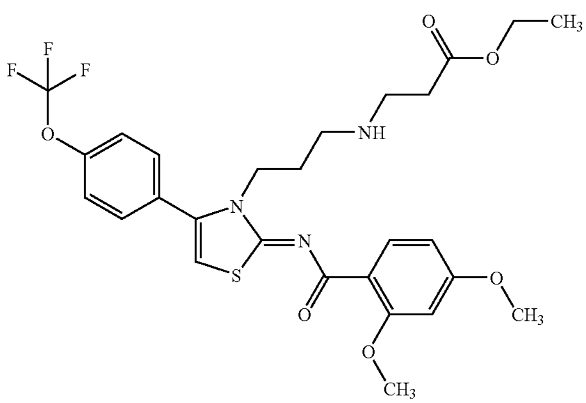 | 581 | 582 | A | 3.80 | 411 |
| 521 | 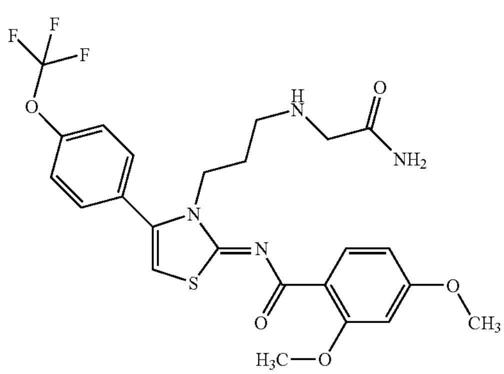 | 538 | 539 | A | 3.47 | 417 |

TABLE 31-continued

| Ex. No. | Structure | Exact MS | m/z | Method for analysis | Retention time (min) | Ref. Ex. |
|---|---|---|---|---|---|---|
| 522 | 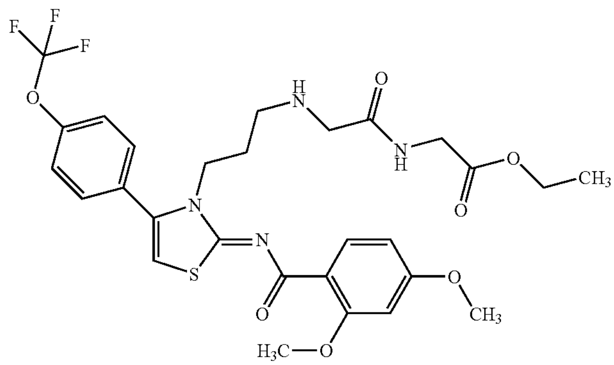 | 624 | 625 | A | 3.71 | 417 |
| 523 | 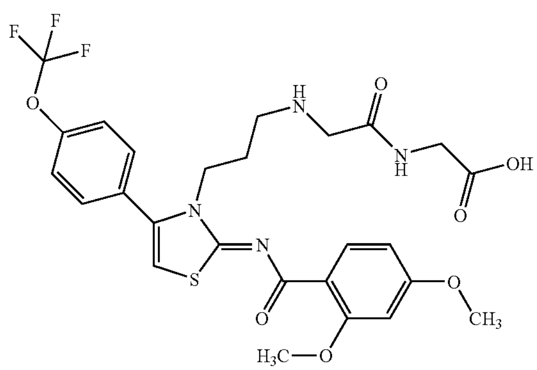 | 596 | 597 | A | 3.51 | 427 |
| 524 | 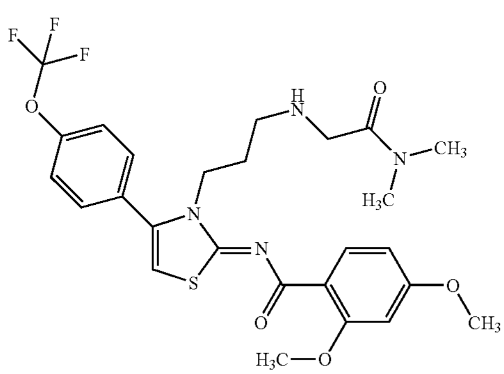 | 566 | 567 | A | 3.62 | 417 |
| 525 | 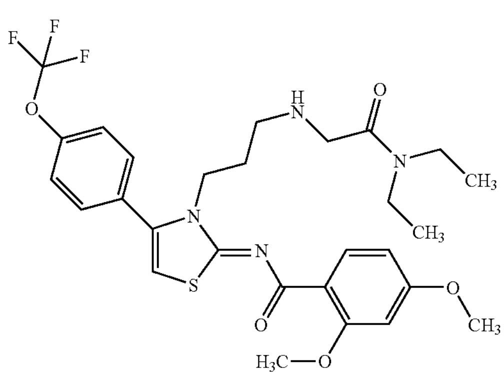 | 594 | 595 | A | 3.79 | 417 |

TABLE 31-continued

| Ex. No. | Structure | Exact MS | m/z | Method for analysis | Retention time (min) | Ref. Ex. |
|---|---|---|---|---|---|---|
| 526 | 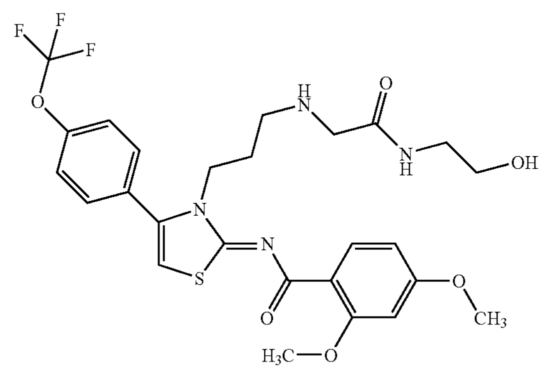 | 582 | 583 | A | 3.46 | 417 |
| 527 | 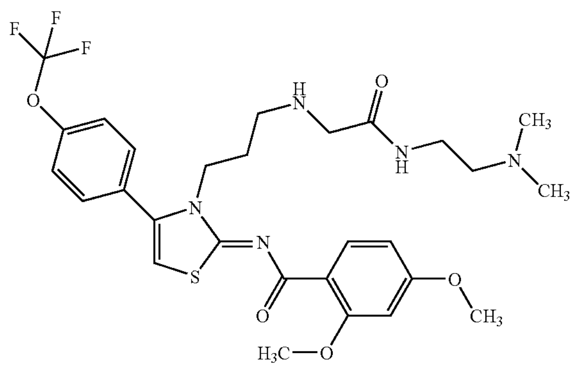 | 609 | 610 | A | 3.26 | 417 |
| 528 | 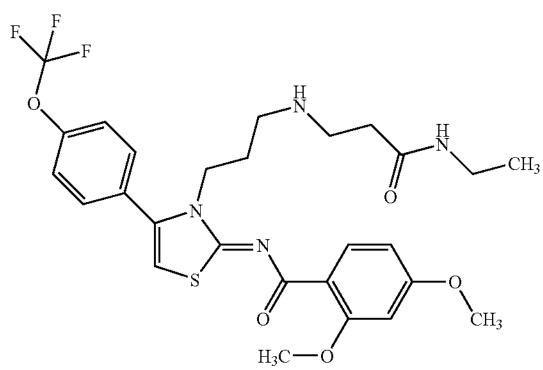 | 580 | 581 | A | 3.62 | 417 |
| 529 | 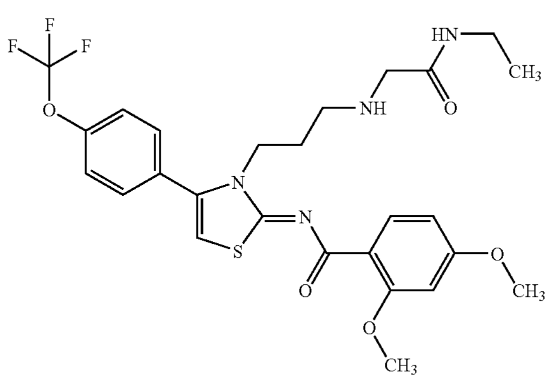 | 566 | 597 | A | 3.58 | 417 |

TABLE 31-continued

| Ex. No. | Structure | Exact MS | m/z | Method for analysis | Retention time (min) | Ref. Ex. |
|---|---|---|---|---|---|---|
| 530 | 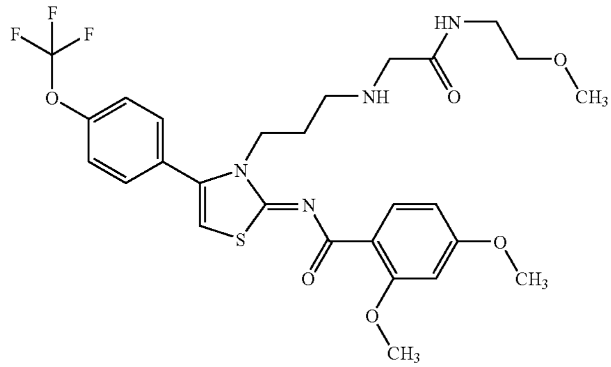 | 596 | 597 | A | 3.55 | 417 |
| 531 | 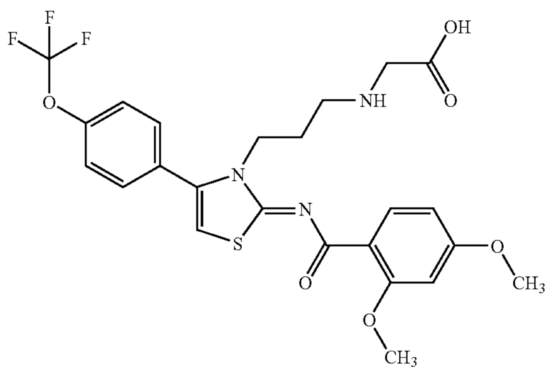 | 539 | 540 | A | 3.52 | 427 |
| 532 | 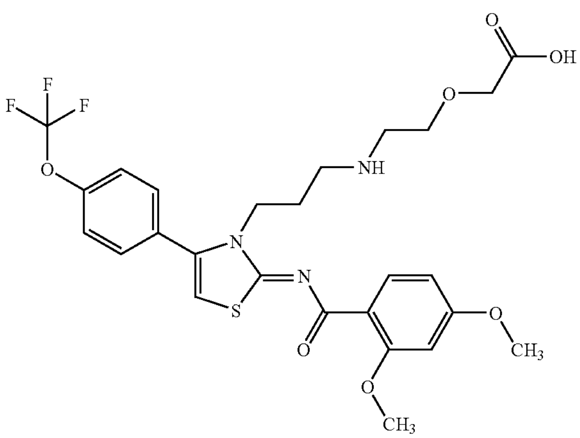 | 583 | 584 | A | 3.55 | 427 |
| 533 | 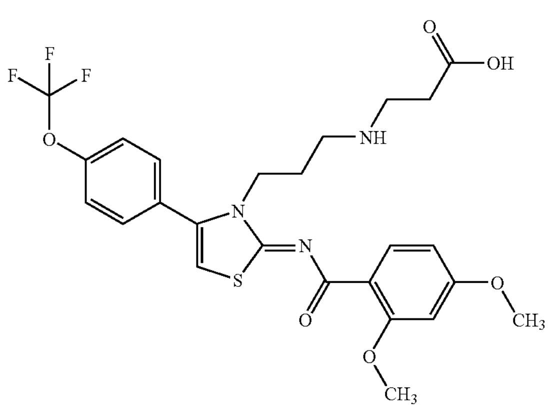 | 553 | 554 | A | 3.56 | 427 |

TABLE 31-continued

| Ex. No. | Structure | Exact MS | m/z | Method for analysis | Retention time (min) | Ref. Ex. |
|---|---|---|---|---|---|---|
| 534 | 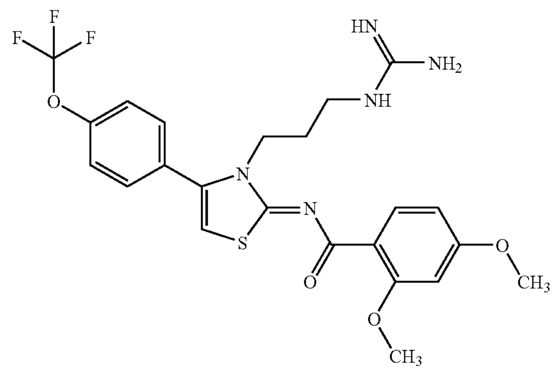 | 523 | 524 | A | 3.39 | 429 |
| 535 | 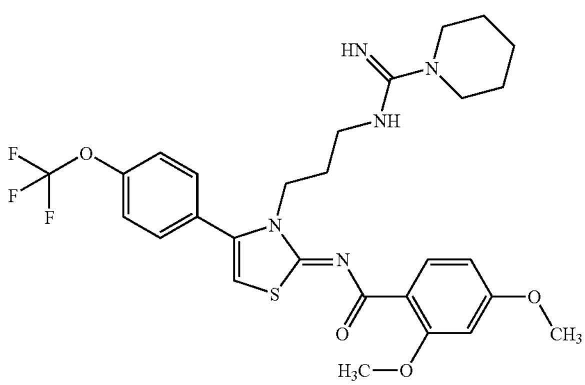 | 591 | 592 | A | 3.70 | 429 |
| 536 | 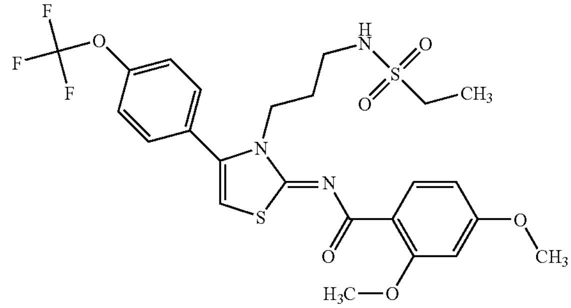 | 573 | 574 | A | 4.09 | 430 |
| 537 | 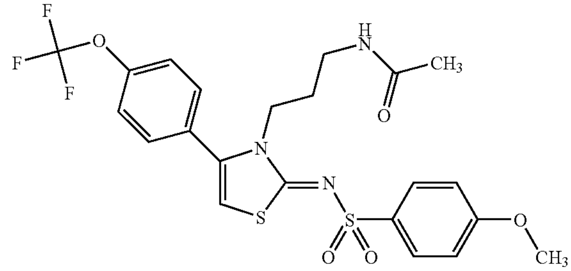 | 529 | 530 | A | 4.15 | 446 |

TABLE 31-continued

| Ex. No. | Structure | Exact MS | m/z | Method for analysis | Retention time (min) | Ref. Ex. |
|---|---|---|---|---|---|---|
| 538 | 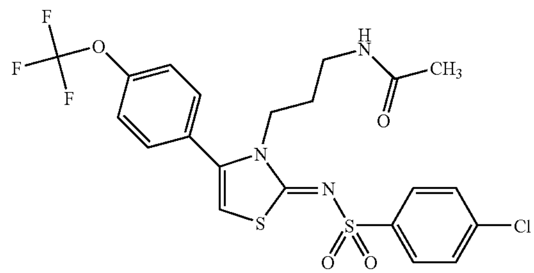 | 533 | 534 | B | 2.75 | 446 |
| 539 | 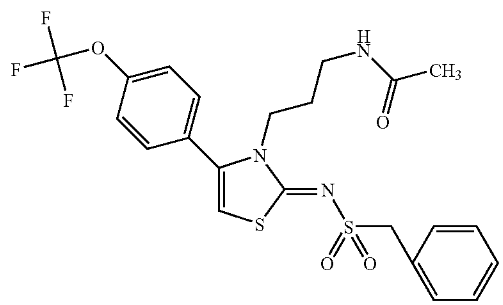 | 513 | 514 | B | 2.09 | 446 |
| 540 | 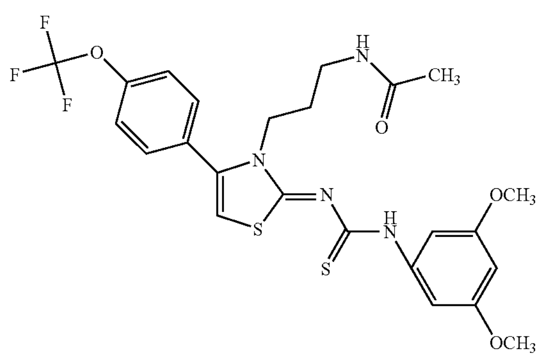 | 554 | 555 | B | 3.21 | 446 |
| 541 | 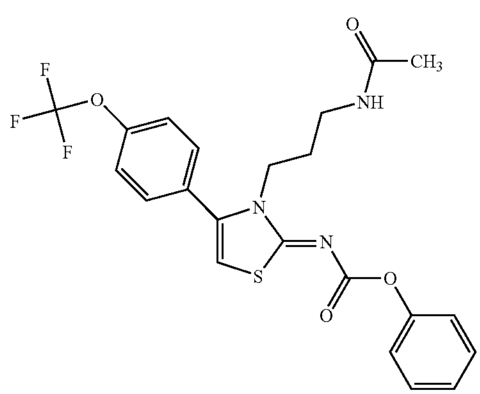 | 479 | 480 | B | 2.71 | 446 |

TABLE 31-continued

| Ex. No. | Structure | Exact MS | m/z | Method for analysis | Retention time (min) | Ref. Ex. |
|---|---|---|---|---|---|---|
| 542 | 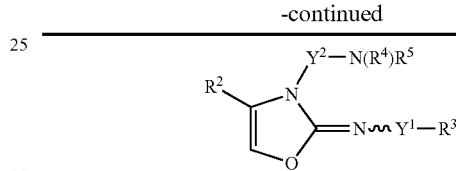 | 508 | 509 | B | 2.63 | 446 |

It was confirmed that the compounds obtained in Example 157 and 480 were (Z)-compounds by X-ray structural analysis.

Preferable examples of the compound (1) wherein X is an oxygen atom are indicated below.

| $R^2$ | $Y^1$—$R^3$ | $Y^2$—$N(R^4)R^5$ |
|---|---|---|
| 4-bromophenyl | phenyl | $(CH_2)_3NMe_2$ |
| 4-methoxyphenyl | phenyl | $(CH_2)_3NMe_2$ |
| 4-bromophenyl | phenyl | $(CH_2)_2NH_2$ |
| 4-bromophenyl | phenyl | $(CH_2)_3NH_2$ |
| 4-methoxyphenyl | phenyl | $(CH_2)_3NH_2$ |
| 4-methoxyphenyl | 4-fluorophenyl | $(CH_2)_3NH_2$ |
| 4-methoxyphenyl | 2,4-dimethoxyphenyl | $(CH_2)_3NH_2$ |
| 3,4-(methylenedioxy)phenyl | 4-fluorophenyl | $(CH_2)_3NH_2$ |
| 3,4-(methylenedioxy)phenyl | 4-methoxyphenyl | $(CH_2)_3NH_2$ |
| 3,4-(methylenedioxy)phenyl | 2,4-dimethoxyphenyl | $(CH_2)_3NH_2$ |
| 4-(trifluoromethoxy)phenyl | 4-methoxyphenyl | $(CH_2)_3NH_2$ |
| 4-(trifluoromethoxy)phenyl | 2,4-dimethoxyphenyl | $(CH_2)_3NH_2$ |
| 4-(trifluoromethoxy)phenyl | 4-chloro-2-methoxyphenyl | $(CH_2)_3NH_2$ |
| 4-morpholinophenyl | 4-fluorophenyl | $(CH_2)_2NH_2$ |
| 4-morpholinophenyl | 4-fluorophenyl | $(CH_2)_3NH_2$ |
| 4-methoxyphenyl | 4-fluorophenyl | $(CH_2)_3NHAc$ |
| 3,4-(methylenedioxy)phenyl | 4-fluorophenyl | $(CH_2)_3NHAc$ |
| 3,4-(methylenedioxy)phenyl | 4-methoxyphenyl | $(CH_2)_3NHAc$ |
| 3,4-(methylenedioxy)phenyl | 2,4-dimethoxyphenyl | $(CH_2)_3NHAc$ |
| 4-(trifluoromethoxy)phenyl | 4-methoxyphenyl | $(CH_2)_3NHAc$ |
| 4-(trifluoromethoxy)phenyl | 2,4-dimethoxyphenyl | $(CH_2)_3NHAc$ |
| 4-(trifluoromethoxy)phenyl | 4-chloro-2-methoxyphenyl | $(CH_2)_3NHAc$ |
| 4-(trifluoromethoxy)phenyl | 4-methoxyphenyl | $(CH_2)_3NHCONHEt$ |
| 4-(trifluoromethoxy)phenyl | 4-methoxyphenyl | $(CH_2)_3NHCONHMe$ |
| 4-(trifluoromethoxy)phenyl | 4-chloro-2-methoxyphenyl | $(CH_2)_3NHCONHEt$ |
| 4-morpholinophenyl | 4-fluorophenyl | $(CH_2)_2NHAc$ |
| 4-morpholinophenyl | 4-fluorophenyl | $(CH_2)_3NHAc$ |
| 4-morpholinophenyl | 4-fluorophenyl | $(CH_2)_2NHCONHEt$ |
| 4-morpholinophenyl | 4-fluorophenyl | $(CH_2)_3NHCONHEt$ |
| 4-morpholinophenyl | 2-pyridyl | $(CH_2)_3NHCONHEt$ |

Reference Example 1 t-Butyl 2-[(anilinocarbothioyl)amino]ethylcarbamate

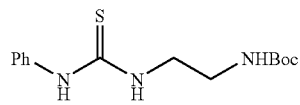

To a solution of t-butyl 2-aminoethylcarbamate (1.76 ml) in ethanol (22 ml) was added dropwise phenyl isothiocyanate (1.5 g), and the mixture was heated at 75° C. for one hour. The reaction mixture was concentrated under reduced pressure and crystallized from n-hexane to give the title compound (3.25 g).

$^1$H-NMR (CDCl$_3$): δ 1.35 (9H, s), 3.33 (2H, m), 3.75 (2H, m), 4.89 (1H, m), 6.86 (1H, m), 7.21-7.46 (5H, m), 7.72 (1H, brs)

Reference Examples 2 to 24

The thiourea compounds as listed in Table 32 were obtained in a similar manner to in Reference Example 1 by reacting various isothiocyanates and amine compounds.

TABLE 32

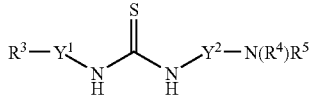

| Ref. Ex. | Y¹—R³ | Y²—N(R⁴)R⁵ |
|---|---|---|
| 2 | phenyl | $(CH_2)_2NMe_2$ |
| 3 | phenyl | $(CH_2)_3NMe_2$ |
| 4 | phenyl | $(CH_2)_3NHBoc$ |
| 5 | 2-methoxyphenyl | $(CH_2)_3NHBoc$ |
| 6 | 3-methoxyphenyl | $(CH_2)_3NHBoc$ |
| 7 | 4-methoxyphenyl | $(CH_2)_3NHBoc$ |
| 8 | 2,4-dimethoxyphenyl | $(CH_2)_3NHBoc$ |
| 9 | 2,5-dimethoxyphenyl | $(CH_2)_3NHBoc$ |
| 10 | 3,4-dimethoxyphenyl | $(CH_2)_3NHBoc$ |
| 11 | 3,5-dimethoxyphenyl | $(CH_2)_3NHBoc$ |
| 12 | 2-chlorophenyl | $(CH_2)_3NHBoc$ |
| 15 | 4-chlorophenyl | $(CH_2)_3NHBoc$ |
| 16 | 4-fluorophenyl | $(CH_2)_3NHBoc$ |
| 17 | 3-pyridyl | $(CH_2)_3NHBoc$ |
| 18 | 3-pyridyl | $(CH_2)_4NHBoc$ |
| 19 | benzoyl | $(CH_2)_3NMe_2$ |
| 20 | benzyl | $(CH_2)_3NHBoc$ |
| 21 | phenyl | $(CH_2)_4NHBoc$ |
| 22 | phenyl | $(CH_2)_5NHBoc$ |
| 23 | phenyl | $CH_2CH(OH)CH_2NHBoc$ |
| 24 | phenyl | $(CH_2)_2CH(OH)CH_2NHBoc$ |

Reference Example 25 t-Butyl 3-{[4-(trifluoromethyl)anilinocarbothioyl]amino}propylcarbamate 1) 4-(Trifluoromethyl)phenylisothiocyanate

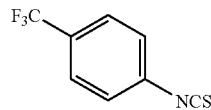

4-(Trifluoromethyl)aniline (1.34 g), thiophosgen (0.73 ml), sodium hydrogen carbonate (5.1 g), chloroform (70 ml) and water (140 ml) were treated by the method disclosed in the literature (Burke, T. R., Jr.; Bajwa, B. S.; Jacobson, A. E.; Rice, K. C.; Streaty, R. A.; Klee, W. A. J. Med. Chem., 1984, 27, 1570-1574) to give the title compound (1.62 g).

¹H-NMR (CDCl₃): δ 7.33 (2H, d, J=8.4), 7.62 (2H, d, J=8.4)

(2) t-Butyl 3-({[4-(trifluoromethyl)anilino]carbothioyl}amino)propyl-carbamate

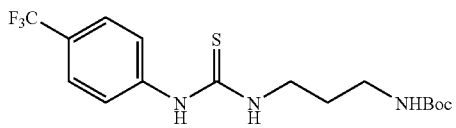

4-(Trifluoromethyl)phenylisothiocyanate (1.62 g) and t-butyl 3-(aminopropyl)carbamate (1.39 g) were reacted in a similar manner to in Reference Example 1 to give the title compound (2.33 g) as yellow oil.

¹H-NMR (CDCl₃): δ 1.35 (9H, s), 1.74 (2H, m), 3.11 (2H, m), 3.70 (2H, m), 4.69 (1H, m), 7.38 (2H, d, J=8.4), 7.56-7.68 (4H, m)

Reference Examples 26 to 32

In a similar manner to in Reference Example 25, various anilines and thiophosgen were reacted to give isothiocyanates, which were reacted with t-butyl 3-(aminopropyl)carbamate to give the thiourea compounds as listed in Table 33.

TABLE 33

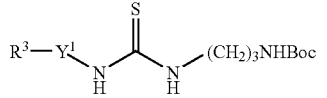

| Ref. Ex. | Y¹—R³ |
|---|---|
| 26 | 2-fluorophenyl |
| 27 | 3-fluorophenyl |
| 28 | 4-fluoro-2-nitrophenyl |
| 29 | 2-methoxy-2-nitrophenyl |
| 30 | 2-bromo-4-(trifluoromethoxy)phenyl |
| 31 | 4-bromo-2-(trifluoromethoxy)phenyl |
| 32 | 3,4-(methylenedioxy)phenyl |

Reference Example 33 t-Butyl 3-({[2-(trifluoromethoxy)anilino]carbothioyl}amino)propyl-carbamate

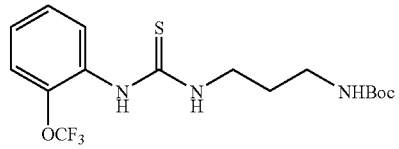

To a solution of 2-(trifluoromethoxy)aniline (1.8 g) and triethylamine (2.9 ml) in tetrahydrofuran (10 ml) was added dropwise thiophosgen (0.8 ml) under nitrogen atmosphere in an ice bath. Then, the mixture was warmed to room temperature, and stirred for 2 hours. To the reaction mixture was added t-butyl 3-(aminopropyl)carbamate (1.39 g), and the mixture was further stirred for 2 hours. To the reaction mixture was added water, and the mixture was extracted with ethyl acetate. The organic layer was washed with a saturated brine, dried over sodium sulfate, and the solvent was evaporated under reduced pressure. The residue was purified by silica gel column chromatography (chloroform) to give the title compound (2.9 g) as brown oil.

¹H-NMR (CDCl₃): δ 1.36 (9H, s), 1.72 (2H, m), 3.11 (2H, m), 3.70 (2H, m), 4.78 (1H, t, J=6.4), 7.27-7.54 (6H, m)

Reference Example 34 t-Butyl 3-{[(2,4,6-trifluoroanilino)carbothioyl]amino}propylcarbamate

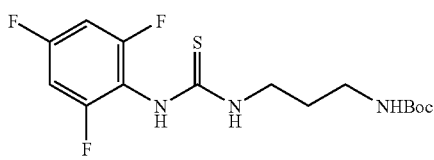

2,4,6-Trifluoroaniline (1.5 g) was treated in a similar manner to in Reference Example 33 to give the title compound (1.1 g).

$^1$H-NMR (CDCl$_3$): δ 1.36 (9H, s), 1.59 (2H, m), 2.91 (2H, m), 3.40 (2H, m), 6.83 (1H, m), 7.24 (2H, t, J=9.0), 7.90 (1H, brs), 8.90 (1H, brs)

Reference Example 35 t-Butyl 3-{[(2,4-dichloro-6-methoxyanilino)carbothioyl]amino}propyl-carbamate

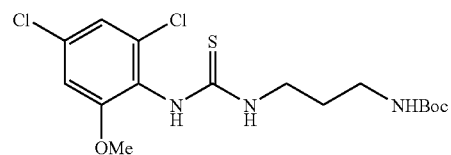

2,4-Dichloro-6-methoxyaniline (1.0 g) was treated in a similar manner to in Reference Example 33 to give the title compound (997 mg).

$^1$H-NMR (CDCl$_3$): δ 1.33 (9H, s), 1.67 (2H, m), 3.10 (2H, m), 3.65 (2H, m), 3.84 (3H, s), 4.71 (1H, m), 6.88 (1H, d, J=2.2), 6.97 (1H, brs), 7.06 (1H, m), 7.11 (1H, d, J=2.2)

Reference Example 36

(1) t-Butyl 3-isothiocyanate propylcarbamate

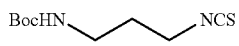

t-Butyl 3-aminopropylcarbamate (17.4 g), triethylamine (1.4 ml), carbon disulfide (30.2 ml) and tetrahydrofuran (100 ml) were treated by the method disclosed in the literature (Li, G. Tajima; H., Ohtani, T. J. Org. Chem., 1997, 62, 4539-4540) to give the title compound (15.2 g).

$^1$H-NMR (CDCl$_3$): δ 1.45 (9H, s), 1.89 (2H, m), 3.25 (2H, m), 3.60 (2H, t, J=6.6), 4.64 (1H, brs)

(2) t-Butyl {[(2,3-methylenedioxyphenylamino)carbothioyl]amino}propyl-carbamate

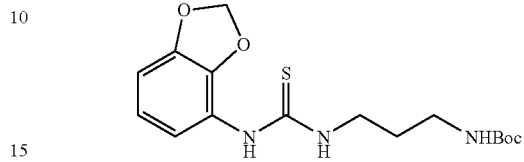

A mixture of 2,3-methylenedioxyphenylamine (698 mg) obtained by the method disclosed in Neville, et al., (Neville, C. F. et al., J. Chem. Soc. Perkin Trans. 1, 1991, 259-262), t-butyl 3-isothiocyanatepropyl-carbamate (1.1 g) and dioxane (10 ml) was heated with reflux under nitrogen atmosphere. Four hours thereafter, the reaction mixture was concentrated under reduced pressure. The residue was crystallized from diethyl ether-n-hexane to give the title compound (803 mg).

$^1$H-NMR (CDCl$_3$): δ 1.37 (9H, s), 1.73 (2H, m), 3.14 (2H, m), 3.71 (2H, m), 4.79 (1H, m), 6.03 (2H, s), 6.71-6.88 (3H, m), 7.12 (1H, m), 7.35 (1H, brs)

Reference Examples 37 to 57

In a similar manner to in Reference Example 36(2), various anilines and t-butyl 3-isothiocyanatopropylcarbamate were reacted to give the thiourea compounds as listed in Table 34.

TABLE 34

$$R^3-Y^1-\underset{H}{N}-\underset{S}{\overset{\|}{C}}-\underset{H}{N}-(CH_2)_3NHBoc$$

| Ref. Ex. | Y$^1$—R$^3$ |
|---|---|
| 37 | 2-hydroxyphenyl |
| 38 | 3-hydroxyphenyl |
| 39 | 4-hydroxyphenyl |
| 40 | 4-(trifluoromethoxy)phenyl |
| 41 | 2-methoxy-4,5-(methylenedioxy)phenyl |
| 42 | 2,4-dichlorophenyl |
| 43 | 2,4-difluorophenyl |
| 44 | 3,4-difluorophenyl |
| 45 | 4-methylphenyl |
| 46 | 4-chloro-2-methoxyphenyl |
| 47 | 4-chloro-2,5-dimethoxyphenyl |
| 48 | 4-chloro-2-methoxy-5-methylphenyl |
| 49 | 2-methoxy-4-(trifluoromethoxy)phenyl |
| 50 | 4-chloro-2,6-dimethoxyphenyl |
| 51 | phenethyl |
| 52 | 3-phenylpropyl |
| 53 | 3-pyridylmethyl |
| 54 | 4-pyridylmethyl |
| 55 | 8-quinolyl |
| 56 | 5-isoquinolyl |
| 57 | benzenesulfonyl |

Reference Example 58

N-[3-(Dimethylamino)propyl]-N'-(2-pyridyl)thiourea

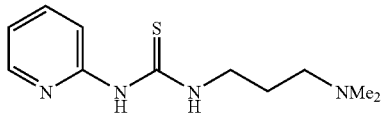

A mixture of ethyl 2-pyridyldithiocarbamate (600 mg), 3-(dimethylamino)propylamine (0.38 ml) and ethanol (6 ml) was heated with reflux under nitrogen atmosphere. One and half hour thereafter, the reaction mixture was concentrated under reduced pressure to give the title compound (786 mg) as crude oil.

$^1$H-NMR (CDCl$_3$): δ 1.89 (2H, m), 2.23 (6H, s), 2.40 (2H, t, J=7.0), 3.76 (2H, m), 6.73 (2H, d, J=8.3), 6.96 (1H, m), 7.64 (1H, m), 8.18 (1H, m), 8.44 (1H, brs), 11.72 (1H, brs)

Reference Example 59 t-Butyl 3-{[(2-pyridylamino)carbothioyl]amino}propylcarbamate

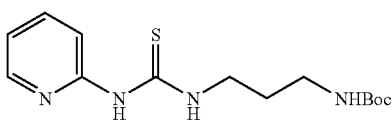

In a similar manner to in Reference Example 58, ethyl 2-pyridyldithiocarbamate (1.98 g) and t-butyl 3-aminopropylcarbamate (1.74 g) were reacted and crystallized from n-hexane-diethyl ether to give the title compound (2.78 g).

$^1$H-NMR (CDCl$_3$): δ 1.45 (9H, s), 1.89 (2H, m), 3.25 (2H, m), 3.84 (2H, m), 5.04 (1H, brs), 6.75 (1H, d, J=8.2), 6.97 (1H, m), 7.65 (1H, m), 8.21 (1H, m), 8.54 (1H, brs), 11.81 (1H, brs)

Reference Example 60 t-Butyl 4-{[(2-pyridylamino)carbothioyl]amino}butylcarbamate

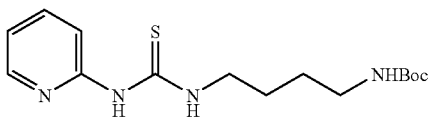

Ethyl 2-pyridyldithiocarbamate (500 mg) and t-butyl 4-amino-butylcarbamate (474 mg) were reacted in a similar manner to in Reference Example 58, and crystallized from n-hexane-diethyl ether to give the title compound (2.78 g).

$^1$H-NMR (CDCl$_3$): δ 1.44 (9H, s), 1.59-1.80 (4H, m), 3.20 (2H, m), 3.76 (2H, m), 4.63 (1H, brs), 6.73 (1H, d, J=8.4), 6.96 (1H, m), 7.65 (1H, m), 8.19 (1H, m), 8.43 (1H, brs), 11.72 (1H, brs)

Reference Example 61 t-Butyl 3-{[(4-pyridylamino)carbothioyl]amino}propylcarbamate

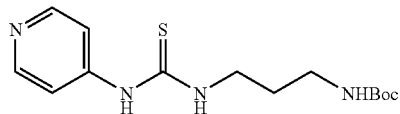

Methyl 4-pyridyldithiocarbamate (350 mg) obtained by the method disclosed in the literature of Hansen, et al. (Hansen, E. T.; Peterson, H. J. Synthetic Commun., 1984, 14, 537-546) and t-butyl 3-aminopropylcarbamate (364 mg) were reacted in a similar manner to in Reference Example 58 to give the title compound (2.78 g).

$^1$H-NMR (CDCl$_3$): δ 1.42 (9H, s), 1.78 (2H, m), 3.18 (2H, m), 3.75 (2H, m), 4.83 (1H, brs), 7.30 (2H, d, J=4.8), 7.97 (1H, brs), 8.52 (2H, d, J=4.8)

Reference Example 62 t-Butyl 3-({[(5-methoxy-2-pyridyl)amino]carbothioyl}amino)propyl-carbamate (1) Methyl 5-methoxy-2-pyridyldithiocarbamate

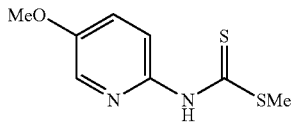

To a solution of 2-amino-5-methoxypyridine (1.26 g) obtained by the method disclosed in the literature of Lombardino (Lombardino, J. G. J. Med. Chem., 1981, 24, 39-42) and triethylamine (1.48 ml) in tetrahydrofuran (5 ml) was added dropwise carbon disulfide (0.61 ml). The mixture was stirred at room temperature overnight, and thereto was added diethyl ether, and the precipitated yellow solid was collected by filtration. To a suspension of the resulting solid (1.7 g) in methanol (6 ml) was added dropwise methyl iodide (0.35 ml), and the mixture was stirred at room temperature. The resulting crystals were collected by filtration to give the title compound (993 mg).

$^1$H-NMR (CDCl$_3$): δ 2.68 (3H, s), 3.87 (3H, s), 7.28 (1H, dd, J=8.2, J=3.1), 8.08 (1H, d, J=3.1), 8.44 (1H, m), 9.69 (1H, brs)

(2) t-Butyl 3-({[(5-methoxy-2-pyridyl)amino]carbothioyl}amino)propyl-carbamate

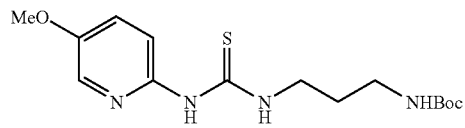

Methyl 5-methoxy-2-pyridyldithiocarbamate (950 mg) and t-butyl 3-aminopropylcarbamate (772 mg) were treated in a similar manner to in Reference Example 58, and crystallized from n-hexane-ethanol to give the title compound (1.51 g).

¹H-NMR (CDCl₃): δ 1.45 (9H, s), 1.88 (2H, m), 3.24 (2H, m), 3.79-3.85 (5H, m), 5.05 (1H, brs), 6.68 (1H, d, J=8.8), 7.26 (1H, dd, J=8.8, J=2.8), 7.88 (1H, d, J=2.8), 8.27 (1H, brs), 11.53 (1H, brs)

Reference Example 63 t-Butyl 3-({[(5-methyl-2-pyridyl)amino]carbothioyl}amino)propyl-carbamate

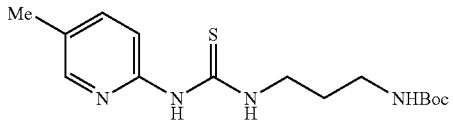

5-Methyl-2-aminopyridine (4 g) was treated in a similar manner to in Reference Example 62 to give the title compound (1.47 g).
¹H-NMR (CDCl₃): δ1.45 (9H, s), 1.88 (2H, m), 2.28 (3H, s), 3.24 (2H, m), 3.82 (2H, m), 5.05 (1H, brs), 6.64 (1H, brs), 7.48 (1H, d, J=7.3), 8.01 (1H, s), 8.27 (1H, m), 11.70 (1H, brs)

Reference Example 64 t-Butyl 3-{[(3,4,5-trimethoxyanilino)carbothioyl]amino}propylcarbamate (1) t-Butyl 3-{[(methylsulfanyl)carbothioyl]amino}propylcarbamate

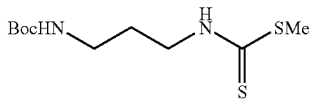

To a solution of t-butyl 3-aminopropylcarbamate (6 g) and triethylamine (5.03 ml) in tetrahydrofuran (10 ml) was added dropwise carbon disulfide (2.07 ml), and the mixture was stirred at room temperature for 2.5 hours. To the reaction mixture was added dropwise methyl iodide (2.14 ml), and the mixture was stirred at room temperature for 0.5 hour. To the reaction mixture was added a saturated aqueous sodium hydrogen carbonate solution, and the mixture was extracted with ethyl acetate. The organic layer was washed with saturated brine, dried over sodium sulfate, and the solvent was evaporated under reduced pressure to give the title compound (11 g) as crude oil.
¹H-NMR (CDCl₃): δ 1.45 (9H, s), 1.78 (2H, m), 2.63 (3H, s), 3.21 (2H, m), 3.83 (2H, m), 4.80 (1H, brs), 8.30 (1H, brs)

(2) t-Butyl 3-{[(3,4, 5-trimethoxyanilino)carbothioyl]amino}-propyl-carbamate

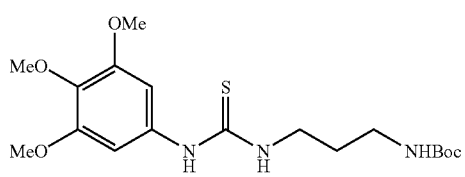

A mixture of t-butyl 3-{[(methylsulfamoyl)carbothionyl]amino}-propylcarbamate (3 g), 3,4,5-trimethoxyaniline (2.07 g) and xylene (20 ml) was heated with reflux under nitrogen atmosphere. Nine hours thereafter, the reaction mixture was concentrated under reduced pressure, and the residue was purified by silica column chromatography [chloroform: ethyl acetate (19:1)] to give the title compound (1.46 g) as amorphous.
¹H-NMR (CDCl₃): δ 1.37 (9H, s), 1.73 (2H, m), 3.12 (2H, m), 3.69 (2H, m), 3.84 (3H, s), 3.85 (6H, s), 4.79 (1H, brs), 6.48 (2H,s), 7.09 (1H, brs), 7.62 (1H, brs)

Reference Example 65 t-Butyl 3-[({[2-(4-pyridyl)ethyl]amino}carbothioyl)amino]propyl-carbamate

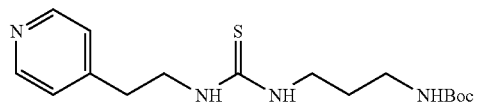

t-Butyl 3-{[(methylsulfamoyl)carbothionyl]amino}propyl-carbamate (1 g), 4-(2-aminoethyl)pyridine (462 mg) and ethanol (10 ml) were reacted in a similar manner to in Reference Example 64 to give the title compound (977 mg).
¹H-NMR (CDCl₃): δ 1.42 (9H, s), 1.70 (2H, m), 3.92 (2H, m), 3.17 (2H, m), 3.61-3.76 (4H, m), 5.03 (1H, m), 6.61 (1H, m), 7.18 (2H, d, J=5.6), 7.19 (1H, m), 8.43 (2H, d, J=5.6)

Reference Examples 66 to 80, and 93

Various isothiocyanates and amine compounds were reacted in a similar manner to in Reference Example 1 to give the thiourea compounds as listed in Table 35.

TABLE 35

$$R^3-Y^1-\underset{\underset{H}{N}}{\overset{S}{\|}}-\underset{\underset{H}{N}}{C}-Y^2-N(R^4)R^5$$

| Ref. Ex. | R³—Y¹ | Y²—N(R⁴)R⁵ |
|---|---|---|
| 66 | 4-fluorophenyl | (CH₂)₂NHBoc |
| 66 | 4-fluorophenyl | (CH₂)₃NHBoc |
| 67 | 4-fluorophenyl | (CH₂)₄NHBoc |
| 68 | 4-fluorophenyl | (CH₂)₅NHBoc |
| 69 | 4-fluorophenyl | (CH₂)₆NHBoc |
| 70 | 2,4-dimethoxybenzoyl | (CH₂)₂NHBoc |
| 71 | 2,4-dimethoxybenzoyl | (CH₂)₃NHBoc |
| 72 | 2,4-dimethoxybenzoyl | (CH₂)₄NHBoc |
| 73 | 2,4-dimethoxybenzoyl | (CH₂)₅NHBoc |
| 74 | 2,4-dimethoxybenzoyl | (CH₂)₆NHBoc |
| 75 | 3,4-(methylenedioxy)benzoyl | (CH₂)₃NHBoc |
| 76 | 2-furoyl | (CH₂)₃NHBoc |
| 77 | 4-chloro-2-methoxybenzoyl | (CH₂)₃NHBoc |
| 78 | 4-fluorobenzoyl | (CH₂)₃NHBoc |
| 79 | 4-methoxybenzoyl | (CH₂)₃NHBoc |
| 80 | diphenylmethyl | (CH₂)₃NHAc |
| 93 | 2,4-dimethoxybenzoyl | (CH₂)₃NHAc |

Reference Examples 81-92

Various amine compounds and t-butyl 3-isothiocyanatopropylc-arbamate were reacted in a similar manner to in Reference Example 36 (2) to give the thiourea compounds as listed in Table 36.

TABLE 36

$$R^3-Y^1-\underset{H}{N}-\underset{S}{\overset{\Vert}{C}}-\underset{H}{N}-Y^2-N(R^4)R^5$$

| Ref. Ex. | R³—Y¹ | Y²—N(R⁴)R⁵ |
|---|---|---|
| 81 | 2-methoxy-4-methylphenyl | (CH₂)₃NHBoc |
| 82 | 4-(methylthio)phenyl | (CH₂)₃NHBoc |
| 83 | 4-(methanesulfonyl)phenyl | (CH₂)₃NHBoc |
| 84 | 4-(morpholino)phenyl | (CH₂)₃NHBoc |
| 85 | 4-(dimethylamino)phenyl | (CH₂)₃NHBoc |
| 86 | 2-pyrimidinyl | (CH₂)₃NHBoc |
| 87 | 2-thiazolyl | (CH₂)₃NHBoc |
| 88 | 5-indolyl | (CH₂)₃NHBoc |
| 89 | 4-(2-imidazolyl)phenyl | (CH₂)₃NHBoc |
| 90 | 2,4-dimethoxybenzyl | (CH₂)₃NHBoc |
| 91 | 4-chlorobenzyl | (CH₂)₃NHBoc |
| 92 | 4-chloro-2-methoxybenzyl | (CH₂)₃NHBoc |

Pharmacological Experiments

Experiment 1

Evaluation Test on Receptor Binding of the Compound in Rat Lung Membranes:

This experiment was carried out according to the method disclosed in Sugasawa et al., (Sugasawa, T. et al., J. Biol. Chem., 272, 21244-21252(1997)).

Preparation of Rat Lung Membranes

The air tube and blood vessels were removed from the lung excised from SD male rats (7-weeks old when used, purchased from Charles River Japan, Inc.), and the lung was chopped, and washed with ice-cold tris-saline buffer (10 mM Tris-HCl, 154 mM sodium chloride, pH 7.4). The lung was homogenized by PHYSCOTRON (maximum speed: 1 minute) in a buffer for homogenization (tris-saline buffer containing 1 mM ethylenediaminetetraacetate (EDTA), 1 mM 4-(2-aminoethyl)-benzenesulfonyl fluoride (AEBSF), 5 μg/ml aprotinin, 5 μg/ml leupeptin) under ice-cooling. The mixture was centrifuged at a low speed (1500×g, 20 minutes, 4° C.), and the supernatant was super-centrifuged (100000×g, 20 minutes, 4° C.). The pellets thus obtained were suspended in tris-saline buffer, and kept at −80° C. The concentration of protein was measured by a Protein Assay Kit manufactured by Bio-Rad using bovine serum albumin (BSA) as standard.

Ligand Binding Assay

To each well of a protein-non-adsorbent round-bottom 96-well assay plate (purchased from IWAKI GLASS CO., LTD.) was added tris-saline buffer (200 μl) containing 1 nM [¹²⁵I]-iodo-cyanopindolol (purchased from Amarsham), 10 μM serotonin, 20 μM dl-propranol, 10 μM phentoramine, 1.1 mM ascorbic acid and 100 μg lung membranes, and the mixture was mixed well by pipetting, and the plate was incubated at 37° C. for 30 minutes. Test compounds were dissolved in 100% dimethylsulfoxide, and added to the plate in an amount of 2 μl (final concentration of DMSO: 1%). In order to obtain non-specific binding, L-threo-3-(3,4-dihydroxyphenyl)-N-[3-(4-fluorophenyl)propyl]-serinepyrrolidinamide was added at a final concentration of 100 μM instead of test compound. During this period, 0.3% polyethyleneimine (PEI)/tris-saline buffer (100 μl) was added to a multiscreen plate (96-well B-glassfiber, milipore Cat. No. MAFB NOB10) and the plate was incubated for more than 30 minutes. The plate was washed by vacuum filtration (by adding ice-cold tris-saline buffer (200 μl) and then vacuum filtration), and the reaction solution on the 96-well assay plate was washed by vacuum filtration onto the multiscreen plate for four times. The B-glassfiber paper filter at the bottom of the multiscreen plate was punched out, and the γ-ray amount of [¹²⁵I]-iodo-cyanopindolol being trapped onto the paper filter was measured as binding amount. The binding amount in the presence of DMSO (final concentration: 1%) was regarded as total binding, and the binding in the presence of L-threo-3-(3,4-dihydroxyphenyl) -N-[3-(4-fluorophenyl)-propyl] serinepyrrolidinamide was regarded as non-specific binding. The value which is calculated by subtracting non-specific binding from total binding is specific binding. The binding activity of the compound can be calculated by the following equation, and expressed in a ratio of inhibiting the specific binding of [¹²⁵I]-iodo-cyanopindorol to SMBS on rat lung membranes.

$$\text{Binding Activity of test compound (\%)} = \left\{ 1 - \frac{\text{Binding in the presence of test compound} - \text{Non-specific binding}}{\text{Total binding amount} - \text{Non-specific binding}} \right\} \times 100$$

The results were shown in Table 37 to Table 39.

TABLE 37

Binding Activity of compounds in Examples (concentration to be used: 30 μM)

| Ex. | R² | Y¹—R³ | Y²—N(R⁴)R⁵ | Binding Activity (30 μM) |
|---|---|---|---|---|
| 1 | 4-bromophenyl | phenyl | (CH₂)₃NMe₂ | 61.3 |
| 9 | 4-methoxyphenyl | phenyl | (CH₂)₃NH₂ | 79.0 |
| 11 | 4-phenylphenyl | phenyl | (CH₂)₃NH₂ | 98.1 |
| 12 | phenyl | phenyl | (CH₂)₃NH₂ | 73.5 |
| 15 | phenyl | 4-methoxyphenyl | (CH₂)₃NH₂ | 79.6 |
| 18 | phenyl | 2,4-dimethoxy-phenyl | (CH₂)₃NH₂ | 95.2 |
| 21 | phenyl | 4-chlorophenyl | (CH₂)₃NH₂ | 71.0 |
| 23 | phenyl | 2-pyridyl | (CH₂)₃NH₂ | 43.4 |
| 27 | phenyl | phenyl | (CH₂)₂CH—(OH)CH₂NH₂ | 38.7 |
| 28 | phenyl | benzyl | (CH₂)₃NH₂ | 91.9 |
| 35 | 4-methoxyphenyl | phenyl | (CH₂)₂NH₂ | 90.3 |
| 38 | 4-methoxyphenyl | 4-methoxyphenyl | (CH₂)₃NH₂ | 110.3 |
| 44 | 4-methoxyphenyl | 4-hydroxyphenyl | (CH₂)₃NH₂ | 75.4 |
| 45 | 4-methoxyphenyl | 3,4-methylene-dioxyphenyl | (CH₂)₃NH₂ | 102.7 |
| 47 | 4-methoxyphenyl | 5-methoxy-2-pyridyl | (CH₂)₃NH₂ | 100.5 |
| 49 | 4-methoxyphenyl | phenethyl | (CH₂)₃NH₂ | 101.9 |

TABLE 38

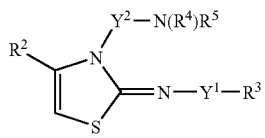

Binding Activity of compounds in Examples (concentration to be used: 30 μM)

| Ex. | $R^2$ | $Y^1$—$R^3$ | $Y^2$—$N(R^4)R^5$ | Binding Activity (30 μM) |
|---|---|---|---|---|
| 52 | 4-methoxyphenyl | 2-(4-pyridylethyl) | $(CH_2)_3NH_2$ | 74.9 |
| 54 | 3,4-dimethoxyphenyl | phenyl | $(CH_2)_3NH_2$ | 47.7 |
| 65 | 4-(methanesulfonyl)phenyl | phenyl | $(CH_2)_3NH_2$ | 38.3 |
| 69 | 3,4-(methylenedioxy)phenyl | 4-methoxyphenyl | $(CH_2)_3NH_2$ | 102.7 |
| 76 | 3,4-(methylenedioxy)phenyl | 2-(trifluoromethoxy)phenyl | $(CH_2)_3NH_2$ | 58.4 |
| 78 | 3,4-(methylenedioxy)phenyl | 4-chloro-2-methoxyphenyl | $(CH_2)_3NH_2$ | 116.9 |
| 102 | 4-fluorophenyl | 4-methoxyphenyl | $(CH_2)_3NH_2$ | 84.1 |
| 106 | 4-fluorophenyl | 4-chloro-2-methoxyphenyl | $(CH_2)_3NH_2$ | 114.4 |
| 109 | 4-fluorophenyl | 4-nitro-2-methoxyphenyl | $(CH_2)_3NH_2$ | 107.2 |
| 113 | 4-fluorophenyl | 4-(trifluoromethyl)phenyl | $(CH_2)_3NH_2$ | 85.6 |
| 116 | 4-fluorophenyl | 4-fluorophenyl | $(CH_2)_3NH_2$ | 94.0 |
| 124 | 4-chlorophenyl | 2-pyridyl | $(CH_2)_3NH_2$ | 67.6 |
| 134 | 4-bromophenyl | benzenesulfonyl | $(CH_2)_3NH_2$ | 69.2 |
| 135 | 4-(methoxycarbonyl)phenyl | phenyl | $(CH_2)_3NH_2$ | 80.1 |

TABLE 39

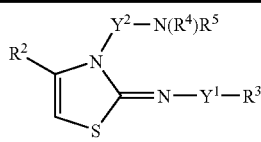

Binding Activity of compounds in Examples (concentration to be used: 30 μM)

| Ex. | $R^2$ | $Y^1$—$R^3$ | $Y^2$—$N(R^4)R^5$ | Binding Activity (30 μM) |
|---|---|---|---|---|
| 137 | 4-hydroxyphenyl | phenyl | $(CH_2)_3NH_2$ | 63.1 |
| 138 | 4-(methylthio)-phenyl | phenyl | $(CH_2)_3NH_2$ | 91.3 |
| 145 | 4-(methanesulfonyl)phenyl | phenyl | $(CH_2)_3NH_2$ | 55.5 |
| 152 | 4-methoxyphenyl | phenyl | $(CH_2)_3NHMe$ | 76.5 |
| 153 | 4-bromophenyl | phenyl | $(CH_2)_3NHAc$ | 89.7 |
| 154 | 4-methoxyphenyl | phenyl | $(CH_2)_2NHAc$ | 6.0 |
| 156 | 4-methoxyphenyl | 4-methoxyphenyl | $(CH_2)_3NHAc$ | 84.7 |
| 164 | 3,4-(methylenedioxy)phenyl | 2-methoxyphenyl | $(CH_2)_3NHAc$ | 61.4 |
| 167 | 4-fluorophenyl | 4-fluorophenyl | $(CH_2)_3NHAc$ | 58.2 |
| 169 | 4-bromophenyl | phenyl | $(CH_2)_3NH$—$COCH_2OH$ | 58.6 |

TABLE 39-continued

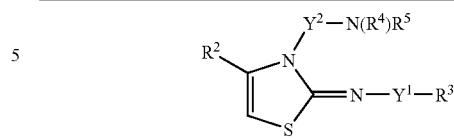

Binding Activity of compounds in Examples (concentration to be used: 30 μM)

| Ex. | $R^2$ | $Y^1$—$R^3$ | $Y^2$—$N(R^4)R^5$ | Binding Activity (30 μM) |
|---|---|---|---|---|
| 172 | 4-methoxyphenyl | phenyl | $(CH_2)_3NH$—$SO_2Me$ | 15.3 |
| 173 | 4-methoxyphenyl | phenyl | $(CH_2)_3NHTs$ | 55.7 |
| 176 | 4-methoxyphenyl | phenyl | $(CH_2)_3NH$—$C(O)OMe$ | 75.2 |
| 178 | 4-methoxyphenyl | phenyl | $(CH_2)_3NH$—$C(O)NHEt$ | 82.2 |
| 181 | 4-methoxyphenyl | phenyl | $(CH_2)_3NHC$—$(S)NHEt$ | 106.0 |
| 185 | 4-carboxyphenyl | phenyl | $(CH_2)_3NH_2$ | 13.9 |

Experiment 2

Evaluation of the Compound in Late Asthmatic Model in Guinea Pigs

The evaluation test was carried out using the compound obtained in Example 1.

Hartley male guinea pigs (purchased from Japan SLC) were prefed for about 1 week after purchasing them, and exposed to a 2% (w/v) solution of ovalbumin (OA) in saline solution in a plastic box (4 animals/box) for 5 minutes and made them inhale it by using an ultrasonic nebulizer (OMRON NE-U12, conditions: maximum amount of atomization and maximum airflow) for sensitization (Day 0). The animals were subjected to the same procedures on the 7th day. On the 14th and 15th days, each one animal was made to inhale a 2% OA for 5 minutes for antigen-challenge. One hour prior to the antigen-challenge, pyrilamine maleate (antihistamic agent; dissolved in saline solution, 10 mg/2 ml/kg) was intraperitoneally administered to each animal. A test compound was suspended in a 0.5% methyl cellulose (MC), and administered intraperitoneally twice to each animal at 2 hours prior to, and 6 hours after the antigen-challenge at a dose of 100 mg/5 ml/kg. To the control group, a 0.5% MC was administered in the same manner instead of a test compound.

The measurement and analysis of the respiratory function were carried out by a modified method of the method of Hutson et al., (cf., Penny A. Hutson et al., Am Rev Respir Dis 1988 137, 548-557). Before the antigen-challenge (before the administration of the drug) and 5 minutes, and 3, 17 and 20 hours after the antigen-challenge, the respiratory function of each animal was measured, and the wave pattern was recorded using Maclab Chart v 3.4 (AD instruments), and the analysis of the respiratory function was carried out later by using thereof. The specific airway conductance (sGaw) was calculated, and the degree of the improvement of the respiratory function was evaluated by using it as an index. The results are shown in Table 40.

TABLE 40

| | Rate of change of sGaw | |
|---|---|---|
| | 5 minutes | 20 hours |
| Control group | −45.1 ± 5.8% | −36.7 ± 4.6% |
| Compound of Example 1 | −33.8 ± 6.8% | −14.2 ± 15.0% |

As is shown in Table 40, in the control group, the significant decrease in sGaw was observed at 5 minutes after the antigen challenge (immediate asthmatic response: IAR), and at 17 and 20 hours after the antigen challenge, the significant decrease in sGaw was observed (late asthmatic response: LAR).

The test compound showed a tendency of inhibiting the IAR that was induced immediately after the antigen challenge. In the 20-hr value in which LAR was induced, the test compound also showed the tendency of inhibiting LAR (the rate of change of sGaw was −36.7±4.6% in the Control group, and −14.2±15.0% in the test compound-treated group, and hence, the inhibitory rate was about 60%).

Experiment 3

Evaluation of the Compound in the Leukocyte Infiltration into the Airway in the Guinea Pig Models:

In the same manner to in Experiment 2, the sensitization, the antigen challenge, and the administration of pyrilamine maleate and a medicament were carried out.

The recovery of bronchoalveolar lavage fluid (BALF) was carried out at 24 hours after the antigen challenge. Namely, the animals were anesthetized by intraperitoneal administration of pentbarbital (50 mg/ml) at a dose of 0.5 ml per animal, and the animals were subjected to an abdominal operation after sufficiently anesthetized. The perineal abdominal aorta was cut and the animals were killed by venesection. The diaphragm was incised and the neck was also incised to expose the trachea. After the trachea was cut, a cannula was inserted thereto, and an ice-cooled saline solution (5 ml) was injected by using a 5 ml syringe. Then, the injection and the suction were repeated three times by using the same solution for recovery. The fluid was collected and filtered through a stainless mesh, and collected in a tube on the ice. These procedures were repeated twice, and the recovery fluid was collected into the same tube (cases wherein the fluid volume was not more than 7 ml were not employed as data).

After the recovery, the fluid volume to be recovered was measured with the eye, and the fluid was centrifuged at 1500 rpm at 4° C. for 3 minutes, and the supernant was discarded. The residue was subjected to hemolysis under hypooncotic conditions. The mixture was centrifuged at 1500 rpm at 4° C. for 3 minutes, and the supernatant was discarded. The cells thus collected were suspended in a phosphoric buffered saline solution (PBS (−))(1 ml) containing a 0.5% BSA. The total number of cells were counted in this suspension by an automated leukocyte counter. After the measurement, a slide preparation was prepared by using Cytospin, which was further stained with a Diff Quick Stainning Kit. The smear slide was observed with an optical microscope, and the numbers of eosinophils, neutrophils, macropharges and lymphocytes in 300 cells were counted. The results are shown in Table 41.

TABLE 41

| | Total number of cells (×$10^5$) | Number of eosinophils (×$10^5$) | Number of lymphocytes (×$10^5$) |
|---|---|---|---|
| Saline-treated group | 53.6 ± 4.6 | 7.3 ± 3.2 | 1.3 ± 0.3 |
| Control | 102.1 ± 19.1 | 38.1 ± 13.1 | 3.6 ± 1.1 |
| Compound of Example 1 | 62.1 ± 8.6 | 13.8 ± 5.1 | 2.0 ± 0.6 |

As is shown in Table 41, as to the total number of cells, there was a significant increase in the control group as compared with the saline-treated group. To this control group, the total number of cells in the test compound-treated compound was reduced by 82%.

As to the number of eosinophils, there was a significant increase in the control group as compared with the saline-treated group. To this control group, the number of eosinophils in the test compound-treated group was reduced by 79%.

As to the number of lymphocytes, there was a significant increase in the control group as compared with the saline-treated group. To this control group, the number of lymphocytes in the test compound-treated group was reduced by 70%.

Experiment 4

In the same manner to in Experiment 1, the receptor binding assay was carried out on the present compounds by using the rat lung membranes. The results are shown in Tables 42-45.

TABLE 42

Binding activity of the compounds of Examples (concentration to be tested: 30 µM)

| Ex. No. | Binding Activity (30 µM) |
|---|---|
| 214 | 99 |
| 215 | 109 |
| 216 | 112 |
| 220 | 101 |
| 221 | 79 |
| 222 | 86 |
| 239 | 50 |
| 245 | 96 |
| 246 | 80 |
| 250 | 98 |
| 251 | 61 |
| 257 | 110 |
| 280 | 99 |
| 284 | 77 |
| 285 | 35 |
| 288 | 34 |
| 290 | 98 |
| 291 | 68 |
| 295 | 18 |
| 297 | 75 |
| 298 | 101 |

TABLE 43

Binding activity of the compounds of Examples (concentration to be tested: 30 µM)

| Ex. No. | Binding Activity (30 µM) |
|---|---|
| 299 | 93 |
| 302 | 27 |

TABLE 43-continued

Binding activity of the compounds of Examples
(concentration to be tested: 30 μM)

| Ex. No. | Binding Activity (30 μM) |
| --- | --- |
| 303 | 23 |
| 305 | 13 |
| 307 | 48 |
| 309 | 100 |
| 311 | 95 |
| 312 | 112 |
| 315 | 115 |
| 316 | 102 |
| 329 | 76 |
| 335 | 101 |
| 342 | 56 |
| 343 | 107 |
| 344 | 101 |
| 349 | 100 |
| 355 | 89 |
| 357 | 86 |
| 359 | 82 |
| 361 | 88 |
| 362 | 117 |
| 373 | 90 |
| 383 | 84 |
| 384 | 107 |
| 402 | 79 |
| 409 | 89 |
| 411 | 118 |
| 417 | 113 |

TABLE 44

Binding activity of the compounds of Examples
(concentration to be tested: 30 μM)

| Ex. No. | Binding Activity (30 μM) |
| --- | --- |
| 427 | 100 |
| 429 | 103 |
| 430 | 89 |
| 368 | 100 |
| 390 | 120 |
| 393 | 80 |
| 396 | 114 |
| 398 | 37 |
| 404 | 109 |
| 405 | 115 |
| 408 | 121 |
| 413 | 96 |
| 423 | 113 |
| 428 | 103 |
| 431 | 95 |
| 446 | 97 |
| 473 | 33 |
| 432 | 42 |
| 435 | 93 |
| 437 | 106 |
| 441 | 61 |
| 444 | 99 |
| 447 | 89 |
| 448 | 77 |
| 449 | 71 |
| 452 | 84 |
| 454 | 38 |
| 458 | 87 |

TABLE 45

Binding activity of the compounds of Examples
(concentration to be tested: 30 μM)

| Ex. No. | Binding Activity (30 μM) |
| --- | --- |
| 461 | 42 |
| 463 | 10 |
| 482 | 85 |
| 484 | 97 |
| 494 | 65 |
| 496 | 80 |
| 508 | 102 |
| 509 | 103 |
| 520 | 99 |
| 521 | 74 |
| 523 | 73 |
| 531 | 32 |
| 534 | 87 |
| 535 | 108 |
| 536 | 67 |

INDUSTRIAL APPLICABILITY

The 5-membered cyclic compounds of the present invention, or a salt thereof, or a prodrug thereof inhibits the infiltration of leukocytes such as eosinophils, lymphocytes, etc., by which it is useful in the treatment of various inflammations.

The invention claimed is:
1. A compound of the formula:

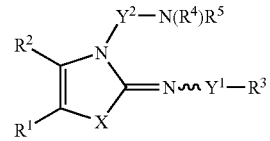

wherein X is a sulfur atom,
$R^1$ is a hydrogen atom, a substituted or unsubstituted alkyl, or a substituted or unsubstituted aryl,
$R^2$ is a hydrogen atom, a substituted or unsubstituted alkyl, or a substituted or unsubstituted aryl,
$Y^1$ is a direct bond, a substituted or unsubstituted alkylene, —CO(CH$_2$)$_n$—, —SO$_2$(CH$_2$)$_n$—, —CONH(CH$_2$)$_n$—, —CSNH(CH$_2$)$_n$—, or —COO(CH$_2$)$_n$—,
n is an integer of from 0 to 5,
the wavy line means (E)-configuration or (Z)-configuration,
$R^3$ is a substituted or unsubstituted pyridyl,
$Y^2$ is a substituted or unsubstituted alkylene, or an alkenylene,
$R^4$ is a hydrogen atom, a substituted or unsubstituted alkanoyl, a substituted or unsubstituted alkyl, —COOR$^8$, —SO$_2$R$^9$, —COR$^{10}$, —CON(R$^{11}$)R$^{12}$, —CSN(R$^{13}$)R$^{14}$, a cycloalkyl, a substituted or unsubstituted aryl, or —C(=NH)N(R$^{15}$)R$^{16}$,
$R^5$ is a hydrogen atom, or a substituted or unsubstituted alkyl,
$R^8$ is a substituted or unsubstituted alkyl, a cycloalkyl, or a substituted or unsubstituted aryl,
$R^9$ is a substituted or unsubstituted alkyl, or a substituted or unsubstituted aryl,
$R^{10}$ is a cycloalkyl, or a substituted or unsubstituted aryl,
$R^{11}$ is a hydrogen atom or an alkyl, R$^{12}$ is a hydrogen atom, a substituted or unsubstituted alkyl, a cycloalkyl, a substituted or unsubstituted aryl, or a substituted or unsubstituted arylcarbonyl, R$^{13}$ is a hydrogen atom or an alkyl, R$^{14}$ is a hydrogen atom, a substituted or unsubstituted alkyl, a cycloalkyl, a substituted or unsubstituted aryl, or a substituted or unsubstituted arylcarbonyl, R$^{15}$ is a hydrogen atom or an alkyl, R$^{16}$ is a hydrogen atom or a substituted or unsubstituted alkyl, or a pharmaceutically acceptable salt thereof, or a prodrug thereof.

2. The compound according to claim 1, which is a compound of the formula:

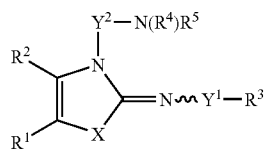

wherein X is a sulfur atom,

R$^1$ is a hydrogen atom; an alkyl; an alkyl being substituted by a hydroxy group or a halogen atom; an aryl; or an aryl which is substituted by one or more groups selected from the group consisting of an alkoxy, a halogen-substituted alkoxy, a hydroxy, a halogen atom, a cyano, an amino, a mono- or di-(alkyl)amino, a nitro, an alkyl, an alkyl being substituted by a halogen atom or a hydroxy, a cycloalkyl, a cycloalkyl-substituted alkyl, a methylenedioxy, an ethylenedioxy, a carboxy, an alkoxycarbonyl, a carbamoyl, an alkylcarbamoyl, a di(alkyl)carbamoyl, an alkylthio, an alkylsulfinyl, an alkylsulfonyl, a sulfamoyl, an alkylsulfamoyl, a di(alkyl)sulfamoyl, an aryl, and an aryl being substituted by an alkyl, an alkoxy, a halogen atom or a hydroxy; R$^2$ is a hydrogen atom; an alkyl; an alkyl being substituted by a hydroxy, a halogen atom or an amino; an aryl; or an aryl being substituted by one or more groups selected from the group consisting of an alkoxy, a halogen-substituted alkoxy, a hydroxy, a halogen atom, a cyano, an amino, a mono- or di-(alkyl)amino, a nitro, an alkyl, an alkyl being substituted by a halogen atom or a hydroxy, a cycloalkyl, a cycloalkyl-substituted alkyl, methylenedioxy, ethylenedioxy, a carboxy, an alkoxycarbonyl, a carbamoyl, an alkylcarbamoyl, a di(alkyl)-carbamoyl, an alkylthio, an alkylsulfinyl, an alkylsulfonyl, sulfamoyl, an alkylsulfamoyl, a di(alkyl)sulfamoyl, an aryl, and an aryl being substituted by an alkyl, an alkoxy, a halogen atom, or a hydroxy;

Y$^1$ is a direct bond; a straight chain or branched chain C$_1$-C$_5$ alkylene; a straight chain or branched chain C$_1$-C$_5$ alkylene being substituted by a hydroxy, a halogen atom or an amino; —CO(CH$_2$)$_n$—; or —SO$_2$(CH$_2$)$_n$—(n is an integer of from 0 to 5), R$^3$ is a pyridyl or a pyridyl being substituted by an alkyl, an alkoxy, a halogen atom or a hydroxy, Y$^2$ is a straight chain or branched chain C$_2$-C$_5$ alkylene; a straight chain or branched chain C$_2$-C$_5$ alkylene being substituted by a hydroxy, an alkoxy, a halogen atom, an amino or an alkanoylamino; or a straight chain or branched chain C$_3$-C$_5$ alkenylene, R$^4$ is a hydrogen atom; an alkanoyl; an aroyl; an alkyl; an alkyl being substituted by a hydroxy, an alkoxy, a halogen atom or an amino: an alkylcarbamoyl, an alkoxycarbonyl; an alkylaminothiocarbonyl; an alkylsulfonyl; an arylsulfonyl; or an alkyl-substituted arylsulfonyl, R$^5$ is a hydrogen atom; an alkyl; or an alkyl being substituted by a hydroxy, a halogen atom or an amino, or a pharmaceutically acceptable salt thereof, or a prodrug thereof.

3. The compound according to claim 1 or 2, wherein Y$^1$ is a direct bond, or a pharmaceutically acceptable salt thereof, or a prodrug thereof.

4. The compound according to claim 1 or 2, wherein R$^1$ is a hydrogen atom, or a pharmaceutically acceptable salt thereof, or a prodrug thereof.

5. The compound according to claim 1 or 2, wherein R$^2$ is a substituted or unsubstituted aryl, or a pharmaceutically acceptable salt thereof, or a prodrug thereof.

6. The compound according to claim 1 or 2, wherein Y$^1$ is a direct bond or a —CO—, or a pharmaceutically acceptable salt thereof, or a prodrug thereof.

7. The compound according to claim 1 or 2, wherein the wavy line means (Z)-configuration, or a pharmaceutically acceptable salt thereof, or a prodrug thereof.

8. The compound according to claim 1 or 2, wherein Y$^2$ is ethylene or trimethylene, or a pharmaceutically acceptable salt thereof, or a prodrug thereof.

9. The compound according to claim 1 or 2, wherein R$^4$ is a substituted or unsubstituted alkanoyl, a substituted or unsubstituted alkyl, a substituted or unsubstituted alkylcarbamoyl, a substituted or unsubstituted alkylaminothiocarbonyl, or a substituted or unsubstituted alkoxycarbonyl, or a pharmaceutically acceptable salt thereof, or a prodrug thereof.

10. The compound according to claim 1 or 2, wherein R$^4$ is a substituted or unsubstituted alkanoyl, a substituted or unsubstituted alkyl, or a substituted or unsubstituted alkylcarbamoyl, or a pharmaceutically acceptable salt thereof, or a prodrug thereof.

11. The compound according to claim 1 or 2, wherein R$^5$ is a hydrogen atom, or a pharmaceutically acceptable salt thereof, or a prodrug thereof.

12. The compound according to claim 1, which is a compound of the formula:

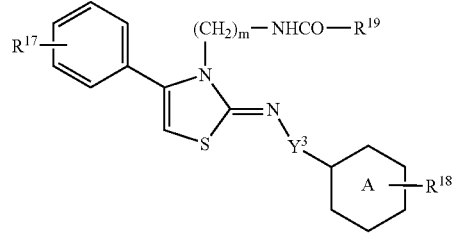

wherein Ring A is a pyridine ring, m is 2 or 3,

Y$^3$ is a direct bond or a carbonyl, the number of R$^{17}$ is 1 or 2, and R$^{17}$s are independently selected from a halogen atom, a C$_1$-C$_4$ alkoxy, a trifluoromethoxy and a methylenedioxy, the number of R$^{18}$ is 1 or 2, and R$^{18}$s are independently selected from a halogen atom, a C$_1$-C$_4$ alkoxy, a trifluoromethoxy and a hydroxy, R$^{19}$ is a C$_1$-C$_4$ alkyl; a C$_1$-C$_4$ alkyl being substituted by a hydroxy, a C$_1$-C$_4$ alkoxy, a mono- or di-(C$_1$-C$_4$ alkyl) amino or a carboxy; a C$_1$-C$_4$ alkylamino; or a C$_1$-C$_4$ alkylamino being substituted by a hydroxy, a C$_1$-C$_4$ alkoxy, a mono- or di-(C$_1$-C$_4$ alkyl)amino, or a carboxy, or a pharmaceutically acceptable salt thereof, or a prodrug thereof.

13. The compound according to claim 12, provided that when $Y^3$ is a direct bond, then $R^{19}$ is not a methyl, or a pharmaceutically acceptable salt thereof, or a prodrug thereof.

14. A pharmaceutical composition, which comprises the compound as set forth in claim 1, 2 or 12, or a pharmaceutically acceptable salt thereof, or a prodrug thereof.

* * * * *

UNITED STATES PATENT AND TRADEMARK OFFICE
CERTIFICATE OF CORRECTION

| | | |
|---|---|---|
| PATENT NO. | : 7,396,842 B2 | Page 1 of 1 |
| APPLICATION NO. | : 11/111845 | |
| DATED | : July 8, 2008 | |
| INVENTOR(S) | : Norio Fujiwara et al. | |

It is certified that error appears in the above-identified patent and that said Letters Patent is hereby corrected as shown below:

On the cover page:

The line reading "(62) Division of application No. 10/312,692, filed on Dec. 30, 2002, now Pat. No. 6,919,361." should read --(62) Division of application No. 10/312,692, filed on Dec. 30, 2002, now Pat. No. 6,919,361 which is a 371 national phase application of international patent application No. PCT/JP01/05540, filed on June 28, 2001--.

Signed and Sealed this
Thirty-first Day of May, 2011

David J. Kappos
*Director of the United States Patent and Trademark Office*